(12) United States Patent
Yu et al.

(10) Patent No.: US 6,911,200 B2
(45) Date of Patent: Jun. 28, 2005

(54) METHODS OF TREATING NEOPLASIA WITH COMBINATION OF TARGET-CELL SPECIFIC ADENOVIRUS, CHEMOTHERAPY AND RADIATION

(75) Inventors: De-Chao Yu, Foster City, CA (US); Yu Chen, Cupertino, CA (US); Daniel R. Henderson, Palo Alto, CA (US)

(73) Assignee: Cell Genesys, Inc., Foster City, CA (US)

( * ) Notice: Subject to any disclaimer, the term of this patent is extended or adjusted under 35 U.S.C. 154(b) by 0 days.

(21) Appl. No.: 09/814,357

(22) Filed: Mar. 21, 2001

(65) Prior Publication Data

US 2003/0068307 A1 Apr. 10, 2003

Related U.S. Application Data

(60) Provisional application No. 60/192,015, filed on Mar. 24, 2000.

(51) Int. Cl.[7] .................. A01N 63/00; A61K 48/00; C12N 15/861
(52) U.S. Cl. .............. 424/93.2; 435/455; 435/456; 435/320.1
(58) Field of Search .................. 435/455, 456, 435/320.1; 424/93.2, 93.21; 514/44

(56) References Cited

U.S. PATENT DOCUMENTS

| | | | |
|---|---|---|---|
| 5,698,443 A | 12/1997 | Henderson et al. | 435/320.1 |
| 5,747,469 A | 5/1998 | Roth et al. | 514/44 |
| 5,776,743 A | 7/1998 | Frisch | 435/172.3 |
| 5,801,029 A | 9/1998 | McCormick | 435/172.3 |
| 5,846,945 A | 12/1998 | McCormick | 514/44 |
| 5,871,726 A * | 2/1999 | Henderson et al. | 424/93.2 |
| 5,998,205 A | 12/1999 | Hallenbeck et al. | 435/325 |

FOREIGN PATENT DOCUMENTS

| | | | | |
|---|---|---|---|---|
| WO | WO 95/19434 | 7/1995 | ........... | C12N/15/11 |
| WO | WO 97/01358 | 1/1997 | .......... | A61K/48/00 |
| WO | WO 97/10007 | 3/1997 | | |
| WO | WO 98/29555 | 7/1998 | ........... | C12N/15/86 |
| WO | WO 98/35554 | 8/1998 | .......... | A01N/37/18 |
| WO | WO 98/37189 | 8/1998 | ........... | C12N/15/11 |
| WO | WO 98/39464 | 9/1998 | | |
| WO | WO 98/39465 | 9/1998 | ........... | C12N/15/86 |
| WO | WO 98/39466 | 9/1998 | ........... | C12N/15/86 |
| WO | WO 98/39467 | 9/1998 | | |
| WO | WO 99/06576 | 2/1999 | ........... | C12N/15/57 |
| WO | WO 99/25860 | 5/1999 | | |
| WO | WO 99/59604 | 11/1999 | | |
| WO | WO 00/15820 | 3/2000 | | |
| WO | WO 00/39319 | 7/2000 | | |

OTHER PUBLICATIONS

Gomez–Navarro et al. Gene Therapy for Cancer, European Journal of Cancer, vol. 6, pp. 867–885, 1999.*
Verma et al. Gene Therapy–promises, problems, and prospects. Nature, vol. 389, pp. 239–242. 1997.*
Gromeier. Viruses for Treating Cancer. ASM News, vol. 68., pp. 438–445, 2002.*
Anderson. Human Gene Therapy, Nature, vol. 392, pp. 25–30 1998.*
Vile et al. Cancer gene therapy: hard lesson and new courses. Gene Therapy. vol. 7, pp. 2–8, 2000.*
Kaminski et al. Prostate cancer gene therapy and the role of radiation. Cancer Treatment Reviews. vol. 28, pp. 49–64, 2002.*
Duque et al. Adenovirus lacking the 19–kDa and 55–kDa E1B genes exerts a marked cytotoxic effect in human malignant cells.Cancer Gene Therapy, vol. 6. pp. 554–563, 1999.*
Gurnani et al. Adenovirus–mediated p53 gene therapy has greater efficacy when combined with chemotherapy against human head and neck, ovarian, prostate, and breast cancer. Cancer Chemother Pharmacol, vol. 44, pp. 143–151, 1999.*

* cited by examiner

*Primary Examiner*—Scott D. Priebe
*Assistant Examiner*—Brian Whiteman
(74) *Attorney, Agent, or Firm*—Steven B. Kelber; DLA Piper Rudnick Gray Cary US LLP

(57) ABSTRACT

The invention provides methods of treating neoplasia using combinations of target cell-specific replication competent adenoviral vectors and chemotherapy, radiation therapy or combinations thereof. The adenoviral vectors are target cell-specific for the particular type of neoplasia for which treatment is necessary and the combination with the chemotherapy and/or radiation leads to synergistic treatment over existing adenoviral therapy or traditional chemotherapy and radiation therapy.

9 Claims, 42 Drawing Sheets

FIG. 37

```
G ATG ACC GGC TCA ACC ATC GCG CCC ACA ACG GAC TAT CGC AAC ACC
46
  Met Thr Gly Ser Thr Ile Ala Pro Thr Thr Asp Tyr Arg Asn Thr
   1           5                  10                  15

ACT GCT ACC GGA CTA ACA TCT GCC CTA AAT TTA CCC CAA GTT CAT GCC
94
Thr Ala Thr Gly Leu Thr Ser Ala Leu Asn Leu Pro Gln Val His Ala
                 20                  25                  30

TTT GTC AAT GAC TGG GCG AGC TTG GAC ATG TGG TGG TTT TCC ATA GCG
142
Phe Val Asn Asp Trp Ala Ser Leu Asp Met Trp Trp Phe Ser Ile Ala
                 35                  40                  45

CTT ATG TTT GTT TGC CTT ATT ATT ATG TGG CTT ATT TGT TGC CTA AAG
190
Leu Met Phe Val Cys Leu Ile Ile Met Trp Leu Ile Cys Cys Leu Lys
         50                  55                  60

CGC AGA CGC GCC AGA CCC CCC ATC TAT AGG CCT ATC ATT GTG CTC AAC
238
Arg Arg Arg Ala Arg Pro Pro Ile Tyr Arg Pro Ile Ile Val Leu Asn
         65                  70                  75

CCA CAC AAT GAA AAA ATT CAT AGA TTG GAC GGT CTG AAA CCA TGT TCT
286
Pro His Asn Glu Lys Ile His Arg Leu Asp Gly Leu Lys Pro Cys Ser
     80                  85                  90                  95

CTT CTT TTA CAG TAT GAT TAA (SEQ ID NO: 17)
307
Leu Leu Leu Gln Tyr Asp (SEQ ID NO: 18)
                100
```

METHODS OF TREATING NEOPLASIA WITH COMBINATION OF TARGET-CELL SPECIFIC ADENOVIRUS, CHEMOTHERAPY AND RADIATION

The above-identified application claims priority to U.S. Provisional application 60/192,015 filed Mar. 24, 2000, which provisional application is hereby incorporated herein in its entirety.

TECHNICAL FIELD

This invention relates to cell transfection, and in particular methods of using adenoviral vectors for the suppression of tumor growth in conjunction with chemotherapy, radiation therapy or combinations thereof.

BACKGROUND ART

Neoplasia, also known as cancer, is the second most common cause of death in the United States. While the survival rates for individuals with cancer have increased considerably in the last few decades, survival of the disease is far from assured. Cancer is a catch-all term for over 100 different diseases, each of which are each fundamentally characterized by the unchecked proliferation of cells. Individual cancer cells are also able to break off from the main tumor, or metastasize, creating additional tumors in other regions of the body.

Due to the mortality rate and incidence of neoplasia in the general population, research into potential cures has been high on the national agenda for decades. This research has led to the development a number of treatments, both systemic and regional (local). Regional treatments include radiation therapy, some types of chemotherapy and surgery. Chemotherapy has most often been used in systemic treatment. Each of these treatment regimes has significant disadvantages and limitations. Chemotherapy and radiation treatments will be discussed below.

Chemotherapy

Chemotherapy refers to the use of chemical compounds or drugs in the treatment of disease, though the term chemotherapy is most often associated with the treatment of cancer. Cancer chemotherapeutic agents are also commonly referred to as antineoplastic agents. There are a number of classes of chemotherapeutic compounds, encompassing nearly 100 individual drugs, as well as numerous drug combination therapies, methods of delivery and schedules of treatment. Each of these chemotherapeutic agents may be classified according to several criteria, such as class of compound and disease state treated. Certain agents have been developed to take advantage of the rapid division of cancer cells and target specific phases in the cell cycle, providing another method of classification. Agents can also be grouped according to the type and severity of their side effects or method of delivery. However, the most common classification of chemotherapeutic agents is by class of compound, which broadly encompasses the mechanism of action of these compounds.

Depending on the reference source consulted, there are slight differences in the classification of antineoplastics. The classes of compounds are described in the Physician's Desk Reference as follows: alkaloids; alkylating agents; antitumor antibiotics; antimetabolites; hormones and hormone analogs; immunomodulators; photosensitizing agents; and miscellaneous other agents. Examples of these antineoplastics are listed in Table 1.

The alkaloid class of compounds are also referred to as mitotic inhibitors, as they are cell cycle phase specific and serve to inhibit mitosis or inhibit the enzymes required for mitosis. They are derived generally from plant alkaloids and other natural products and work during the M-phase of the cell cycle. This class of compounds is often used to treat neoplasias such as acute lymphoblastic leukemia, Hodgkin's and non-Hodgkin's lymphoma; neuroblastomas and cancers of the lung, breast and testes.

Alkylating agents make up a large class of chemotherapeutic agents, including of the following sub-classes, which each represent a number of individual drugs: alkyl sulfonates; aziridines; ethylenimines and methylmelamines; nitrogen mustards; nitrosoureas; and others. Alkylating agents attack neoplastic cells by directly alkylating the DNA of cells and therefore causing the DNA to be replication incompetent. This class of compounds is commonly used to treat a variety of diseases, including chronic leukemias, non-Hodgkin's lymphoma, Hodgkin's lymphoma, multiple myeloma and certain lung, breast and ovarian cancers.

Nitrosoureas are often categorized as alkylating agents, and have a similar mechanism of action, but instead of directly alkylating DNA, they inhibit DNA repair enzymes causing replication failure. These compounds have the advantage of being able to cross the blood-brain barrier and therefore can be used to treat brain tumors.

Antitumor antibiotics have antimicrobial and cytotoxic activity and also interfere with DNA by chemically inhibiting enzymes and mitosis or by altering cell membranes. They are not cell cycle phase specific and are widely used to treat a variety of cancers.

The antimetabolite class of antineoplastics interfere with the growth of DNA and RNA and are specific to the S-phase of the cell-cycle. They can be broken down further by type of compound, which include folic acid analogs, purine analogs, and pyrimidine analogs. They are often employed in the treatment of chronic leukemia, breast, ovary, and gastrointestinal tumors.

There are two classes of hormones or hormone analogs used as antineoplastic agents, the corticosteroid hormones and sex hormones. While some corticosteroid hormones can both kill cancer cells and slow the growth of tumors, and are used in the treatment of lymphoma, leukemias, etc., sex hormones function primarily to slow the growth of breast, prostate and endometrial cancers. There are numerous sub-classes of hormones and hormone analogs, including, androgens, antiadrenals, antiandrogens, antiestrogens, aromatase inhibitors, estrogens, leutenizing hormone releasing hormone (LHRH) analogs and progestins.

An additional smaller class of antineoplastics is classified as immunotherapy. These are agents which are intended to stimulate the immune system to more effectively attack the neoplastic cells. This therapy is often used in combination with other therapies.

There are also a number of compounds, such as campothectins, which are generally listed as 'other' antineoplastic agents and can be used to treat a variety of neoplasias.

While there is a plethora of antineoplastic agents, the efficacy of these compounds is often outweighed by the severity of the side effects produced by the agent. This comparison is often referred to as the therapeutic index, which describes the balance between the required dose to accomplish the destruction of the cancer cells compared to the dose at which the substance is unacceptably toxic to the individual. The drawback to most antineoplastic agents is the relatively small range of the therapeutic index, (i.e, the narrow dosage range in which cancer cells are destroyed without unacceptable toxicity to the individual). This characteristic limits the frequency and dosage where an agent is useful, and often the side effects become intolerable before the cancer can be fully eradicated.

The severe side effects experienced with the majority of cancer chemotherapeutics are a result of the non-specific nature of these drugs, which do not distinguish between healthy and cancerous cells, and instead destroy both. The cell cycle specific drugs attempt to lessen these effects, targeting phases of the cell cycle involved in cell replication and division. These drugs do not, however, distinguish between cancerous cells and healthy cells which are undergoing normal cell division. The cells most at risk from these types of chemotherapy are those which undergo cell division often, including blood cells, hair follicle cells, and cells of the reproductive and digestive tracts.

The most common side effects of antineoplastic agents are nausea and vomiting. A large proportion of individuals also suffer from myelosuppression, or suppression of the bone marrow, which produces red blood cells, white blood cells and platelets. These and other side effects are also exacerbated by the suppression of the immune system concomitant with the destruction and lack of production of white blood cells, and associated risk of opportunistic infection.

Other side effects common to a wide range of antineoplastic agents include: hair loss (alopecia); appetite loss; weight loss; taste changes; stomatitis and esophagitis (inflammation and sores); constipation; diarrhea; fatigue; heart damage; nervous system changes; lung damage; reproductive tissue damage; liver damage; kidney and urinary system damage.

The wide range of the side effects associated with most antineoplastic agents and their severity in individuals who are already debilitated with disease and possibly immune compromised has led researches to search for mechanisms by which they can alleviate some of the side effects while maintaining the efficacy of the treatment. Several approaches to this problem have been taken. They include combination chemotherapy, where multiple antineoplastics are administered together; adjuvant therapies, where additional agents are prescribed along with the antineoplastic agent to fight the side effects of the antineoplastic; alternative delivery vehicles for the administration of chemotherapeutics, such as the encapsulation of antineoplastic agents in liposomes; and combined modality treatments, where chemotherapy is combined with radiation and/or surgery.

One difficulty with respect to combination chemotherapy is that many antineoplastic agents have similar side effects, so while their toxicity profiles are different, the individual will still suffer greatly and may not be able to finish the recommended course of treatment.

Another aspect of combination chemotherapy is the addition of hormones to the combination of drugs administered. While the hormone or hormonal analog treatment is generally not cytotoxic, hormonal manipulation helps to prevent or slow cell division and therefore slows the growth of the tumor. This type of therapy is often used for hormone dependent tumors of, for instance, the prostate, breast or ovaries. One well known example is the treatment of breast cancer with tamoxifen.

An additional method of combating the side effects associated with antineoplastics and, more importantly, extending the therapeutic dosage of these agents is adjuvant therapy, where additional agents are co-administered to the individual in order to ameliorate the side effects or toxicity of the antineoplastic agent. Examples of such adjuvant therapy includes the administration of chemoprotective agents, such as the uroprotective agent mesna, the antimetastatic agent batimastat, the folic acid replenisher folinic acid. Additional therapies include the administration of granulocyte colony stimulating factors, granulocyte-macrophage colony stimulating factor and even the transplantation of hematopoietic stem cells. These last three therapies aim to treat lessen the chance of opportunistic infection due to myelosuppression concomitant with many chemotherapy regimens. However, despite the recent advances in antineoplastic and adjuvant therapy there are still numerous cancers, for example ovarian cancer, that are resistant to current treatments, and leave the individual at risk for potentially serious infection.

Radiation Therapy

Along with chemotherapy and surgery, radiation is one of the most commonly used treatment modalities, used in approximately 60% of treatment regimens. Radiation, in any of several forms, is often used as the primary therapy for basal cell carcinomas of the skin, head and neck, prostate cancers, bladder cancers, and others. Often combined with chemotherapy and/or surgery, radiation therapy encompasses both local and total body administration as well as a number of new advances, including radioimmunotherapy.

The cytotoxic effect of radiation on neoplastic cells arises from the ability of radiation to cause a break in one or both strands of the DNA molecule inside the cells. Cells in all phases of the cell cycle are susceptible to this effect. However, the DNA damage is more likely to be lethal in cancerous cells because they are less capable of repairing DNA damage. Healthy cells, with functioning cell cycle check proteins and repair enzymes, are far more likely to be able to repair the radiation damage and function normally after treatment.

Tumors and tissues themselves are also characterized by a range of susceptibilities to radiation therapy. Lymphoma and leukemias are very sensitive to radiation therapy, while renal cancer and gland tumors are fairly insensitive to radiation. A tumor that is considered radiosensitive is one which can be eradicated by a dose(s) of radiation that is also well tolerated by the surrounding tissues. Unsurprisingly, different tissue types within the body tolerate radiation at different doses. Tissues that undergo frequent cell division are most effected by treatment, similar to their sensitivity to certain cell cycle specific chemotherapy agents.

The radiosensitivity of tumors is also effected by hypoxia, or a lack of oxygen in the interiors of larger tumors. Hypoxic tumors can be 2–3 times less responsive to radiation treatment. Certain agents used in conjunction with radiation treatment, such as some of the radiosensitizing agents, work by increasing the singlet oxygen species in the vicinity of the tumor and therefore increasing its radiosensitivity. Other compounds used in conjunction with radiation therapy include radioprotectants which are designed to protect surrounding tissue from some of the effects of radiation therapy. Sources of radiation include: Americium, chromic phosphate, radioactive, Cobalt, $^{131}$I-ethiodized oil, Gold (radioactive, colloidal) iobenguane, Radium, Radon, sodium iodide (radioactive), sodium phosphate (radioactive).

Radiation therapy itself can be classified according to two primary types, internal and external radiation therapy. External therapy involves the administration of radiation via a machine capable of producing high-energy external beam radiation. This therapy can include either total body irradiation, or can be localized to the region of the tumor. With external radiation treatments, the bodily secretions of the individual are not radioactive after treatment. The radiation itself can be either electromagnetic (X-ray or gamma radiation) or particulate ($\alpha$ or $\beta$ particles). The treatment requirements will differ depending upon the characteristics of the tumor. External radiation is often used pre- or post-operatively; either to shrink the tumor before surgery, or to mop up remaining cancer cells after surgery.

Internal radiation therapy, also termed brachytherapy, involves implantation of a radioactive isotope as the source of the radiation. There a variety of methods of delivery, including permanent, temporary, sealed, unsealed, intracavity or interstitial implants. The choice of implant is determined by a variety of factors, including the location and extent of the tumor.

A third, but still experimental, type of radiation therapy is often termed radioimmunotherapy. This involves the attachment of radioisotopes to monoclonal antibodies specific for the tumor cells. Upon administration the antibodies specifically seek out and destroy the cancer cells.

The side effects of radiation are similar to those of chemotherapy and arise for the same reason, the damage of healthy tissue. Radiation is usually more localized than chemotherapy, but treatment is still accompanied by damage to previously healthy tissue. Many of the side effects are unpleasant, and radiation also shares with chemotherapy the disadvantage of being mutagenic, carcinogenic and teratogenic in its own right. While normal cells usually begin to recover from treatment within two hours of treatment, mutations may be induced in the genes of the healthy cells. These risks are elevated in certain tissues, such as those in the reproductive system. It has also been found that people tolerate radiation differently. Doses that may not lead to new cancers in one individual may in fact spawn additional cancers in another individual. This could be due to pre-existing mutations in cell cycle check proteins or repair enzymes, but current practice would not be able to predict at what dose a particular individual is at risk. Common side effects of radiation include: bladder irritation; fatigue; diarrhea; low blood counts; mouth irritation; taste alteration; loss of appetite; alopecia; skin irritation; change in pulmonary function; enteritis; sleep disorders; and others.

Adenovirus Vectors

Until relatively recently, the virtually exclusive focus in development of adenoviral vectors for gene therapy has been use of adenovirus merely as a vehicle for introducing the gene of interest, not as an effector in itself. Replication of adenovirus had previously been viewed as an undesirable result, largely due to the host immune response. More recently, however, the use of adenovirus vectors as effectors has been described. International Patent Application Nos. PCT/US98/04084, PCT/US98/04080; PCT/US98/04133, PCT/US98/04132, PCT/US98/16312, PCT/US95/00845, PCT/US96/10838, PCT/EP98/07380, U.S. Pat. No. 5,998, 205 and U.S. Pat. No. 5,698,443. The use of IRES in vectors have been described. See, for example, International Patent Application No. PCT/US98/03699 and International Patent Application No. PCT/EP98/07380. Adenovirus E1A and E1B genes are disclosed in Rao et al. (1992, *Proc. Natl. Acad. Sci.* USA vol. 89: 7742–7746).

Publications describing various aspects of adenovirus biology and/or techniques relating to adenovirus include the following. PCT/US95/14461; Graham and Van de Eb (1973) *Virology* 52:456–467; Takiff et al. (1981) *Lancet* ii:832–834; Berkner and Sharp (1983) *Nucleic Acid Research* 6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806 describe adenoviruses that have been genetically modified to produce replication-defective gene transfer vehicles. In these vehicles, the early adenovirus gene products E1A and E1B are deleted and provided in trans by the packaging cell line 293 developed by Frank Graham (Graham et al. (1987) *J. Gen. Birol.* 36:59–72 and Graham (1977) *J. Genetic Virology* 68:937–940). The gene to be transduced is commonly inserted into adenovirus in the deleted E1A and E1B region of the virus genome Bett et al. (1994), supra. Adenovirus vectors as vehicles for efficient transduction of genes have been described by Stratford-Perricaudet (1990) *Human Gene Therapy* 1:2–256; Rosenfeld (1991) *Science* 252:431–434; Wang et al. (1991) *Adv. Exp. Med. Biol.* 309:61–66; Jaffe et al. (1992) *Nat Gent.* 1:372–378; Quantin et al. (1992) *Proc Natl. Acad. Sci. USA* 89:2581–2584; Rosenfeld et al. (1992) *Cell* 68:143–155; Stratford-Perricaudet et al. (1992) *J. Clin. Invest.* 90:626–630; Le Gal La Salle et al. (1993) *Science* 259:988-990; Mastrangeli et al. (1993) *J. Clin. Invest.* 91:225–234; Ragot et al. (1993) *Nature* 361:647–650; Hayaski et al. (1994) *J. Biol. Chem.* 269:23872–23875.

There are several other experimental cancer therapies which utilize various aspects of adenovirus or adenovirus vectors. See, U.S. Pat. No. 5,776,743; U.S. Pat. No. 5,846, 945; U.S. Pat. No. 5,801,029; PCT/US99/08592; U.S. Pat. No. 5,747,469; PCT/US98/03514; and PCT/US97/22036.

Of particular interest is the development of more specific, targeted forms of cancer therapy, especially in cancers that are difficult to treat successfully, such as prostate, bladder or ovarian cancer. In contrast to conventional cancer therapies, which result in relatively non-specific and often serious toxicity, more specific treatment modalities attempt to inhibit or kill malignant cells selectively while leaving healthy cells intact. There is, therefore a serious need for developing specific, less toxic cancer therapies.

All references cited herein are hereby incorporated by reference in their entirety.

SUMMARY OF THE INVENTION

The invention provides methods for the administration of combinations of a target cell-specific adenoviral vector and at least one antineoplastic agent(s) and/or radiation to an individual in need thereof, such as, an individual with neoplasia.

Accordingly, in one aspect, the invention provides methods of suppressing tumor growth in an individual comprising the steps of: a) administering to the individual a composition comprising a replication-competent target cell-specific adenoviral vector wherein said vector comprises an adenovirus gene essential for replication (preferably an early gene) under transcriptional control of a target cell specific transcriptional regulatory element (TRE); and b) administering an antineoplastic agent to the individual, wherein the adenoviral vector and antineoplastic agent are administered in amounts sufficient to suppress tumor growth. In some embodiments, the amount of adenovirus vector and/or anitneoplastic agent administered is less than that known in the art to be effective for suppressing tumor growth when either is administered alone. In one embodiment, the antineoplastic agent includes alkaloids, alkylating agents, antibiotics, antimetabolites, immunomodulators, nitrosoureas, hormone antagonists/agonists and analogs, or photosensitizing agents.

In another aspect, the invention provides methods of suppressing tumor growth in an individual comprising the following steps: a) administering to the individual a composition comprising a replication-competent target cell-specific adenoviral vector wherein said vector comprises an adenovirus gene essential for replication (preferably an early gene) under transcriptional control of a target cell specific transcriptional regulatory element (TRE); and b) administering an effective amount of radiation. In some embodiments, the amount of adenovirus vector and/or radiation administered is less than that known in the art to be effective for suppressing tumor growth when administered alone. In one embodiment, the radiation includes X-rays, gamma rays, alpha particles, beta particles, electrons, photons, neutrons, other ionizing radiation or radioactive isotopes.

In yet another aspect, the present invention provides methods for suppressing tumor growth in an individual comprising the following steps, in any order: a) administering to the individual an effective amount of a replication-competent target cell-specific adenoviral vector and an effective amount of at least one antineoplastic agent; and b) administering an effective amount of an appropriate course of radiation therapy to the individual. In one embodiment, the method may further comprise, c) administering to the individual an additional dose of the adenoviral/chemotherapeutic solution or radiation as necessary to treat the individual's neoplasia. In another embodiment, the method may further comprise a delay between any of steps a), b) and c). In some embodiments, the amount of adenovirus vector and/or anitneoplastic agent and/or radiation administered will be less than that known in the art to be effective for suppressing tumor growth when either is administered alone.

Any TRE which directs cell-specific expression can be used in the disclosed adenovirus vectors. In one embodiment, TREs include, for example, TREs specific for prostate cancer cells, breast cancer cells, hepatoma cells, melanoma cells, bladder cells or colorectal cancer cells. In another embodiment, the TREs include, probasin (PB) TRE; prostate-specific antigen (PSA) TRE; mucin (MUC1) TRE; α-fetoprotein (AFP) TRE; hKLK2 TRE; tyrosinase TRE; human uroplakin II TRE (hUPII) or carcinoembryonic antigen (CEA) TRE. In other embodiments, the target cell-specific TRE is a cell status-specific TRE. In yet other embodiments, the target cell-specific TRE is a tissue specific TRE.

In one aspect, the adenovirus vectors comprise adenovirus genes essential for viral replication. An essential gene can be an early viral gene, including for example, E1A; E1B; E2; and/or E4, or a late viral gene. In another aspect, the adenovirus vector comprises E3.

In some embodiments, the adenovirus vectors comprise an adenovirus gene having an inactivation of its endogenous promoter. In one embodiment, the adenovirus gene is essential for viral replication under control of a target cell-specific TRE. In another embodiment, the adenovirus gene is E1A wherein the E1A promoter is inactivated and wherein the E1A gene is under transcriptional control of a heterologous cell-specific TRE. In another embodiment, the adenovirus gene is E1B wherein the E1B promoter is inactivated and wherein the E1B gene is under transcriptional control of a heterologous cell-specific TRE. In other embodiments, the adenovirus vectors comprise the adenovirus gene, E1B, having a deletion of the 19-kDa region.

In other embodiments, an enhancer element for the adenovirus genes is inactivated, such as an inactivation of E1A enhancer. In yet other embodiments, the E1A promoter is inactivated and the E1A enhancer I is inactivated. In further embodiments, the TRE has its endogenous silencer element inactivated.

In another embodiment, the replication competent adenovirus vectors comprise co-transcribed first and second genes under transcriptional control of a heterologous, target cell-specific transcriptional regulatory element (TRE), wherein the second gene is under translational control of an internal ribosome entry site (IRES). In one aspect, the first and/or second genes are adenovirus genes and in another aspect, the first and/or second adenovirus genes are essential for viral replication. An essential gene can be an early viral gene, including for example, E1A; E1B; E2; and/or E4, or a late viral gene. In another aspect an early gene is E3.

In one embodiment, the first gene is an adenovirus gene and the second gene is a therapeutic gene. In another embodiment, both genes are adenovirus genes. In an additional embodiment, the first adenovirus gene is E1A, and the second adenovirus gene is E1B. Optionally, the endogenous promoter for one of the co-transcribed adenovirus gene essential for viral replication, such as for example, E1A, is inactivated, placing the gene under sole transcriptional control of a target cell-specific TRE.

In additional embodiments, the adenovirus vector comprises at least one additional co-transcribed gene under the control of the cell-specific TRE. In another embodiment, an additional co-transcribed gene is under the translational control of an IRES.

In another aspect of the present invention, adenovirus vectors further comprise a transgene such as, for example, a cytotoxic gene. In one embodiment, the transgene is under the transcriptional control of the same TRE as the first gene and second genes and optionally under the translational control of an internal ribosome entry site. In another embodiment, the transgene is under the transcriptional control of a different TRE that is functional in the same cell as the TRE regulating transcription of the first and second genes and optionally under the translational control of an IRES.

Figure 7:
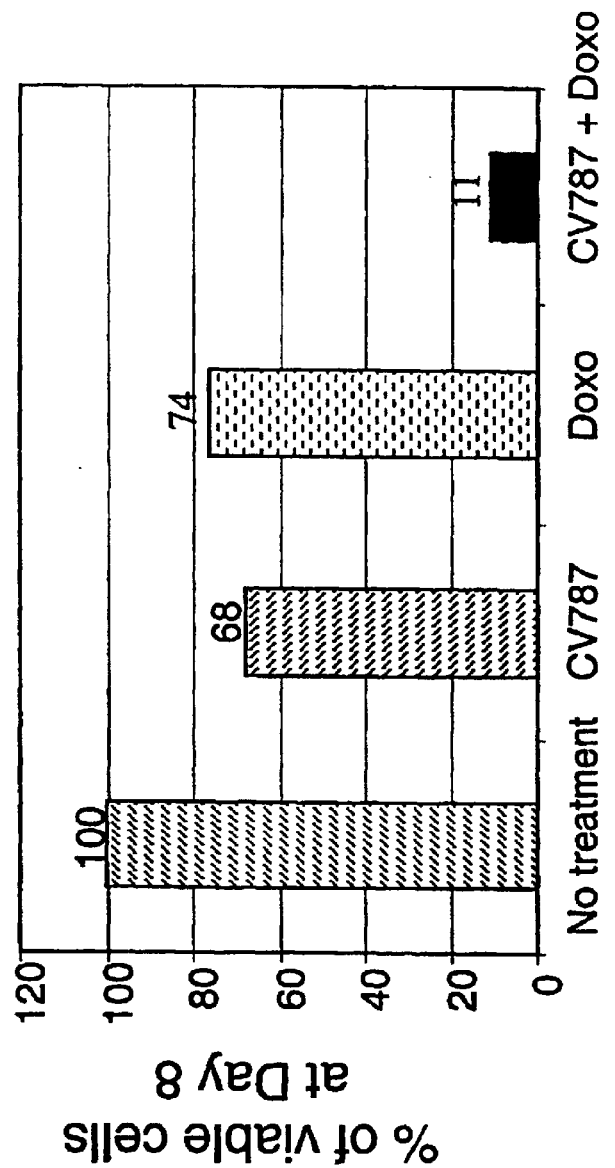

FIG. 7 is a bar graph depicting percent viable LNCaP prostate tumor cells with no treatment; CV787 treatment (MOI 0.01); doxorubicin treatment (50 ng/ml); and CV787 plus doxorubicin (Doxo) treatment on day 8 (CV787 was administered first).

Figure 8:
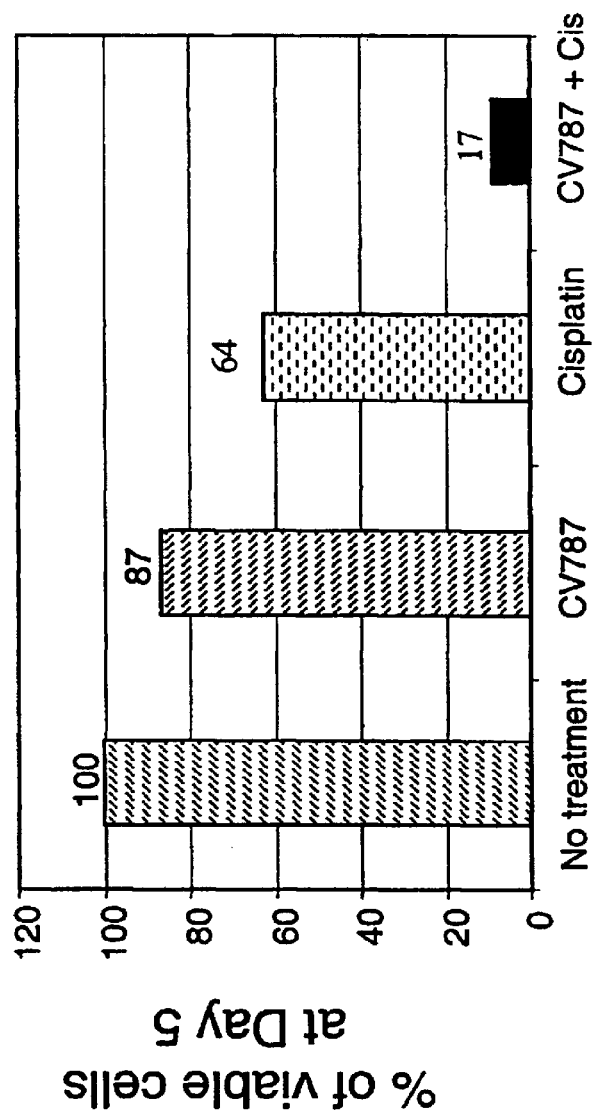

FIG. 8 is a bar graph depicting percent viable LNCaP prostate tumor cells with no treatment; CV787 treatment (MOI 0.1); cisplatin treatment (8.25 µM); and CV787 plus cisplatin (Cis) treatment on day 5 (Cisplatin was administered first).

Figure 9:
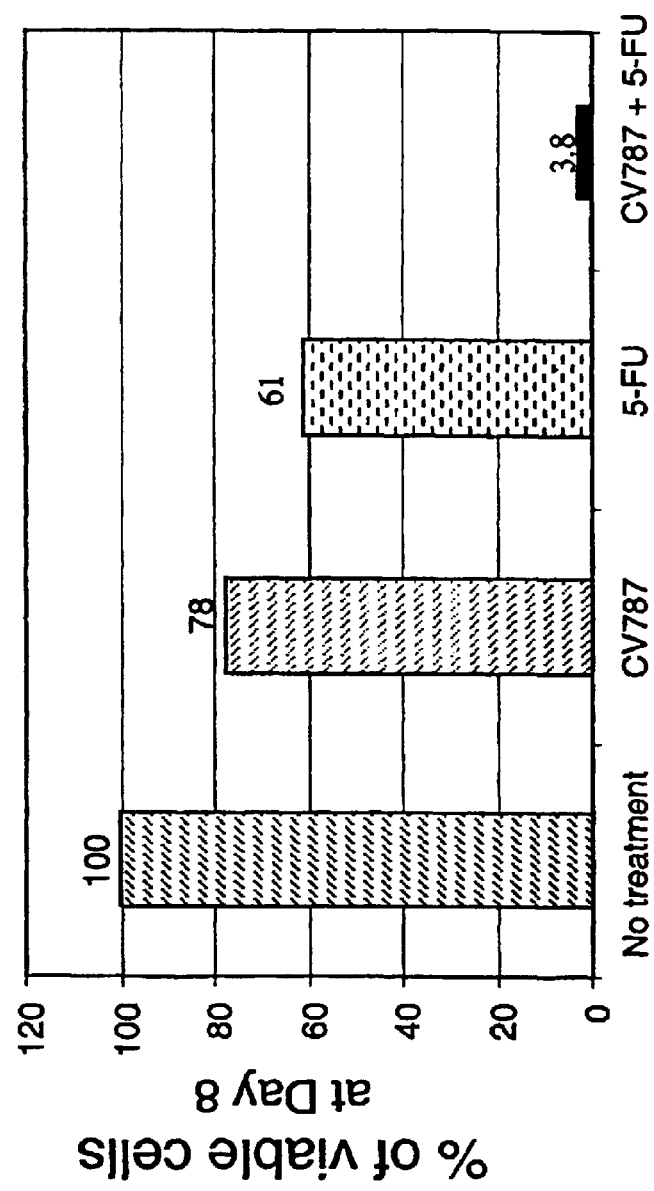

FIG. 9 is a bar graph depicting percent viable LNCaP prostate tumor cells with no treatment; CV787 treatment (MOI 0.01); 5-fluorouracil (5-FU; 35 µM) treatment; and CV787 plus 5-fluorouracil treatment on day 8 (5-fluorouracil was administered first).

Figure 10:
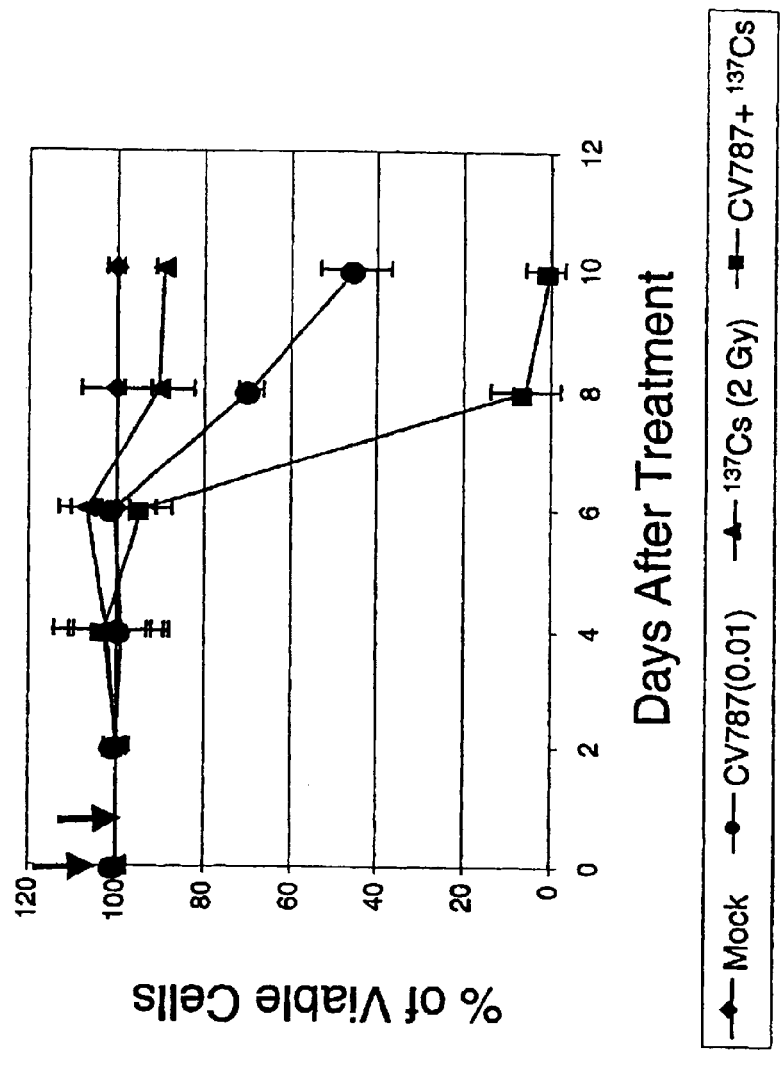

FIG. 10 is a graph depicting percent viable LNCaP prostate tumor cells treated with CV787 adenovirus vector (solid circles; MOI 0.01); CV787 and radiation (solid squares); radiation alone (solid triangles; $^{137}$Cs; 2 Gy); and mock infected control (diamonds). For combination administration, CV787 was administered first, 24 hours prior to radiation.

Figure 11:
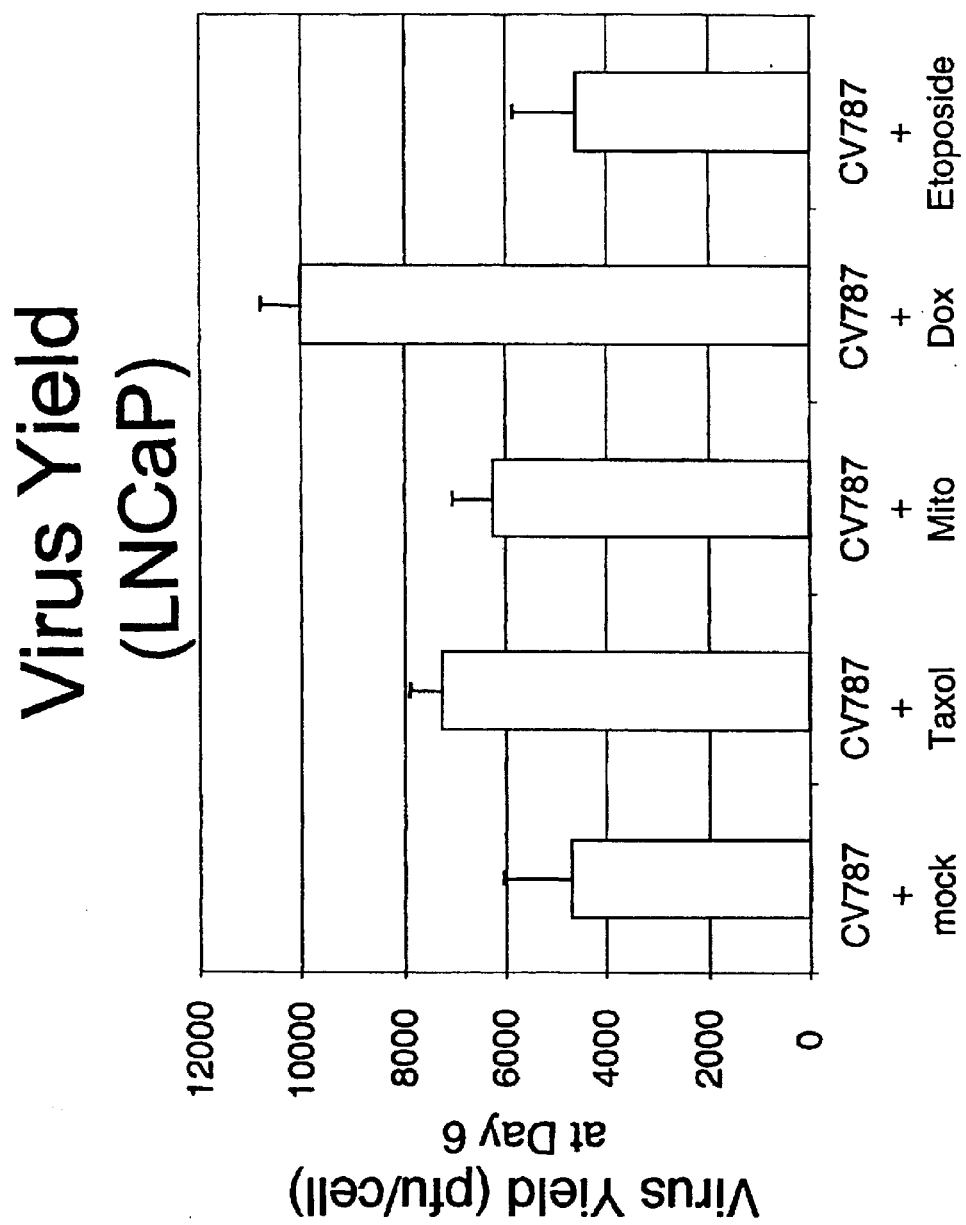

FIG. 11 is a graph depicting CV787 adenovirus yield in LNCaP prostate tumor cells treated with CV787 (MOI 0.1) and mock infected control; CV787 and TAXOL™ (6.25 nM); CV787 and mitoxantrone (Mito; 100 nM); CV787 and doxorubicin (Dox; 50 ng/ml); and CV787 and etoposide (500 ng/ml), on day 6 of treatment. For all combination administration, CV787 was administered first.

Figure 12:
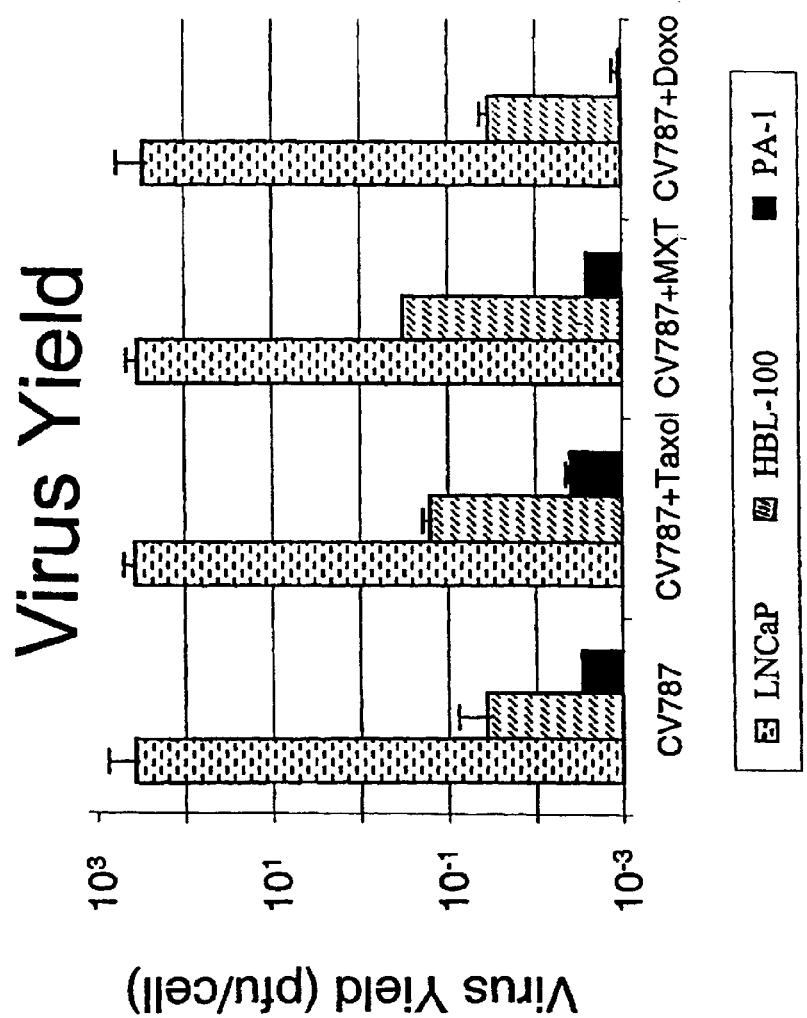

FIG. 12 is a bar graph depicting CV787 adenovirus yield in LNCaP prostate tumor cells (dashed shading); HBL-100 breast epithelial cells (horizontal shading); and PA-I ovary cells (solid shading) when treated with CV787 adenovirus vector (MOI 0.1); CV787 and TAXOL™ (6.25 nM); CV787 and mitoxantrone (MTX; 100 nM);and CV787 and doxorubicin (Doxo; 50 ng/ml). For combination administration, CV787 was administered first with virus yield measured at 72 hours after infection.

Figure 13:
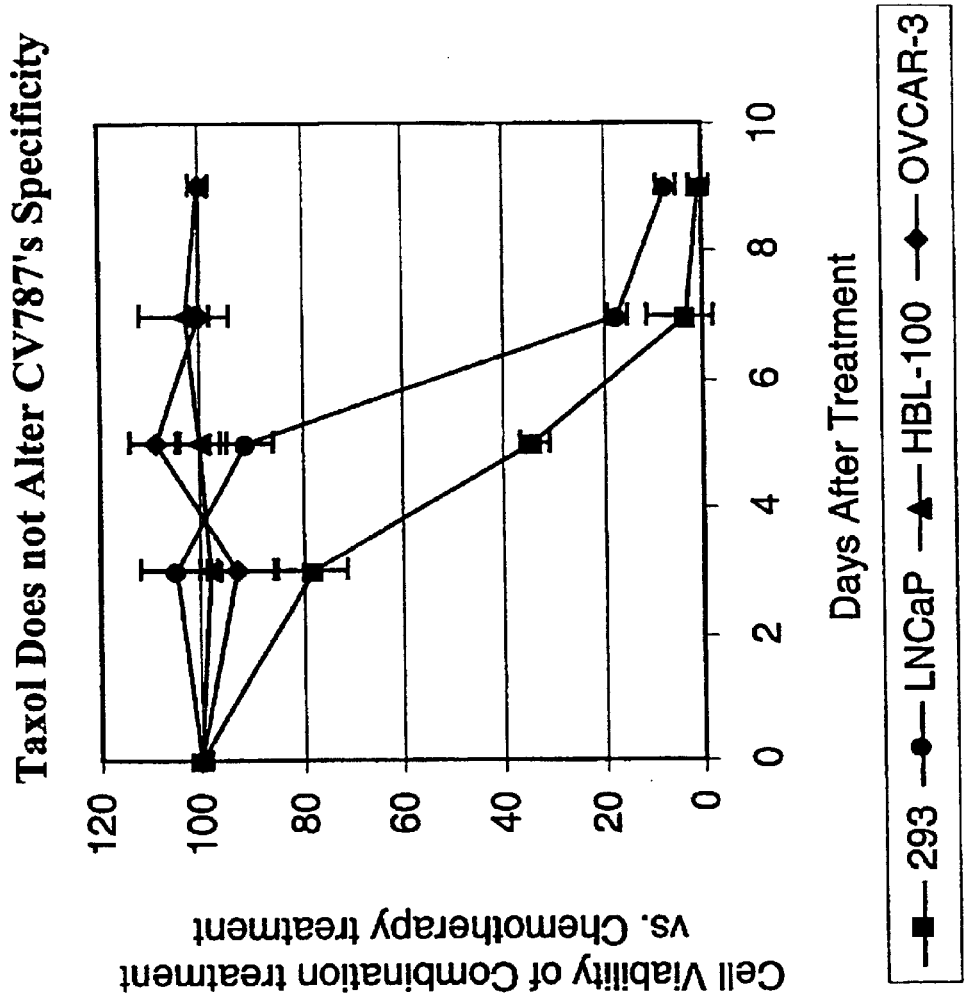

FIG. 13 is a graph depicting relative percent viable cells for combination treatment compared to chemotherapeutic agent alone over time when treated with CV787 adenovirus vector (MOI 0.01) and TAXOL™ (6.25 nM). LNCaP, prostate tumor cells (solid circles); HBL-100, breast epithelial tissue cells (solid triangles); OVCAR-3, ovarian cancer cells (solid diamonds); and 293, human embryonic kidney cells (solid squares), E1A and E1B permissible. For combination administration, CV787 was administered first.

Figure 14:
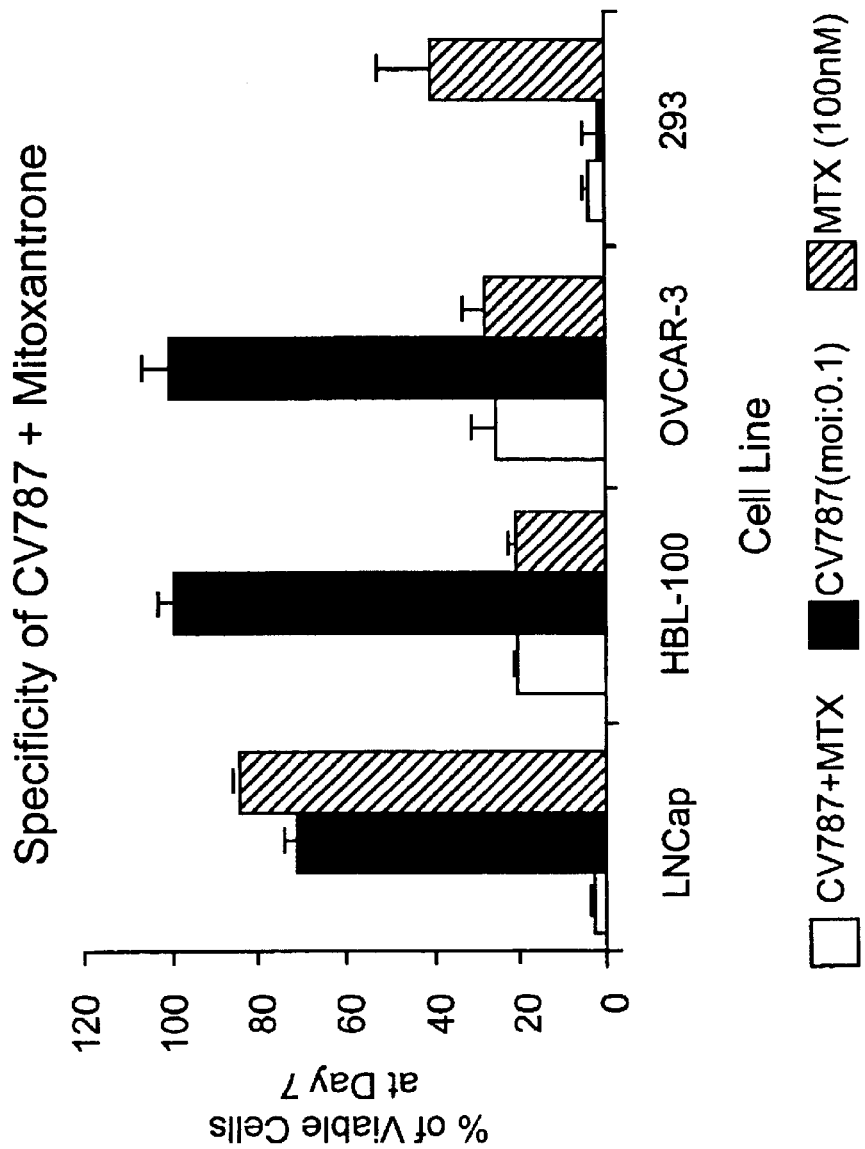

FIG. 14 is a bar graph depicting percent viable cells when treated with CV787 adenovirus vector (dark shading; MOI 0.1); CV787 and mitoxantrone (MTX; outlined; 100 nM) and mitoxantrone alone (horizontal shading) on day 7 of treatment. LNCaP, prostate tumor cells; HBL-100, breast epithelial tissue cells; OVCAR-3, ovarian cancer cells; and 293, human embryonic kidney cells, E1A and E1B permissible. For combination administration, CV787 was administered first.

Figure 15:
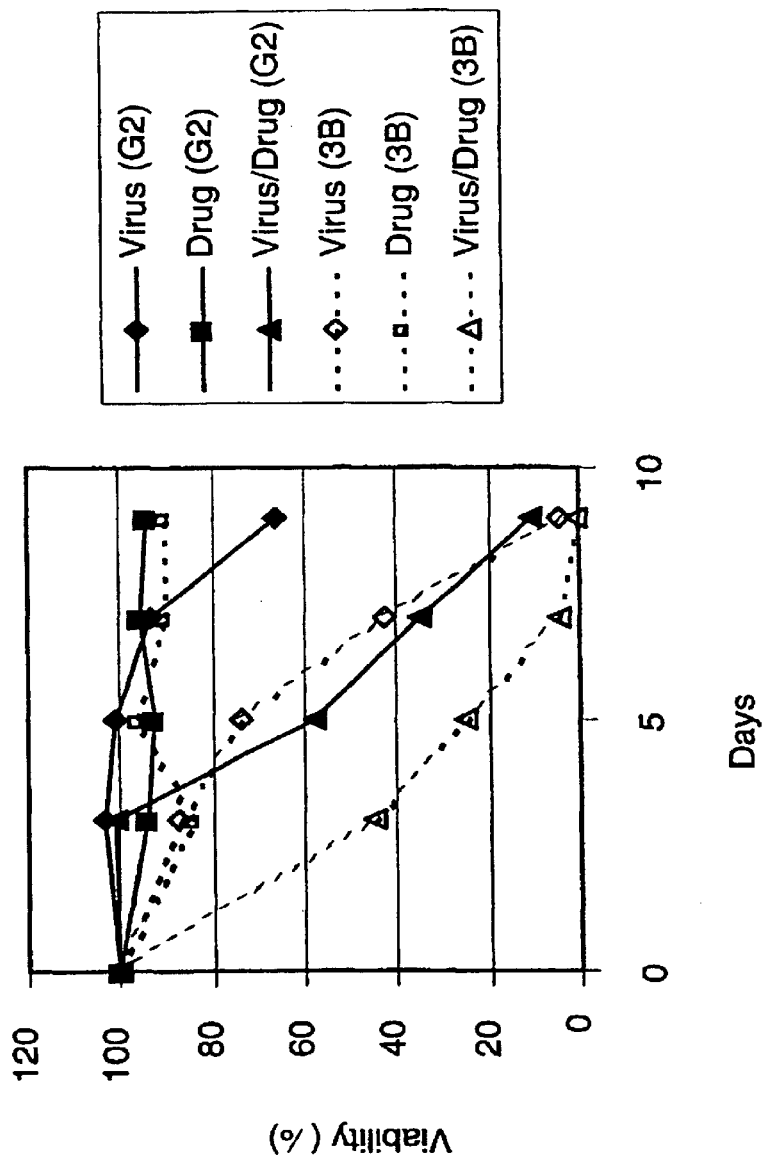

FIG. 15 is a graph depicting percent viable Hep3B (3B) and HepG2 (G2) hepatoma cells treated with CV790 adenovirus vector (diamonds; MOI 0.01); and doxorubicin (triangles); and doxorubicin alone (squares; 10 ng/ml). For combination administration, CV790 was administered first.

Figure 16:
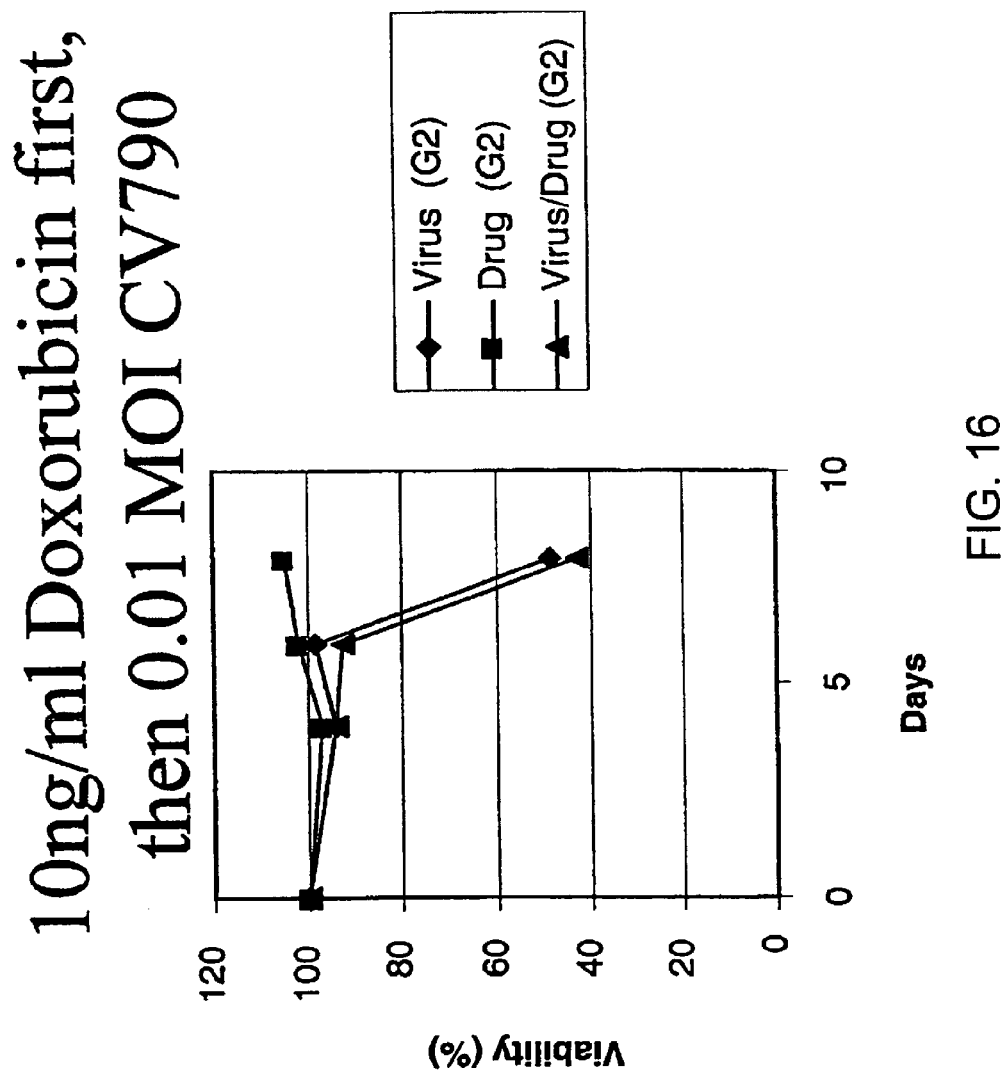

FIG. 16 is a graph depicting percent viable HepG2 (G2) hepatoma cells treated with CV790 adenovirus vector (solid diamonds; MOI 0.01); CV790 and doxorubicin (solid triangles); and doxorubicin alone (solid squares; 10 ng/ml). For combination administration, Doxorubicin was administered first.

Figure 17:
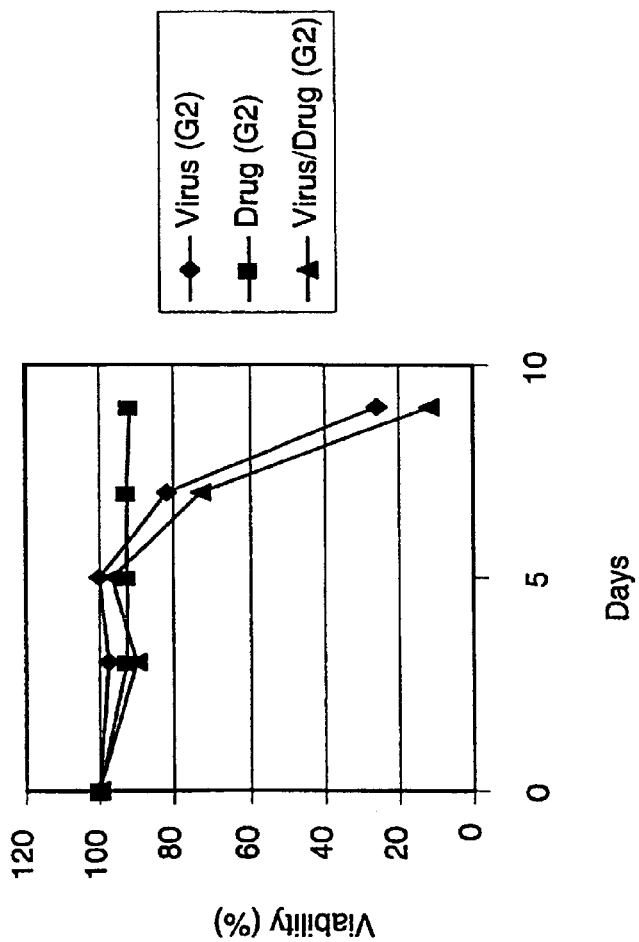

FIG. 17 is a graph depicting percent viable HepG2 (G2) hepatoma cells treated with CV790 adenovirus vector (solid diamonds; MOI 0.01); CV790 and doxorubicin (solid triangles); and doxorubicin alone (solid squares; 10 ng/ml). For combination administration, CV790 and doxorubicin were administered together.

Figure 18:
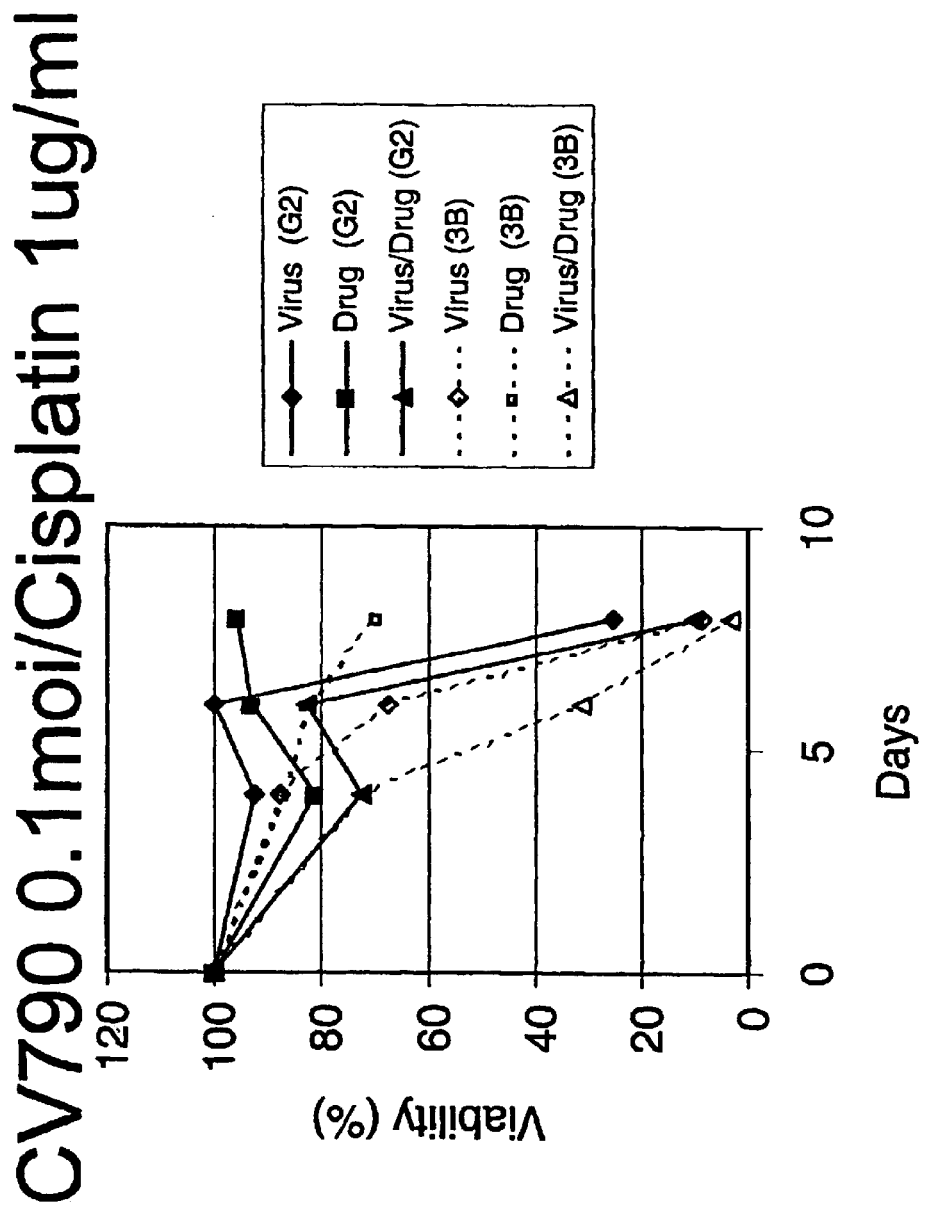

FIG. 18 is a graph depicting percent viable HepG2 (G2) and Hep3B (3B) hepatoma cells treated with CV790 adenovirus vector (diamonds; MOI 0.1); CV790 and cisplatin (triangles); and cisplatin alone (squares; 1 µg/ml). For combination administration, CV790 was administered first.

Figure 19:
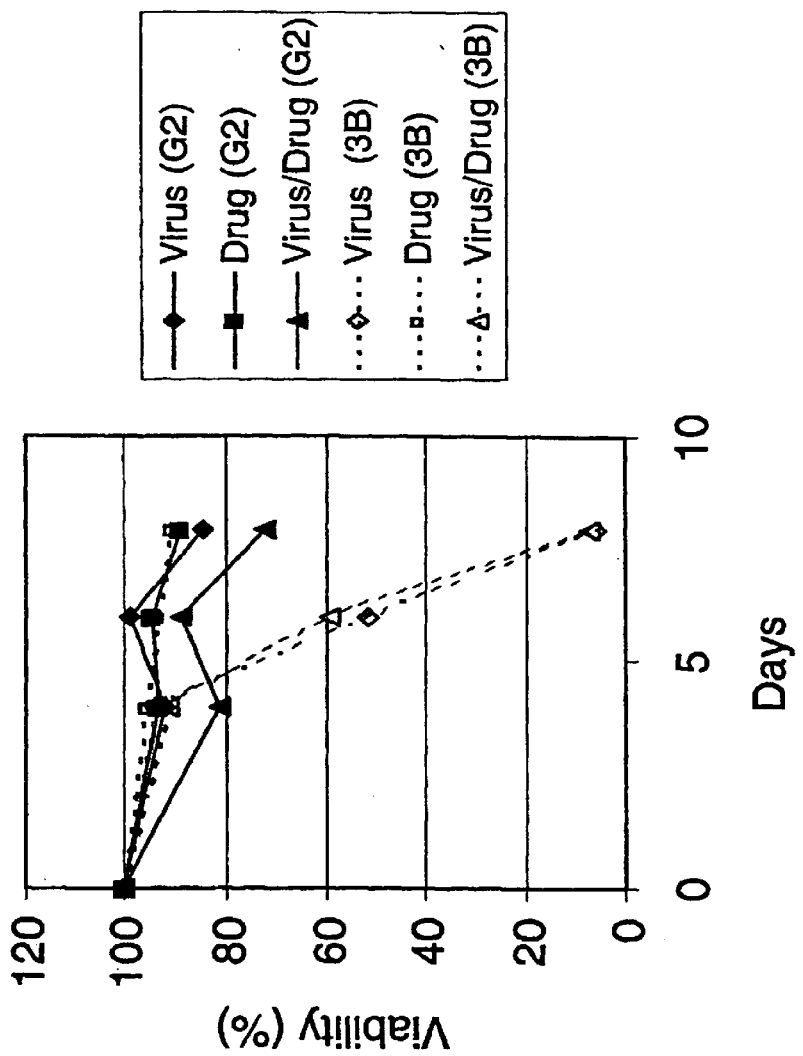

FIG. 19 is a graph depicting percent viable HepG2 (G2) and Hep3B (3B) hepatoma cells treated with CV790 adenovirus vector (diamonds; MOI 0.1); CV790 and TAXOL™ (paclitaxel; triangles); and TAXOL™ alone (squares; 0.5 ng/ml). For combination administration, CV790 was administered first.

Figure 20:
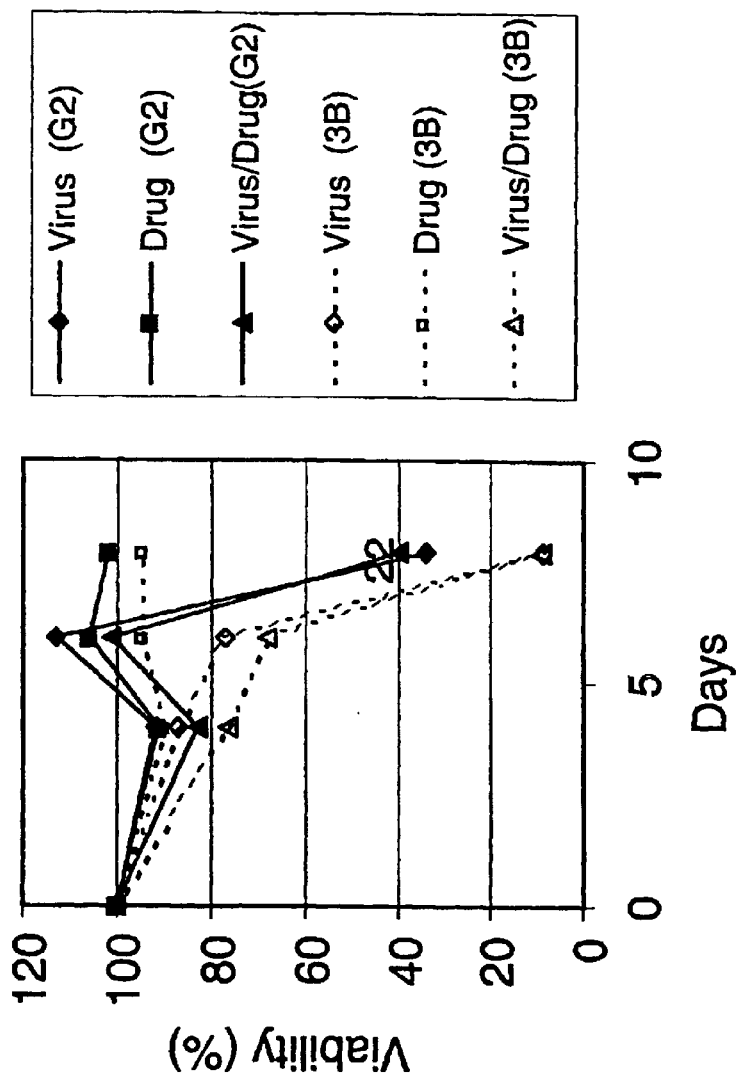

FIG. 20 is a graph depicting percent viable HepG2 (G2) and Hep3B (3B) hepatoma cells treated with CV790 adenovirus vector (diamonds; MOI 0.1); CV790 and 5-fluorouracil (triangles); and 5-fluorouracil alone (squares; 10 ng/ml). For combination administration, CV790 was administered first.

Figure 21:
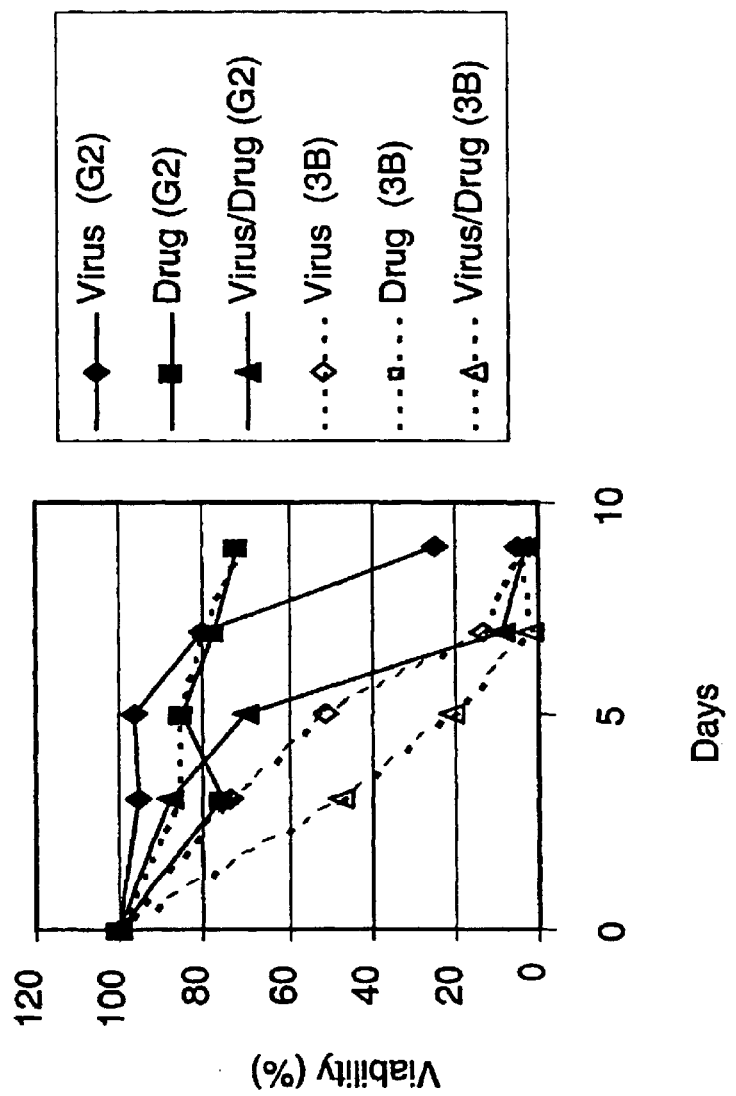

FIG. 21 is a graph depicting percent viable HepG2 (G2) and Hep3B (3B) hepatoma cells treated with CV790 adenovirus vector (diamonds; MOI 0.1); CV790 and mitoxantrone (triangles); and mitoxantrone alone (squares; 4 ng/ml). For combination administration, CV790 was administered first.

Figure 22:
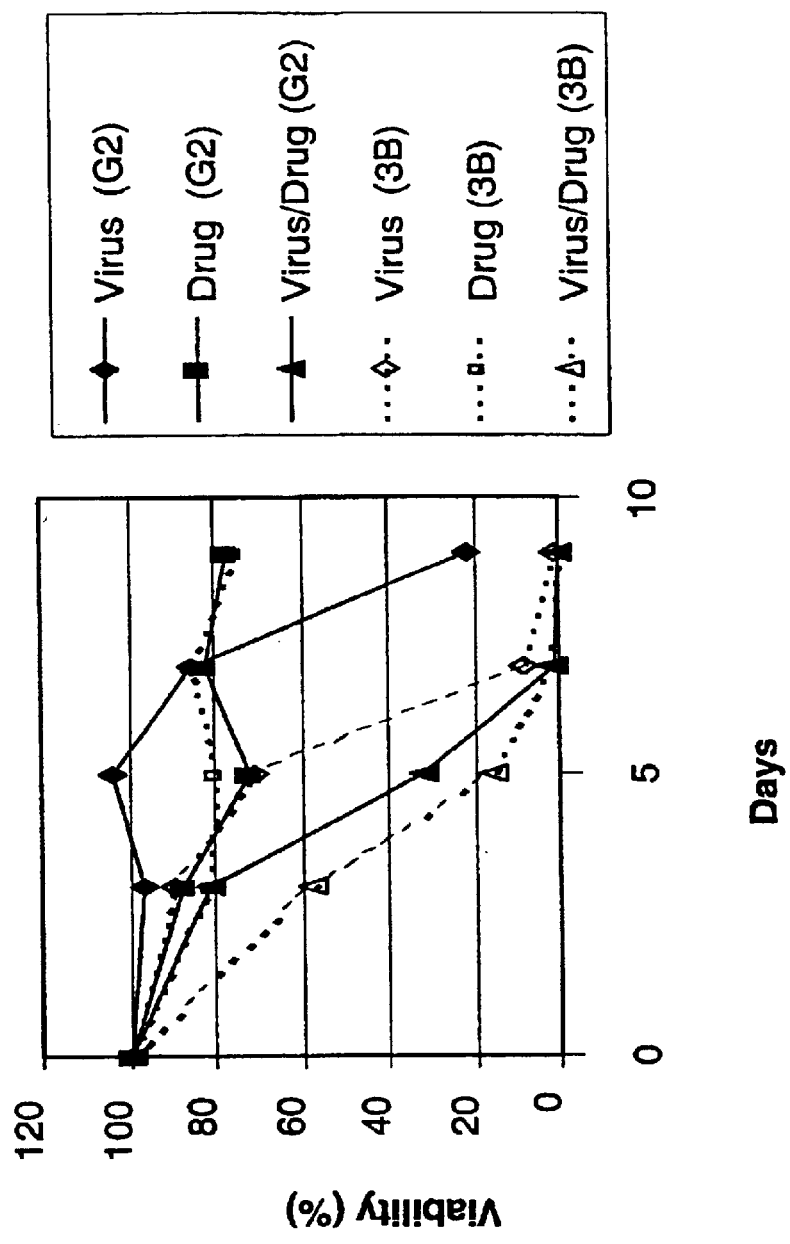

FIG. 22 is a graph depicting percent viable HepG2 (G2) and Hep3B (3B) hepatoma cells treated with CV790 adenovirus vector (diamonds; MOI 0.1); CV790 and mitomycin C (triangles); and mitomycin C alone (squares; 10 ng/ml). For combination administration, CV790 was administered first.

Figure 23:
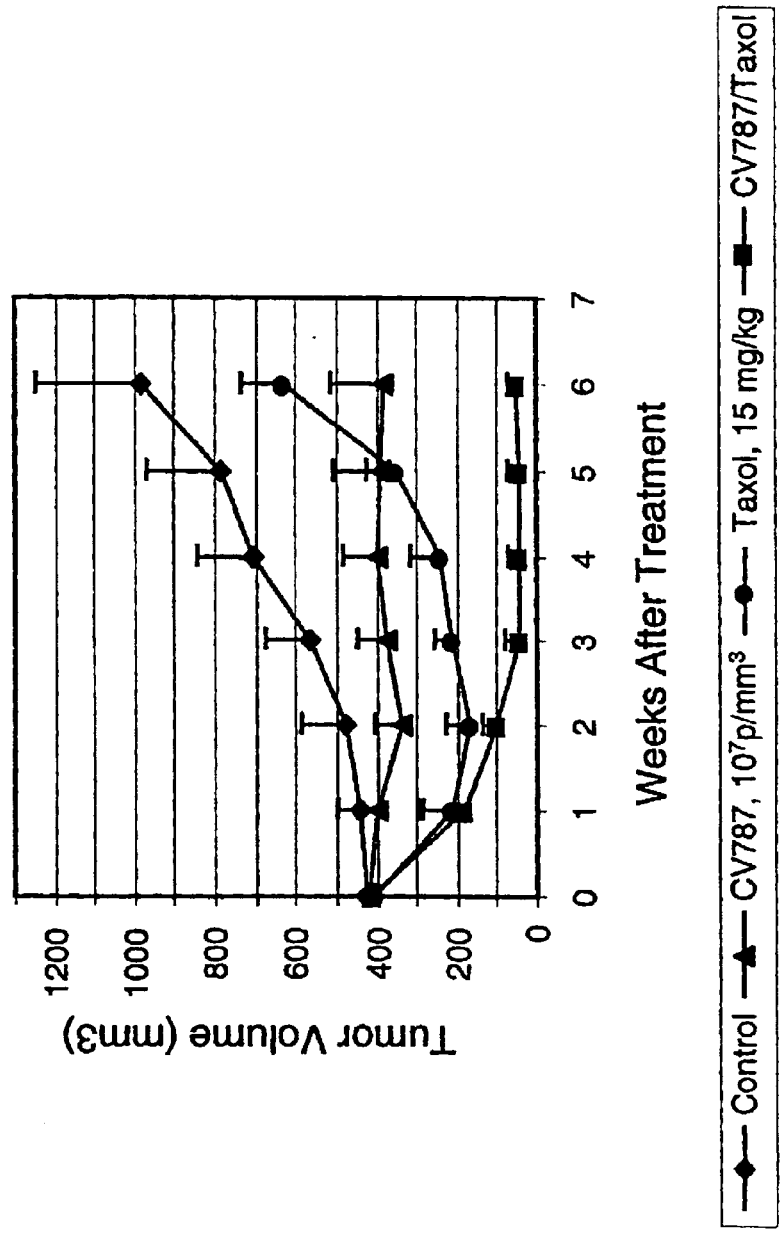

FIG. 23 is a graph depicting the tumor volume of LNCaP prostate tumor xenografts treated with CV787 adenovirus vector (triangles; $1 \times 10^7$ particles/mm$^3$); CV787 and TAXOL™ (solid squares); TAXOL™ alone (paclitaxel; solid circles; 15 mg/kg); and mock infected control (solid diamonds). For combination administration, CV787 was administered first on day 0 via intra-tumor injection. TAXOL™ was administered on day 1, 2, 3, and 4.

Figure 24:
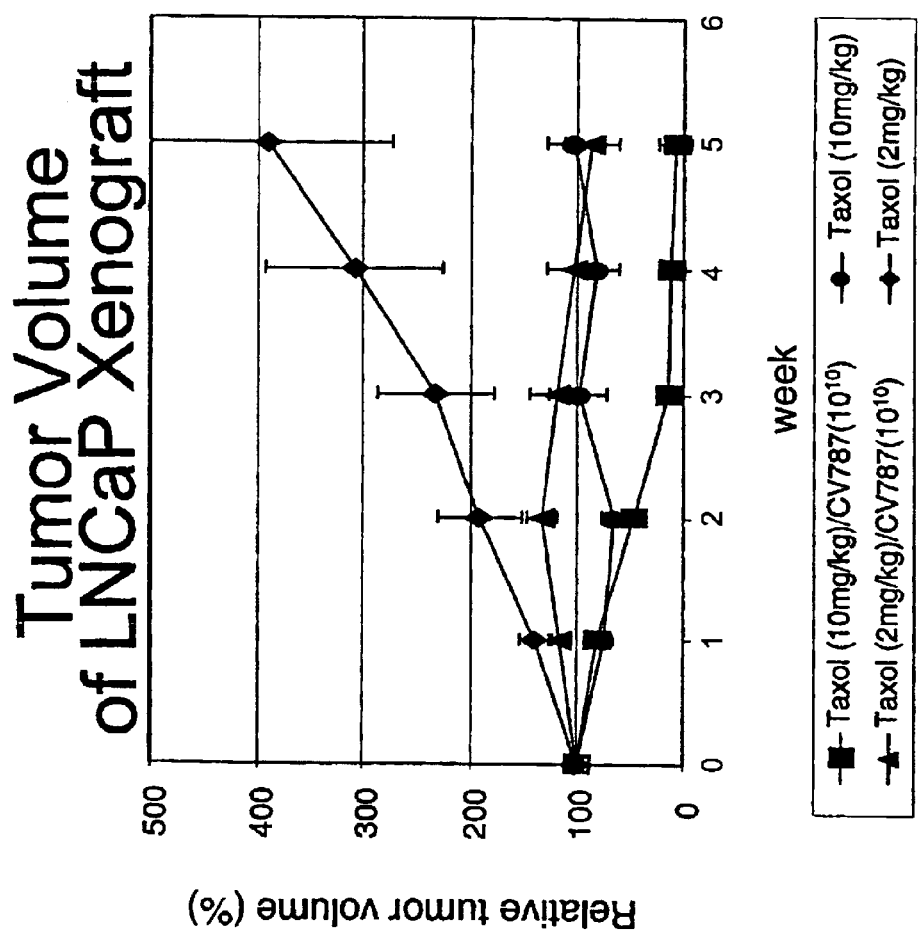

FIG. 24 is a graph depicting the relative percent of tumor volume of LNCaP prostate tumor xenografts treated with TAXOL™ and CV787 adenovirus vector (triangles; TAXOL™ 2 mg/kg; $1 \times 10^{10}$ particles); CV787 and TAXOL™ (solid squares; TAXOL™ 10 mg/kg); TAXOL™ alone (solid circles; 10 mg/kg); and TAXOL™ alone (solid diamonds; 2 mg/kg). For combination administration, TAXOL™ was administered first via intravenous administration.

Figure 25:
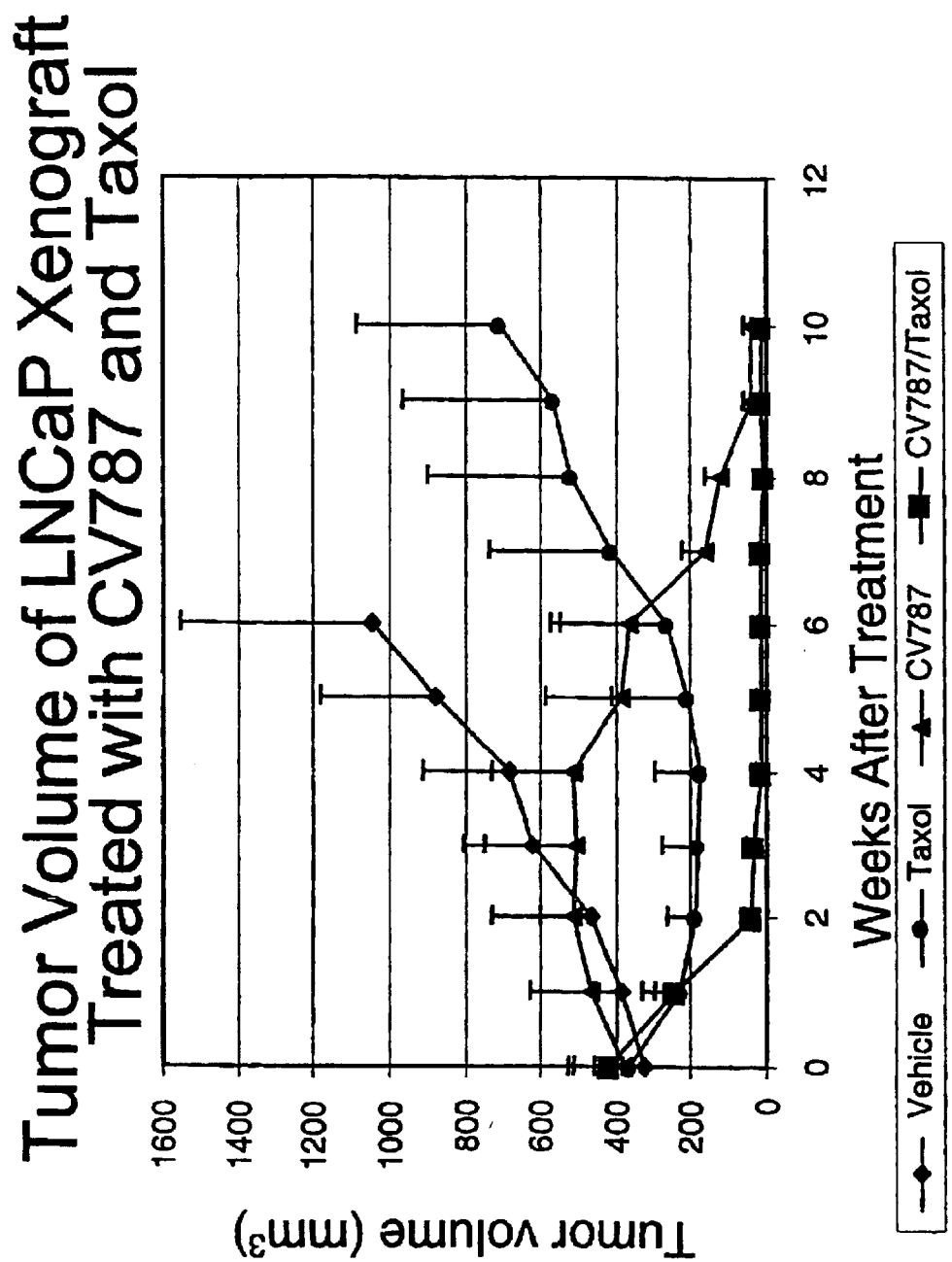

FIG. 25 is a graph depicting the tumor volume of LNCaP prostate tumor xenografts treated with CV787 adenovirus vector (triangles; $1 \times 10^{10}$ particles); CV787 and TAXOL™ (solid squares); TAXOL™ alone (solid circles; 20 mg/kg); mock infected control (vehicle; solid diamonds). For combination administration, CV787 was administered first via intravenous delivery.

Figure 26:
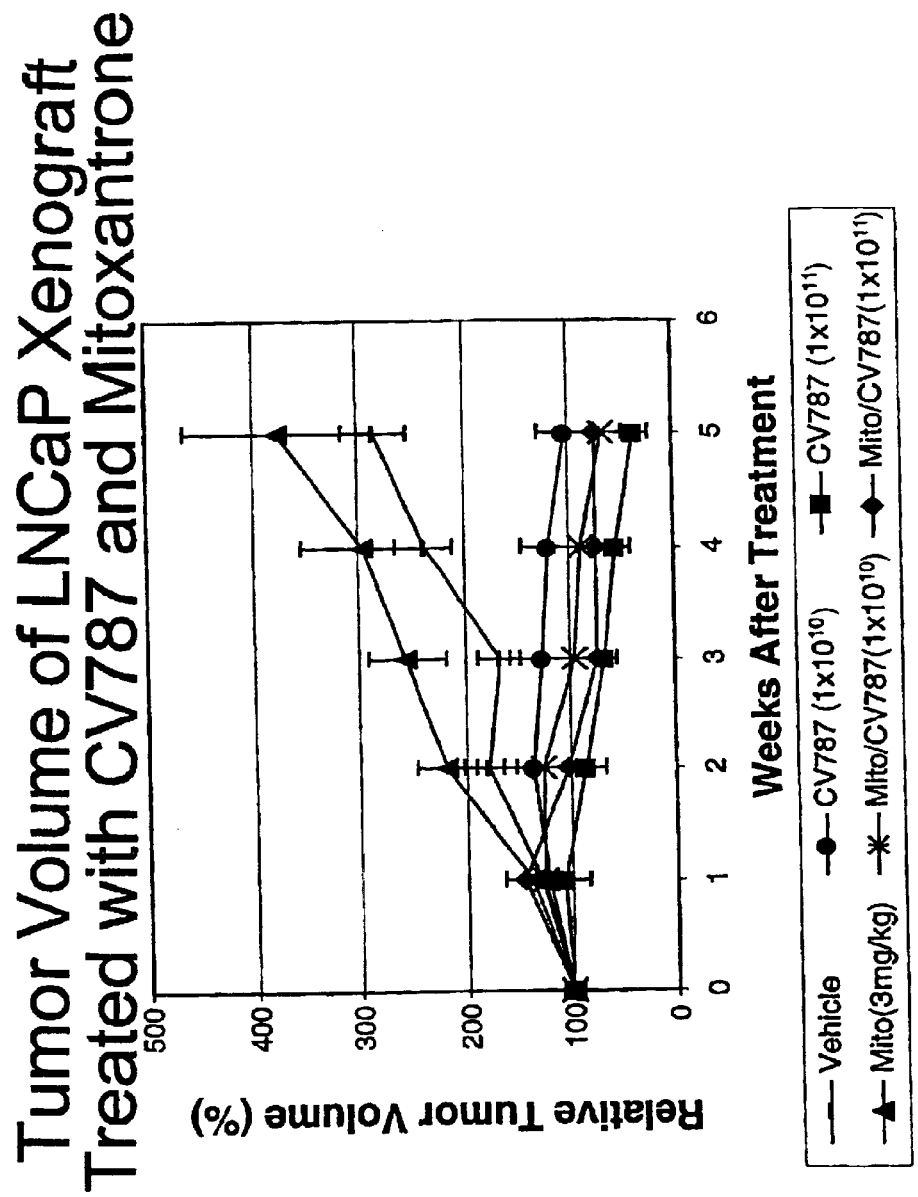

FIG. 26 is a graph depicting the relative percent tumor volume of LNCaP prostate tumor xenografts treated with CV787 adenovirus vector (shaded squares; $1 \times 10^{11}$ particles); CV787 (solid circles; $1 \times 10^{10}$ particles); CV787 ($1 \times 10^{10}$ particles) and mitoxantrone (Mito; "X"; 3 mg/kg); CV787 ($1 \times 10^{11}$ particles) and mitoxantrone (solid diamonds; 3 mg/kg); mitoxantrone alone (solid triangles; 3 mg/kg) and mock infected control (vehicle; "-"). For combination administration, CV787 was administered first.

Figure 27:
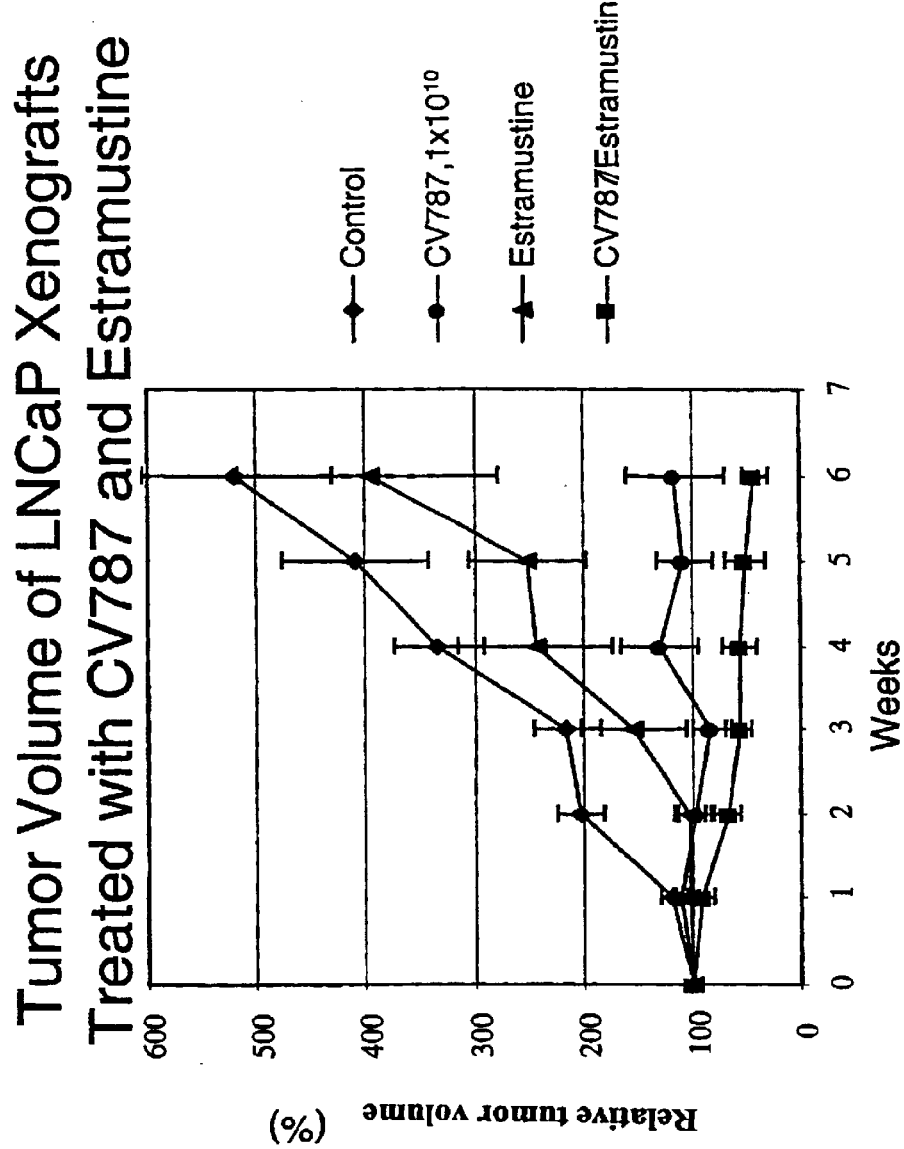

FIG. 27 is a graph depicting the relative percent tumor volume of LNCaP prostate tumor xenografts treated with CV787 adenovirus vector (solid circles; $1 \times 10^{10}$ particles); CV787 and estramustine (solid squares); estramustine alone (triangles); and mock infected control (solid diamonds). For combination administration, CV787 was administered first. Estramustine was administered at 14 mg/kg on days 2–5, 7–11, 13–17 and 20–24.

Figure 28:
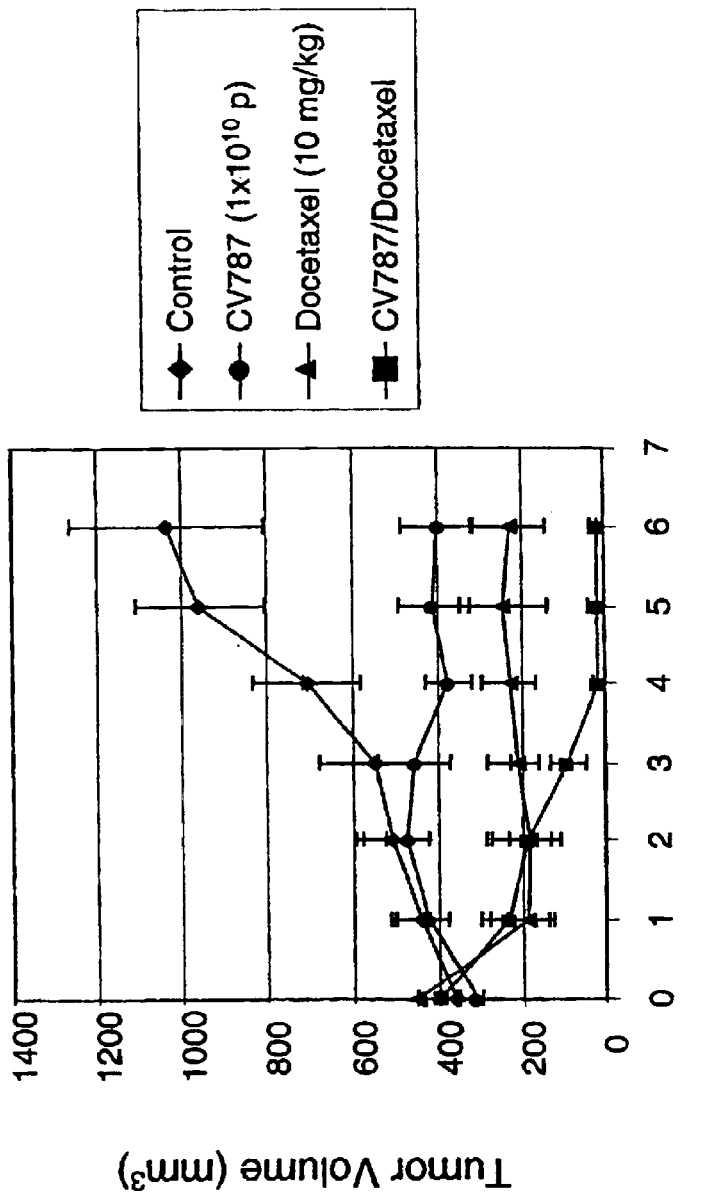

FIG. 28 is a graph depicting the tumor volume of LNCaP prostate tumor xenografts treated with CV787 adenovirus vector (solid circles; $1 \times 10^{10}$ particles), CV787 and docetaxel (solid squares; $1 \times 10^{10}$ particles, 10 mg/kg); docetaxel alone (solid triangles; 10 mg/kg); and mock infected control (shaded diamonds). For combination administration, CV787 was administered first.

Figure 29:
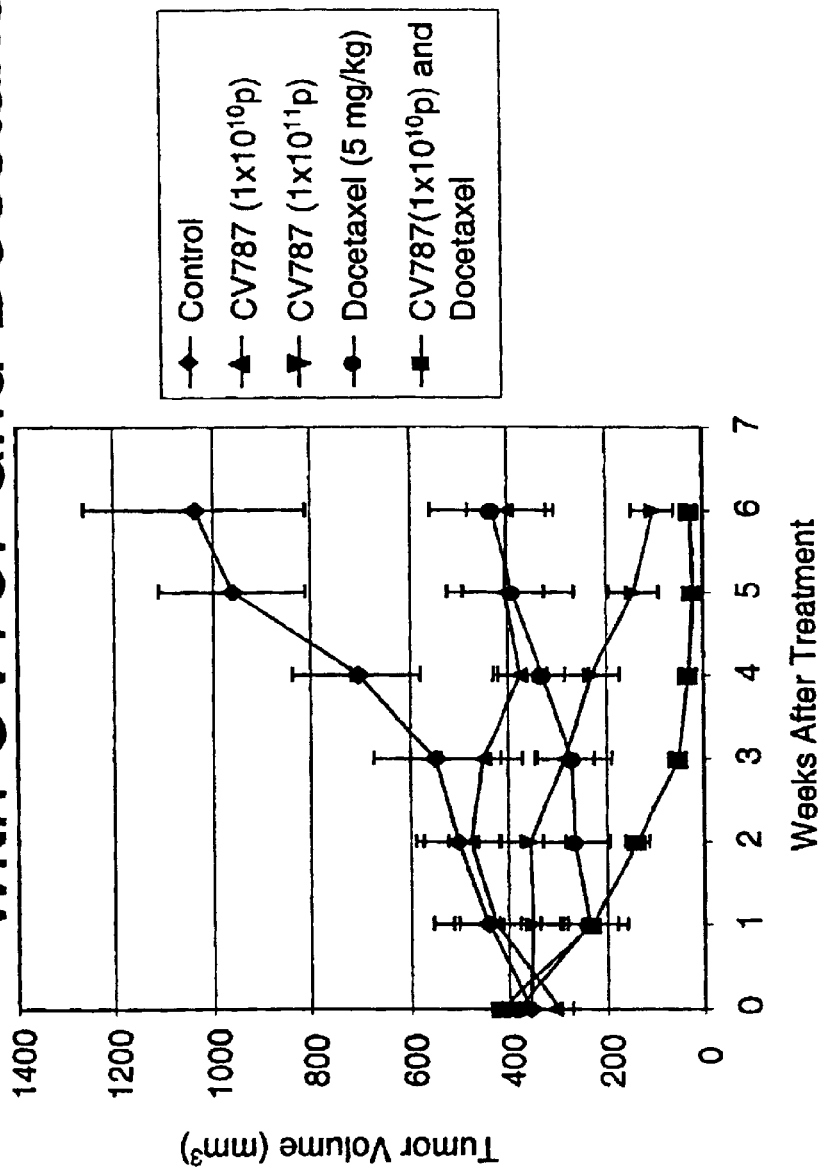

FIG. 29 is a graph depicting the tumor volume of LNCaP prostate tumor xenografts treated with CV787 adenovirus vector (shaded triangles; $1 \times 10^{10}$ particles), CV787 (unfilled triangles; $1 \times 10^{11}$ particles); CV787 and docetaxel (solid squares; $1 \times 10^{10}$ particles, 5 mg/kg); docetaxel alone (solid circles; 5 mg/kg); and mock infected control (solid diamonds). For combination administration, CV787 was administered first.

Figure 30:
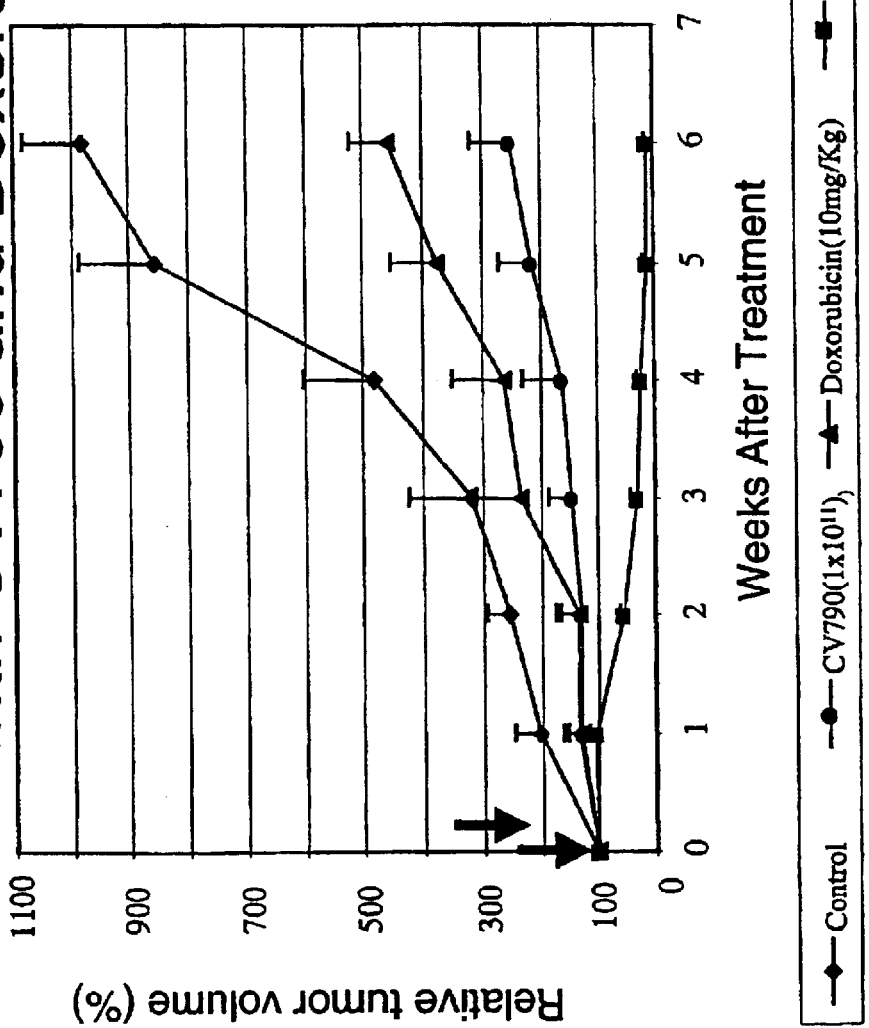

FIG. 30 is a graph depicting the relative percent tumor volume of Hep3B hepatoma xenografts treated with CV790 adenovirus vector (solid circles; $1 \times 10^{11}$ particles); CV790 and doxorubicin (Doxo; solid squares); doxorubicin alone (triangles; 10 mg/kg); and mock infected control (solid diamonds). For combination administration, CV790 was administered first.

Figure 31:
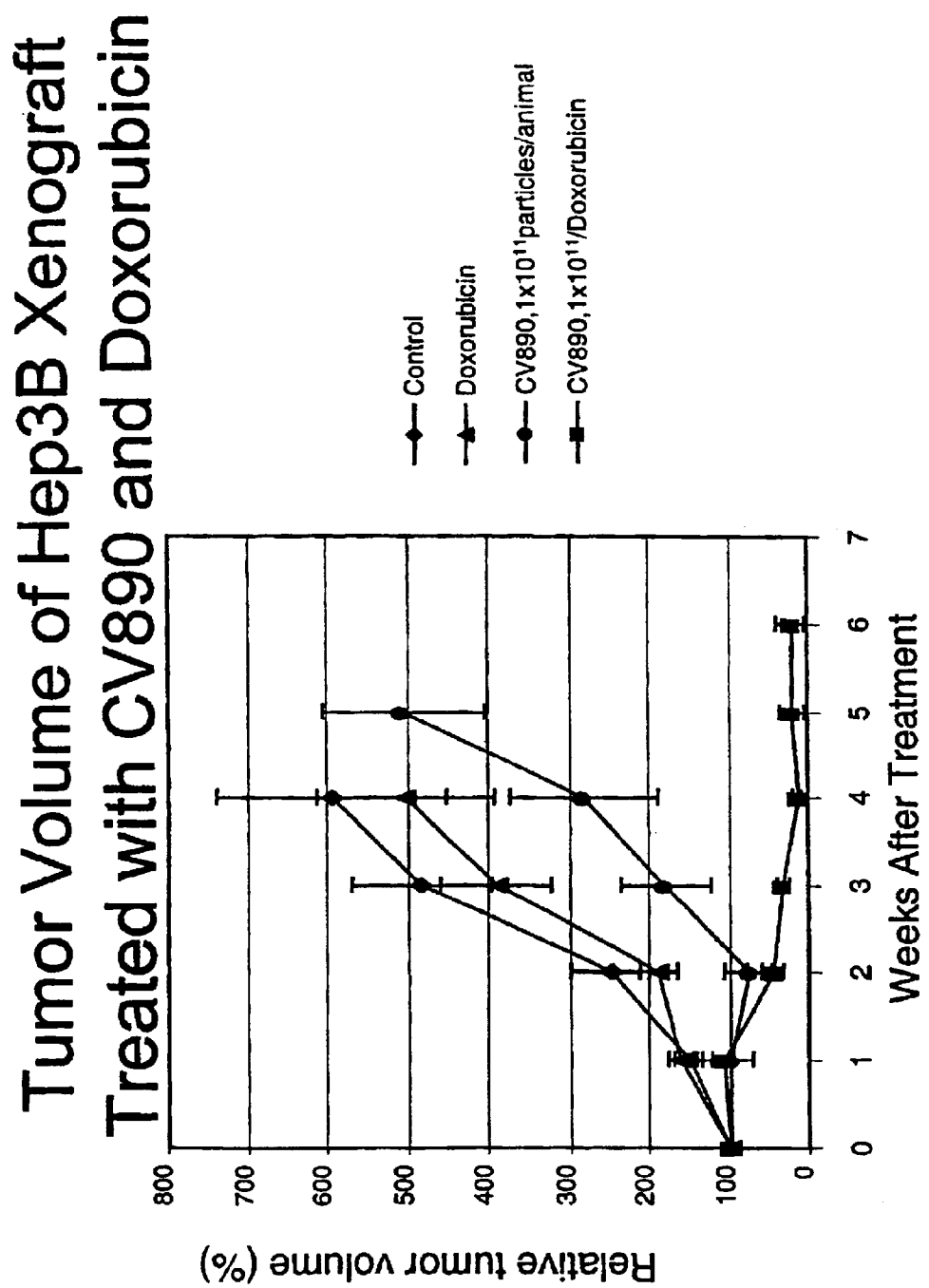

FIG. 31 is a graph depicting the relative percent tumor volume of Hep3B hepatoma xenografts treated with CV890 adenovirus vector (solid circles; $1 \times 10^{11}$ particles); CV890 and doxorubicin (solid squares); doxorubicin alone (triangles; 10 mg/kg); and mock infected control (solid diamonds). For combination administration, CV890 was administered first.

Figure 32:
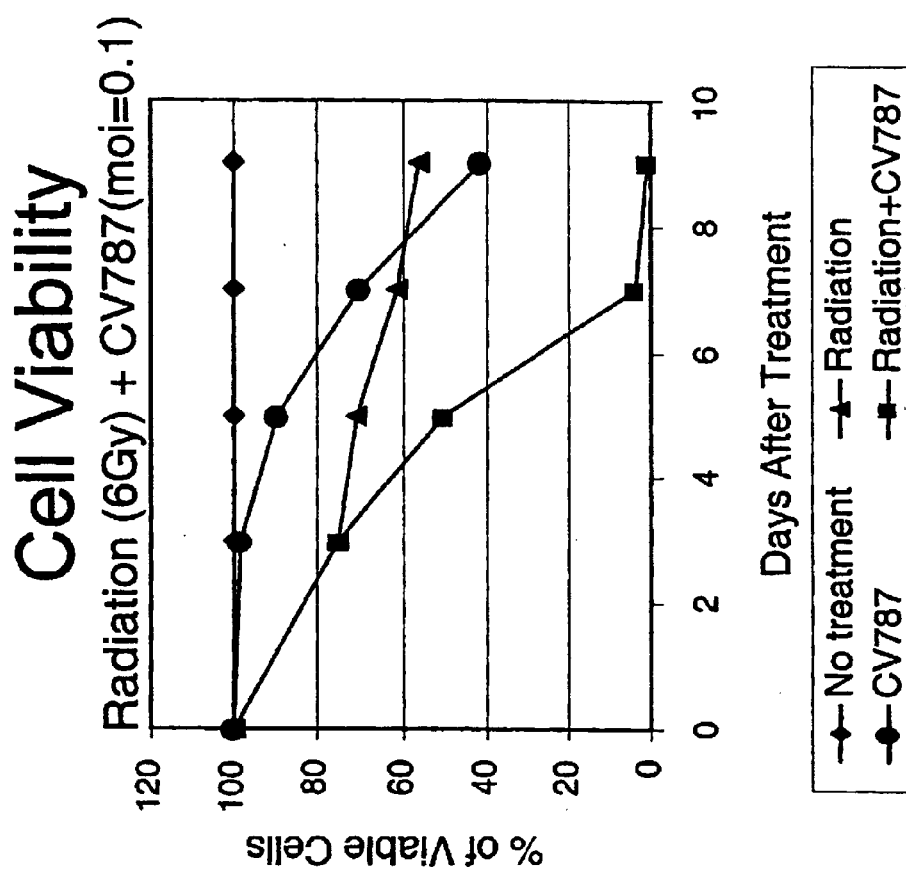

FIG. 32 is a graph depicting percent viable LNCaP prostate tumor cells treated with CV787 adenovirus vector (solid circles; MOI 0.1); CV787 and radiation (solid squares); radiation alone (solid triangles; 6 Gy); and no treatment (diamonds). In combination administration, radiation was administered first.

Figure 33:
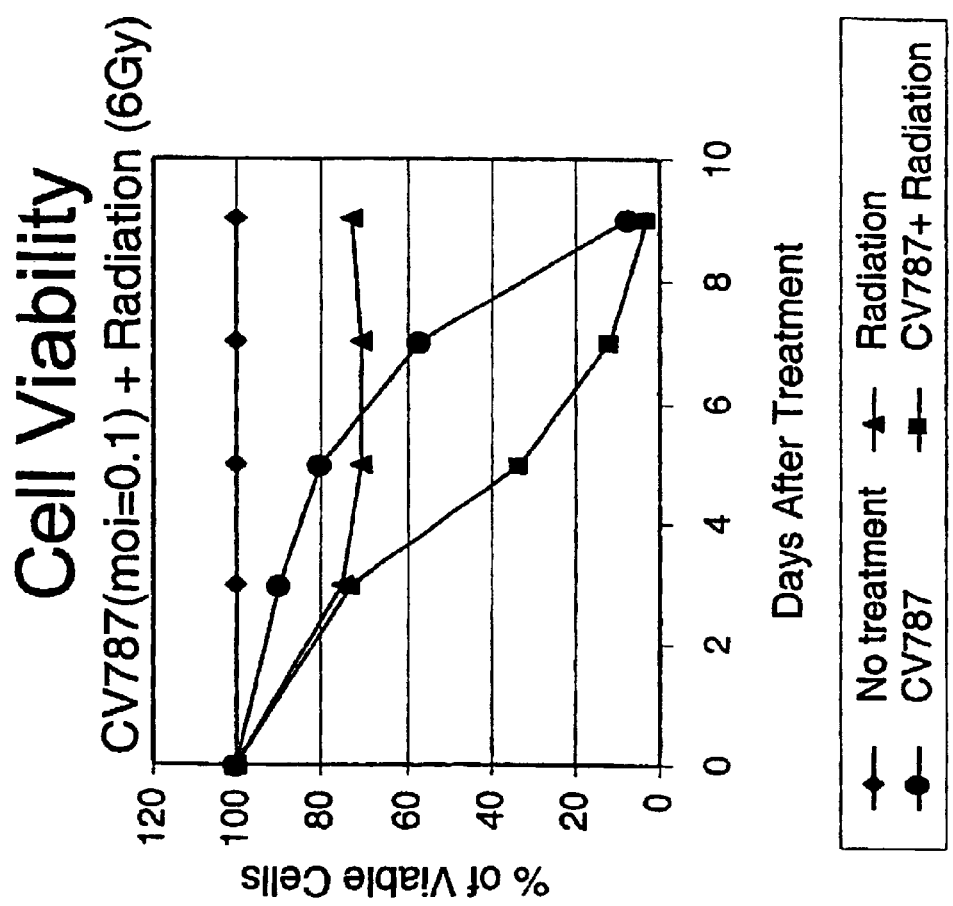

FIG. 33 is a graph depicting percent viable LNCaP prostate tumor cells treated with CV787 adenovirus vector (solid circles; MOI 0.1); CV787 and radiation (solid squares); radiation alone (solid triangles; 6 Gy); and no treatment (diamonds). In combination administration, CV787 was administered first.

Figure 34:
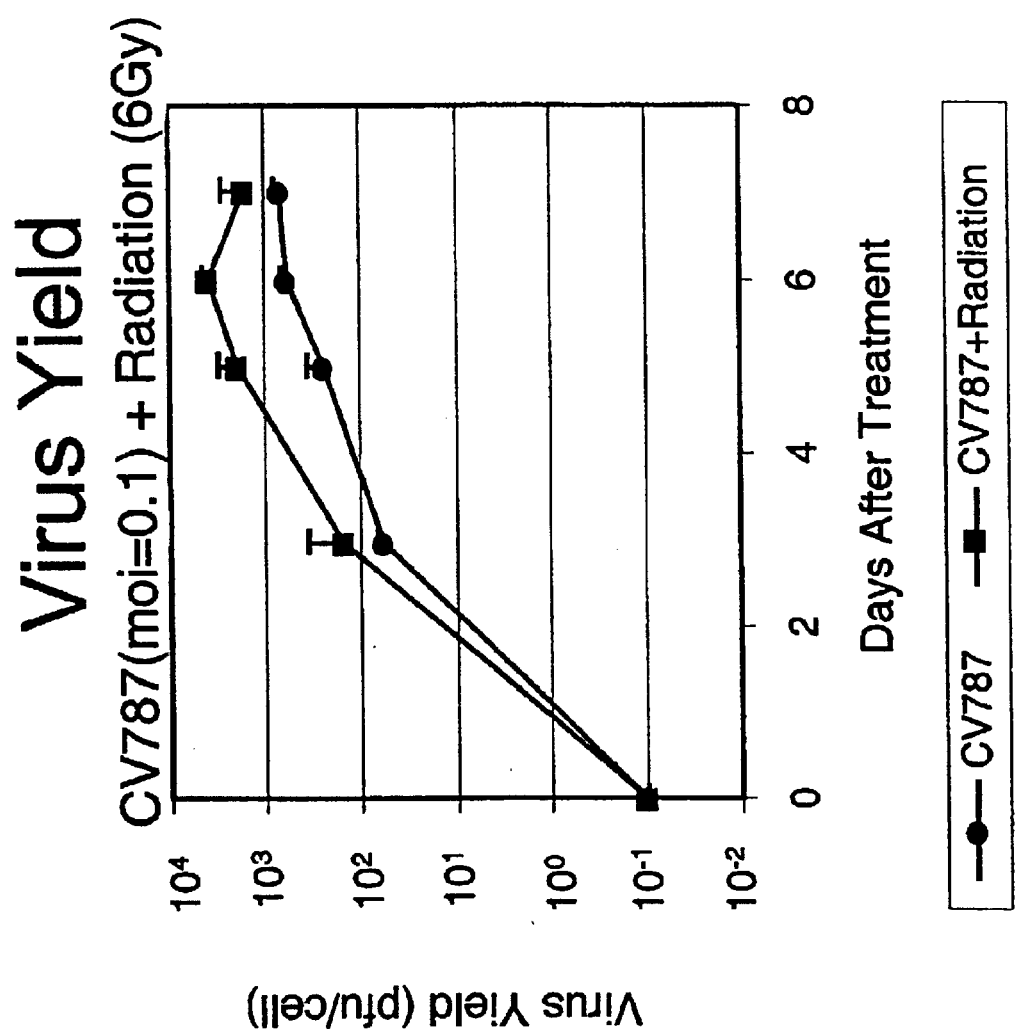

FIG. 34 is a graph depicting the virus yield of CV787 adenovirus vector over time for CV787 administered with radiation first (solid squares; MOI 0.1; 6 Gy) and CV787 administered without radiation (solid circles).

Figure 35:
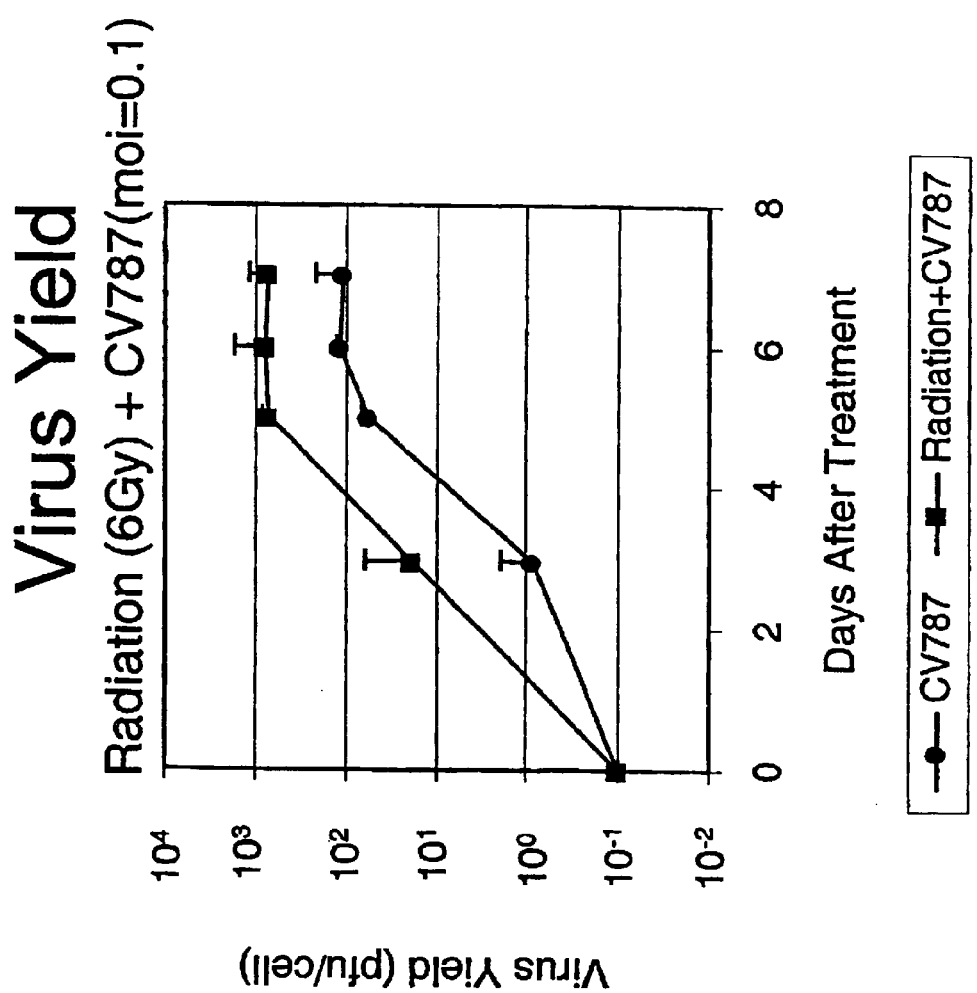

FIG. 35 is a graph depicting the virus yield of CV787 adenovirus vector over time for CV787 administered before radiation (solid squares; MOI 0.1; 6 Gy) and CV787 administered without radiation (solid circles).

Figure 36:
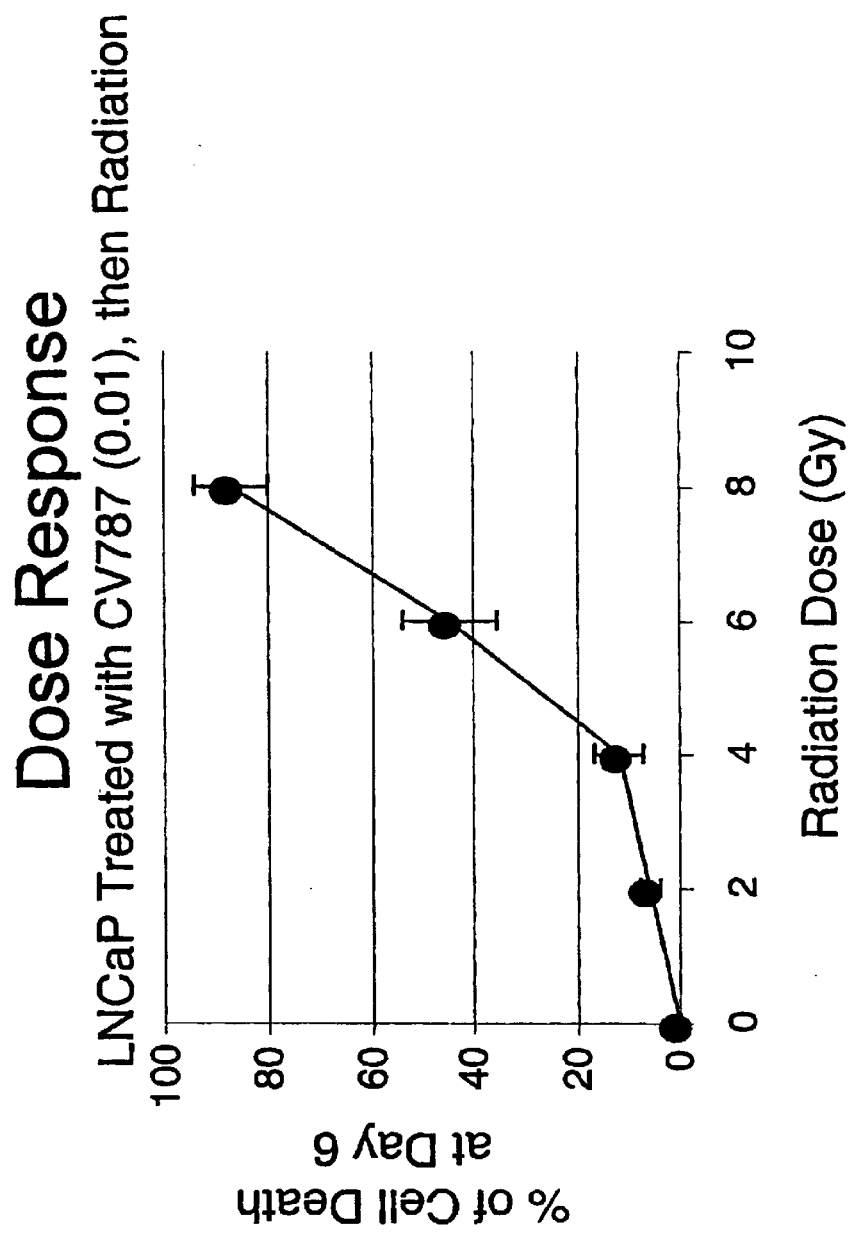

FIG. 36 is a graph depicting percent of cell death of LNCaP prostate tumor cells treated with CV787 adenovirus vector (MOI 0.01) and increasing doses of radiation, on day 6 of treatment. CV787 was administered first.

FIG. 37 depicts a nucleotide SEQ ID NO: 17 and amino acid sequence SEQ ID NO: 18 for ADP.

Figure 38:
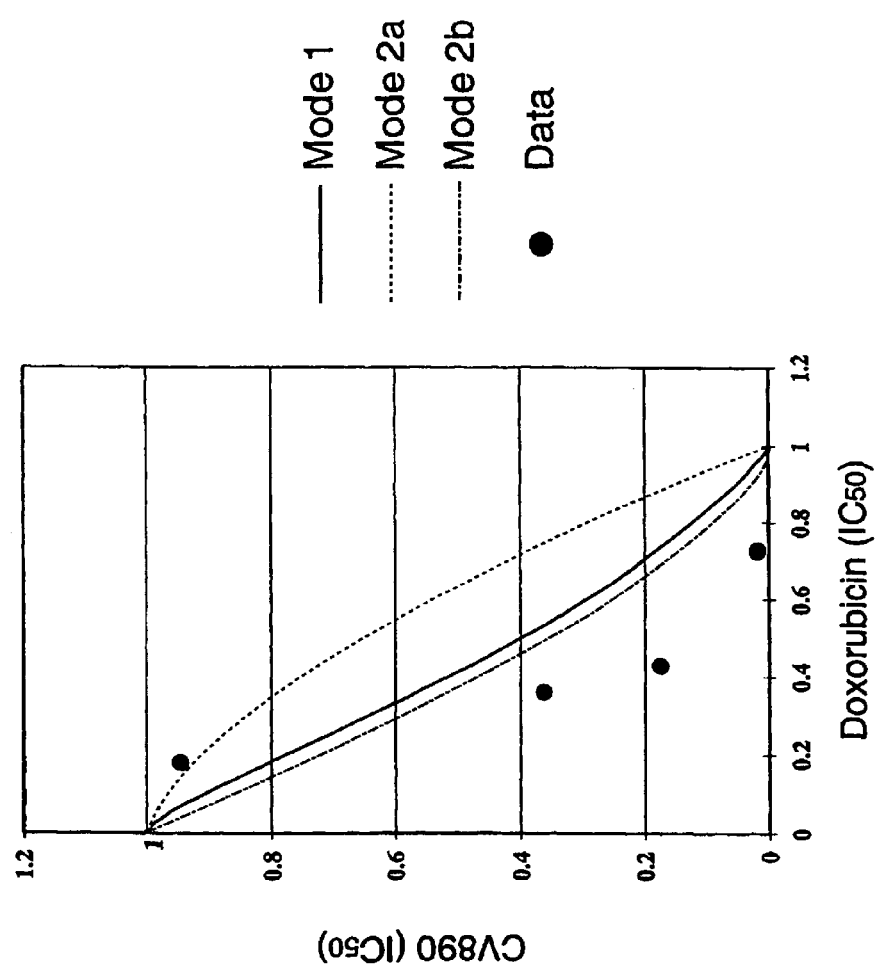

FIG. 38 depicts an $IC_{50}$ isobologram of doxorubicin and CV 890 on Hep3B cells at day 5.

Figure 39:
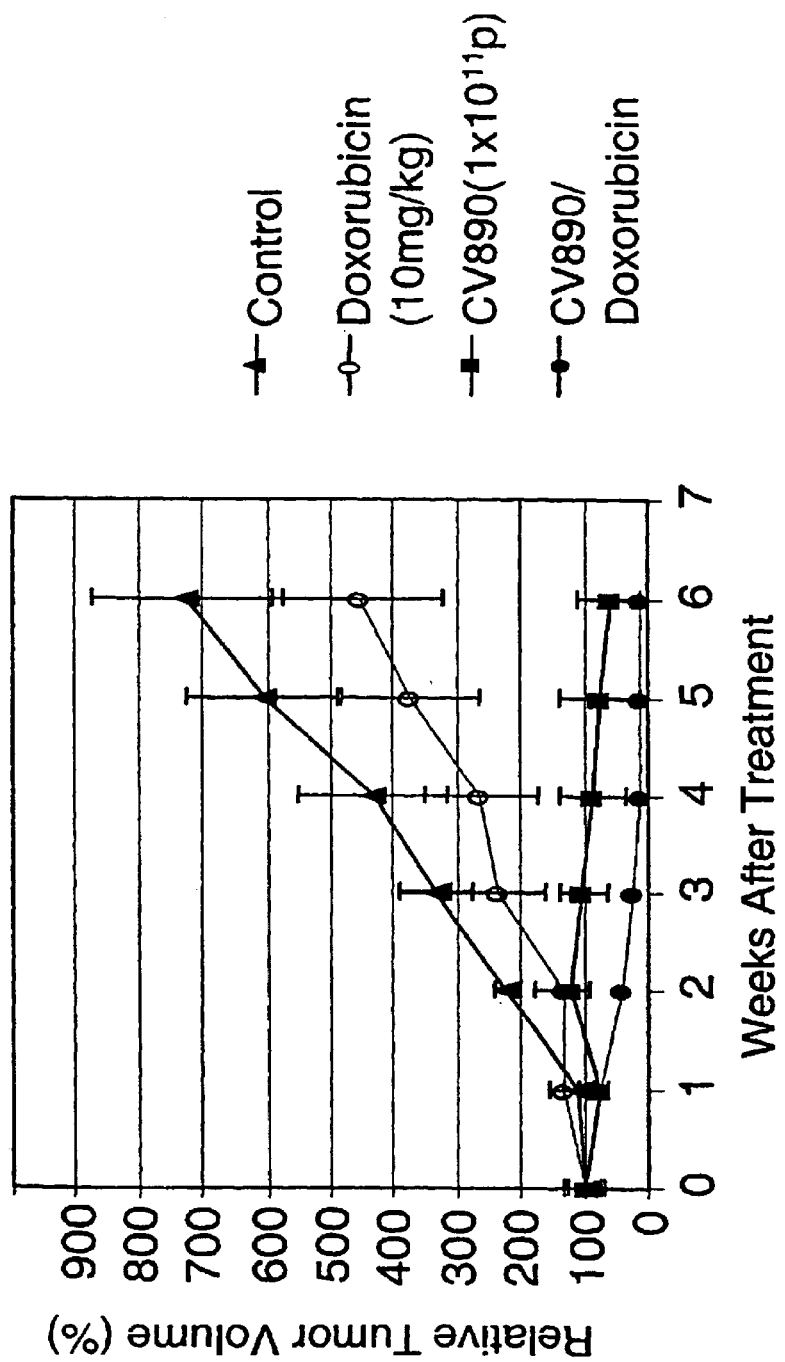

FIG. 39 depicts in vivo efficacy of CV890 with doxorubicin. Hep3B nude mouse xenografts were grouped (n—6) and treated with CV890 alone ($1 \times 10^{11}$ particles/dose, iv), doxorubicin alone (10 mg/kg, ip), CV890 and doxorubicin combination ($1 \times 10^{11}$ particles of CV890 through tail vein and 10 mg/kg doxorubicin ip), or vehicle control. Tumor size was measured weekly and the tumor volume were normalized as 100% at the day of treatment. Error bars represent the standard error of the mean.

Figure 40:
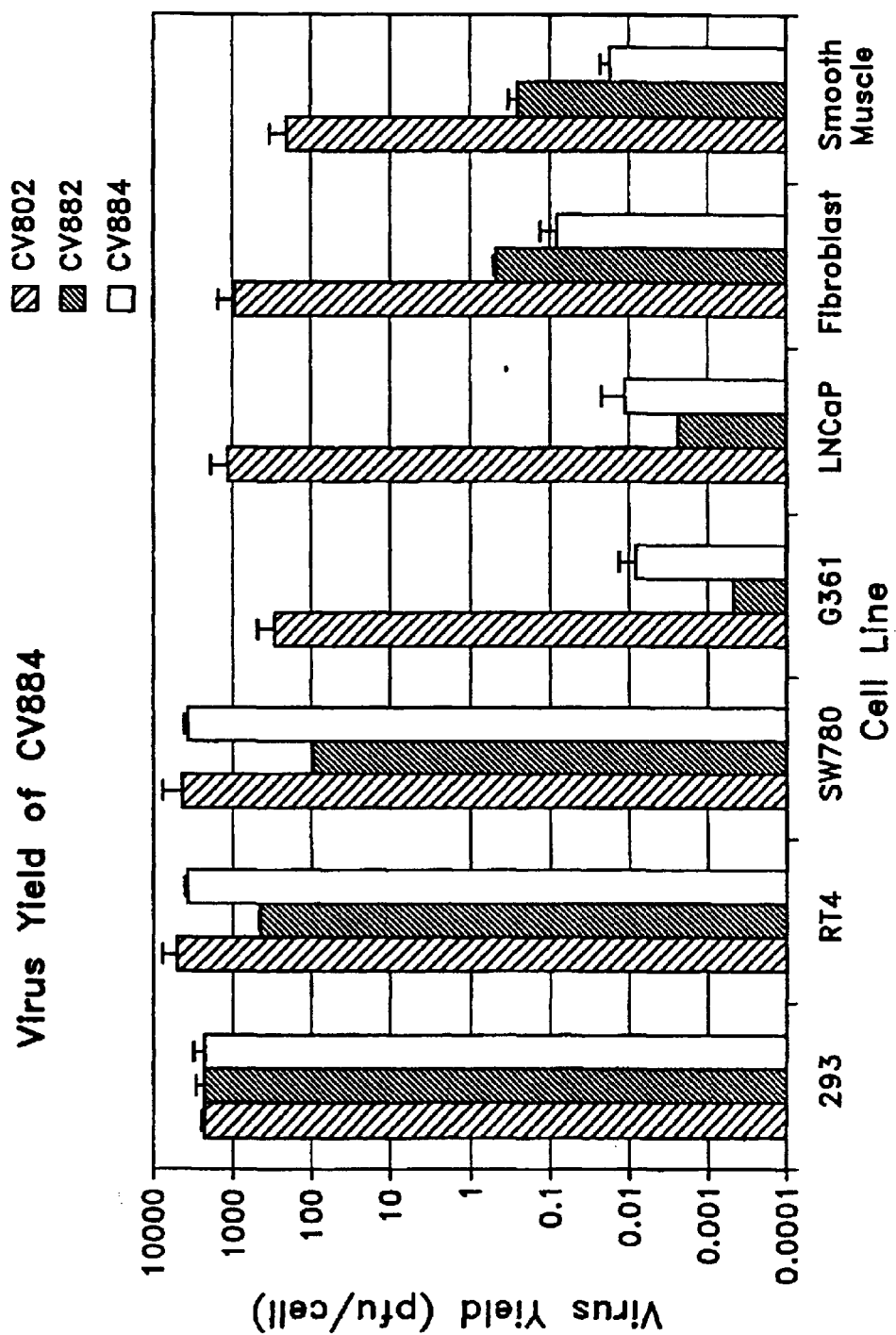

FIG. 40 shows the virus yield of CV802, CV882 and CV884 in cell lines.

Figure 41:
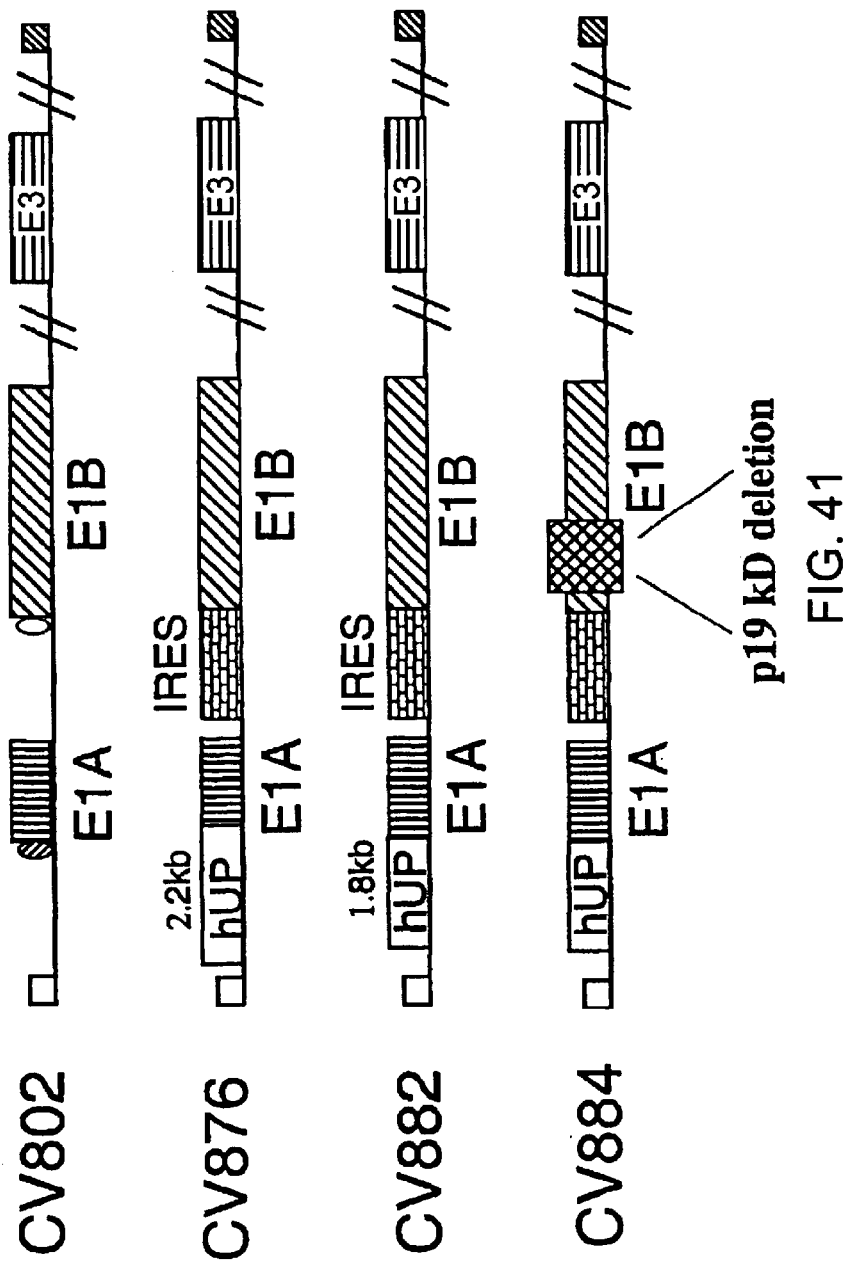

FIG. 41 are schematic depictions of various adenovirus constructs described herein.

MODES FOR CARRYING OUT THE INVENTION

We have discovered methods of using replication-competent, target cell-specific adenovirus vectors in combination with single chemotherapeutic agents, combinations of chemotherapeutic agents, radiation therapy treatment and the combination of radiation therapy and chemotherapeutic agents. The target cell-specific replication-competent adenovirus vectors comprise an adenovirus gene essential for replication, preferably an early gene, under the transcriptional control of a cell type-specific transcriptional regulatory element (TRE). By providing for cell type-specific transcription through the use of one or more cell type-specific TREs, the adenovirus vectors effect cell-specific cytotoxicity due to selective replication. We have observed synergy with respect to these adenoviral vectors and various chemotherapeutic agents as well as radiation compared to results using adenovirus or chemotherapy or radiation alone.

Although chemotherapeutic agents are used to treat a wide variety of cancers, the success rate is highly variable and the chemotherapeutic agents themselves are highly toxic, causing highly undesirable side effects and possibly contributing additional mutagenic or carcinogenic results in an already immune-compromised individual. Because the combination of adenoviral vectors and chemotherapeutics can synergistically enhance the efficacy of treatment, this in turn permits a lower effective dose of virus and/or chemotherapeutic agent, reducing the toxicity of the treatment and the suffering of the individual. An additional potential benefit is reduced length of treatment, as we have observed that tumors respond to the combined viral therapy more quickly than to chemotherapy or viral therapy alone.

We have also discovered that, in spite of their potential to damage viral DNA and thus compromise adenoviral vector function, viral replication is not appreciably changed in the presence of chemotherapeutic agent(s) and/or radiation, and that simultaneous administration of target-cell specific adenovirus and chemotherapeutic agent(s) is effective for killing tumor cells.

In some embodiments, the methods are for suppressing tumor growth. In other embodiments, the methods are for reducing size and/or extent of a tumor. In other embodiments, the methods are for delaying development of a tumor. In other embodiments, the methods are for treating a neoplasia. In still other embodiments, the methods are for killing tumor cells.

With respect to all methods described herein, target cells (i.e., neoplastic, proliferative cells) are contacted with an appropriate adenovirus vector described herein (preferably in the form of an adenovirus particle) such that the vector enters the cell and viral replication initiates. Target cell(s) are also contacted with another agent which kills tumor cells, such as a chemotherapeutic agent(s) and/or radiation.

Individuals suitable for treatment by these methods include individuals who have or are suspected of having neoplasia, including individuals in the early or late stages of the disease, as well as individuals who have previously been treated (e.g., are in the adjuvant setting). Other individuals suitable for the methods described herein are those who are considered high risk for developing a tumor, such as those who have a genetic predisposition to development of a neoplasia and/or who have been exposed to an agent(s) which is correlated with development of a neoplasia.

Treatment regimes include both the eradication of tumors or other forms of the disease as well as palliation of the disease. These methods of treatment are suitable for numerous forms of neoplasia, including, but not limited to bladder cancer, prostate cancer, liver cancer, breast cancer, colon cancer, melanoma, ovarian pancreatic, lung, and brain cancer.

The presence of neoplasia and the suitability of the individual for receiving the methods described herein may be determined by any of the techniques known in the art, including diagnostic methods such as imaging techniques, analysis of serum tumor markers, and biopsy.

The various methods of the invention will be described below. Certain embodiments of the methods use replication-competent target cell-specific adenoviral vectors such as CV706 (prostate specific); CV787(prostate specific); CV790 (liver specific); CV829(bladder specific); CV884 (bladder specific); CV859(melanoma specific); CV873(colon/breast specific); CV890 (liver specific); CV874(bladder specific); CV875(bladder specific); CV876(bladder specific); CV877 (bladder specific) and CV855(melanoma specific), as described herein. A summary of the components of these vectors is included in the Examples section as Table 4. Although methods of tumor suppression are exemplified in the discussion below, it is understood that the alternative methods described above are equally applicable and suitable for these methods, and that the endpoints of these methods are measured using methods standard in the art, including the diagnostic and assessment methods described above.

General Techniques

The practice of the present invention will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Felgner and Ringold (1989) *Nature* 337:387–388; Berkner and Sharp (1983) *Nucl. Acids Res.* 11:6003-6020; Graham (1984) *EMBO J.* 3:2917–2922; Bett et al. (1993) *J. Virology* 67:5911-5921; Bett et al. (1994) *Proc. Natl. Acad. Sci. USA* 91:8802–8806.

Definitions

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

The terms "antineoplastic agent", "antineoplastic chemotherapeutic agent", "chemotherapeutic agent", "antineoplastic" and "chemotherapeutic" are used interchangeably herein and refer to chemical compounds or drugs which are used in the treatment of cancer e.g., to kill cancer cells and/or lessen the spread of the disease.

"Radiation therapy" is a term commonly used in the art to refer to multiple types of radiation therapy including internal and external radiation therapy, radioimmunotherapy, and the use of various types of radiation including X-rays, gamma rays, alpha particles, beta particles, photons, electrons, neutrons, radioisotopes, and other forms of ionizing radiation. As used herein, the term "radiation therapy" is inclusive of all of these types of radiation therapy, unless otherwise specified.

As used herein, "suppressing tumor growth" refers to reducing the rate of growth of a tumor, halting tumor growth completely, causing a regression in the size of an existing tumor, eradicating an existing tumor and/or preventing the occurrence of additional tumors upon treatment with the compositions, kits or methods of the present invention. "Suppressing" tumor growth indicates a growth state that is curtailed when compared to growth without contact with, i.e., transfection by, an adenoviral vector combined with administration of chemotherapeutic agents and radiation as described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

"Delaying development" of a tumor means to defer, hinder, slow, retard, stabilize, and/or postpone development of the disease. This delay can be of varying lengths of time, depending on the history of the disease and/or individual being treated.

As used herein, "synergy" or "synergistic effect" when referring to combination administration of adenovirus vector and antineoplastic agent and/or radiation means that the effect of the combination is more than additive when compared to administration of adenovirus vector, antineoplastic agent or radiation alone.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

As used herein, a "transcription response element" or "transcriptional regulatory element", or "TRE" is a polynucleotide sequence, preferably a DNA sequence, which increases transcription of an operably linked polynucleotide sequence in a host cell that allows that TRE to function. A TRE can comprise an enhancer and/or a promoter. A "transcriptional regulatory sequence" is a TRE. A "target cell-specific transcriptional response element" or "target cell-specific TRE" is a polynucleotide sequence, preferably a DNA sequence, which is preferentially functional in a specific type of cell, that is, a target cell. Accordingly, a target cell-specific TRE transcribes an operably linked polynucleotide sequence in a target cell that allows the target cell-specific TRE to function. The term "target cell-specific", as used herein, is intended to include cell type specificity, tissue specificity, developmental stage specificity, and tumor specificity, as well as specificity for a cancerous state of a given target cell. "Target cell-specific TRE" includes cell type-specific and cell status-specific TRE, as well as "composite" TREs. The term "composite TRE" includes a TRE which comprises both a cell type-specific and a cell status-specific TRE. A target cell-specific TRE can also include a heterologous component, including, for example, an SV40 or a cytomegalovirus (CMV) promoter(s). An example of a target cell specific TRE which is tissue specific is a CMV TRE which contains both promoter(s) and enhancer(s).

As described in more detail herein, a target cell-specific TRE can comprise any number of configurations, including, but not limited to, a target cell-specific promoter; and target cell-specific enhancer; a heterologous promoter and a target cell-specific enhancer; a target cell-specific promoter and a heterologous enhancer; a heterologous promoter and a heterologous enhancer; and multimers of the foregoing. The promoter and enhancer components of a target cell-specific TRE may be in any orientation and/or distance from the coding sequence of interest, as long as the desired target cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to) the target cell-specific TRE. As discussed herein, a target cell-specific TRE can be of varying lengths, and of varying sequence composition. As used herein, the term "cell status-specific TRE" is preferentially functional, i.e., confers transcriptional activation on an operably linked polynucleotide in a cell which allows a cell status-specific TRE to function, i.e., a cell which exhibits a particular physiological condition, including, but not limited to, an aberrant physiological state. "Cell status" thus refers to a given, or particular, physiological state (or condition) of a cell, which is reversible and/or progressive. The physiological state may be generated internally or externally; for example, it may be a metabolic state (such as in response to conditions of low oxygen), or it may be generated due to heat or ionizing radiation. "Cell status" is distinct from a "cell type", which relates to a differentiation state of a cell, which under normal conditions is irreversible. Generally (but not necessarily), as discussed herein, a cell status is embodied in an aberrant physiological state, examples of which are given below.

A "functional portion" of a target cell-specific TRE is one which confers target cell-specific transcription on an operably linked gene or coding region, such that the operably linked gene or coding region is preferentially expressed in the target cells.

By "transcriptional activation" or an "increase in transcription," it is intended that transcription is increased above basal levels in the target cell (i.e., target cell) by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-target cell (i.e., a different cell type), or the level of activity (if any) of a reporter construct lacking a target cell-specific TRE as tested in a target cell line.

A "functionally-preserved variant" of a target cell-specific TRE is a target cell-specific TRE which differs from another target cell-specific TRE, but still retains target cell-specific transcription activity, although the degree of activation may be altered (as discussed below). The difference in a target cell-specific TRE can be due to differences in linear sequence, arising from, for example, single base mutation(s), addition(s), deletion(s), and/or modification(s) of the bases. The difference can also arise from changes in the sugar(s), and/or linkage(s) between the bases of a target cell-specific TRE. For example, certain point mutations within sequences of TREs have been shown to decrease transcription factor binding and stimulation of transcription. See Blackwood, et al. (1998) *Science* 281:60–63 and Smith et al. (1997) *J. Biol. Chem.* 272:27493–27496. One of skill in the art would recognize that some alterations of bases in and around transcription factor binding sites are more likely to negatively affect stimulation of transcription and cell-specificity, while alterations in bases which are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

As used herein, a TRE derived from a specific gene is referred to by the gene from which it was derived and is a polynucleotide sequence which regulates transcription of an operably linked polynucleotide sequence in a host cell that expresses said gene. For example, as used herein, a "human glandular kallikrein transcriptional regulatory element", or "hKLK2-TRE" is a polynucleotide sequence, preferably a DNA sequence, which increases transcription of an operably linked polynucleotide sequence in a host cell that allows an hKLK2-TRE to function, such as a cell (preferably a mammalian cell, even more preferably a human cell) that expresses androgen receptor, such as a prostate cell. An hKLK2-TRE is thus responsive to the binding of androgen receptor and comprises at least a portion of an hKLK2 promoter and/or an hKLK2 enhancer (i.e., the ARE or androgen receptor binding site).

As used herein, a "probasin (PB) transcriptional regulatory element", or "PB-TRE" is a polynucleotide sequence, preferably a DNA sequence, which selectively increases transcription of an operably-linked polynucleotide sequence in a host cell that allows a PB-TRE to function, such as a cell (preferably a mammalian cell, more preferably a human cell, even more preferably a prostate cell) that expresses androgen receptor. A PB-TRE is thus responsive to the binding of androgen receptor and comprises at least a portion of a PB promoter and/or a PB enhancer (i.e., the ARE or androgen receptor binding site).

As used herein, a "prostate-specific antigen (PSA) transcriptional regulatory element", or "PSA-TRE", or "PSE-TRE" is a polynucleotide sequence, preferably a DNA sequence, which selectively increases transcription of an operably linked polynucleotide sequence in a host cell that allows a PSA-TRE to function, such as a cell (preferably a mammalian cell, more preferably a human cell, even more preferably a prostate cell) that expresses androgen receptor. A PSA-TRE is thus responsive to the binding of androgen receptor and comprises at least a portion of a PSA promoter and/or a PSA enhancer (i.e., the ARE or androgen receptor binding site).

As used herein, a "carcinoembryonic antigen (CEA) transcriptional regulatory element", or "CEA-TRE" is a polynucleotide sequence, preferably a DNA sequence, which selectively increases transcription of an operably linked polynucleotide sequence in a host cell that allows a CEA-TRE to function, such as a cell (preferably a mammalian cell, even more preferably a human cell) that expresses CEA. The CEA-TRE is responsive to transcription factors and/or co-factor(s) associated with CEA-producing cells and comprises at least a portion of the CEA promoter and/or enhancer.

As used herein, an "α-fetoprotein (AFP) transcriptional regulatory element", or "AFP-TRE" is a polynucleotide sequence, preferably a DNA sequence, which selectively increases transcription (of an operably linked polynucleotide sequence) in a host cell that allows an AFP-TRE to function, such as a cell (preferably a mammalian cell, even more preferably a human cell) that expresses AFP. The AFP-TRE is responsive to transcription factors and/or co-factor(s) associated with AFP-producing cells and comprises at least a portion of the AFP promoter and/or enhancer.

As used herein, an "a mucin gene (MUC) transcriptional regulatory element", or "MUC1-TRE" is a polynucleotide sequence, preferably a DNA sequence, which selectively increases transcription (of an operably-linked polynucleotide sequence) in a host cell that allows a MUC1-TRE to function, such as a cell (preferably a mammalian cell, even more preferably a human cell) that expresses MUC1. The MUC1-TRE is responsive to transcription factors and/or co-factor(s) associated with MUC 1-producing cells and comprises at least a portion of the MUC1 promoter and/or enhancer.

As used herein, a "urothelial cell-specific transcriptional response element", or "urothelial cell-specific TRE" is polynucleotide sequence, preferably a DNA sequence, which increases transcription of an operably linked polynucleotide sequence in a host cell that allows a urothelial-specific TRE to function, i.e., a target cell. A variety of urothelial cell-specific TREs are known, are responsive to cellular proteins (transcription factors and/or co-factor(s)) associated with urothelial cells, and comprise at least a portion of a urothelial-specific promoter and/or a urothelial-specific enhancer. Methods are described herein for measuring the activity of a urothelial cell-specific TRE and thus for determining whether a given cell allows a urothelial cell-specific TRE to function.

As used herein, a "melanocyte cell-specific transcriptional response element", or "melanocyte cell-specific TRE" is polynucleotide sequence, preferably a DNA sequence, which increases transcription of an operably linked polynucleotide sequence in a host cell that allows a melanocyte-specific TRE to function, i.e., a target cell. A variety of melanocyte cell-specific TREs are known, are responsive to cellular proteins (transcription factors and/or co-factor(s)) associated with melanocyte cells, and comprise at least a portion of a melanocyte-specific promoter and/or a melanocyte-specific enhancer. Methods are described herein for measuring the activity of a melanocyte cell-specific TRE and thus for determining whether a given cell allows a melanocyte cell-specific TRE to function.

As used herein, a target cell-specific TRE can comprise any number of configurations, including, but not limited to, a target cell-specific promoter; a target cell-specific enhancer; a target cell-specific promoter and a target cell-specific enhancer; a target cell-specific promoter and a heterologous enhancer; a heterologous promoter and a target cell-specific enhancer; and multimers of the foregoing. The promoter and enhancer components of a target cell-specific TRE may be in any orientation and/or distance from the coding sequence of interest, as long as the desired target cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to) the target cell-specific TRE.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. Jackson R J, Howell M T, Kaminski A (1990) *Trends Biochem Sci* 15(12): 477–83) and Jackson RJ and Kaminski, A. (1995) *RNA* 1(10):985–1000). The present invention encompasses the use of any IRES element which is able to promote direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, *Trends Biochem Sci* 15(12):477–483); and IRES obtainable from viral or cellular mRNA sources, such as for example, immunogloublin heavy-chain binding protein (BiP), the vascular endothelial growth factor (VEGF) (Huez et al. (1998) *Mol. Cell. Biol.* 18(11):6178–6190), the fibroblast growth factor 2, and insulin-like growth factor, the translational initiation factor eIF4G, yeast transcription factors TFIID and HAP4. IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) *J. Virol* 66(3): 1602–1609). In another illustrative embodiment disclosed herein, the IRES is from VEGF. Table I and Table II disclose a variety of IRES sequences useful in the present invention. In some embodiments, an adenovirus vector comprising an IRES exhibits greater specificity for the target cell than an adenovirus vector comprising a target cell-specific TRE operably linked to a gene and lacking an IRES. In some embodiments, specificity is conferred by preferential transcription and/or translation of the first and second genes due to the presence of a target cell specific TRE. In other embodiments, specificity is conferred by preferential replication of the adenovirus vectors in target cells due to the target cell-specific TRE driving transcription of a gene essential for replication.

A "multicistronic transcript" refers to an mRNA molecule which contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions of polynucleotides are under transcriptional control of single transcriptional control element.

A "gene" refers to a coding region of a polynucleotide. A "gene" may or may not include non-coding sequences and/or regulatory elements.

"Replicating preferentially", as used herein, means that the adenovirus replicates more in a target cell than a non-target cell. Preferably, the adenovirus replicates at a significantly higher rate in target cells than non target cells; preferably, at least about 2-fold higher, preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1 \times 10^6$ higher. Most preferably, the adenovirus replicates solely in the target cells (that is, does not replicate or replicates at a very low levels in non-target cells).

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothioate linkage can be used in place of a phosphodiester linkage. Braun et al. (1988) *J. Immunol.* 141: 2084–9; Latimer et al. (1995) *Molec. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

An "E3 region" (used interchangeably with "E3") is a term well understood in the art and means the region of the adenoviral genome that encodes the E3 products (discussed herein). Generally, the E3 region is located between about 28583 and 30470 of the adenoviral genome. The E3 region has been described in various publications, including, for example, Wold et al. (1995) *Curr. Topics Microbiol Immunol.* 199:237–274.

A "portion" of the E3 region means less than the entire E3 region, and as such includes polynucleotide deletions as well as polynucleotides encoding one or more polypeptide products of the E3 region. As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, 3H-thymidine uptake, and plaque assays.

An "E1B 19-kDa region" (used interchangeably with "E1B 19-kDa genomic region") refers to the genomic region of the adenovirus E1B gene encoding the E1B 19-kDa product. According to wild-type Ad5, the E1B 19-kDa region is a 261 bp region located between nucleotide 1714 and nucleotide 2244. The E1B 19-kDa region has been described in, for example, Rao et al., *Proc. Natl. Acad. Sci. USA*, 89:7742–7746. The present invention encompasses deletion of part or all of the E1B 19-kDa region as well as embodiments wherein the E1B 19-kDa region is mutated, as long as the deletion or mutation lessens or eliminates the inhibition of apoptosis associated with E1B-19 kDa.

The term "selective cytotoxicity", as used herein, refers to the cytotoxicity conferred by an adenovirus vector of the present invention on a cell which allows or induces a target cell-specific TRE to function (a target cell) when compared to the cytotoxicity conferred by an adenoviral vector of the present invention on a cell which does not allow a target cell-specific TRE to function (a non-target cell). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes are provided below.

In the context of adenovirus, a "heterologous" promoter or enhancer is one which is not associated with or derived from an adenovirus gene.

In the context of adenovirus, an "endogenous" promoter, enhancer, or TRE is native to or derived from adenovirus. In the context of promoter, an "inactivation" means that there is a mutation of or deletion in part or all of the of the endogenous promoter, ie, a modification or alteration of the endogenous promoter, such as, for example, a point mutation or insertion, which disables the function of the promoter.

In the context of a target cell-specific TRE, a "heterologous" promoter or enhancer is one which is derived from a gene other than the gene from which a reference target cell-specific TRE is derived.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

An "ADP coding sequence" is a polynucleotide that encodes ADP or a functional fragment thereof. In the context of ADP, a "functional fragment" of ADP is one that exhibits cytotoxic activity, especially cell lysis, with respect to adenoviral replication. Ways to measure cytotoxic activity are known in the art and are described herein.

A polynucleotide that "encodes" an ADP polypeptide is one that can be transcribed and/or translated to produce an ADP polypeptide or a fragment thereof. The anti-sense strand of such a polynucleotide is also said to encode the sequence.

An "ADP polypeptide" is a polypeptide containing at least a portion, or region, of the amino acid sequence of an ADP and which displays a function associated with ADP, particularly cytotoxicity, more particularly, cell lysis. As discussed herein, these functions can be measured using techniques known in the art. It is understood that certain sequence variations may be used, due to, for example, conservative amino acid substitutions, which may provide ADP polypeptides.

"Androgen receptor," or AR, as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones other than androgens. Encompassed in the term "androgen receptor" are mutant forms of an androgen receptor, such as those characterized by amino acid additions, insertions, truncations and deletions, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

A polynucleotide sequence that is "depicted in" a SEQ ID NO means that the sequence is present as an identical contiguous sequence in the SEQ ID NO. The term encompasses portions, or regions of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, rodents, primates, and pets.

An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

A given TRE is "derived from" a given gene if it is associated with that gene in nature.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

Combination Adenoviral and Chemotherapeutic Therapy

Embodiments of the present invention include methods for the administration of combinations of a target cell-specific adenoviral vector and at least one antineoplastic agent(s) to an individual with neoplasia. The antineoplastic agent includes those listed in Table 1. These include agents from each of the major classes of chemotherapeutics, including but not limited to: alkylating agents, alkaloids, antimetabolites, anti-tumor antibiotics, nitrosoureas, hormonal agonists/antagonists and analogs, immunomodulators, photosensitizers, enzymes and others. In some embodiments, the antineoplastic is an alkaloid, an antimetabolite, an antibiotic or an alkylating agent. In certain embodiments the antineoplastic agents include, for example, thiotepa, interferon alpha-2a, and the M-VAC combination (methotrexate-vinblastine, doxorubicin, cyclophosphamide). Preferred antineoplastic agents include, for example, 5-fluorouracil, cisplatin, 5-azacytidine, and gemcitabine. Particularly preferred embodiments include, but are not limited to, doxorubicin, estramustine, etoposide, mitoxantrone, docetaxel (TAXOTERE™), paclitaxel (TAXOL™), and mitomycin C.

TABLE 1

| | | | Antineoplastic Agents | | |
|---|---|---|---|---|---|
| ALKALOIDS | ALKYLATING AGENTS | ANTIBIOTICS AND ANALOGS | ANTIMETABOLITES | ENZYMES | IMMUNOMODULATORS |
| Docetaxel (TAXOTERE ™) | Alkyl Sulfonates | Aclacinomycins | Folic Acid Analogs | L-Asparaginase | Interferon-α |
| Etoposide | Busulfan | Actinomycin $F_1$ | Denopterin | Pegasargase | Interferon-β |
| Irinotecan | Improsulfan | Anthramycin | Edatrexate | | Interferon-γ |
| Paclitaxel (TAXOL ™) | Piposulfan | Azaserine | Methotrexate | | Interferon-α-2a |
| Teniposide | | Bleomycins | Piritrexim | | Interleukin-2 |
| Topotecan | Aziridines | Cactinomycin | Pteropterin | | Lentinan |
| Vinblastine | Benzodepa | Carubicin | Tomudex ® | | Propagermanium |
| Vincristine | Carboquone | Carzinophilin | Trimetrexate | | PSK |
| Vendesine | Meturedepa | Chromomycins | | | Roquinimex |
| Vinorelbine | Uredepa | Dactinomycin | Purine Analogs | | Rituximab |
| | | Daunorubicin | Cladribine | | Sizofiran |
| | Ethylenimines and Methylmelamines | 6-Diazo-5-oxo-L-norleucine | Fludarabine | | Trastuzumab |
| | Altretamine | Doxorubicin | 6-Mercaptopurine | | Ubenimex |
| | Triethylenemel-amine | Epirubicin | Thiamiprine | | |
| | Triethylenephos-phoramide | Idarubicin | Thioguanine | | |
| | Triethylenethio-phosphoramide | Menogaril | | | |
| | | Mitomycins | | | |
| | | Mitoxantrone | Pyrimidine Analogs | | |
| | Nitrogen Mustards | Mycophenolic Acid | Ancitabine | | |
| | Chlorambucil | Nogalamycin | 5-Azacytidine | | |
| | Chlomaphazine | Olivomycins | 6-Azauridine | | |
| | Cyclophos-phamide | Peplomycin | Carmofur | | |
| | Estramustine | Pirarubicin | Cytarabine | | |
| | Ifosfamide | Plicamycin, | Doxifluridine | | |
| | Mechlorethamine | Porfiromycin | Emitefur | | |
| | Mechlorethamine Oxide | Puromycin | Enocitabine | | |

TABLE 1-continued

| | | | |
|---|---|---|---|
| Hydrochloride | | | |
| Melphalan | Streptonigrin | Floxuridine | |
| Novembichin | Streptozocin | Fluorouracil | |
| | Valrubicin | | |
| Perfosfamide | Tubercidin | Gemcitabine | |
| Phenesterine | Zinostatin | Tegafur | |
| Prednimustine | Zorubicin | | |
| Trofosfamide | | | |
| Uracil Mustard | | | |
| Carboplatin | | | |
| Cisplatin | | | |
| Miboplatin | | | |
| Oxaliplatin | | | |
| Others | | | |
| | | | |
| Dacarbazine | | | |
| Mannomustine | | | |
| Mitobronitol | | | |
| Mitolactol | | | |
| Thiotepa | | | |
| Pipobroman | | | |
| Temozolomide | | | |

| NITROSOUREAS | OTHERS | HORMONE ANTAGONISTS/AGONISTS & ANALOGS | PHOTOSENSITIZER |
|---|---|---|---|
| Carmustine | Aceglatone | Dexamethasone | Porfimer Sodium |
| Chlorozotocin | Amsacrine | Prednisone | |
| Fotemustine | Bisantrene | | |
| Lomustine | Defosfamide | Androgens | |
| | | | |
| Nimustine | Demecolcine | Calusterone | |
| Ranimustine | Diaziquone | Dromostanolone | |
| | Eflornithine | Epitiostanol | |
| | Elliptinium Acetate | Mepitiostane | |
| | Etoglucid | Testolactone | |
| | Fenretinide | | |
| | Finasteride | Antiadrenals | |
| | | | |
| | Gallium Nitrate | Aminoglutethimide | |
| | Hydroxyurea | Mitotane | |
| | Lonidamine | Trilostane | |
| | Miltefosine | | |
| | Mitoguazone | | |
| | Mopidamol | Antiandrogens | |
| | Nitracrine | Bicalutamide | |
| | Pentostatin | Flutamide | |
| | Phenamet | Nilutamide | |
| | Podophyllinic Acid 2-Ethylhydrazide | Antiestrogens | |
| | | | |
| | Procarbazine | Droloxifene | |
| | Razoxane | Tamoxifen | |
| | Sobuzoxane | Toremifene | |
| | Spirogermanium | Exemestane | |
| | Amsacrine | Aromatase Inhibitors | |
| | Tretinoin | Aminoglutethimide | |
| | Tenuazonic Acid | Anastrozole | |
| | Triaziquone | | |
| | 2,2',2"-Triclorotriethylamine, | Fadrozole | |
| | Urethan | Formestane | |
| | Topotecan | Letrozole | |
| | | | |
| | | Estrogens | |
| | | | |
| | | Fosfestrol | |
| | | Hexestrol | |
| | | Polyestradiol Phosphate | |

TABLE 1-continued

LHRH Analogs

Buserelin
Goserelin
Leuprolide
Triptorelin,
Progestogens
Chlormadinone
Acetate
Medroxyprogesterone
Megestrol Acetate
Melengestrol This section provides exemplary non-inclusive vector and chemotherapeutic combinations. The adenoviral vector used in the methods described herein is generally a replication-competent, target-cell specific adenoviral vector comprising an adenovirus gene essential for replication under transcriptional control of a TRE, embodiments of which are described infra. In some embodiments, the gene essential for replication in the adenoviral vector is an early gene, preferably E1A and/or E1B. In some embodiments the E1A and E1B genes are under transcriptional of identical TREs. In other embodiments E1A and E1B genes are under transcriptional control of non-identical (or heterologous) TREs. In some embodiments, the adenovirus vector comprises a transgene. In other embodiments, the adenovirus vector comprises ADP. In some embodiments, the adenovirus vector contains an E3 region.

In other embodiments, the adenovirus vectors comprise co-transcribed first and second genes under transcriptional control of a heterologous, target cell-specific transcriptional regulatory element (TRE), wherein the second gene is under translational control of an internal ribosome entry site (IRES).

The choice of adenoviral vector is primarily determined by the identity of the target cells and therefore the type of cancer to be treated. As explained below in detail, an adenoviral vector comprising a PSA-TRE, PB-TRE, or hKLK2-TRE would preferentially replicate in prostate cells; an adenoviral vector comprising a CEA-TRE would preferentially replicate in colorectal, gastric, pancreatic, breast and lung cells; an AFP-TRE would preferentially replicate in hepatoma cells, or liver tumors; a urothelial cell-specific TRE (such as uroplakin) would preferentially replicate in bladder cells; a MUC-TRE would preferentially replicate in breast cells; a melanocyte specific TRE (such as tyrosinase) would preferentially replicate in melanoma cells.

Certain combinations of adenoviral vector and chemotherapeutic are particularly effective for the treatment of particular types of cancer using the methods described above. Based on our in vitro studies, not all combinations of target cell-specific adenoviral vector and chemotherapeutic result in synergy. As shown in Tables 5 and 6 in Examples 1 and 2, gemcitabine used with CV790 (a liver-specific virus with E1A and E1B under transcriptional control of two identical AFP-TREs) results in synergy. However, when gemcitabine is used with CV787 (a prostate-specific virus with E1A under transcriptional control of a PB-TRE and E1B under transcriptional control of a PSE-TRE), synergy is not observed. 5-fluorouracil used with prostate-specific adenovirus CV787 results in synergy, but when used with liver-specific adenovirus CV790, synergy is not observed. In another embodiment disclosed herein, CV884 used with doxorubicin provides synergistic effect.

For example, with respect to treatment of prostate tumors, a replication-competent adenovirus in which a gene essential for replication, preferably one or more early genes, is under transcriptional control of a prostate specific TRE, as discussed below, may be used in conjunction with an antineoplastic agent that is in the alkaloid, antimetabolite, antibiotic, or alkylating agent class of antineoplastics. Preferred examples of antineoplastic agents include doxorubicin, mitoxantrone, paclitaxel, estramustine, etoposide and docetaxel. Additional examples of antineoplastic agents include, 5-fluorouracil or cisplatin.

In some embodiments of the adenovirus vector, E1A is under transcriptional control of a prostate specific TRE. In other embodiments E1B is under transcriptional control of a prostate specific TRE. In yet other embodiments, both E1A and E1B are under transcriptional control of prostate specific TREs, which may or may not be the same sequence. An example of a suitable prostate specific replication-competent adenoviral vector is one comprising probasin (PB)-TRE controlling transcription of E1A, and PSE-TRE controlling transcription of E1B, such as CV787 as described in the examples. Particularly preferred embodiments include administration of the combination of 5-fluorouracil with a prostate specific adenoviral vector in which a PSA-TRE controls transcription of E1A. An example of a suitable adenoviral vector is CV706.

In some embodiments, a prostate specific adenoviral vector comprising E1A and E1B under transcriptional control of two non-identical prostate specific TREs, is administered in conjunction with any of the following antineoplastic agents: paclitaxel; docetaxel; cisplatin; doxorubicin; estramustine; etoposide; mitoxantrone; and 5-fluorouracil. In some embodiments, the prostate specific TRE controlling transcription of E1A and the prostate specific TRE controlling transcription of E1B are heterologous (i.e., of different sequence) with respect to each other. In some embodiments, the prostate specific TRE controlling transcription of E1A is derived from probasin (PB) and the prostate specific TRE controlling transcription of E1B is derived from prostate specific antigen (PSA). In other embodiments, the prostate specific TRE controlling transcription of E1A is derived from PSA, and the prostate specific TRE controlling transcription of E1B is derived from probasin. PSA-derived and PB-derived TREs are described herein. In some embodiments, the adenoviral vector is CV787. In some embodiments, an IRES is translationally linked to an adenovirus gene essential for replication, such as E1B and in preferred embodiments, E1B has its endogenous promoter deleted and the IRES and E1B are in frame. In other embodiments, the 19-kDa region of E1B is deleted.

Preferably, the prostate specific adenovirus vectors used in these methods also contains an E3 region, as described herein. For example, CV787 contains an E3 region.

With respect to liver tumors (hepatoma), any liver cell specific adenoviral vector may be used with the chemotherapeutic agents described herein. Preferably, the TRE is derived from AFP. The liver specific adenovirus vectors may be used with chemotherapeutic agents from any of the following classes: antimetabolites (especially DNA damaging agents); alkylating agents (especially platinum containing agents); antibiotics; alkaloids. Preferably, the chemotherapeutic agent is an antibiotic such as doxorubicin, mitoxantrone, or mitomycin-C. In some embodiments, the chemotherapeutic agent is paclitaxel, 5-azacytidine, gemcitabine, etoposide, or cisplatin. In some embodiments, E1A is under transcriptional control of an AFP-TRE. In other embodiments, E1B is under transcriptional control of an AFP-TRE. In yet other embodiments, E1A and E1B are under transcriptional control of two AFP-TREs (which may be identical or non-identical). These vectors may or may not contain an E3 region. In some embodiments, E1A and E1B are co-transcribed and under transcriptional control of an AFP-TRE, and E1B is under translational control of an IRES (with E1B promoter preferably deleted and preferably with the IRES and E1B in frame). In other embodiments, the 19-kDa region of E1B is deleted.

An example of a suitable vector is CV790, in which E1A and E1B are each under transcriptional control of identical AFP-TREs, and which further comprises an E3 region. Another example of a suitable vector is CV890, in which E1A and E1B are co-transcribed and under transcriptional control of an AFP-TRE wherein E1B is under translational control of an IRES. Vectors such as these have displayed in vivo synergy in conjunction with doxorubicin. Accordingly, in some embodiments, the target cell-specific adenoviral vector has E1A under transcriptional control of an AFP-TRE and E1B under translational control of an IRES, and further comprising an E3 region (such as CV890), and the antineoplastic is chosen from the antibiotic class of agents. Preferably, the antineoplastic is doxorubicin.

With respect to bladder tumors, any bladder cell specific adenoviral vector may be used with the chemotherapeutic agents described herein. Preferably, the TRE is derived from uroplakin. The bladder specific adenovirus vectors may be used with chemotherapeutic agents from any of the following classes: antimetabolites (especially DNA damaging agents); alkylating agents (especially platinum containing agents); antibiotics; alkaloids, hormone antagonists/agonists and analogs and immunomodulators. Preferably, the chemotherapeutic agent is an antibiotic such as doxorubicin, mitoxantrone, bleomycin, valrubicin, or mitomycin C. In some embodiments, the chemotherapeutic agent is paclitaxel, etoposide, docetaxel, gemcitabine, 5-fluorouracil, vinblastine, ifosfamide, thiotepa, interferon alpha-2a, methotrexate, goserelin, leuprolide, gallium nitrate, cyclophosphamide, vincristine, carboplatin or cisplatin. Preferably the chemotherapeutic agent is cisplatin, thiotepa, mitomycin C, or interferon alpha-2a. In some embodiments, E1A is under transcriptional control of an uroplakin-TRE. In other embodiments, E1B is under transcriptional control of uroplakin-TRE. In yet other embodiments, E1A and E1B are under transcriptional control of uroplakin-TREs (which may be identical or non-identical). Examples of suitable vectors include CV829 and CV877, in which E1A and E1B are each under transcriptional control of heterologous uroplakin-derived TREs, and which further comprise an E3 region. These vectors may or may not contain an E3 region. In some embodiments of the vector, E1A and E1B are co-transcribed and under transcriptional control of an uroplakin-TRE, and E1B is under translational control of an IRES (with the E1B promoter preferably deleted and preferably IRES and E1B are in frame). In other embodiments, the 19-kDa region of E1B is deleted. These vectors may or may not contain an E3 region. Examples of vectors include CV874, CV875 and CV876, which comprise an E3 region. Another example includes CV884.

With respect to colorectal or breast tumors, any colorectal or breast cell specific adenoviral vector may be used with the chemotherapeutic agents described herein. Preferably, the TRE is derived from CEA. The colorectal or breast specific adenovirus vectors may be used with chemotherapeutic agents from any of the following classes: antimetabolites (especially DNA damaging agents); alkylating agents (especially platinum containing); antibiotics; alkaloids; hormone antagonists/agonists and analogs (especially anti-estrogens). Preferably, the chemotherapeutic agent is an antibiotic such as doxorubicin, mitoxantrone, epirubicin, or mitomycin-C. In some embodiments, the chemotherapeutic agent is paclitaxel, 5-fluorouracil, thiotepa, goserelin, exemestane, methotrexate, irinotecan, edatrexate, letrozole, leuprolide, cyclophosphamide, vinblastine, prednisone, docetaxel, paclitaxel, or cisplatin. Preferably the chemotherapeutic agent is a hormone or hormone analog anti-estrogen such as tamoxifen, anastrozole, exemestane or letrozole. In some embodiments, E1A is under transcriptional control of an CEA-TRE. In other embodiments, E1B is under transcriptional control of an CEA-TRE. In yet other embodiments, E1A and E1B are each under transcriptional control of CEA-TREs (which may be identical or non-identical). These vectors may or may not contain an E3 region. In some embodiments, E1A is co-transcribed with E1B and under transcriptional control of an CEA-TRE, and E1B is under translational control of an IRES (with the E1B promoter preferably deleted and preferably IRES and E1B are in frame). In other embodiments, the 19-kDa region of E1B is deleted. These vectors may or may not contain an E3 region. An example of a suitable vector is CV873, in which E1A is under transcriptional control of a CEA-TRE and E1B is under translational control of an IRES, and which further comprises an E3 region.

With respect to melanoma, any melanoma specific adenoviral vector may be used with the chemotherapeutic agents described herein. Preferably, the TRE is derived from tyrosinase. The melanoma specific adenovirus vectors may be used with chemotherapeutic agents from any of the following classes: antimetabolites (especially DNA damaging agents); alkylating agents (especially platinum containing agents); antibiotics; alkaloids, hormone antagonists/agonists and analogs, nitrosoureas. In some embodiments, the chemotherapeutic agent is 5-fluorouracil, gemcitabine, doxorubicin, miroxantrone, mitomycin, dacarbazine, carmustine, vinblastine, lomustine, tamoxifen, docetaxel, paclitaxel or cisplatin. In some embodiments, E1A is under transcriptional control of a tyrosinase-TRE. In other embodiments, E1B is under transcriptional control of a tyrosinase-TRE. In yet other embodiments, E1A and E1B are each under transcriptional control of a tyrosinase-TREs (which may be identical or non-identical). These vectors may or may not contain an E3 region. In some embodiments, E1A is co-transcribed with E1B and under transcriptional control of a tyrosinase-TRE, and E1B is under translational control of an IRES (with the E1B promoter preferably deleted and preferably IRES and E1B are in frame). In other embodiments, the 19-kDa region of E1B is deleted. These vectors may or may not contain an E3 region. An example is CV859, having E1A co-transcribed with E1B and under transcriptional control of a tyrosinase-TRE and E1B under translational control of an IRES and an intact E3 region.

The specific choice of both the target cell-specific adenoviral vector and the chemotherapeutic agent(s) is dependent upon, inter alia, the characteristics of the disease to be treated. These characteristics include, but are not limited to, the type of cancer, location of the tumor, identity of the target cell, stage of the disease and the individual's response to previous treatments, if any. It is well established that certain antineoplastic agents are more efficacious for certain types of cancer than others, for instance the use of tamoxifen in the treatment of breast cancer, the use of mitoxantrone or estramustine to treat prostate tumors or the use of doxorubicin and 5-fluorouracil to treat hepatoma.

In addition to the use of single antineoplastic agents in combination with a particular adenoviral vector, the invention also includes the use of more than one agent in conjunction with an adenoviral vector. Table 2 lists non-limiting examples of common combinations of antineoplastic agents. These combinations of antineoplastics when used to treat neoplasia are often referred to as combination chemotherapy and are often part of a combined modality treatment which may also include surgery and/or radiation, depending on the characteristics of an individual's cancer. It is contemplated that the combined adenoviral/chemotherapy of the present invention can also be used as part of a combined modality treatment program. Preferred combinations of chemotherapeutic agents include, but are not limited to, doxorubicin and cisplatin; doxorubicin; and mitomycin C; doxorubicin and mitoxantrone; and doxorubicin and paclitaxel (TAXOL™). In some embodiments, these combinations are used with an adenovirus specific for AFP producing cells, such as liver cells. An example of a suitable vector is CV790.

In other embodiments, preferred combinations of chemotherapeutic agents include, but are not limited to, mitoxantrone and estramustine; paclitaxel (TAXOL™) and estramustine; and docetaxel (TAXOTERE™) and estramustine. In some embodiments, these combinations are used with an adenovirus specific for prostate cells, such as adenoviruses containing PSA-TRE, hKLK-TRE or PB-TRE. Examples of such adenoviruses include CV787 and CV706.

In other embodiments, preferred combinations of chemotherapeutic agents include, but are not limited to M-VAC (methotrexate-vinblastine, doxorubicin, cyclophosphamide), CISCA (cyclophosphamide, doxorubicin, cisplatin), CMV (cisplatin, methotrexate, vinblastine), CAP (cyclophosphamide, doxorubicin, cisplatin), or MVMJ (methotrexate, vinblastine, mitoxantrone, carboplatin). In some embodiments, these combinations are used with an adenovirus specific for bladder cells, such as those containing a uroplakin TRE. Examples of such adenoviruses include vectors such as CV829, CV874, CV875, CV876, CV877, and CV884 described herein.

In other embodiments, preferred combinations include DBPT (dacarbazine, cisplatin, carmustine, tamoxifen), VDD (vinblastine, dacarbazine, cisplatin). In some embodiments these combinations are used with adenovirus vectors specific for melanoma, such as those containing a tyrosinase-TREs. An example of a suitable vector is CV859, described herein.

In other embodiments preferred combinations include levamisole and 5-fluorouracil or leucovorin and fluorouracil. In particular embodiments these combinations can be used with colorectal specific adenoviral vectors, such as those containing a CEA-TRE. An example of a vector is CV873, described herein.

In other embodiments preferred combinations include CAF (cyclophosphamide, doxorubicin, 5-fluorouracil), CMF (cyclophosphamide, methotrexate, 5-fluorouracil), CNF (cyclophosphamide, mitoxantrone, 5-fluorouracil), FAC (5-fluorouracil, doxorubicin, cyclophosphamide), MF (methotrexate, 5-fluorouracil, leucovorin), MV (mitomycin C, vinblastine), CMFP (cyclophosphamide, methotrexate, 5-fluorouracil, prednisone), VATH (vinblastine, doxorubicin, thiotepa, fluoxymesterone). In particular embodiments these combinations can be used with breast specific adenoviral vectors, such as those containing a CEA-TRE. An example of such a vector is CV873, described herein.

Listed below are selected acronyms for combination cancer chemotherapy regimens comprising substances in *The Merck Index*.

TABLE 2

Cancer Combination Chemotherapy Drug Regimens

| Acronym | Drug regimens |
| --- | --- |
| AA | cytarabine + doxorubicin |
| ABP | doxorubicin + bleomycin + prednisone |
| ABVD | doxorubicin + bleomycin + vinblastine + dacarbazine |
| AC | doxorubicin + cyclophosphamide |
| ACVB | doxorubicin + cyclophosphamide + vindesine + bleomycin |
| ADIC | doxorubicin + dacarbazine |
| APO | doxorubicin + prednisone + vincristine + 6-mercaptopurine + asparaginase + methotrexate |
| AV | doxorubicin ~ vincristine |
| AVDP | asparaginase + vincristine + daunorubicin + prednisone |
| BACOP | bleomycin + doxorubicin + cyclophosphamide + vincristine + prednisone |
| BAPP | bleomycin + doxorubicin +, cisplatin + prednisone |
| B – CAVe | bleomycin + lomustine + doxorubicin + vincristine |
| BCD | methotrexate + doxorubicin + cisplatin |
| BCP | carmustine + cyclophosphamide + prednisone |
| BCVPP | carmustine + cyclophosphamide + vinblastine + procarbazine + prednisone |
| B – DOPA | bleomycin + dacarbazine + vincristine + prednisone + doxorubicin |
| BEP | bleomycin + etoposide + cisplatin |
| BMP | bleomycin + methotrexate + cisplatin |
| BOLD | bleomycin + vincristine + lomustine + dacarbazine |
| CA | cyclophosphamide + doxorubicin |
| CAF | cyclophosphamide + doxorubicin + fluorouracil |
| CAMF | cyclophosphamide + doxorubicin + methotrexate + fluorouracil |
| CAP | cyclophosphamide + doxorubicin + cisplatin |
| CAP-BOP | cyclophosphamide + doxorubicin + procarbazine + bleomycin + vincristine + prednisone |
| CAV | cyclophosphamide + doxorubicin + vincristine |
| CAVE | cyclophosphamide + doxorubicin + vincristine + etoposide |
| CAVEP | cyclophosphamide + doxorubicin + vincristine + etoposide + cisplatin |
| CBV | cyclophosphamide + carmustine + etoposide |
| CC | carboplatin + cyclophosphamide |
| CD | cytarabine + duanorubicin |
| CFP | cyclophosphamide + fluorouracil + prednisone |
| CFPMV | cyclophosphamide + fluorouracil + prednisone + methotrexate + vincristine |
| CFPT | cyclophosphamide + fluorouracil + prednisone + tamoxifen |
| CHAD | cyclophosphamide + hexamethylmelamine + doxorubicin + cisplatin |
| CHAMOCA | cyclophosphamide + hydroxyurea + dactinomycin + methotrexate + vincristine + doxorubicin |
| CHAP-5 | cyclophosphamide + hexamethylmelamine + doxorubicin + cisplatin |
| CHF | cyclophosphamide + hexamethylmelamine + fluorouracil |
| ChIVPP | chlorambucil + vinblastine + procarbazine + prednisone |
| CHO | cyclophosphamide + doxorubicin + vincristine |
| CHOP | cyclophosphamide + doxorubicin + vincristine + prednisone |

TABLE 2-continued
Cancer Combination Chemotherapy Drug Regimens

| Acronym | Drug regimens |
|---|---|
| CHOP-B | cyclophosphamide + doxorubicin + vincristine + prednisone + bleomycin |
| CMF | cyclophosphamide + methotrexate + fluorouracil |
| CMFP | cyclophosphamide + methotrexate + fluorouracil + prednisone |
| CMFVP | cyclophosphamide + methotrexate + fluorouracil + vincristine + prednisone |
| C-MOPP | cyclophosphamide + mechlorethamine + vincristine + procarbazine + prednisone |
| CMV | cisplatin + methotrexate + vinblastine |
| COAP | cyclophosphamide + vincristine + cytarabine + prednisolone |
| CODE | cisplatin + vincristine + doxorubicin + etoposide |
| COMLA | cyclophosphamide + vincristine + methotrexate + cytarabine |
| COMP | cyclophosphamide + vincristine + methotrexate + prednisone |
| COP | cyclophosphamide + vincristine + prednisone |
| COP-BLAM | cyclophosphamide + vincristine + prednisone + bleomycin + doxorubicin + procarbazine |
| COPP | cyclophosphamide + vincristine + prednisone + procarbazine |
| CVF | cyclophosphamide + vincristine + fluorouracil |
| CVP | cyclophosphamide + vincristine + prednisone |
| CVPP | bleomycin + lomustine + doxorubicin + vinblastine |
| CYVADIC | cyclophosphamide + vincristine + doxorubicin + dacarbazine |
| DCT | daunorubicin + cytarabine + thioguanine |
| DICEP | cyclophosphamide + etoposide + cisplatin |
| DVP | duanorubicin + vincristine + prednisone |
| EAP | etoposide + doxorubicin + cisplatin |
| EFP | etoposide + fluorouracil + cisplatin |
| ELF | etoposide + leucovorin + fluorouracil |
| EMA-CO | etoposide + methotrexate + dactinomycin + cyclophosphamide + vincristine |
| ESHAP | etoposide + methylprednisolone + cytarabine + cisplatin |
| FA | fluorouracil + doxorubicin |
| FAC | fluorouracil + doxorubicin + cyclophosphamide |
| FAM | fluorouracil + doxorubicin + mitomycin C |
| FAMTX | fluorouracil + doxorubicin + methotrexate |
| FAP | fluorouracil + doxorubicin + cisplatin |
| FEB | fluorouracil + epirubicin + carmustine |
| FUVAC | fluorouracil + vinblastine + doxorubicin + cyclophosphamide |
| HAD | hexamethylmelamine + doxorubicin + cisplatin |
| H-CAP | hexamethylmelamine + cyclophosphamide + doxorubicin + cisplatin |
| Hexa-CAF | hexamethylmelamine + cyclophosphamide + methotrexate + fluorouracil |
| ICE | ifosfamide + carboplatin + etoposide |
| IMVP - 16 | ifosfamide + methotrexate + etoposide |
| LOPP | chlorambucil + vincristine + procarbazine + prednisone |
| LSA$_2$L$_2$ | cyclophosphamide + vincristine + prednisone + daunorubicin + methotrexate + cytarabine + thioguanine + colaspase + hydroxyurea + carmustine |
| M - 2 | vincristine + carmustine + cyclophosphamide + melphalan + prednisone |
| MAC | methotrexate + dactinomycin + chlorambucil |
| MACC | methotrexate + doxorubicin + cyclophosphamide + lomustine |
| MACOP-B | methotrexate + doxorubicin + cyclophosphamide + vincristine + prednisone + bleomycin |
| M-BACOD | methotrexate + bleomycin + doxorubicin + cyclophosphamide + vincristine + dexamethasone |
| MBD | methotrexate + bleomycin + cisplatin |
| MC | mitoxantrone + cytarabine |
| MCF | mitoxantrone + cyclophosphamide + fluorouracil |
| MeCP | methyl-CCNU + cyclophosphamide + prednisone |
| MINE | mesna + ifosfamide + mitoxantrone + etoposide |
| MIP | mitomycin + ifosfamide + cisplatin |
| MM | mercaptopurine + methotrexate |
| MMM | mitoxantrone + methotrexate + mitomycin |
| MOP | mechlorethamine + vincristine + procarbazine |
| MOPP | mechlorethamine + vincristine + procarbazine + prednisone |
| MP | melphalan + prednisone |
| M-VAC | methotrexate + vinblastine + doxorubicin + cisplatin |
| MV | mitroxantrone + etoposide |
| MVP | mitomycin + vindesine + cisplatin |
| MPPP | mechlorethamine + vinblastine + procarbazine + prednisone |
| PAC | cisplatin + doxorubicin + cyclophosphamide |
| PC | cisplatin + cyclophosphamide |
| PCV | procarbazine + lomustine + vincristine |
| PE | cisplatin + etoposide |
| PEB | cisplatin + etoposide + bleomycin |
| PF | L – PAM and fluorouracil |
| PMF | cisplatin + mitomycin C + fluorouracil |
| ProMACE | prednisone + methotrexate + doxorubicin + cyclophosphamide + etoposide |
| ProMACE-CytaBOM | prednisone + methotrexate + doxorubicin + cyclophosphamide + etoposide + cytarabine + bleomycin + vincristine + methotrexate |
| ProMACE-MOPP | prednisone + methotrexate + doxorubicin + cyclophosphamide + etoposide + mechlorethamine + vincristine + procarbazine + prednisone |
| PVP - 16B | VP - 16 + bleomycin + cisplatin |
| PVB | cisplatin + vinblastine + bleomycin |
| SMF | streptozocin + mitomycin + fluorouracil |
| TC | thioguanine + cytarabine |
| VAB-6 | vinblastine + dactinomycin + bleomycin + cisplatin + cyclophosphamide |
| VAC | vincristine + dactinomycin + cyclophosphamide |
| VAD | vincristine + doxorubicin + dexamethasone |
| VAMP | vincristine + prednisone + methotrexate + 6-mercaptopurine |
| VAP-cyclo | vincristine + doxorubicin + prednisolone + cyclophosphamide |
| VBAP | vincristine + carmustine + dexamethasone + prednisone |
| VCAP | vincristine + cyclophosphamide + doxorubicin + prednisone |
| VIP | vindesine + ifosfamide + cisplatin |
| VMF | etoposide + methotrexate + fluorouracil |
| VP | vindesine + cisplatin |

Administration and Assessment

There are a variety of delivery methods for the administration of antineoplastic agents, which are well known in the art, including oral and parenteral methods. There are a number of drawbacks to oral administration for a large number of antineoplastic agents, including low bioavailability, irritation of the digestive tract and the necessity of remembering to administer complicated combinations of drugs. The majority of parenteral administration of antineoplastic agents is intravenously, as intramuscular and subcutaneous injection often leads to irritation or damage to the tissue. Regional variations of parenteral injections include intra-arterial, intravesical, intra-tumor, intrathecal, intrapleural, intraperitoneal and intracavity injections.

Delivery methods for chemotherapeutic agents include intravenous, intraparenteral and introperitoneal methods as well as oral administration. Intravenous methods also include delivery through a vein of the extremities as well as including more site specific delivery, such as an intravenous drip into the portal vein of the liver. Other intraparenteral methods of delivery include direct injections of an antineoplastic solution, for example, subcutaneously, intracavity or intra-tumor.

Delivery of adenoviral vectors is discussed infra and is generally accomplished by either site-specific injection or intravenously. Site-specific injections of either vector or antineoplastic agent(s) may include, for example, injections into the portal vein of the liver as well as intraperitoneal, intrapleural, intrathecal, intra-arterial, intra-tumor injections or topical application. These methods are easily accommodated in treatments using the combination of adenoviral vectors and chemotherapeutic agents.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are in vitro or in vivo). If used as a packaged adenovirus, adenovirus vectors may be administered in an appropriate physiologically acceptable carrier at a dose of about 1 to about 10 The multiplicity of infection will generally be in the range of about 0.001 to 100. If administered as a polynucleotide construct (i.e., not packaged as a virus) about 0.01 $\mu$g to about 1000 $\mu$g of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Generally, the adenovirus and chemotherapeutic agent are administered as compositions in a pharmaceutically acceptable excipient (and may or may not be in the same compositions), including, but not limited to, saline solutions, suitable buffers, preservatives, stabilizers, and may be administered in conjunction with suitable agents such as antiemetics. In some embodiments, an effective amount of an adenoviral vector and an effective amount of at least one antineoplastic agent are combined with a suitable excipient and/or buffer solutions and administered simultaneously from the same solution by any of the methods listed herein or those known in the art. This may be applicable when the antineoplastic agent does not compromise the viability and/or activity of the adenoviral vector itself. Where more than one antineoplastic agent is administered, the agents may be administered together in the same composition; sequentially in any order; or, alternatively, administered simultaneously in different compositions. If the agents are administered sequentially, administration may further comprise a time delay.

The chemotherapeutic agent and adenovirus may be administered simultaneously or sequentially, with various time intervals for sequential administration. In some embodiments, chemotherapeutic agent(s) and adenovirus vector(s) are administered simultaneously. As shown in the Examples, at least some antineoplastics do not appear to compromise viral replication or specificity. The method of delivery will depend upon both the choice of the adenoviral vector and chemotherapeutic agent(s) and by the characteristics of the cancer under treatment.

In other embodiments, a chemotherapeutic agent and adenoviral vector can be administered sequentially. This may be appropriate, for example, in instances where the antineoplastic agent is an alkylating agent, antimetabolite, nitrosourea or other DNA damaging agent which may compromise the viability and/or activity or the viral vector, or in instances in which it has been indicated that sequential administration optimizes effectiveness of the combination therapy. Sequential administration may be in any order, and accordingly encompasses the administration of an effective amount of an adenoviral vector first, followed by the administration of an effective amount of the chemotherapeutic agent. The interval between administration of adenovirus and chemotherapeutic agent may be in terms of at least (or, alternatively, less than) minutes, hours, or days. Sequential administration also encompasses administration of a chosen antineoplastic agent followed by the administration of the adenoviral vector. The interval between administration may be in terms of at least (or, alternatively, less than) minutes, hours, or days.

Administration of the above-described methods may also include repeat doses or courses of target-cell specific adenovirus and chemotherapeutic agent depending, inter alia, upon the individual's response and the characteristics of the individual's disease. Repeat doses may be undertaken immediately following the first course of treatment (i.e., within one day), or after an interval of days, weeks or months to achieve and/or maintain suppression of tumor growth. A particular course of treatment according to the above-described methods, for example, combined adenoviral and chemotherapy, may later be followed by a course of combined radiation and adenoviral therapy.

Generally, an effective amount of adenovirus vector and chemotherapeutic agent(s) is administered, i.e., amounts sufficient to achieve the desired result, based on general empirical knowledge of a population's response to such amounts. Some individuals are refractory to these treatments, and it is understood that the methods encompass administration to these individuals. The amount to be given depends, inter alia, on the type of cancer, the condition of the individual, the extent of disease, the route of administration, how many doses will be administered, and the desired objective.

A chemotherapeutic agent(s) is administered in a physiologically acceptable carrier appropriate to the method of delivery, as are known in the art and described herein. The amount of chemotherapeutic agent(s) administered is determined by the characteristics of the individual's disease, the method of delivery and the weight, age, general health and response of the individual. In some embodiments the amount of chemotherapeutic agent(s) administered will be the dosage known in the art to be effective given the characteristics of the individual and their disease. In other embodiments, due to the synergistic effect of the combination of adenoviral vector and chemotherapeutic agent, the amount of chemotherapeutic agent(s) administered will be about 2×, about 5×, about 10×, or about 5× less than that known in the art to be effective for the particular individual and characteristics of the disease. In some embodiments, the amount of chemotherapeutic agent(s) administered will be about 20×, about 50×, about 100× or about 1000× less than that known in the art to be effective for the particular individual and characteristics of the disease. Dosages include courses of chemotherapy and repeat administrations of the chemotherapeutic agent(s) over the course of days, weeks or months and may include an increase or decrease in the interval between doses during administration of the course of chemotherapy, or increases or decreases in the actual amount of chemotherapeutic agent administered.

Examples of dosages known in the art for chemotherapeutic agents include, but are not limited to, doses of 60–75 mg/m$^2$ for doxorubicin at 21 day intervals when administered as a single agent, and doxorubicin doses of 40–60 mg/m$^2$ when administered as a component in a combination of chemotherapeutic agents. Typical doses known in the art for cisplatin are from 20 mg/m$^2$ to 100 mg/m$^2$; for etoposide 35–100 mg/m$^2$; for paclitaxel 135–175 mg/m$^2$; for docetaxel 60–100 mg/m$^2$; for mitomycin C 30–40 mg/m$^2$; gemcitabine 1000–1250 mg/m$^2$; mitoxantrone 12–14 mg/m$^2$ per cycle, 12–212 mg/m$^2$ cumulative over course of treatment; thiotepa 0.3–0.8 mg/kg; 5-azacytidine 50–200 mg/m$^2$/day; 5-fluorouracil 7–12 mg/kg/day, not more than 800 mg/day. These dose may be administered on a variety of schedules known to those of skill in the art and depending on the response of the individual and the characteristic of the individual cancer.

Any of the methods described herein may further be used in conjunction with combined modality treatment for suppressing tumor growth. Such combined modality treatment may or may not include surgery as a component of the treatment.

Assessment may be determined by any of the techniques known in the art, including diagnostic methods such as imaging techniques, analysis of serum tumor markers (which may be measured, for example, by ELISA), biopsy (which could indicate the presence of killed tumor cells), and the presence, absence or amelioration of tumor associated symptoms.

Compositions and Kits of Adenoviral Vectors and Chemotherapeutic Agents

The invention also includes compositions comprising at least one antineoplastic agent, such as those listed in Table 1, and a target cell-specific adenoviral vector(s) as described herein, where the stability, activity, and/or viability of the adenoviral vector is not compromised by the antineoplastic agent(s) (ie, the adenovirus vector retains some to all activity). These compositions can further comprise suitable pharmaceutical such as, saline solutions, suitable buffers, preservatives, stabilizers.

In some embodiments, the composition comprises a target cell-specific adenoviral vector comprising E1A under transcriptional control of a PB-TRE, E1B under transcriptional control of a PSA-TRE, further comprising an E3 region (such as CV787) and the antineoplastic is 5-fluorouracil or cisplatin. In other embodiments, the antineoplastic is doxorubicin, estramustine, etoposide, mitoxantrone, docetaxel (TAXOTERE™) or paclitaxel (TAXOL™). In other embodiments, the composition comprises an adenovirus vector comprising E1A under transcriptional control of a PSA-TRE (such as CV706) and the composition further comprises 5-fluorouracil or cisplatin. In other embodiments, the antineoplastic is doxorubicin, estramustine, etoposide, mitoxantrone, docetaxel (TAXOTERE™) or paclitaxel (TAXOL™). In other embodiments, the composition comprises an adenoviral vector comprising an early gene under transcriptional control of an AFP-TRE (for example, E1A under transcriptional control of an AFP-TRE), E1B under transcriptional control of an AFP-TRE, an intact E3 region (such as CV790) and the composition further comprises 5-azacytidine, cisplatin, etoposide or gemcitabine, doxorubicin, mitomycin C, mitoxantrone, paclitaxel or a combination of antineoplastic agents such as, doxorubicin and cisplatin, or doxorubicin and mitomycin C or doxorubicin and mitoxantrone or doxorubicin and paclitaxel (TAXOL™).

In some embodiments, the adenovirus vector comprises co-transcribed first and second genes, preferably adenovirus genes, under transcriptional control of a heterologous, target cell-specific transcriptional regulatory element (TRE), wherein the second gene is under translational control of an internal ribosome entry site (IRES).

Kits comprising the combined antineoplastic agent(s), target cell-specific adenoviral vector, and suitable excipient, packaging, and labeling are also included in the present invention. The kit provides suitable dosages of each of the antineoplastic agent(s) and adenoviral vector. Embodiments include kits comprising, for example, all of the compositions listed above. The kits preferably contain instructions for administration to individuals for appropriate cancer to effect suppression of tumor growth.

In some embodiments, the chemotherapeutic agent and adenoviral vector are packaged separately in appropriate packaging. In other embodiments, the chemotherapeutic agent and adenoviral vector are packaged together. Examples of suitable agents and adenoviral vectors have been discussed above and are described herein.

Combination Adenoviral and Radiation Therapy

The invention also provides combination methods which employ the replication competent target cell specific adenoviral vectors as described herein and radiation. As explained in more detail in Example 6, the combined treatment of neoplasia with a target cell-specific adenoviral vector and radiation results in a synergistic effect, with earlier eradication of the tumor compared to no treatment, radiation alone or virus alone. When used in combination with target cell-specific adenoviral vectors, the type of radiation treatment used is dependent upon the characteristics of the individual cancer being treated. The choice of suitable radiation therapy is well known by a person skilled in the art and decided on an individual basis. The choice of the target cell-specific adenoviral vector is largely governed by the identity of the target (neoplastic) cells and includes X-rays, gamma rays, alpha particles, beta particles, radioactive isotopes, photons, neutrons, electrons and other forms of ionizing radiation. Sources of radiation include Americium, chromic phosphate, radioactive Cobalt, $^{131}$I-ethiodized oil, Gold (radioactive, colloidal) iobenguane, Radium, Radon, sodium iodide (radioactive), sodium phosphate (radioactive), and $^{137}$Cesium. Radioimmunotherapy can also be used. In some embodiments, radiation therapy includes use of one or more radiosensitizing agent(s) or radiation protectants.

Accordingly, the present invention includes methods of suppressing tumor growth in an individual comprising the following steps:
  a) administration of an effective amount of a replication-competent target cell-specific adenoviral vector to an individual with neoplasia; and
  b) administration of an effective amount of an appropriate course of radiation wherein radiation includes X-rays, gamma rays, alpha particles, beta particles, electrons, photons, neutrons, other ionizing radiation and radioactive isotopes.

In some embodiments, step (a) is performed before step (b). In other embodiments, step (b) is performed before step (a). In other embodiments, steps (a) and (b) are performed simultaneously.

The replication-competent target cell-specific adenoviral vector may be any of the replication-competent target cell-specific adenoviral vectors disclosed herein, comprising a gene essential for replication, preferably an early gene, under transcriptional control of a TRE. Preferably, the gene essential for replication is E1A or E1B or both. Discussion of exemplary embodiments of suitable adenoviral vectors in the previous section, as well as the section describing adenovirus vectors below, are applicable to these methods.

In some embodiments, the gene essential for replication is E1A or E1B and in some embodiments, the vector comprises both E1A and E1B under transcriptional control of a cell-specific TRE. In some embodiments, the E1A and E1B genes are under transcriptional control of the same or similar TREs. The vectors may or may not include an E3 region. In some embodiments, the adenovirus vector comprises co-transcribed first and second genes, preferably adenovirus genes, under transcriptional control of a heterologous, target cell-specific transcriptional regulatory element (TRE), wherein the second gene is under translational control of an internal ribosome entry site (IRES). In some embodiments, the first and second genes are E1A and E1B, respectively. In this embodiment it is preferred that E1B has its endogenous promoter deleted and in one embodiment, IRES and E1B are in frame.

In other embodiments, the adenovirus vector comprises E1A wherein the E1A promoter is deleted and wherein the E1A gene is under transcriptional control of a target cell-specific TRE. In other embodiments, the adenovirus gene is E1B wherein the E1B promoter is deleted and wherein the E1B gene is under transcriptional control of a target cell-specific TRE. In other embodiments, the vector comprises ETA wherein the E1A promoter is deleted and E1B wherein the E1B promoter is deleted.

In other embodiments, an enhancer element for the first and/or second adenovirus genes is deleted. In some embodiments, the E1A enhancer is deleted. In yet other embodiments, the E1A promoter is deleted and E1A enhancer I is deleted. In further embodiments, the TRE has its endogenous silencer element deleted. In other embodiments, the adenovirus vector comprises E1B having a deletion in the 19-kDa region. These embodiments apply to any and all methods described herein.

Administration and Assessment

As is well-known in the art, radiation therapy includes treatment with X-rays and gamma-rays, as well as alpha and beta particles, photons, electrons, neutrons, implants of radioactive isotopes and other forms of ionizing radiation. Recent experimental therapy employs monoclonal antibodies specific to the malignant tumor to deliver radioactive isotopes directly to the site of the tumor, termed radioimmunotherapy. The most common type of radiation treatment is radiation directed to the body area containing the neoplastic tumor, which is known as regional or local radiation therapy.

The combined modality treatment of radiation and target cell-specific adenoviral therapy can be carried out in a number of ways, including delivery of the adenoviral vector followed by radiation therapy, or where vector delivery is followed by a time delay of seconds, minutes, hours or days and before radiation treatment. The combined modality treatment also incorporates administration of the radiation treatment followed by the adenoviral treatment, including but not necessarily requiring a time interval between radiation treatment and delivery of the adenovirus, of seconds, minutes, hours or days.

Repeat dosages of adenoviral vector and/or radiation may be administered. Administration of adenovirus vectors has been described above. Administration of radiation therapy can include methods well known in the art, such as internal and external radiation therapy. External therapy includes the administration of radiation via high-energy external beam radiation, administered either regionally (locally) to the tumor site or whole body irradiation. Examples of internal radiation (brachytherapy) include the implantation of radioactive isotopes in permanent, temporary, sealed, unsealed, intracavity or interstitial implants. The choice of implant is determined by the characteristics of the neoplasia, including the location and extent of the tumor. The choice between external or internal radiation treatment and type of external radiation treatment is also determined by the characteristics of the neoplasia and can be determined by those skilled in the art. An additional type of radiation therapy is radioimmunotherapy in which radioisotopes are attached to monoclonal antibodies specific for the tumor cells.

The amount/course of radiation administered to the individual is determined by the characteristics of the individual's disease, the method of delivery and the weight, age, general health and response of the individual. For radiation therapy in particular, the location of the tumor is a determining factor in the administration of radiation, as the radiosensitivity of the tumor and surrounding tissue are variable according to tissue type (see Table 3), oxygen supply and other factors. In some embodiments the amount of radiation administered will be the dosage known in the art to be effective given the characteristics of the individual and the disease. In other embodiments, the amount of radiation administered will be about 2×, about 5×, about 10×, or about 15× less than that known in the art to be effective for the particular individual and characteristics of the disease. In some embodiments, the amount of radiation administered will be about 20×, about 50×, about 100× or about 1000× less than that known in the art to be effective for the particular individual and characteristics of the disease.

Radiation treatment may also entail the administration of a radiosensitizing agent or radioprotectant to facilitate the treatment. Recent evidence suggests that the antineoplastic agent TAXOL™ (paclitaxel) may function as a radiosensitizer. Liebmann et al., *J. National Cancer Inst.* 86:441, 1994;. Similar evidence has been found for TAXOTERE™ (docetaxel). Creane et al., *Int. J. Radiat. Biol.* 75:731, 1999; Sikov et al., *Front. Biosci.* May 1: 221, 1997. Other radiation sensitizers include E2F-1, anti-ras single chain antibody, p53, GM-CSF, and cytosine deaminase. A tumor specific adenovirus may further comprise a radiation sensitizer, such as p53 for example, or a chemo sensitizer.

Repeat doses may be undertaken immediately following the first course of treatment or after an interval of days, weeks or months to achieve suppression of tumor growth. A particular course of treatment according to the above-described methods, for example, combined adenoviral and radiation therapy, may later be followed by a course of combined chemotherapy and adenoviral therapy.

TABLE 3

Radiosensitivity of Various Tissues

| Tumor or Tissue Type | Relative Radiosensitivity |
|---|---|
| lymphoma, leukemia, seminoma, dysgerminoma | high |
| squamous cell, cancer of the oropharyngeal glottis, bladder, skin & cervical epithelia adenocarinomas of the alimentary tract | fairly high |
| vascular & connective tissue (elements of all tumors) secondary neurovascularization, astrocytomas | medium |
| salivary gland tumors, hepatoma, renal cancer, pancreatic cancer, chondrosarcoma, osteogenic sarcomas | fairly low |
| rhabdomyosarcoma, leiomyosarcoma & ganglioneurofibrosarcoma | low |

Assessment may be determined by any of the techniques known in the art, including diagnostic methods such as imaging techniques, analysis of serum tumor markers, biopsy, the presence, absence or amelioration of tumor associated symptoms.

Combination Treatment With Adenoviral, Chemotherapy and Radiation

Chemotherapy and radiation are commonly used as components of a combined modality treatment, and the choice of chemotherapeutic agent(s) and type and course of radiation therapy is generally governed by the characteristics of the individual cancer and the response of the individual. While target cell-specific adenoviral vectors can be used with either radiation or chemotherapy, as separate courses of treatment, they can also be combined with both methods of treatment in the same course of therapy. Accordingly, the present invention encompasses combinations of the methods discussed above.

Accordingly, the invention includes methods for suppressing tumor growth in an individual comprising the following steps, in any order:
 a) administering to the individual an effective amount of a target cell-specific adenoviral vector and at least one antineoplastic agent; and
 b) administering an effective amount of an appropriate course of radiation therapy to the individual.

The method may further comprise the step of:
 c) administering to the individual an additional dose of the adenoviral/chemotherapeutic solution or radiation as necessary to treat the individual's neoplasia.

The method may further comprise time delays after any one of steps a), b) and c). A time delay interval may be days, weeks or months.

The antineoplastic may be chosen from the agents listed in Table 1 or a combination of agents may be chosen from the list in Table 2. Additional agents or combinations of agents known to those of skill in the art may also be used. The replication-competent target cell-specific adenoviral vector is chosen from the replication-competent target cell-specific adenoviral vectors disclosed herein.

In preferred embodiments the gene essential for replication in the adenoviral vector is an early gene. Even more preferably the gene essential for replication is E1A or E1B or both. In particularly preferred embodiments the E1A and E1B genes are under transcriptional of the same or similar TREs. The vector may or may not contain an E3 region.

In some embodiments, the adenovirus vector comprises co-transcribed first and second genes under transcriptional control of a heterologous, target cell-specific transcriptional regulatory element (TRE), wherein the second gene is under translational control of an internal ribosome entry site (IRES). An adenovirus vector may further comprise E3.

In particular embodiments of the above described methods, the adenoviral gene(s) essential for replication is under the control of TRE(s) specific for target cells such as, but not limited to liver, prostate, bladder, colorectal, breast or melanoma cells.

In certain preferred embodiments of the above described methods, the adenoviral gene(s) essential for replication is under the control of a TRE(s) such as, but not limited to the PB-TRE, PSA-TRE, the MUC-TRE, the AFP-TRE, the CEA-TRE, the hKLK2-TRE, tyrosinase-TRE, and uroplakin-TRE, as described herein.

Illustrative embodiments of target cell-specific adenoviral vectors include CV787, CV790, CV890, CV706, CV829, CV859, CV873, CV874, CV875, CV876, CV877, and CV884 as described herein.

In a preferred embodiment, the adenoviral vector comprises a prostate specific TRE or a liver specific TRE and at least one of the chemotherapeutic agents is from the alkaloid class.

In another preferred embodiment, the adenoviral vector comprises a prostate specific TRE or a liver specific TRE and at least one of the chemotherapeutic agents is paclitaxel (TAXOL™) or docetaxel (TAXOTERE™) or a paclitaxel derivative.

In another preferred embodiment the adenoviral vector comprises a urothelial specific TRE and least one of the chemotherapeutic agents is paclitaxel (TAXOL™) or docetaxel (TAXOTERE™) or a paclitaxel derivative.

Administration and Assessment

Administration of adenoviral vectors, chemotherapeutic agents and radiation has been described above. The choice of the adenoviral vector, chemotherapeutic agent(s) and radiation are dependent on the characteristics of the individual cancer and the individual's response to therapy. Such considerations are known to those skilled in the art. The invention encompasses embodiments which include the replication-competent target cell-specific adenoviral vectors discussed herein as well as those known to persons of skill in the art. The invention also encompasses embodiments which include the combinations of target cell-specific adenoviral vectors and chemotherapeutic agents discussed herein which can be further combined with radiation therapy.

The above-described methods include administration of the adenoviral vector, radiation and chemotherapeutic(s) in any order and may include sequential administration or simultaneous administration of all or some of the components (i.e. simultaneous administration of chemotherapy and adenovirus followed sequentially by radiation therapy or sequential administration of adenovirus first, radiation second and thirdly, chemotherapy, etc.).

Repeat doses may be undertaken immediately following the first course of treatment or after an interval of days, weeks or months to achieve suppression of tumor growth. Repeat doses of a particular component of the therapy may also be administered before the administration of the remaining components (i.e. administration of multiple doses of chemotherapeutic agent(s) followed by sequential administration of radiation and adenovirus or administration of multiple doses of radiation therapy followed by simultaneous administration of chemotherapy and adenovirus, etc.). A particular course of treatment according to the above-described methods, for example, combined adenoviral, chemotherapeutic and radiation therapy, may later be followed by a course of combined chemotherapy and adenoviral therapy.

Any of the methods described herein may further be used in conjunction with combined modality treatment for suppressing tumor growth. Such combined modality treatment may include surgery as a component of the treatment.

Assessment of the suppression of tumor growth may be determined by any of the techniques known in the art, including diagnostic methods such as imaging techniques, analysis of serum tumor markers, biopsy, the presence, absence or amelioration of tumor associated symptoms.

Adenoviral Vectors

The adenoviral vectors used in the methods described herein are replication-competent target-cell specific adenoviral vectors comprising an adenovirus gene, preferably a gene essential for replication under transcriptional control of a target cell specific TRE. The vector may or may not include an E3 region. In other embodiments, an adenovirus vector is a replication competent, target cell specific vector comprising E1B, wherein E1B has a deletion of part or all of the 19-kDa region.

In some embodiments the adenoviral gene essential for replication is an early gene, preferably E1A or E1B or both.

In some embodiments, the adenovirus vector comprises co-transcribed first and second genes under transcriptional control of a heterologous, target cell-specific transcriptional regulatory element (TRE), wherein the second gene is under translational control of an internal ribosome entry site (IRES). The adenovirus vector may further comprise E3.

The adenovirus vectors used in this invention replicate preferentially in TRE functional cells referred to herein as target cells. This replication preference is indicated by comparing the level of replication (i.e., titer) in cells in which the TRE is active to the level of replication in cells in which the TRE is not active (i.e., a non-target cell). The replication preference is even more significant, as the adenovirus vectors used in the invention actually replicate at a significantly lower rate in TRE non-functional cells than wild type virus. Comparison of the adenovirus titer of a target cell to the titer of a TRE inactive cell type provides a key indication that the overall replication preference is enhanced due to the replication in target cells as well as depressed replication in non-target cells. This is especially useful in the cancer context, in which targeted cell killing is desirable. The TRE's preferably control genes necessary for replication, where the gene(s) necessary for replication is an early gene(s) of the adenovirus, preferentially the E1A or E1B genes. Particularly preferred embodiments include where TRE's control both the E1A and E1B genes within the same viral construct. In another particularly preferred embodiment, the adenovirus vector comprises co-transcribed first and second genes under transcriptional control of a heterologous, target cell-specific transcriptional regulatory element (TRE), wherein the second gene is under translational control of an internal ribosome entry site (IRES). In this embodiment, it is preferred that the second gene has its endogenous promoter mutated or deleted and in one embodiment, the IRES and second gene are in frame. In some embodiments, an adenovirus vector of the present invention further comprises E3.

Runaway infection is prevented due to the cell-specific requirements for viral replication. Without wishing to be bound by any particular theory, production of adenovirus proteins can serve to activate and/or stimulate the immune system, either generally or specifically toward target cells producing adenoviral proteins which can be an important consideration in the cancer context, where individuals are often moderately to severely immunocompromised.

In particular embodiments, the adenoviral vector may be a replication-competent target-cell specific adenoviral vector where the vector comprises an adenoviral gene. In one embodiment, the adenoviral gene is essential for replication and is under transcriptional control of a target cell-specific TRE.

In certain embodiments, the adenoviral vector may be a replication-competent target-cell specific adenoviral vector wherein the gene essential for replication is an early gene. In other embodiments the gene essential for replication may be a late gene.

In preferred embodiments the gene essential for replication is E1A or E1B. In particular embodiments, the adenovirus comprises both E1A and E1B. In further embodiments, the gene essential for replication is E1B wherein E1B has a deletion of part or all of the 19-kDa region.

In some embodiments, the adenovirus vector comprises co-transcribed first and second genes under transcriptional control of a heterologous, target cell-specific transcriptional regulatory element (TRE), wherein the second gene is under translational control of an internal ribosome entry site (IRES). In this embodiment, it is preferred that the endogenous promoter of the second gene be mutated or deleted and in one embodiment, the IRES and second gene are in frame.

In some embodiments of the adenovirus vector, E1A has a mutation in or deletion of its endogenous promoter. In some embodiments, E1B has a mutation in or a deletion of its endogenous promoter. In some embodiments, E1A has a mutation in or deletion of its endogenous enhancer. In other embodiments, E1B has a deletion in part or all of the 19-kDa region.

In particular preferred embodiments, the target cell specific adenoviral vector is specific for target cells including bladder, liver, prostate, breast, colorectal and melanoma cells.

In certain preferred embodiments, the adenoviral gene(s) essential for replication is under the control of a TRE(s) such as, but not limited to PB-TRE, PSA-TRE, MUC-TRE, AFP-TRE, CEA-TRE, tyrosinase-TRE, hKLK2-TRE, and uroplakin-TRE, as described herein.

Illustrative adenoviral vectors are summarized in Table 4.

In one aspect of the present invention, the adenovirus vectors comprise an intergenic IRES element(s) which links the translation of two or more genes, thereby removing any potential for homologous recombination based on the presence of identical TREs in the vector. Adenovirus vectors comprising an IRES are stable and in some embodiments provide better specificity than vectors not containing an IRES. Another advantage of an adenovirus vector comprising an intergenic IRES is that the use of an IRES rather than a second TRE may provide additional space in the vector for an additional gene(s) such as a therapeutic gene.

Thus, the adenovirus vectors comprising a second gene under control of an IRES retain a high level of target cell specificity and remain stable in the target cell. Accordingly, in one aspect of the invention, the viral vectors disclosed herein comprise at least one IRES within a multicistronic transcript, wherein production of the multicistronic transcript is regulated by a heterologous, target cell-specific TRE. For adenovirus vectors comprising a second gene under control of an IRES, it is preferred that the endogenous promoter of a gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and the second gene are in frame. Alternatively, if the IRES does not contain an initiation codon or if the initiation codon is removed from the IRES, the initiation codon of the second gene is used. In one embodiment, the adenovirus vectors comprises the adenovirus essential genes, E1A and E1B genes, under the transcriptional control of a heterologous, cell-specific TRE, and an IRES introduced between E1A and E1B. Thus, both E1A and E1B are under common transcriptional control, and translation of E1B coding region is obtained by virtue of the presence of the IRES. In one embodiment, E1A has its endogenous promoter deleted. In another embodiment, E1A has an endogenous enhancer deleted and in yet an additional embodiment, E1A has its endogenous promoter deleted and E1A enhancer I deleted. In another embodiment, E1B has its endogenous promoter deleted. In yet further embodiments, E1B has a deletion of part or all of the 19-kDa region.

To provide cytotoxicity to target cells, one or more transgenes having a cytotoxic effect may be present in the vector. Additionally, or alternatively, an adenovirus gene that contributes to cytotoxicity and/or cell death, such as the adenovirus death protein (ADP) gene, can be included in the vector, optionally under the selective transcriptional control of a heterologous TRE and optionally under the translational control of an IRES.

The subject vectors can be used for a wide variety of purposes. The purpose will vary with the target cell. Suitable target cells are characterized by the transcriptional activation of the cell specific transcriptional response element in the adenovirus vehicle. The transcription initiation region will usually be activated in less than about 5%, more usually less than about 1%, and desirably by less than about 0.1% of the cells in the host.

Transcriptional Response Elements (TREs)

The adenovirus vectors of the invention comprise target cell specific TREs which direct preferential expression of an operatively linked gene (or genes) in a particular target cell. A TRE can be tissue-specific, tumor-specific, developmental stage-specific, cell status specific, etc., depending on the type of cell present in the tissue or tumor.

Cell- and tissue-specific transcriptional regulatory elements, as well as methods for their identification, isolation, characterization, genetic manipulation and use for regulation of operatively linked coding sequences, are well known in the art. A TRE can be derived from the transcriptional regulatory sequences of a single gene, or sequences from different genes can be combined to produce a functional TRE. A cell-specific TRE is preferentially functional in a limited population (or type) of cells, e.g., prostate cells or liver cells. Accordingly, in some embodiments, the TRE used is preferentially functional in any of the following cell types: prostate; liver; breast; urothelial cells (bladder); colorectal; lung; ovarian; pancreas; stomach; and uterine. In other embodiments, in accordance with cell status, the TRE is functional in or during: low oxygen conditions (hypoxia); certain stages of cell cycle, such as S phase; elevated temperature; ionizing radiation.

As is known in the art, activity of TREs can be inducible. Inducible TREs generally exhibit low activity in the absence of inducer, and are up-regulated in the presence of inducer. Inducers include, for example, nucleic acids, polypeptides, small molecules, organic compounds and/or environmental conditions such as temperature, pressure or hypoxia. Inducible TREs may be preferred when expression is desired only at certain times or at certain locations, or when it is desirable to titrate the level of expression using an inducing agent. For example, transcriptional activity from the PSA-TRE, PB-TRE and hKLK2-TRE is inducible by androgen, as described herein and in PCT/US98/04080. Accordingly, in one embodiment of the present invention, an adenovirus vector comprises an inducible heterologous TRE.

TRE multimers are also useful in the disclosed vectors. For example, a TRE can comprise a tandem series of at least two, at least three, at least four, or at least five promoter fragments. Alternatively, a TRE can comprise one or more promoter regions along with one or more enhancer regions. TRE multimers can also comprise promoter and/or enhancer sequences from different genes. The promoter and enhancer components of a TRE can be in any orientation with respect to each other and can be in any orientation and/or any distance from the coding sequence of interest, as long as the desired cell-specific transcriptional activity is obtained.

The disclosed vectors are designed such that replication is preferentially enhanced in target cells in which the TRE(s) is (are) functional. More than one TRE can be present in a vector, as long as the TREs are functional in the same target cell. However, it is important to note that a given TRE can be functional in more than one type of target cell. For example, the CEA-TRE functions in, among other cell types, gastric cancer cells, colorectal cancer cells, pancreatic cancer cells and lung cancer cells.

A TRE for use in the present vectors may or may not comprise a silencer. The presence of a silencer (i.e., a negative regulatory element known in the art) can assist in shutting off transcription (and thus replication) in non-target cells. Thus, presence of a silencer can confer enhanced cell-specific vector replication by more effectively preventing replication in non-target cells. Alternatively, lack of a silencer may stimulate replication in target cells, thus conferring enhanced target cell-specificity.

As is readily appreciated by one skilled in the art, a TRE is a polynucleotide sequence, and, as such, can exhibit function over a variety of sequence permutations. Methods of nucleotide substitution, addition, and deletion are known in the art, and readily-available functional assays (such as the CAT or luciferase reporter gene assay) allow one of ordinary skill to determine whether a sequence variant exhibits requisite cell-specific transcription regulatory function. Hence, functionally preserved variants of TREs, comprising nucleic acid substitutions, additions, and/or deletions, can be used in the vectors disclosed herein. Accordingly, variant TREs retain function in the target cell but need not exhibit maximal function. In fact, maximal transcriptional activation activity of a TRE may not always be necessary to achieve a desired result, and the level of induction afforded by a fragment of a TRE may be sufficient for certain applications. For example, if used for treatment or palliation of a disease state, less-than-maximal responsiveness may be sufficient if, for example, the target cells are not especially virulent and/or the extent of disease is relatively confined.

Certain base modifications may result in enhanced expression levels and/or cell-specificity. For example, nucleic acid sequence deletions or additions within a TRE can move transcription regulatory protein binding sites closer or farther away from each other than they exist in their normal configuration, or rotate them so they are on opposite sides of the DNA helix, thereby altering spatial relationship among TRE-bound transcription factors, resulting in a decrease or increase in transcription, as is known in the art. Thus, while not wishing to be bound by theory, the present disclosure contemplates the possibility that certain modifications of a TRE will result in modulated expression levels as directed by the TRE, including enhanced cell-specificity. Achievement of enhanced expression levels may be especially desirable in the case of more aggressive forms of neoplastic growth, and/or when a more rapid and/or aggressive pattern of cell killing is warranted (for example, in an immunocompromised individual).

Transcriptional activity directed by a TRE (including both inhibition and enhancement) can be measured in a number of ways known in the art (and described in more detail below), but is generally measured by detection and/or quantitation of mRNA and/or of a protein product encoded by the sequence under control of (i.e., operably linked to) a TRE.

As discussed herein, a TRE can be of varying lengths, and of varying sequence composition. The size of a heterologous TRE will be determined in part by the capacity of the viral vector, which in turn depends upon the contemplated form of the vector (see infra). Generally minimal sizes are preferred for TREs, as this provides potential room for insertion of other sequences which may be desirable, such as transgenes (discussed infra) and/or additional regulatory sequences. In a preferred embodiment, such an additional regulatory sequence is an IRES. However, if no additional sequences are contemplated, or if, for example, an adenoviral vector will be maintained and delivered free of any viral packaging constraints, larger TRE sequences can be used as long as the resultant adenoviral vector remains replication-competent.

In a preferred embodiment, a viral vector is an adenoviral vector. An adenoviral vector can be packaged with extra sequences totaling up to about 5% of the genome size, or approximately 1.8 kb, without requiring deletion of viral sequences. If non-essential sequences are removed from the adenovirus genome, an additional 4.6 kb of insert can be tolerated (i.e., for a total insertion capacity of about 6.4 kb). Examples of non-essential adenoviral sequences that can be deleted are E3, and E4 sequences other than those which encode E4 ORF6.

To minimize non-specific replication, endogenous (e.g., adenovirus) TREs are preferably removed from the vector. Besides facilitating target cell-specific replication, removal of endogenous TREs also provides greater insert capacity in a vector, which may be of special concern if an adenoviral vector is to be packaged within a virus particle. Even more importantly, deletion of endogenous TREs prevents the possibility of a recombination event whereby a heterologous TRE is deleted and the endogenous TRE assumes transcriptional control of its respective adenovirus coding sequences (thus allowing non-specific replication). In one embodiment, an adenoviral vector is constructed such that the endogenous transcription control sequences of adenoviral genes are deleted and replaced by one or more heterologous TREs. However, endogenous TREs can be maintained in the adenovirus vector(s), provided that sufficient cell-specific replication preference is preserved. These embodiments are constructed by inserting heterologous TREs between an endogenous TRE and a replication gene coding segment. Requisite cell-specific replication preference is determined by conducting assays that compare replication of the adenovirus vector in a cell which allows function of the heterologous TREs with replication in a cell which does not.

Generally, a TRE will increase replication of a vector in a target cell by at least about 2-fold, preferably at least about 5-fold, preferably at least about 10-fold more preferably at least about 20-fold, more preferably at least about 50-fold, more preferably at least about 100-fold, more preferably at least about 200-fold, even more preferably at least about 400- to about 500-fold, even more preferably at least about 1000-fold, compared to basal levels of replication in the absence of a TRE. The acceptable differential can be determined empirically (by measurement of mRNA levels using, for example, RNA blot assays, RNase protection assays or other assays known in the art) and will depend upon the anticipated use of the vector and/or the desired result.

Replication-competent adenovirus vectors directed at specific target cells can be generated using TREs that are preferentially functional in a target cell. In one embodiment of the present invention, the target cell is a tumor cell. Non-limiting examples of tumor cell-specific heterologous TREs, and their respective target cells, include: probasin (PB), target cell, prostate cancer (PCT/US98/04132); α-fetoprotein (AFP), target cell liver cancer (PCT/US98/04084); mucin-like glycoprotein DF3 (MUC1), target cell, breast carcinoma (PCT/US98/04080); carcinoembryonic antigen (CEA), target cells, colorectal, gastric, pancreatic, breast, and lung cancers (PCT/US98/04133); plasminogen activator urokinase (uPA) and its receptor gene, target cells, breast, colon, and liver cancers (PCT/US98/04080); E2F1 (cell cycle S-phase specific promoter); target cell, tumors with disrupted retinoblastoma gene function, and HER-2/neu (c-erbB2/neu), target cell, breast, ovarian, stomach, and lung cancers (PCT/US98/04080); tyrosinase, target cell, melanoma cells as described herein and uroplakins, target cell, bladder cells as described herein. Methods for identification, isolation, characterization and utilization of additional target cell-specific TREs are readily available to those of skill in the art.

In addition, tumor-specific TREs can be used in conjunction with tissue-specific TREs from the following exemplary genes (tissue in which the TREs are specifically functional are in parentheses): hypoxia responsive element, vascular endothelial growth factor receptor (endothelium), albumin (liver), factor VII (liver), fatty acid synthase (liver), Von Willebrand factor (brain endothelium), alpha-actin and myosin heavy chain (both in smooth muscle), synthetase I (small intestine) Na$^+$—K$^+$—Cl-transporter (kidney). Additional tissue-specific TREs are known in the art.

In one embodiment of the present invention, a target cell-specific, heterologous TRE is tumor cell-specific. A vector can comprise a single tumor cell-specific TRE or multiple heterologous TREs which are tumor cell-specific and functional in the same cell. In another embodiment, a vector comprises one or more heterologous TREs which are tumor cell-specific and additionally comprises one or more heterologous TREs which are tissue specific, whereby all TREs are functional in the same cell.

Prostate-specific TREs

In one embodiment, adenovirus vectors comprise heterologous TREs that are prostate cell specific. For example, TREs that function preferentially in prostate cells and can be used to target adenovirus replication to prostate neoplasia, include, but are not limited to, TREs derived from the prostate-specific antigen gene (PSA-TRE) (Henderson U.S. Pat. No. 5,698,443); the glandular kallikrein-1 gene (from the human gene, hKLK2-TRE) (PCT US98/16312), and the probasin gene (PB-TRE) (PCT/US98/04132). All three of these genes are preferentially expressed in prostate cells and their expression is androgen-inducible. Generally, expression of genes responsive to androgen induction is mediated by an androgen receptor (AR).

Prostate-specific Antigen (PSA)

PSA is synthesized exclusively in prostatic epithelial cells and is synthesized in these cells whether they are normal, hyperplastic, or malignant. This tissue-specific expression of PSA has made it an excellent biomarker for benign prostatic hyperplasia (BPH) and prostatic carcinoma (CaP). Normal serum levels of PSA are typically below 5 ng/ml, with elevated levels indicative of BPH or CaP. Lundwall et al. (1987) *FEBS Lett.* 214:317; Lundwall (1989) *Biochem. Biophys. Res. Comm.* 161:1151; and Riegmann et al. (1991) *Molec. Endocrin.* 5:1921.

The region of the PSA gene that provides androgen-dependent cell specificity, particularly in prostate cells, involves approximately 6.0 kilobases (kb). Schuur et al. (1996) *J. Biol. Chem.* 271:7043–7051. An enhancer region of approximately 1.5 kb in humans is located between nt −5322 and nt −3739, relative to the transcription start site of the PSA gene. Within these enhancer sequences is an androgen response element (ARE) a sequence which binds androgen receptor. The sequence coordinates of the PSA promoter are from about nt −540 to nt +8 relative to the transcription start site. Juxtapositioning of the enhancer and promoter yields a fully functional, minimal prostate-specific TRE (PSA-TRE). Other portions of this approximately 6.0 kb region of the PSA gene can be used in the vectors described herein, as long as requisite functionality is maintained.

Human Glandular Kallikrein (hKLK2)

Human glandular kallikrein (hKLK2, encoding the hK2 protein) is expressed exclusively in the prostate and its expression is up-regulated by androgens, primarily through transcriptional activation. Wolf et al. (1992) *Molec. Endocrinol.* 6:753–762; Morris (1989) *Clin. Exp. Pharm. Physiol.*

16:345–351; Qui et al. (1990) *J. Urol.* 144:1550–1556; and Young et al. (1992) *Biochem.* 31:818–824. The levels of hK2 found in various tumors and in the serum of patients with prostate cancer indicate that hK2 antigen may be a significant marker for prostate cancer. Charlesworth et al. (1997) *Urology* 49:487–493. Expression of hK2 has been detected in each of 257 radical prostatectomy specimens analyzed. Darson et al. (1997) *Urology* 49:857–862. The intensity and extent of hK2 expression, detected using specific antibodies, was observed to increase from benign epithelium to high-grade prostatic intraepithelial neoplasia (PIN) and adenocarcinoma.

The activity of the hKLK2 promoter has been described and a region up to nt −2256 relative to the transcription start site was previously disclosed. Schedlich et al. (1987) *DNA* 6:429–437. The hKLK2 promoter is androgen responsive and, in plasmid constructs wherein the promoter alone controls the expression of a reporter gene, expression of the reporter gene is increased approximately 10-fold in the presence of androgen. Murtha et al. (1993) *Biochem.* 32:6459–6464. hKLK2 enhancer activity is found within a polynucleotide sequence approximately nt −12,014 to nt −2257 relative to the start of transcription and, when this sequence is operably linked to an hKLK2 promoter and a reporter gene, transcription of operably-linked sequences in prostate cells increases in the presence of androgen to levels approximately 30-fold to approximately 100-fold greater than the level of transcription in the absence of androgen. This induction is generally independent of the orientation and position of the enhancer sequences. Enhancer activity has also been demonstrated in the following regions (all relative to the transcription start site): about nt −3993 to about nt −3643, about nt −4814 to about nt −3643, about nt −5155 to about nt −3387, about nt −6038 to about nt −2394.

Thus, a hKLK2 enhancer can be operably linked to an hKLK2 promoter or a heterologous promoter to form a hKLK2 transcriptional regulatory element (hKLK2-TRE). A hKLK2-TRE can then be operably linked to a heterologous polynucleotide to confer hKLK2-TRE-specific transcriptional regulation on the linked gene, thus increasing its expression.

Probasin

The rat probasin (PB) gene encodes an androgen and zinc-regulated protein first characterized in the dorsolateral prostate of the rat. Dodd et al. (1983) *J. Biol. Chem.* 258:10731–10737; Matusik et al. (1986) *Biochem. Cell. Biol.* 64:601–607; and Sweetland et al. (1988) *Mol. Cell. Biochem.* 84:3–15. The dorsolateral lobes of the murine prostate are considered the most homologous to the peripheral zone of the human prostate, where approximately 68% of human prostate cancers are thought to originate.

A PB-TRE has been shown to exist in an approximately 0.5 kb fragment of sequence upstream of the probasin coding sequence, from about nt −426 to about nt +28 relative to the transcription start site. This minimal promoter sequence from the PB gene appears to provide sufficient information to direct prostate-specific developmental—and hormone—regulated expression of an operably linked heterologous gene in transgenic mice. Greenberg et al. (1994) *Mol. Endocrinol.* 8:230–239.

Alpha-fetoprotein

α-fetoprotein (AFP) is an oncofetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. High serum AFP levels in patients appear to be due to AFP expression in hepatocellular carcinoma (HCC), but not in surrounding normal liver. Thus, expression of the AFP gene appears to be characteristic of hepatoma cells. An AFP-TRE is described in for example PCT/US98/04084.

According to published reports, the AFP-TRE is responsive to cellular proteins (transcription factors and/or co-factor(s)) associated with AFP-producing cells, such as AFP-binding protein (see, for example, U.S. Pat. No. 5,302, 698) and comprises at least a portion of an AFP promoter and/or an AFP enhancer. Cell-specific TREs from the AFP gene have been identified. For example, the cloning and characterization of human AFP-specific enhancer activity is described in Watanabe et al. (1987) *J. Biol. Chem.* 262:4812–4818. A 5' AFP regulatory region (containing the promoter, putative silencer, and enhancer) is contained within approximately 5 kb upstream from the transcription start site.

Within the AFP regulatory region, a human AFP enhancer region is located between about nt −3954 and about nt −3335, relative to the transcription start site of the AFP gene. The human AFP promoter encompasses a region from about nt −174 to about nt +29. Juxtapositioning of these two genetic elements, yields a fully functional AFP-TRE. Ido et al. (1995) *Cancer Res.* 55:3105–3109 describe a 259 bp promoter fragment (nt −230 to nt +29) that is specific for expression in HCC cells. The AFP enhancer, located between nt −3954 and nt −3335 relative to the transcription start site, contains two regions, denoted A and B. The promoter region contains typical TATA and CAAT boxes. Preferably, the AFP-TRE contains at least one enhancer region. More preferably, the AFP-TRE contains both enhancer regions.

Suitable target cells for vectors containing AFP-TREs are any cell type that allow an AFP-TRE to function. Preferred are cells that express or produce AFP, including, but not limited to, tumor cells expressing AFP. Examples of such cells are hepatocellular carcinoma (HCC) cells, gonadal and other germ cell tumors (especially endodermal sinus tumors), brain tumor cells, ovarian tumor cells, acinar cell carcinoma of the pancreas (Kawamoto et al. (1992) *Hepato-gastroenterology* 39:282–286), primary gall bladder tumor (Katsuragi et al (1989) *Rinsko Hoshasen* 34:371–374), uterine endometrial adenocarcinoma cells (Koyama et al. (1996) *Jpn. J. Cancer Res.* 87:612–617), and any metastases of the foregoing (which can occur in lung, adrenal gland, bone marrow, and/or spleen). In some cases, metastatic disease to the liver from certain pancreatic and stomach cancers produce AFP. Especially preferred as target cells for an AFP-TRE are hepatocellular carcinoma cells and any of their metastases.

AFP production can be measured (and hence AFP-producing cells can be identified) using immunoassays standard in the art, such as RIA, ELISA or protein immunoblotting (Western blots) to determine levels of AFP protein production; and/or RNA blotting (Northern blots) to determine AFP mRNA levels. Alternatively, such cells can be identified and/or characterized by their ability to activate transcriptionally an AFP-TRE (i.e., allow an AFP-TRE to function).

See also co-owned PCT WO98/39465 regarding AFP-TREs. As described in more detail therein, an AFP-TRE can comprise any number of configurations, including, but not limited to, an AFP promoter; an AFP enhancer; an AFP promoter and an AFP enhancer; an AFP promoter and a heterologous enhancer; a heterologous promoter and an AFP enhancer; and multimers of the foregoing. The promoter and enhancer components of an AFP-TRE can be in any orientation and/or distance from the coding sequence of interest, as long as the desired AFP cell-specific transcriptional activity is obtained. An adenovirus vector of the present invention can comprise an AFP-TRE endogenous silencer element or the AFP-TRE endogenous silencer element can be deleted.

Urokinase Plasminogen Activator

The protein urokinase plasminogen activator (uPA) and its cell surface receptor, urokinase plasminogen activator receptor (uPAR), are expressed in many of the most frequently-occurring neoplasms and appear to represent important proteins in cancer metastasis. Both proteins are implicated in breast, colon, prostate, liver, renal, lung and ovarian cancer. Sequence elements that regulate uPA and uPAR transcription have been extensively studied. Riccio et al. (1985) *Nucleic Acids Res.* 13:2759–2771; Cannio et al (1991) *Nucleic Acids Res.* 19:2303–2308.

Carcinoembryonic Antigen (CEA)

CEA is a 180,000 Dalton, tumor-associated, glycoprotein antigen present on endodermally-derived neoplasms of the gastrointestinal tract, such as colorectal, gastric (stomach) and pancreatic cancer, as well as other adenocarcinomas such as breast and lung cancers. CEA is of clinical interest because circulating CEA can be detected in the great majority of patients with CEA-positive tumors. In lung cancer, about 50% of total cases have circulating CEA, with high concentrations of CEA (greater than 20 ng/ml) often detected in adenocarcinomas. Approximately 50% of patients with gastric carcinoma are serologically positive for CEA.

The 5'-flanking sequence of the CEA gene has been shown to confer cell-specific activity. The CEA promoter region, approximately the first 424 nucleotides upstream of the transcriptional start site in the 5' flanking region of the gene, was shown to confer cell-specific activity by virtue of providing higher promoter activity in CEA-producing cells than in non-producing HeLa cells. Schrewe et al. (1990) *Mol. Cell. Biol.* 10:2738–2748. In addition, cell-specific enhancer regions have been found. See PCT/GB/02546 The CEA promoter, putative silencer, and enhancer elements appears to be contained within a region that extends approximately 14.5 kb upstream from the transcription start site. Richards et al. (1995); PCT/GB/02546. Further characterization of the 5'-flanking region of the CEA gene by Richards et al. (1995) supra indicated that two upstream regions (one between about –13.6 and about –10.7 kb, and the other between about –6.1 and about –4.0 kb), when linked to the multimerized promoter, resulted in high-level and selective expression of a reporter construct in CEA-producing LoVo and SW1463 cells. Richards et al. (1995) supra also localized the promoter region between about nt –90 and about nt +69 relative to the transcriptional start site, with the region between about nt –41 and about nt –18 being essential for expression. PCT/GB/02546 describes a series of 5'-flanking CEA fragments which confer cell-specific activity, including fragments comprising the following sequences: about nt –299 to about nt +69; about nt –90 to about nt +69; nt –14,500 to nt –10,600; nt –13,600 to nt –10,600; and nt –6100 to nt –3800, with all coordinates being relative to the transcriptional start point. In addition, cell-specific transcription activity is conferred on an operably linked gene by the CEA fragment from nt –402 to nt +69.

CEA-TREs for use in the vectors disclosed herein are derived from mammalian cells, including, but not limited to, human cells. Thus, any of the CEA-TREs can be used as long as the requisite desired functionality is displayed by the vector.

Mucin

The protein product of the MUC1 gene (known as mucin, MUC1 protein; episialin; polymorphic epithelial mucin or PEM; EMA; DF3 antigen; NPGP; PAS-O; or CA1 5.3 antigen) is normally expressed mainly at the apical surface of epithelial cells lining the glands or ducts of the stomach, pancreas, lungs, trachea, kidney, uterus, salivary glands, and mammary glands. Zotter et al. (1988) *Cancer Rev.* 11–12:55–101; and Girling et al. (1989) *Int. J. Cancer* 43:1072–1076. However, mucin is overexpressed in 75–90% of human breast carcinomas. Kufe et al. (1984) *Hybridoma* 3:223–232. For reviews, see Hilkens (1988) *Cancer Rev.* 11–12:25–54; and Taylor-Papadimitriou, et al. (1990) *J. Nucl. Med. Allied Sci.* 34:144–150. Mucin protein expression correlates with the degree of breast tumor differentiation. Lundy et al (1985) *Breast Cancer Res. Treat.* 5:269–276.

Overexpression of the MUC1 gene in human breast carcinoma cells MCF-7 and ZR-75-1 appears to occur at the transcriptional level. Kufe et al. (1984) supra; Kovarik (1993) *J. Biol. Chem.* 268:9917–9926; and Abe et al (1990) *J. Cell. Physiol.* 143:226–231. The regulatory sequences of the MUC1 gene have been cloned, including the approximately 0.9 kb upstream of the transcription start site which contains a TRE that appears to be involved in cell-specific transcription. Abe et al. (1993) *Proc. Natl. Acad. Sci. USA* 90:282–286; Kovarik et al. (1993) supra; and Kovarik et al. (1996) *J. Biol. Chem.* 271:18140–18147.

MUC1-TREs are derived from mammalian cells, including but not limited to, human cells. Preferably, the MUC1-TRE is human. In one embodiment, the MUC1-TRE contains the entire 0.9 kb 5' flanking sequence of the MUC1 gene. In other embodiments, MUC1-TREs comprise the following sequences (relative to the transcription start site of the MUC1 gene) operably-linked to a promoter: about nt –725 to about nt +31, about nt –743 to about nt +33, about nt –750 to about nt +33, and about nt –598 to about nt +485.

c-erbB2/HER-2/neu

The c-erbB2/neu gene (HER-2/neu or HER) is a transforming gene that encodes a 185 kD epidermal growth factor receptor-related transmembrane glycoprotein. In humans, the c-erbB2/neu protein is expressed during fetal development and, in adults, the protein is weakly detectable (by immunohistochemistry) in the epithelium of many normal tissues. Amplification and/or over-expression of the c-erbB2/neu gene has been associated with many human cancers, including breast, ovarian, uterine, prostate, stomach and lung cancers. The clinical consequences of overexpression of the c-erbB2/neu protein have been best studied in breast and ovarian cancer. c-erbB2/neu protein overexpression occurs in 20 to 40% of intraductal carcinomas of the breast and 30% of ovarian cancers, and is associated with a poor prognosis in subcategories of both diseases.

Human, rat and mouse c-erbB2/neu TREs have been identified and shown to confer transcriptional activity specific to c-erbB2/neu-expressing cells. Tal et al. (1987) *Mol. Cell. Biol.* 7:2597–2601; Hudson et al. (1990) *J. Biol. Chem.* 265:4389–4393; Grooteclaes et al. (1994) *Cancer Res.* 54:4193–4199; Ishii et al. (1987) *Proc. Natl. Acad. Sci. USA* 84:4374–4378; and Scott et al. (1994) *J Biol. Chem.* 269:19848–19858.

Melanocyte-specific TRE

It has been shown that some genes which encode melanoma proteins are frequently expressed in melanoma/ melanocytes, but silent in the majority of normal tissues. A variety of melanocyte-specific TRE are known, are responsive to cellular proteins (transcription factors and/or co-factor(s)) associated with melanocytes, and comprise at least a portion of a melanocyte-specific promoter and/or a melanocyte-specific enhancer. Known transcription factors that control expression of one or more melanocyte-specific genes include the microphthalmia associated transcription factor MITF. Yasumoto et al. (1997) *J. Biol. Chem.* 272:503–509. Other transcription factors that control expression of one or more melanocyte specific genes include MART-1/Melan-A, gp100, TRP-1 and TRP-2.

Methods are described herein for measuring the activity of a melanocyte-specific TRE and thus for determining whether a given cell allows a melanocyte-specific TRE to function.

The melanocyte-specific TREs used in this invention are derived from mammalian cells, including but not limited to, human, rat, and mouse. Any melanocyte-specific TREs may be used in the adenoviral vectors of the invention. Rodent and human 5' flanking sequences from genes expressed specifically or preferentially in melanoma cells have been described in the literature and are thus made available for practice of this invention and need not be described in detail herein. The following are some examples of melanocyte-specific TREs which can be used. A promoter and other control elements in the human tyrosinase gene 5' flanking region have been described and sequences have been deposited as GenBank Accession Nos. X16073 and D10751. Kikuchi et al. (1989) *Biochim. Biophys. Acta* 1009:283–286; and Shibata et al. (1992) *J. Biol. Chem.* 267:20584–20588. A cis-acting element has been defined that enhances melanocyte-specific expression of human tyrosinase gene. This element comprises a 20-bp sequence known as tyrosinase distal element (TDE), contains a CATGTG motif, and lies at positions about −1874 to about −1835 relative to the human tyrosinase gene transcription start site. Yasumoto et al. (1994) *Mol. Cell. Biol.* 14:8058–8070. A promoter region comprising sequences from about −209 to +61 of the human tyrosinase gene was found to direct melanocyte-specific expression. Shibata (1992). Similarly, the mouse tyrosinase 5' flanking region has been analyzed and a sequence deposited as GenBank Accession Nos. D00439 and X51743. Klüppel et al. (1991) *Proc. Natl. Acad. Sci. USA* 88:3777–3788. A minimal promoter has been identified for the mouse TRP-1 gene, and was reported to encompass nucleotides −44 to +107 relative to the transcription start site. Lowings et al. (1992) *Mol. Cell. Biol.* 12:3653–3662. Two regulatory regions required for melanocyte-specific expression of the human TRP-2 gene have been identified. Yokoyama et al. (1994) *J. Biol. Chem.* 269:27080–27087. A human MART-1 promoter region has been described and deposited as GenBank Accession No. U55231. Melanocyte-specific promoter activity was found in a 233-bp fragment of the human MART-1 gene 5' flanking region. Butterfield et al. (1997) *Gene* 191:129–134. A basic-helix-loop-helix/leucine zipper-containing transcription factor, MITF (microphthalmia associated transcription factor) was reported to be involved in transcriptional activation of tyrosinase and TRP-1 genes. Yasumoto et al. (1997) *J. Biol. Chem.* 272:503–509.

In some embodiments, a melanocyte-specific TRE comprises sequences derived from the 5' flanking region of a human tyrosinase gene depicted in Table 14. In some of these embodiments, the melanocyte-specific TRE comprises tyrosinase nucleotides from about −231 to about +65 relative to the transcription start site (from about nucleotide 244 to about nucleotid 546 of SEQ ID NO:10) and may further comprise nucleotides from about −1956 to about −1716 relative to the human tyrosinase transcription start site (from about nucleotide 6 to about nucleotide −243 of SEQ ID NO:10). A tyrosinase TRE can comprise nucleotides from about −231 to about +65 juxtaposed to nucleotides from about −1956 to about −1716. It has been reported that nucleotides from about −1956 to about −1716 relative to the human tyrosinase transcription start site can confer melanocyte-specific expression of an operably linked reporter gene with either a homologous or a heterologous promoter. Accordingly, in some embodiments, a melanocyte-specific TRE comp ses nucleotides from about −1956 to about −1716 operably linked to a heterologous promoter. Accordingly, in some embodiments, a melanocyte-specific TRE comprises nucleotides from about −1956 to about −1716 operably linked to a heterologous promoter.

A melanocyte-specific TRE can also comprise multimers. For example, a melanocyte-specific TRE can comprise a tandem series of at least two, at least three, at least four, or at least five tyrosinase promoter fragments. Alternatively, a melanocyte-specific TRE could have one or more tyrosinase promoter regions along with one or more tyrosinase enhancer regions. These multimers may also contain heterologous promoter and/or enhancer sequences.

Cell Status-specific TREs

Cell status-specific TREs for use in the adenoviral vectors of the present invention can be derived from any species, preferably a mammal. A number of genes have been described which are expressed in response to, or in association with, a cell status. Any of these cell status-associated genes may be used to generate a cell status-specific TRE.

An example of a cell status is cell cycle. An exemplary gene whose expression is associated with cell cycle is E2F-1, a ubiquitously expressed, growth-regulated gene, which exhibits peak transcriptional activity in S phase. Johnson et al. (1994) *Genes Dev.* 8:1514–1525. The RB protein, as well as other members of the RB family, form specific complexes with E2F-1, thereby inhibiting its ability to activate transcription. Thus, E2F-1-responsive promoters are down-regulated by RB. Many tumor cells have disrupted RB function, which can lead to de-repression of E2F-1-responsive promoters, and, in turn, de-regulated cell division.

Accordingly, in one embodiment, the invention provides an E3-containing adenoviral vector in which an adenoviral gene (preferably a gene necessary for replication) is under transcriptional control of a cell status-specific TRE, wherein the cell status-specific TRE comprises a cell cycle-activated TRE. In one embodiment, the cell cycle-activated TRE is an E2F 1 TRE.

Another group of genes that are regulated by cell status are those whose expression is increased in response to hypoxic conditions. Bunn and Poyton (1996) *Physiol. Rev.* 76:839–885; Dachs and Stratford (1996) *Br. J. Cancer* 74:5126–5132; Guillemin and Krasnow (1997) *Cell* 89:9–12. Many tumors have insufficient blood supply, due in part to the fact that tumor cells typically grow faster than the endothelial cells that make up the blood vessels, resulting in areas of hypoxia in the tumor. Folkman (1989) *J. Natl. Cancer Inst.* 82:4–6; and Kallinowski (1996) *The Cancer J.* 9:37–40. An important mediator of hypoxic responses is the transcriptional complex HIF-1, or hypoxia inducible factor-1, which interacts with a hypoxia-responsive element (HRE) in the regulatory regions of several genes, including vascular endothelial growth factor, and several genes encoding glycolytic enzymes, including enolase-1. Murine HRE sequences have been identified and characterized. Firth et al. (1994) *Proc. Natl. Acad. Sci. USA* 91:6496–6500. An HRE from a rat enolase-1 promoter is described in Jiang et al. (1997) *Cancer Res.* 57:5328–5335. An HRE from a rat enolase-1 promoter is depicted in Table 14.

Accordingly, in one embodiment, an adenovirus vector comprises an adenovirus gene, preferably an adenoviral gene essential for replication, under transcriptional control of a cell status-specific TRE comprising an HRE. In one embodiment, the cell status-specific TRE comprises the HRE depicted in Table 14.

Other cell status-specific TREs include heat-inducible (i.e., heat shock) promoters, and promoters responsive to radiation exposure, including ionizing radiation and UV radiation. For example, the promoter region of the early growth response-1 (Egr-1) gene contains an element(s) inducible by ionizing radiation. Hallahan et al. (1995) *Nat. Med.* 1:786–791; and Tsai-Morris et al. (1988) *Nucl. Acids. Res.* 16:8835–8846. Heat-inducible promoters, including heat-inducible elements, have been described. See, for example Welsh (1990) in "Stress Proteins in Biology and Medicine", Morimoto, Tisseres, and Georgopoulos, eds. Cold Spring Harbor Laboratory Press; and Perisic et al. (1989) *Cell* 59:797–806. Accordingly, in some embodiments, the cell status-specific TRE comprises an element(s) responsive to ionizing radiation. In one embodiment, this TRE comprises a 5' flanking sequence of an Egr-1 gene. In other embodiments, the cell status-specific TRE comprises a heat shock responsive element.

The cell status-specific TREs listed above are provided as non-limiting examples of TREs that would function in the instant invention. Additional cell status-specific TREs are known in the art, as are methods to identify and test cell status specificity of suspected cell status-specific TREs.

Urothelial Cell-specific TREs

Any urothelial cell-specific TRE may be used in the adenoviral vectors of the invention. A number of urothelial cell-specific proteins have been described, among which are the uroplakins. Uroplakins (UP), including UPIa and UPIb (27 and 28 kDa, respectively), UPII (15 kDa), and UPIII (47 kDa), are members of a group of integral membrane proteins that are major proteins of urothelial plaques. These plaques cover a large portion of the apical surface of mammalian urothelium and may play a role as a permeability barrier and/or as a physical stabilizer of the urothelial apical surface. Wu et al. (1994) *J. Biol. Chem.* 269:13716–13724. UPs are bladder-specific proteins, and are expressed on a significant proportion of urothelial-derived tumors, including about 88% of transitional cell carcinomas. Moll et al. (1995) *Am. J. Pathol.* 147:1383–1397; and Wu et al. (1998) *Cancer Res.* 58:1291–1297. The control of the expression of the human UPII has been studied, and a 3.6-kb region upstream of the mouse UPII gene has been identified which can confer urothelial-specific transcription on heterologous genes (Lin et al. (1995) *Proc. Natl. Acad. Sci. USA* 92:679–683).

Preferred urothelial cell-specific TREs include TREs derived from the uroplakins UPIa, UPIb, UPII, and UPIII, as well as urohingin. A uroplakin TRE may be from any species, depending on the intended use of the adenovirus, as well as the requisite functionality is exhibited in the target or host cell. Significantly, adenovirus constructs comprising a urothelial cell-specific TREs have observed that such constructs are capable of selectively replicating in urothelial cells as opposed to smooth muscle cells, which adjoin urothelial cells in the bladder.

Uroplakin

Urothelial-specific TREs derived from the hUPII gene are described herein. Accordingly, in some embodiments, an adenovirus vector of the invention comprises an adenovirus gene, preferably an adenoviral gene essential for replication, under transcriptional control of a urothelial cell-specific TRE which comprises the 2.2 kb sequence from the 5' flanking region of hUPII gene, as shown in Table 14. In other embodiments, an adenovirus vector of the invention comprises an adenovirus gene, preferably an adenoviral gene essential for replication, under transcriptional control of a urothelial cell-specific TRE which comprises a 1.8 kb sequence from the 5' flanking region of hUPII gene, from nucleotides 430 to 2239 as shown in Table 14. In other embodiments, the urothelial cell-specific TRE comprises a functional portion of the 2.2 kb sequence depicted in Table 14, or a functional portion of the 1.8 kb sequence of nucleotides 430 to 2239 of the sequence depicted in Table 14, such as a fragment of 2000 bp or less, 1500 bp or less, or 1000 bp or less, 600 bp less, or at least 200 bp which includes the 200 bp fragment of the hUPII 5'-flanking region.

A 3.6 kb 5'-flanking sequence located from the mouse UPII (mUPII) gene which confers urothelial cell-specific transcription on heterologous genes is one urothelial cell-specific TRE useful in vectors of the instant invention (Table 14). Smaller TREs (i.e., 3500 bp or less, more preferably less than about 2000 bp, 1500 bp, or 1000 bp) are preferred. Smaller TREs derived from the mUPII 3.6 kb fragment are one group of preferred urothelial cell-specific TREs. In particular, Inventors have identified an approximately 600 bp fragment from the 5' flanking DNA of the mUPII gene, which contains 540 bp of 5' untranslated region (UTR) of the mUPII gene, that confers urothelial cell-specific expression on heterologous genes.

Accordingly, in some embodiments, an adenovirus vector comprises an adenovirus gene, preferably an adenoviral gene essential for replication, under transcriptional control of a urothelial cell-specific TRE which comprises the 3.6 kb sequence from the 5' flanking region of mouse UPII gene, as shown in Table 14. In other embodiments, the urothelial cell-specific TRE comprises a functional portion of the 3.6 kb sequence depicted in Table 14, such as a fragment of 3500 bp or less, 2000 bp or less, 1500 bp or less, or 1000 bp or less which includes the 540 bp fragment of 5' UTR. The urothelial cell-specific TRE may also be a sequence which is substantially identical to the 3.6 kb mUPII 5'-flanking region or any of the described fragments thereof.

As an example of how urothelial cell-specific TRE activity can be determined, a polynucleotide sequence or set of such sequences can be generated using methods known in the art, such as chemical synthesis, site-directed mutagenesis, PCR, and/or recombinant methods. The sequence(s) to be tested is inserted into a vector containing an appropriate reporter gene, including, but not limited to, chloramphenicol acetyl transferase (CAT), β-galactosidase (encoded by the lacZ gene), luciferase (encoded by the luc gene), a green fluorescent protein, alkaline phosphatase, and horse radish peroxidase. Such vectors and assays are readily available, from, inter alia, commercial sources. Plasmids thus constructed are transfected into a suitable host cell to test for expression of the reporter gene as controlled by the putative target cell-specific TRE using transfection methods known in the art, such as calcium phosphate precipitation, electroporation, liposomes (lipofection) and DEAE dextran. Suitable host cells include any urothelial cell type, including but not limited to, KU-1, MYP3 (a non-tumorigenic rat urothelial cell line), 804G (rat bladder carcinoma cell line), cultured human urothelial cells (HUC), HCV-29, UM-UC-3, SW780, RT4, HL60, KG-1, and KG-1A. Non-urothelial cells, such as LNCaP, HBL-100, HLF, HLE, 3T3, Hep3B, HuH7, CADO-LC9, and HeLa are used as a control. Results are obtained by measuring the level of expression of the reporter gene using standard assays. Comparison of expression between urothelial cells and control indicates presence or absence of transcriptional activation.

Comparisons between or among various urothelial cell-specific TREs can be assessed by measuring and comparing levels of expression within a single urothelial cell line. It is understood that absolute transcriptional activity of a urothelial cell-specific TRE will depend on several factors, such as the nature of the target cell, delivery mode and form of the urothelial cell-specific TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the CMV immediate early promoter. This analysis can also indicate negative regulatory regions, i.e., silencers.

Alternatively a putative urothelial cell-specific TRE can be assessed for its ability to confer adenoviral replication preference for cells that allow a urothelial cell-specific TRE to function. For this assay, constructs containing an adenovirus gene essential to replication operatively linked to a putative urothelial cell-specific TRE are transfected into urothelial cells. Viral replication in those cells is compared, for example, to viral replication by wild type adenovirus in those cells and/or viral replication by the construct in non-urothelial cells.

TRE Configurations

A TRE as used in the present invention can be present in a variety of configurations. A TRE can comprise multimers. For example, a TRE can comprise a tandem series of at least two, at least three, at least four, or at least five target cell-specific TREs. These multimers may also contain heterologous promoter and/or enhancer sequences.

Optionally, a transcriptional terminator or transcriptional "silencer" can be placed upstream of the target cell-specific TRE, thus preventing unwanted read-through transcription of the coding segment under transcriptional control of the target cell-specific TRE. Also, optionally, the endogenous promoter of the coding segment to be placed under transcriptional control of the target cell-specific TRE can be deleted.

A target cell-specific TRE may or may not lack a silencer. The presence of a silencer (i.e., a negative regulatory element) may assist in shutting off transcription (and thus replication) in non-permissive cells (i.e., a non-target cell). Thus, presence of a silencer may confer enhanced target cell-specific replication by more effectively preventing adenoviral vector replication in non-target cells. Alternatively, lack of a silencer may assist in effecting replication in target cells, thus conferring enhanced target cell-specific replication due to more effective replication in target cells.

It is also understood that the invention includes a target cell-specific TRE regulating the transcription of a bicistronic mRNA in which translation of the second mRNA is associated by an IRES. An adenovirus vector may further include an additional heterologous TRE which may or may not be operably linked to the same gene(s) as the target cell-specific TRE. For example a TRE (such as a cell type-specific or cell status-specific TRE) may be juxtaposed to a second type of target-cell-specific TRE. "Juxtaposed" means a target cell-specific TRE and a second TRE transcriptionally control the same gene. For these embodiments, the target cell-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene.

As is readily appreciated by one skilled in the art, a target cell-specific TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite target cell-specific transcription function. Hence, the invention also includes functionally-preserved variants of the TRE nucleic acid sequences disclosed herein, which include nucleic acid substitutions, additions, and/or deletions. The variants of the sequences disclosed herein may be 80%, 85%, 90%, 95%, 98%, 99% or more identical, as measured by, for example, ALIGN Plus (Scientific and Educational Software, Pennsylvania), preferably using efault parameters, which are as follows: mismatch=2; open gap=0; extend gap=2 to any of the urothelial cell-specific TRE sequences disclosed herein. Variants of target cell-specific TRE sequences may also hybridize at high stringency, that is at 68° C. and 0.1× SSC, to any of the target cell-specific TRE sequences disclosed herein.

In terms of hybridization conditions, the higher the sequence identity required, the more stringent are the hybridization conditions if such sequences are determined by their ability to hybridize to a sequence of a TRE disclosed herein. Accordingly, the invention also includes polynucleotides that are able to hybridize to a sequence comprising at least about 15 contiguous nucleotides (or more, such as about 25, 35, 50, 75 or 100 contiguous nucleotides) of a sequence of a TRE disclosed herein. The hybridization conditions would be stringent, i.e., 80° C. (or higher temperature) and 6M SSC (or less concentrated SSC). Another set of stringent hybridization conditions is 68° C. and 0.1× SSC. For discussion regarding hybridization reactions, see below.

Hybridization reactions can be performed under conditions of different "stringency". Conditions that increase stringency of a hybridization reaction of widely known and published in the art. See, for example, Sambrook et al. (1989) at page 7.52. Examples of relevant conditions include (in order of increasing stringency): incubation temperatures of 25° C., 37° C., 50° C. and 68° C.; buffer concentrations of 10× SSC, 6× SSC, 1× SSC, 0.1× SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6× SSC, 1× SSC, 0.1× SSC, or deionized water. An exemplary set of stringent hybridization conditions is 68° C. and 0.1× SSC.

"$T_m$" is the temperature in degrees Celcius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m=81.5+16.6 log[X^+]+0.41(\%G/C)-0.61 (\%F)-600/L$$

where [$X^+$] is the cation concentration (usually sodium ion, $Na^+$) in mol/L; (%G/C) is the number of G and C residues as a percentage of total residues in the duplex; (%F) is the percent formamide in solution (wt/vol); and L is the number of nucleotides in each strand of the duplex.

While not wishing to be bound by a single theory, the inventors note that it is possible that certain modifications will result in modulated resultant expression levels, including enhanced expression levels. Achievement of modulated resultant expression levels, preferably enhanced expression levels, may be especially desirable in the case of certain, more aggressive forms of cancer, or when a more rapid and/or aggressive pattern of cell killing is warranted (due to an immunocompromised condition of the individual, for example).

Determination of TRE Activity

Activity of a TRE can be determined, for example, as follows. A TRE polynucleotide sequence or set of such sequences can be generated using methods known in the art, such as chemical synthesis, site-directed mutagenesis, PCR, and/or recombinant methods. The sequence(s) to be tested can be inserted into a vector containing a promoter (if no promoter element is present in the TRE) and an appropriate reporter gene encoding a reporter protein, including, but not limited to, chloramphenicol acetyl transferase (CAT), β-galactosidase (encoded by the lacZ gene), luciferase (encoded by the luc gene), alkaline phosphatase (AP), green fluorescent protein (GFP), and horseradish peroxidase (HRP). Such vectors and assays are readily available, from, inter alia, commercial sources. Plasmids thus constructed are transfected into a suitable host cell to test for expression of the reporter gene as controlled by the putative TRE using transfection methods known in the art, such as calcium phosphate precipitation, electroporation, liposomes, DEAE dextran-mediated transfer, particle bombardment or direct injection. TRE activity is measured by detection and/or quantitation of reporter gene-derived mRNA and/or protein. Reporter protein product can be detected directly (e.g., immunochemically) or through its enzymatic activity, if any, using an appropriate substrate. Generally, to determine cell specific activity of a TRE, a TRE-reporter gene construct is introduced into a variety of cell types. The amount of TRE activity is determined in each cell type and compared to that of a reporter gene construct lacking the TRE. A TRE is determined to be cell-specific if it is preferentially functional in one cell type, compared to a different type of cell.

Internal Ribosome Entry Site (IRES)

IRES elements were first discovered in picomavirus mRNAs (Jackson R J, Howell M T. Kaminski A (1990) *Trends Biochern Sci* 15(12):477–83) and Jackson R J and Kaminiski, A. (1995) *RNA* 1(10):985–1000). The present invention provides improved adenovirus vectors comprising co-transcribed first and second genes under transcriptional control of a heterologous, target cell-specific TRE, and wherein the second gene (i.e., coding region) is under translatioal control of an internal ribosome entry site (IRES). Any IRES may be used in the adenovirus vectors of the invention, as long as they exhibit requisite function in the vectors. Example of IRES which can be used in the present invention include those provided in Table I and referenced in Table II. Examples of IRES elements include the enceph-elomycarditis virus (EMCV) which is commercially available from Novagen (Duke et al. (1992) *J. Viral* 66(3): 1602–9) the sequence fo which is depicted in Table 12 (SEQ ID NO:1). Another example of an IRES element disclosed herein is the VEGF IRES (Huez et al. (1998) *Mol Cell Biol* 18(11):6178–90). This IRES has a ort segment and the sequence is depicted in Table 12 (SEQ ID NO:2).

The IRES promotes direct internal ribosome entry to the initiation codon of a downstream cistron, leading to cap-independent translation. Thus, the product of a downstream cistron can be expressed from a bicistronic (or multicistronic) mRNA, without requiring either cleavage of a polyprotein or generation of a monocistronic mRNA. Therefore, in one illustrative embodiment of the present invention, an adenovirus vector comprising E1B under translational control of an IRES allows translation of E1B from a bicistronic E1A-E1B mRNA under control of a target cell-specific TRE.

Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. See Jackson et al. (1990).

Three major classes of picornavirus IRES have been identified and characterized: (1) the cardio- and aphthovirus class (for example, the encephelomycarditis virus, Jang et al. (1990) *Gene Dev* 4:1560–1572); (2) the entero- and rhinovirus class (for example, polioviruses, Borman et al. (1994) *EMBO J.* 13:314903157); and (3) the hepatitis A virus (HAV) class, Glass et al. (1993) *Virol* 193:842–852). For the first two classes, two general principles apply. First, most of the 450-nucleotide sequence of the IRES functions to maintain particular secondary and tertiary structures conducive to ribosome binding and translational initiation. Second, the ribosome entry site is an AUG triplet located at the 3' end of the IRES, approximately 25 nucleotides downstream of a conserved oligopyrimidine tract. Translation initiation can occur either at the ribosome entry site (cardioviruses) or at the next downstream AUG (entero/rhinovirus class). Initiation occurs at both sites in aphthoviruses.

HCV and pestiviruses such as bovine viral diarrhea virus (BVDV) or classical swine fever virus (CSFV) have 341 nt and 370 nt long 5'-UTR respectively. These 5'-UTR fragments form similar RNA secondary structures and can have moderately efficient IRES function (Tsukiyama-Kohara et al. (1992) *J. Virol.* 66:1476–1483; Frolov I et al., (1998) *RNA* 4:1418–1435). Table I depicts the 5'-UTR region from HCV genome sequence (GenBank accession D14853).

Leishmania RNA virus 1 (LRV1) is a double-stranded RNA virus. Its 128 nt long 5'-UTR has IRES activity to facilitate the cap-independent translation, (Maga et al. (1995) *Mol Cell Biol* 15:4884–4889). This fragment also forms conserved stemloop secondary structure and at least the front part is essential.

Recent studies showed that both Friend-murine leukemia virus (MLV) 5'-UTR and rat retrotransposon virus-like 30S (VL30) sequences contain IRES structure of retroviral origin (Torrent et al. (1996) *Hum Gene Ther* 7:603–612). These fragments are also functional as packing signal when used in retroviruse derived vectors. Studies of avian reticuloendotheliosis virus type A (REV-A) show that its IRES maps downstream of the packaging/dimerization (E/DLS) sequence and the minimal IRES sequence appears to be within a 129 nt fragment (452–580) of the 5' leader, immediately upstream of the gag AUG codon (Lopez-Lastra et al. (1997) *Hum Gene Ther* 8:1855–1865).

In eukaryotic cells, translation is normally initiated by the ribosome scanning from the capped mRNA 5' end, under the control of initiation factors. However, several cellular mRNAs have been found to be with IRES structure to mediate the cap-independent translation (van der Velde, et al. (1999) *Int J Biochem Cell Biol.* 31:87–106). Examples are immunoglobulin heavy-chain binding protein (BiP) (Macejak et al. (1991) *Nature* 353:90–94), antennapedia mRNA of Drosophilan (Oh et al. (1992) *Gene and Dev* 6:1643–1653), fibroblast growth factor-2 (FGF-2) (Vagner et al. (1995) *Mol Cell Biol* 15:35–44), platelet-derived growth factor B (PDGF-B) (Bernstein et al. (1997) *J Biol Chem* 272:9356–9362), insulin-like growth factor II (Teerink et al. (1995) *Biochim Biophys Acta* 1264:403–408), and the translation initiation factor eIF4G (Gan et al. (1996) *J Biol Chem* 271:623–626). Table 1 depicts the 5'-noncoding region for BiP and PDGF. Recently, vascular endothelial growth factor (VEGF) was also found to have IRES element (Stein et al. (1998) *Mol Cell Biol* 18:3112–3119; Huez et al. (1998) *Mol Cell Biol* 18:6178–6190).

Apart from the oligopyrimidine tract, nucleotide sequence per se does not appear to be important for IRES function. Without wishing to be bound by theory, a possible explanation for the function of an IRES is that it forms secondary and/or tertiary structures which orient particular single-stranded regions of its sequence in a three-dimensional configuration that is conducive to interaction with a mammalian ribosome (either ribosomal protein and/or ribosomal RNA components) and/or initiation factor(s) and/or RNA binding proteins which interact with ribosomes and/or initiation factors. It is also possible that the three-dimensional structure of the IRES is determined or stabilized by one or more RNA-binding proteins. Thus it is possible to devise synthetic IRES sequences having similar single-stranded regions in a similar three-dimensional configuration.

In certain cases, one or more trans-acting cellular proteins may be required for IRES function. For example, the HAV and entero/rhinovirus IRESes function inefficiently in vitro in reticulocyte lysates. Supplementation of a reticulocyte lysate with a cytoplasmic extract from HeLa, Krebs II ascites, or L-cells restores activity of entero/rhinovirus IRESes. See, for example, Brown et al. (1979) *Virology* 97:396–405; and Dorner et al. (1984) *J. Virol.* 50:507–514. Activity of the HAV IRES in vitro is stimulated by liver cytoplasmic extracts. Glass et al. (1993) *Virology* 193:1047–1050. These observations indicate that cell-specific translational regulation can be achieved through the use of a cell-specific IRES. Furthermore, coordinated cell-specific transcriptional and translational regulatory elements can be included in a vector to further increase cell specificity of viral replication. For example, the combination of an AFP-TRE and a HAV-IRES can be used to direct preferential replication of a vector in hepatic cells. Thus, in one illustrative embodiment, a vector comprises an AFP-TRE regulating the transcription of a bicistronic E1A-E1B mRNA in which E1B translation is regulated by an ECMV IRES. In another illustrative embodiment, the vector comprises a probasin-TRE regulating the transcription of a bicistronic E1A-E1B mRNA in which E1B translation is regulated by an ECMV IRES. In yet another illustrative embodiment, a vector comprises a CMV-TRE regulating the transcription of a bicistronic E1A-E1B mRNA in which E1B translation is regulated by an ECMV IRES. In examples disclosed herein, E1B has a deletion of the 19-kDa region.

Examples of IRES which can be used in the present invention include those provided in Table 12 and Table 13. In order to test for an IRES sequence which may be used in the present invention, a test vector is produced having a reporter gene, such as luciferase, for example, placed under translational control of an IRES to be tested. A desired cell type is transfected with the vector containing the desired IRES-reporter gene and an assay is performed to detect the presence of the reporter gene. In one illustrative example, the test vector comprises a co-transcribed chloramphenicol transferase (CAT) and luciferase encoding gene transcriptionally driven by a CMV promoter wherein the luciferase encoding gene is translationally driven by an IRES to be tested. Host cells are transiently transfected with the test vector by means known to those of skill in the art and assayed for the presence of luciferase.

IRES may be prepared using standard recombinant and synthetic methods known in the art, and as described in the Examples. For cloning convenience, restriction sites may be engineered into the ends of the IRES fragments to be used.

Adenovirus Early Genes

The adenovirus vectors of the invention comprise adenovirus genes under the control of a target cell-specific TRE. Preferably an adenovirus gene essential for replication. Any gene that is essential for adenovirus replication, such as E1A, E1B, E2, E4 or any of the late genes, is useful. The adenovirus may also comprise E3. In addition, one or more of the genes can be a transgene or heterologous gene. Any of the various adenovirus serotypes can be used, such as, for example, Ad2, Ad5, Ad12 and Ad40. For purposes of illustration, the Ad5 serotype is exemplified herein.

The E1A gene is expressed immediately (between 0 and 2 hours) after viral infection, before any other viral genes. E1A protein is a trans-acting positive transcriptional regulatory factor, and is required for the expression of the other early viral genes E1B, E2, E3, E4, and the promoter-proximal major late genes. Despite the nomenclature, the promoter proximal genes driven by the major late promoter are also expressed during early times after Ad5 infection. Flint (1982) *Biochem. Biophys. Acta* 651:175–208; Flint (1986) *Advances Virus Research* 31:169–228; and Grand (1987) *Biochem. J.* 241:25–38. In the absence of a functional E1A gene, viral infection does not proceed, because the gene products necessary for viral DNA replication are not produced. Nevins (1989) *Adv. Virus Res.* 31:35–81. The transcription start site of Ad5 E1A is at coordinate 498 and the ATG start site of the E1A protein is at coordinate 560 in the virus genome.

The E1B protein is necessary in trans for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey et al. (1993) *Virology* 193:631; Bailey et al. (1994) *Virology* 202:695–706. The E1B promoter of Ad5 consists of a single high-affinity recognition site for Spl and a TATA box, and extends from Ad5 nt 1636 to 1701.

Adenovirus E1B 19-kDa (19K) protein is a potent inhibitor of apoptosis and cooperates with E1A to produce oncogenic transformation of primary cells (Rao, et al., 1992, *Cell Biology*, 89:7742–7746). During productive adenovirus infection, E1A stimulates host cell DNA synthesis, thereby causing cells to aberrantly go through the cell cycle. In response to cell cycle deregulation, the host cell undergoes apoptosis. As a defense mechanism, the E1B 19-kDa protein inhibits this E1A-induced apoptosis and allows assembly of viral progeny to be completed before the cell commits suicide. E1B 19-kDa conducts anti-apoptotic function by multiple mechanisms. E1B 19-kDa inhibits the apoptosis of multiple stimuli, including E1a, p53 and TNF, for example. According to wild-type Ad5, the E1B 19-kDa region is located between nucleotide 1714 and nucleotide 2244. The E1B 19-kDa region has been described in, for example, Rao et al., *Proc. Natl. Acad. Sci. USA,* 89:7742–7746.

In a preferred embodiment, expression of the E1A and E1B regions of the Ad genome is facilitated in a cell-specific fashion by placing a cell-specific TRE upstream of E1A and a internal ribosome entry site between E1A and E1B.

The E2 region of adenovirus encodes proteins related to replication of the adenoviral genome, including the 72 kD DNA-binding protein, the 80 kD precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 early promoter of Ad5 is located between nucleotides 27,050 and 27,150, and consists of a major and a minor transcription initiation site (the latter accounting for about 5% of E2 transcripts), two non-canonical TATA boxes, two E2F transcription factor binding sites and an ATF transcription factor binding site. For a detailed review of E2 promoter architecture see Swaminathan et al. (1995) *Curr. Topics in Micro. and Imm.* 199 part 3:177–194.

The E2 late promoter overlaps with the coding sequences of a gene encoded by the counterstrand and is therefore not amenable for genetic manipulation. However, the E2 early promoter overlaps by only a few base pairs with sequences on the counterstrand which encode a 33 kD protein. Notably, an SpeI restriction site (Ad5 position 27,082) is part of the stop codon for the above mentioned 33 kD protein and conveniently separates the major E2 early transcription initiation site and TATA box from the upstream E2F and ATF binding sites. Therefore, insertion of a heterologous TRE having SpeI ends into the SpeI site disrupts the endogenous E2 early promoter of Ad5 and allows TRE-regulated expression of E2 transcripts.

An E3 region refers to the region of the adenoviral genome that encodes the E3 products. The E3 region has been described in various publications, including, for example, Wold et al. (1995) *Curr. Topics Microbiol. Immunol.* 199:237–274. Generally, the E3 region is located between about 28583 and about 30470 of the adenoviral genome. An E3 region for use in the present invention may be from any adenovirus serotype. An E3 sequence is a polynucleotide sequence that contains a sequence from an E3 region. In some embodiments, the sequence encodes ADP. In other embodiments, the sequence encodes other than ADP and excludes a sequence encoding only ADP. As is well known in the art, the ADP coding region is located in the E3 region within the adenoviral genome from about 29468 bp to about 29773 bp; including the Y leader, the location of ADP is from about 28375 bp to about 29773 bp for Ad5. Other ADP regions for other serotypes are known in the art. An E3 sequence includes, but is not limited to, deletions; insertions; fusions; and substitutions. An E3 sequence may also comprise an E3 region or a portion of the E3 region. It is understood that, as an "E3 sequence" is not limited to an "E3 region", alternative references herein to an "E3 region" or "E3 sequence" do not indicate that these terms are interchangeable. Assays for determining a functional E3 sequence for purposes of this invention are described herein.

The E4 gene has a number of transcription products and encodes two polypeptides (the products of open reading frames (ORFs) 3 and 6) which are responsible for stimulating the replication of viral genomic DNA and stimulating late gene expression, through interaction with heterodimers of cellular transcription factors E2F-1 and DP-1. The ORF 6 protein requires interaction with the E1B 55 kD protein for activity while the ORF 3 protein does not. In the absence of functional ORF 3- and ORF 6-encoded proteins, efficiency of plaque formation is less than $10^{-6}$ that of wild type virus.

To further increase cell-specificity of replication, it is possible to take advantage of the interaction between the E4 ORF 6 gene product and the E1B 55 kD protein. For example, if E4 ORFs 1–3 are deleted, viral DNA replication and late gene synthesis becomes dependent on E4 ORF6 protein. By generating such a deletion in a vector in which the E1B region is regulated by a cell-specific TRE, a virus is obtained in which both E1B and E4 functions are dependent on the cell-specific TRE which regulates E1B.

Late genes relevant to the disclosed vectors are L1, L2 and L3, which encode proteins of the virion. All of these genes (typically coding for structural proteins) are probably required for adenoviral replication. All late genes are under the control of the major late promoter (MLP), which is located in Ad5 between nucleotides 5986 and 6048.

In one embodiment, an adenovirus early gene is under transcriptional control of a cell specific, heterologous TRE. In additional embodiments, the early gene is selected from the group including E1A, E1B, E2, E3, E4. In another embodiment, an adenovirus late gene is under transcriptional control of a cell specific, heterologous TRE. In further embodiments, two or more early genes are under the control of heterologous TREs that function in the same target cell. The heterologous TREs can be the same or different, or one can be a variant of the other. In additional embodiments, two or more late genes are under the control of heterologous TREs that function in the same target cell. The heterologous TREs can be the same or different, or one can be a variant of the other. In yet another embodiment, one or more early gene(s) and one or more late gene(s) are under transcriptional control of the same or different heterologous TREs, wherein the TREs function in the same target cell.

In some embodiments of the present invention, the adenovirus vector comprises the essential gene E1A and the E1A promoter is deleted. In other embodiments, the adenovirus vector comprises the essential gene E1A and the E1A enhancer I is deleted. In yet other embodiments, the E1A promoter is deleted and E1A enhancer I is deleted. In other embodiments, an internal ribosome entry site (IRES) is inserted upstream of E1B (so that E1B is translationally linked), and a target cell-specific TRE is operably linked to E1A. In still other embodiments, an (IRES) is inserted upstream of E1B (so that E1B is translationally linked), and target cell-specific TRE is operably linked to E1A, which may or may not maintain the E1A promoter and/or enhancer I (i.e., the E1A promoter and/or enhancer I may be, but not necessarily be, deleted). In other embodiments, the 19-kDa region of E1B is deleted. For adenovirus vectors comprising a second gene under control of an IRES, it is preferred that the endogenous promoter of a gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and second gene are in frame. Alternatively, if the IRES does not contain an initiation codon or if the initiation codon is removed from the IRES, the initiation codon of the second gene is used.

Adenovirus Death Protein (ADP) Gene and Gene Product

In the construction of adenovirus vectors, the E3 region is often deleted to facilitate insertion of one or more TREs and/or transgenes. In some embodiments, however, the adenovirus death protein (ADP), encoded within the E3 region, is retained in an adenovirus vector. The ADP gene, under control of the major late promoter (MLP), appears to code for a protein (ADP) that is important in expediting host cell lysis. Tollefson et al. (1992) *J. Virol.* 66:3633; and Tollefson et al. (1996) *J. Virol.* 70:2296. Thus, inclusion of an ADP gene in a viral vector can render the vector more potent, making possible more effective treatment and/or a lower dosage requirement.

An ADP coding sequence is obtained preferably from Ad2 (since this is the strain in which the ADP has been most fully characterized) using techniques known in the art, such as PCR. Preferably, the Y leader (which is an important sequence for correct expression of late genes) is also obtained and placed in operative linkage to the ADP coding sequence. The ADP coding sequence (with or without the Y leader) is then introduced into an adenoviral genome, for example, in the E3 region, where expression of the ADP coding sequence will be driven by the MLP. The ADP coding sequence can, of course, also be inserted in other locations of the adenovirus genome, such as the E4 region. Alternatively, the ADP coding sequence can be operably linked to a heterologous TRE, including, but not limited to, another viral TRE or a target cell-specific TRE (see infra). In another embodiment, the ADP gene is present in a viral genome such that it is transcribed as part of a multi-cistronic mRNA in which its translation is associated with an IRES.

E3-containing Target Cell-specific Adenoviral Vectors

Figure 6:
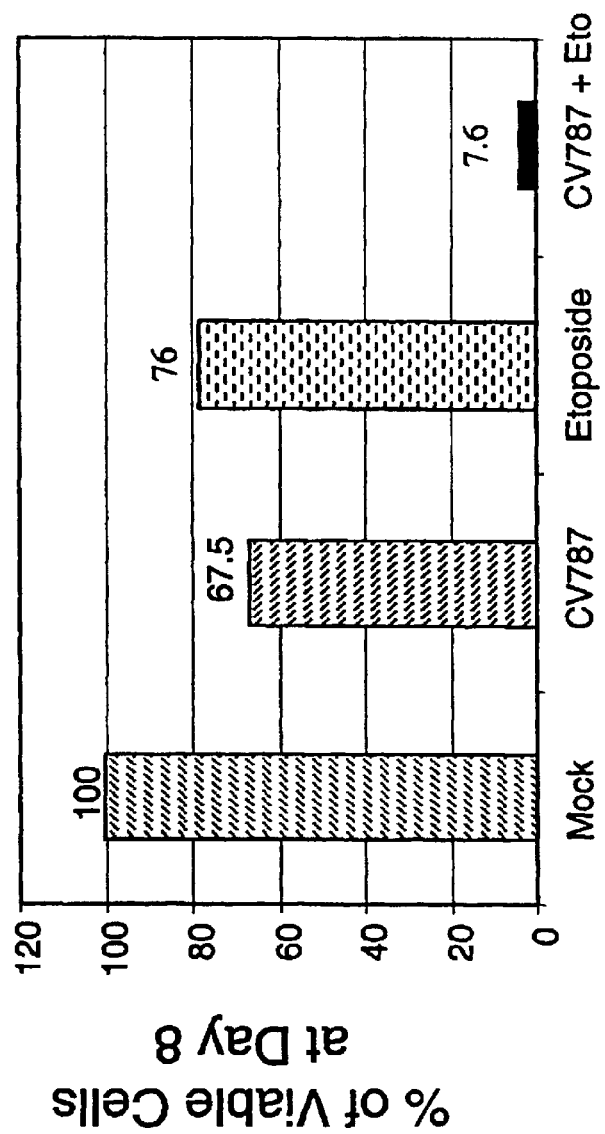
FIG. 6 is a bar graph depicting percent viable LNCaP prostate tumor cells with no treatment (mock); CV787 treatment (MOI 0.01); etoposide treatment (500 ng/ml); and CV787 plus etoposide (Eto) treatment on day 8 (Etoposide was administered first).

In some embodiments, the adenovirus vectors contain an E3 region, or a portion of an E3 region. Inclusion of the E3 region of adenovirus can enhance cytotoxicity of the target cell-specific adenoviral vectors of the present invention. Adenoviral vectors containing an E3 region may maintain their high level of specificity and can be (a) significantly more cytotoxic; (b) produce higher virus yield including extracellular virus yield; (c) form larger plaques; (d) produce rapid cell death; and (e) kill tumors more efficiently in vivo than vectors lacking the E3 region. The adenoviral vectors of this invention may contain the E3 region or a portion of the E3 region. It is understood that, as inclusion of E3 confers observable and measurable functionality on the adenoviral vectors, for example, increased replication and production, functionally equivalent (in which functionality is essentially maintained, preserved, or even enhanced or diminished) variants of E3 may be constructed. For example, portions of E3 may be used. A portion may be, non-inclusively, either of the following: (a) deletion, preferably at the 3' end; (b) inclusion of one or more various open reading frames of E3. Five proteins which are encoded by the Ad-E3 region have been identified and characterized: (1) a 19-kDa glycoprotein (gp19 k) is one of the most abundant adenovirus early proteins, and is known to inhibit transport of the major histocompatibility complex class I molecules to the cell surface, thus impairing both peptide recognition and clearance of Ad-infected cells by cytotoxic T lymphocytes (CTLs); (2) E3 14.7 k protein and the E3 10.4 k/14.5 k complex of proteins inhibit the cytotoxic and inflammatory responses mediated by tumor necrosis factor (TNF); (3) E3 10.4 k/14.5 k protein complex down regulates the epidermal growth factor receptor, which may inhibit inflammation and activate quiescent infected cells for efficient virus replication; (4) E3 11.6 k protein (adenoviral death protein, ADP) from adenovirus 2 and 5 appears to promote cell death and release of virus from infected cells. The functions of three E3-encoded proteins—3.6 k, 6.7 k and 12.5 k—are unknown. A ninth protein having a molecular weight of 7.5 kDa has been postulated to exist, but has not been detected in cells infected with wild-type adenovirus. Wold et al. (1995) *Curr. Topics Microbiol. Immunol.* 199:237–274. The E3 region is schematically depicted in FIG. 6. These intact, portions, or variants of E3 may be readily constructed using standard knowledge and techniques in the art. Preferably, an intact E3 region is used.

In the adenovirus vectors of the present invention, E3 may or may not be under transcriptional control of native adenoviral transcriptional control element(s). The E3 promoter is located within the coding sequence for virion protein VIII, an essential protein which is highly conserved among adenovirus serotypes. In some embodiments, E3 is under transcriptional control of a heterologous TRE, including, but not limited to, a target cell-specific TRE. Accordingly, in one embodiment, the invention provides an adenoviral vector, preferably replication competent, that comprises E3 region (or a portion of E3) under transcriptional control of a target cell-specific TRE. In other embodiments, the E3 region is under transcriptional control of a native adenoviral TRE, and the vector further comprises an adenoviral gene essential for replication under transcriptional control of a target cell-specific TRE. In other embodiments, the E3 region is under transcriptional control of a target cell-specific TRE, and the vector further comprises an adenoviral gene essential for replication under transcriptional control of a target cell-specific TRE.

Transgenes Under Transcriptional Control of a Target Cell-specific TRE

Various other replication-competent adenovirus vectors can be made according to the present invention in which, in addition to having a single or multiple adenovirus gene(s) under control of a target cell-specific TRE, a transgene(s) is/are also under control of a target cell-specific TRE and optionally under translational control of an IRES. Transgenes include, but are not limited to, therapeutic transgenes and reporter genes. Transgenes can be inserted into the adenoviral vector to produce, for example, certain chemotherapeutic agents, chemoprotectants, chemosensitizers, radioprotectants and radiosensitizers. Examples of such genes include, for example, genes encoding, p53, Adenovirus E1A, HSV-TK, Cytosine deaminase (CDA), Cytochrome p450, TAXOL™ or others.

Reporter Genes

For example, a target cell-specific TRE can be introduced into an adenovirus vector immediately upstream of and operably linked to an early gene such as E1A or E1B, and this construct may further comprise a second co-transcribed gene under translational control of an IRES. The second gene may be a reporter gene. The reporter gene can encode a reporter protein, including, but not limited to, chloramphenicol acetyl transferase (CAT), β-galactosidase (encoded by the lacZ gene), luciferase, alkaline phosphatase, a green fluorescent protein, and horse radish peroxidase. For detection of a putative cancer cell(s) in a biological sample, the biological sample may be treated with modified adenoviruses in which a reporter gene (e.g., luciferase) is under control of a target cell-specific TRE. The target cell-specific TRE will be transcriptionally active in cells that allow the target cell-specific TRE to function, and luciferase will be produced. This production will allow detection of target cells, including cancer cells in, for example, a human host or a biological sample. Alternatively, an adenovirus can be constructed in which a gene encoding a product conditionally required for survival (e.g., an antibiotic resistance marker) is under transcriptional control of a target cell-specific TRE. When this adenovirus is introduced into a biological sample, the target cells will become antibiotic resistant. An antibiotic can then be introduced into the medium to kill the non-cancerous cells.

Therapeutic Transgenes

Transgenes also include genes which may confer a therapeutic effect, such as enhancing cytotoxicity so as to eliminate unwanted target cells. In this way, various genetic capabilities may be introduced into target cells, particularly cancer cells. For example, in certain instances, it may be desirable to enhance the degree and/or rate of cytotoxic activity, due to, for example, the relatively refractory nature or particular aggressiveness of the cancerous target cell. This could be accomplished by coupling the target cell-specific cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin (Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J Biochem.* 148: 265; Frankel et al. (1989) *Mol Cell. Biol.* 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-$\alpha$, -$\beta$, -$\chi$, TNF-$\alpha$, -$\beta$, TGF-$\alpha$, -$\beta$, NGF, and the like. The positive effector genes could be used in an earlier phase, followed by cytotoxic activity due to replication.

Preparation of the Adenovirus Vectors

The adenovirus vectors of this invention can be prepared using recombinant techniques that are standard in the art. Generally, a target cell-specific TRE is inserted 5' to the adenoviral gene of interest, preferably an adenoviral replication gene, more preferably one or more early replication genes (although late gene(s) can be used). A target cell-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for a target cell-specific TRE. Accordingly, convenient restriction sites for annealing (i.e., inserting) a target cell-specific TRE can be engineered onto the 5' and 3' ends of a UP-TRE using standard recombinant methods, such as PCR.

Polynucleotides used for making adenoviral vectors of this invention may be obtained using standard methods in the art, such as chemical synthesis, recombinant methods and/or obtained from biological sources.

Adenoviral vectors containing all replication-essential elements, with the desired elements (e.g., E1A) under control of a target cell-specific TRE, are conveniently prepared by homologous recombination or in vitro ligation of two plasmids, one providing the left-hand portion of adenovirus and the other plasmid providing the right-hand region, one or more of which contains at least one adenovirus gene under control of a target cell-specific TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from a target cell-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003–6020; Bridge et al. (1989) *J. Virol.* 63: 631–638.

For convenience, plasmids are available that provide the necessary portions of adenovirus. Plasmid pXC.1 (McKinnon (1982) *Gene* 19:33–42) contains the wild-type left-hand end of Ad5. pBHG10 (Bett et al. (1994); Microbix Biosystems Inc., Toronto) provides the right-hand end of Ad5, with a deletion in E3. The deletion in E3 provides room in the virus to insert a 3 kb target cell-specific TRE without deleting the endogenous enhancer/promoter. The gene for E3 is located on the opposite strand from E4 (r-strand). PBHG11 provides an even larger E3 deletion (an additional 0.3 kb is deleted). Bett et al. (1994). Alternatively, the use of pBHGE3 (Microbix Biosystems, Inc.) provides the right hand end of Ad5, with a full-length of E3.

For manipulation of the early genes, the transcription start site of Ad5 E1A is at 498 and the ATG start site of the E1A coding segment is at 560 in the virus genome. This region can be used for insertion of a target cell-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of target cell-specific TRE at that site.

A similar strategy may also be used for insertion of a target cell-specific TRE element to regulate E1B. The E1B promoter of Ad5 consists of a single high-affinity recognition site for Sp1 and a TATA box. This region extends from Ad5 nt 1636 to 1701. By insertion of a target cell-specific TRE in this region, one can provide for cell-specific transcription of the E1B gene. By employing the left-hand region modified with the cell-specific response element regulating E1A, as the template for introducing a target cell-specific TRE to regulate E1B, the resulting adenovirus vector will be dependent upon the cell-specific transcription factors for expression of both E1A and E1B. In some embodiments, part or all of the 19-kDa region of E1B is deleted.

Similarly, a target cell-specific TRE can be inserted upstream of the E2 gene to make its expression cell-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Micro. and Immunol.* (1995) 199(part 3):177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor binding sites E2F and ATF. Therefore, insertion of a target cell-specific TRE having SpeI ends into the SpeI site in the 1-strand would disrupt the endogenous E2 early promoter of Ad5 and should allow target cell-restricted expression of E2 transcripts.

For E4, one must use the right hand portion of the adenovirus genome. The E4 transcription start site is predominantly at about nt 35605, the TATA box at about nt 35631 and the first AUG/CUG of ORF I is at about nt 35532. Virtanen et al. (1984) *J. Virol.* 51: 822–831. Using any of the above strategies for the other genes, a UP-TRE may be introduced upstream from the transcription start site. For the construction of full-length adenovirus with a target cell-specific TRE inserted in the E4 region, the co-transfection and homologous recombination are performed in W162 cells (Weinberg et al. (1983) *Proc. Natl. Acad. Sci.* 80:5383–5386) which provide E4 proteins in trans to complement defects in synthesis of these proteins.

Adenoviral constructs containing an E3 region can be generated wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 region can be introduced into cells, for example 293 cells, along with an adenoviral construct or an adenoviral plasmid construct, where they can undergo homologous recombination to yield adenovirus containing an E3 region. In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Insertion of an IRES into a vector is accomplished by methods and techniques that are known in the art and described herein supra, including but not limited to, restriction enzyme digestion, ligation, and PCR. A DNA copy of an IRES can be obtained by chemical synthesis, or by making a cDNA copy of, for example, a picornavirus IRES. See, for example, Duke et al. (1995) *J. Vvirol.* 66(3):1602–9) for a description of the EMCV IRES and Huez et al. (1998), *Mol. Cell. Biol.* 18(11):6178–90) for a description of the VEGF IRES. The internal translation initiation sequence is inserted into a vector genome at a site such that it lies upstream of a 5'-distal coding region in a multicistronic mRNA. For example, in a preferred embodiment of an adenovirus vector in which production of a bicistronic E1A-E1B mRNA is under the control of a target cell-specific TRE, the E1B promoter is deleted or inactivated, and an IRES sequence is placed between E1A and E1B. In other embodiments, part or all of the 19-kDa region of E1B is deleted. IRES sequences of cardioviruses and certain aphthoviruses contain an AUG codon at the 3' end of the IRES that serves as both a ribosome entry site and as a translation initiation site. Accordingly, this type of IRES is introduced into a vector so as to replace the translation initiation codon of the protein whose translation it regulates. However, in an IRES of the entero/rhinovirus class, the AUG at the 3' end of the IRES is used for ribosome entry only, and translation is initiated at the next downstream AUG codon. Accordingly, if an entero/rhinovirus IRES is used in a vector for translational regulation of a downstream coding region, the AUG (or other translation initiation codon) of the downstream gene is retained in the vector construct.

Methods of packaging polynucleotides into adenovirus particles are known in the art and are also described in co-owned PCT PCT/US98/04080.

The following examples are offered by way of illustration and should not be considered as limiting the scope of the invention. The specific examples exemplify the adenovirus 5 serotype, however, persons skilled in the art will realize these techniques may be applied to other adenoviral serotypes.

EXAMPLES

Table 4 summarizes descriptions of the various replication-competent target-cell specific adenoviral constructs used in these studies, and described previously herein. Preparation of these adenoviral vectors (including their components) employ standard techniques in the art. See also PCT/US99/03117, PCT/US98/16312, PCT/US98/04133, PCT/US98/04132, PCT/US98/04084, PCT/US98/04080, PCT/US97/13888, PCT/US96/10838, PCT/US95/00845. In these publications, a CV designation is also denoted as CN. For example, CV706 is also denoted as CN706.

TABLE 4

Summary Description of Adenoviral Constructs

| ADENO-VIRAL VECTOR | TARGET CELL TYPE | E1A TRE | E1B TRE | E3 +/− | E1A PRO-MO-TER | E1B PRO-MO-TER |
|---|---|---|---|---|---|---|
| CV706 | Prostate | PSE | N/A | − | + | + |
| CV787 | Prostate | PB | PSE | + | + | + |
| CV790 | Liver | AFP (0.827 kb) | AFP (0.827 kb) | + | + | + |
| CV829 | Bladder | hUPII | mUPII | + | − | + |
| CV859 | Melanoma | tyrosinase | IRES | + | − | − |
| CV873 | Colorectal Breast | CEA | IRES | + | − | − |
| CV874 | Bladder | mUPII (2 kb) | IRES | + | − | − |
| CV875 | Bladder | hUPII (1 kb) | IRES | + | − | − |

TABLE 4-continued

Summary Description of Adenoviral Constructs

| ADENO-VIRAL VECTOR | TARGET CELL TYPE | E1A TRE | E1B TRE | E3 +/− | E1A PRO-MO-TER | E1B PRO-MO-TER |
|---|---|---|---|---|---|---|
| CV876 | Bladder | hUPII (2 kb) | IRES | + | − | − |
| CV877 | Bladder | mUPII (1 kb) | hUPII (1 kb) | + | − | − |
| CV890 | Liver | AFP | IRES | + | − | − |
| CV884 | Bladder | hUPII (1.8 kb) | IRES | + | − | − |

For all constructs the E1A enhancer is present.

PSA, prostate specific enhancer/promoter; PB, rat probasin promoter; AFP, α-fetoprotein promoter; mUPII, mouse uroplakin II promoter; hUPII, human uroplakin II promoter; tyrosinase, melanocyte specific TRE; IRES, internal ribosome entry site.

Example 1

Treatment of in vitro Tumor Cells With Combined Prostate Cell Specific Adenoviral Vector CV787 and Chemotherapy and in vivo Assessment.

In vitro Assessment.

CV787 is a prostate-specific, replication competent adenovirus vector that preferentially replicates in prostate cancer cells. In this vector, E1A is under transcriptional control of a 452 bp PB TRE, and E1B is under transcriptional control of 1.6 kb PSA-TRE. CV787 alone can, in a single intratumoral dose ($1 \times 10^8$ particles per mm³ of tumor) or a single intravenous dose ($1 \times 10^{11}$ particles per animal) eliminate established tumors within 6 weeks in nude mouse xenografts. The data below demonstrate that CV787-mediated, replication-dependent oncolytic cytotoxicity can be enhanced in conjunction with standard chemotherapeutic agents including paclitaxel (TAXOL™), doxorubicin, mitoxantrone and docetaxel (TAXOTERE™), while the specificity of CV787-based cytopathogenicity remains specific to prostate cancer cells. These data suggest that the combination of CV787 with chemotherapy is more effective than chemotherapy treatment alone or virus treatment alone.

Cell Lines and Culture

The human LNCAP (prostate carcinoma), HBL-100 (breast epithelia), and OVCAR-3 (ovarian carcinoma) were obtained from the American Type Culture Collection (Rockville, Md.). The human embryonic kidney cell line, 293, which expresses the adenoviral E1A and E1B gene products serves as a production cell line, and was purchased from Microbix Biosystem, Inc. (Toronto, Canada). Cells were maintained at 37 C with 5% $CO_2$ in RPMI 1640 (Life Technologies, Gaithersburg, Md.) supplemented with 100 units/ml penicillin and 100 μg/ml of streptomycin (Life Technologies, Gaithersburg, Md.).

Chemotherapeutic Agents and Virus

Paclitaxel (TAXOL™, Bristol-Myers Squibb, Princeton, N.J.), docetaxel (TAXOTERE™, Rhone-Poulenc Rorer Pharmaceuticals, Inc., Collegeville, Pa.), and the chemotherapeutic agents listed in Table 5, were purchased from the Stanford University Hospital pharmacy (Palo Alto, Calif.). These agents were diluted with medium without fetal bovine serum (FBS) just before use for in vitro studies and with 0.9% NaCl for in vivo studies.

CV787 is a prostate-specific replication-competent adenovirus. Yu et al. (1999) *Cancer Res.* 59:4200. Two prostate-specific transcription response elements (TRE), the rat probasin promoter and the human prostate-specific antigen (PSE) promoter/enhancer, were inserted upstream of the E1A and E1B encoding regions in the viral genome, respectively, using methods known in the art. The expression of the E1A gene and the E1B gene are then controlled by these TREs.

Combination Study of CV787 With Paclitaxel (TAXOL™), Docetaxel (TAXOTERE™) or Other Chemotherapeutic Agents in vitro In preliminary experiments, we examined the chemosensitivity to different agents, as well as the oncolytic effect of CV787 in the prostate carcinoma LNCaP cells. Cells were plated in 96-well plates at a density of 20,000 cells per well. Twenty-four hours later, the cells were infected with CV787 at various multiplicities of infection (MOI). Subsequently, medium (50 μl) containing 10% heat-inactivated serum and various concentrations of chemotherapeutic agents were added to the appropriate wells. Cells were incubated at 37° C. in 5% $CO_2$ for an additional two days. Cell viability was measured using the MTT assay. Mosmann et al., (1983). Briefly, 50 μl of 1 mg/ml MTT vital dye (Sigma, St. Louis, Mo.) was added to each well and allowed to incubate for 3 h at 37° C. and 5% $CO_2$. Then, plates were drained to remove untransformed MTT and blot. 100 μl of isopropanol was added to each well, the plate was incubated for 15 minutes and vigorously shaken (Microshaker II, Dynatech) in order to ensure solubilization of the blue formazan. The optical density of each well was quantitated using an automatic plate reader (Molecular Devices, Sunnyvale, Calif.) with a 560 nm test wavelength and 690 nm reference wavelength. Cell viability was defined as the ratio of the mean absorbance of 9 treatment wells minus the blank to the mean absorbance of 6 untreated matched controls minus the blank. Blank is defined as the mean absorbance of six wells containing medium alone. Each experiment was performed at least twice.

Other chemotherapeutics were tested, using the protocols described above.

Results of in vitro Experiments

Figure 1A:
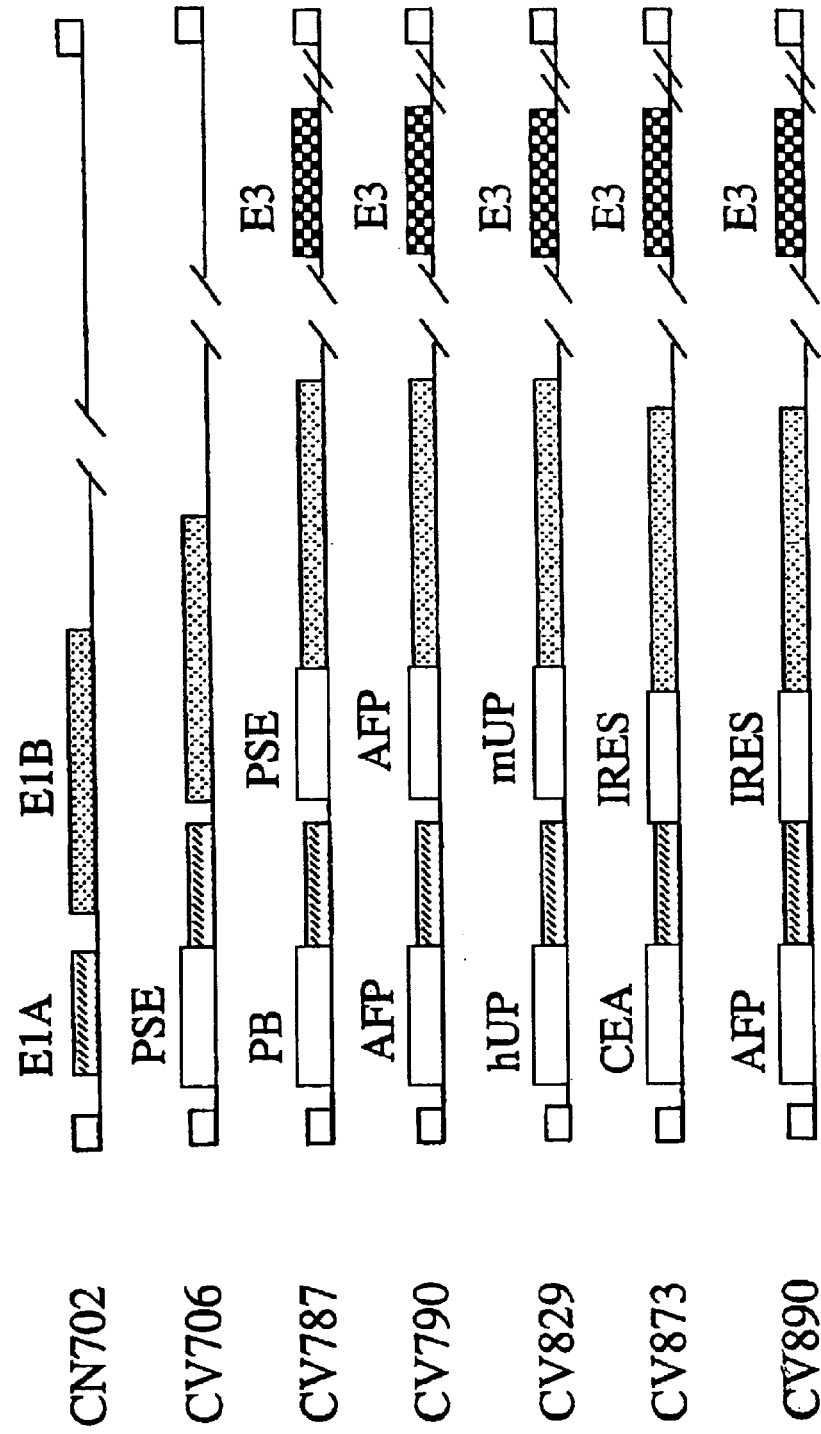
FIGS. 1A–1B is a schematic depicting target cell-specific adenovirus vectors described in the Examples.
Figure 1B:
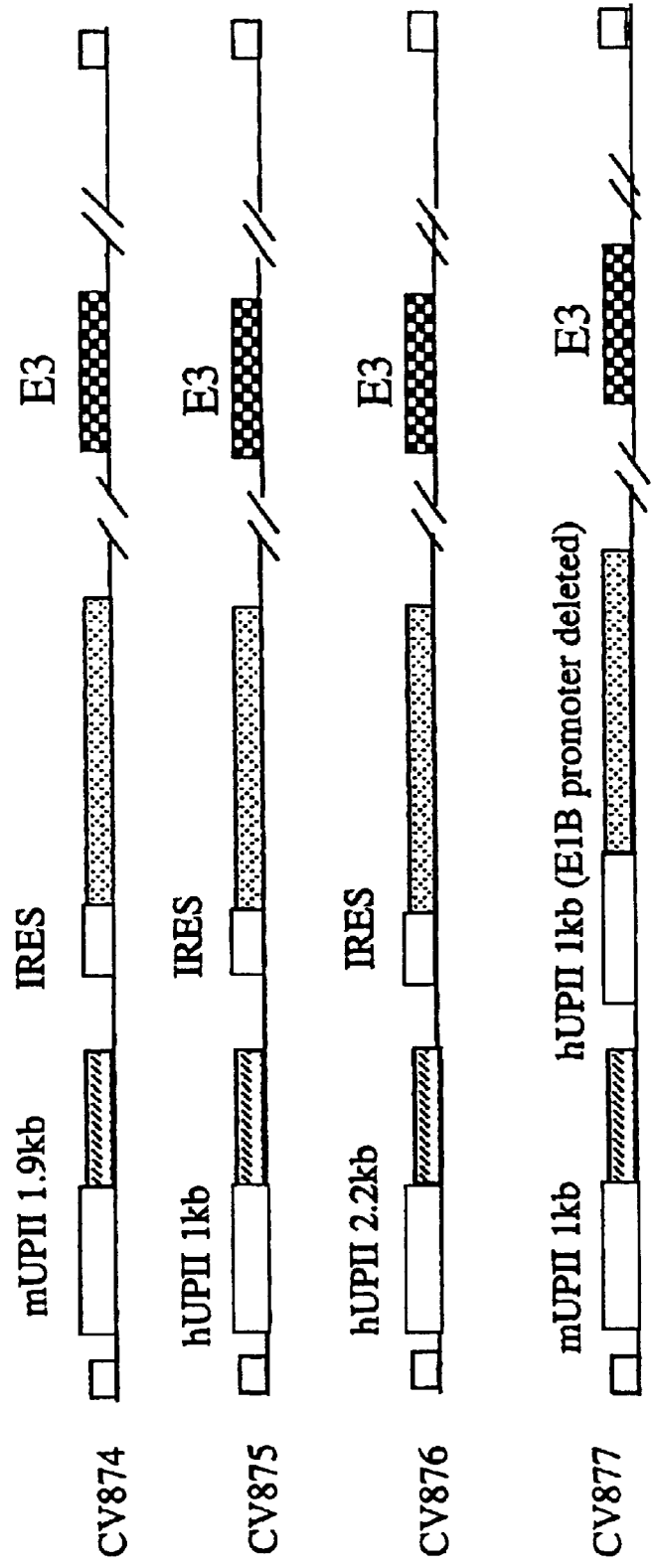
Figure 2:
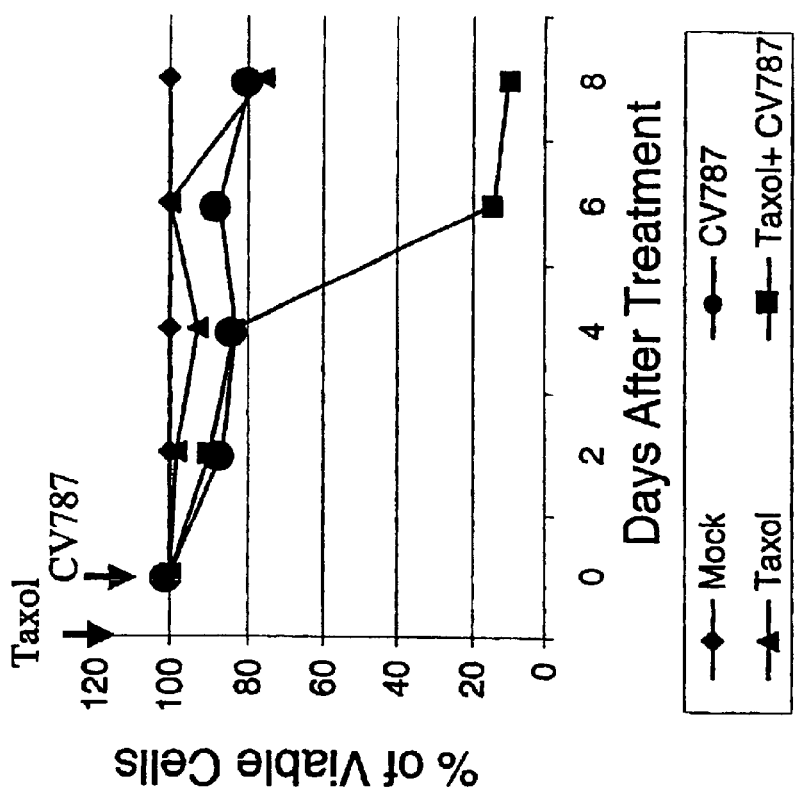
FIG. 2 is a graph depicting percent viable LNCaP prostate tumor cells treated with CV787 adenovirus vector (solid circles; MOI 0.01); CV787 and TAXOL™ (paclitaxel; solid squares); TAXOL™ alone (solid triangles; 6.25 nM) and mock infected control (diamonds). For the combined administration of CV787 and TAXOL™, TAXOL™ was administered first, 24 hrs prior to CV787.
Figure 3:
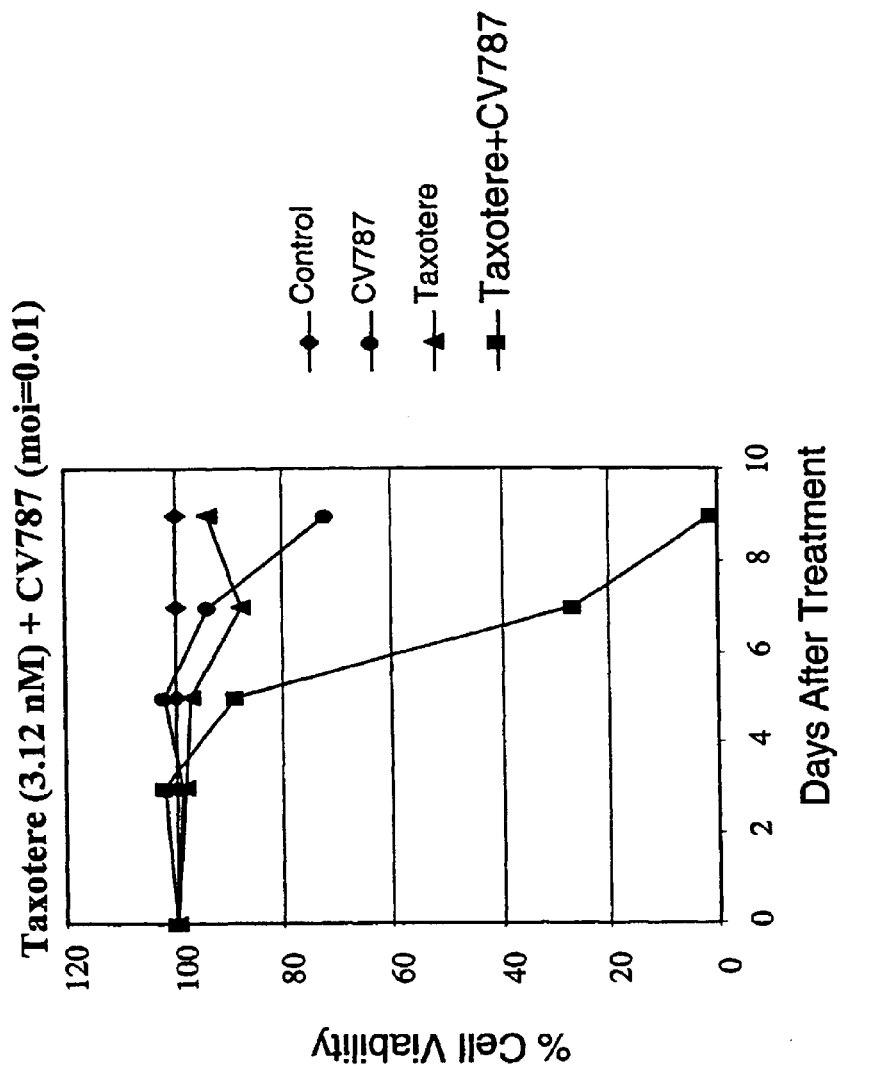
FIG. 3 is a graph depicting percent viable LNCaP prostate tumor cells treated with CV787 adenovirus vector (solid circles; MOI 0.01); CV787 and TAXOTERE™ (docetaxel; solid squares;); TAXOTERE™ alone (triangles; 3.12 nM); and mock infected control (diamonds) In the combination administration, TAXOTERE™ was administered first.
Figure 4:
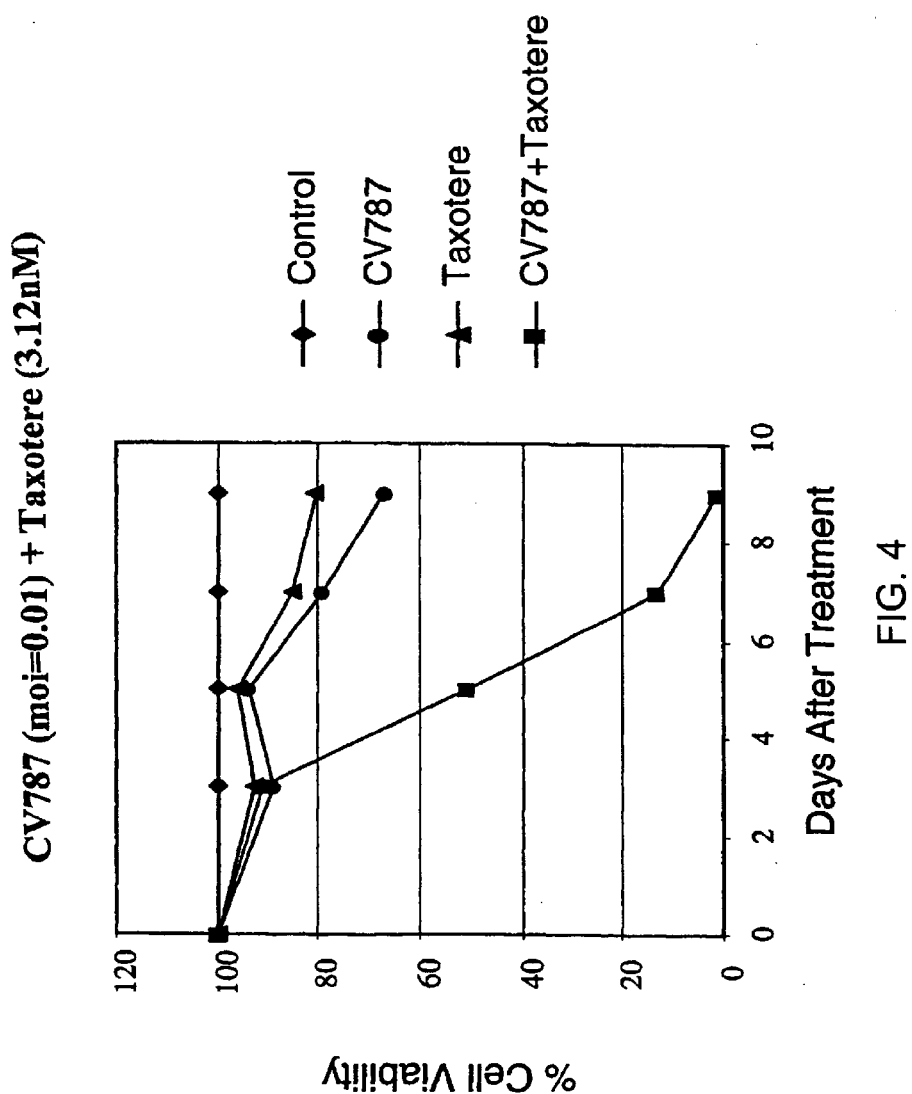
FIG. 4 is a graph depicting percent viable LNCaP prostate tumor cells treated with CV787 adenovirus vector (solid circles; MOI 0.01); CV787 and TAXOTERE™ (docetaxel; solid squares); TAXOTERE™ alone (triangles; 3.12 nM); and mock infected control (diamonds) For the combination administration, CV787 was added first.
Figure 5:
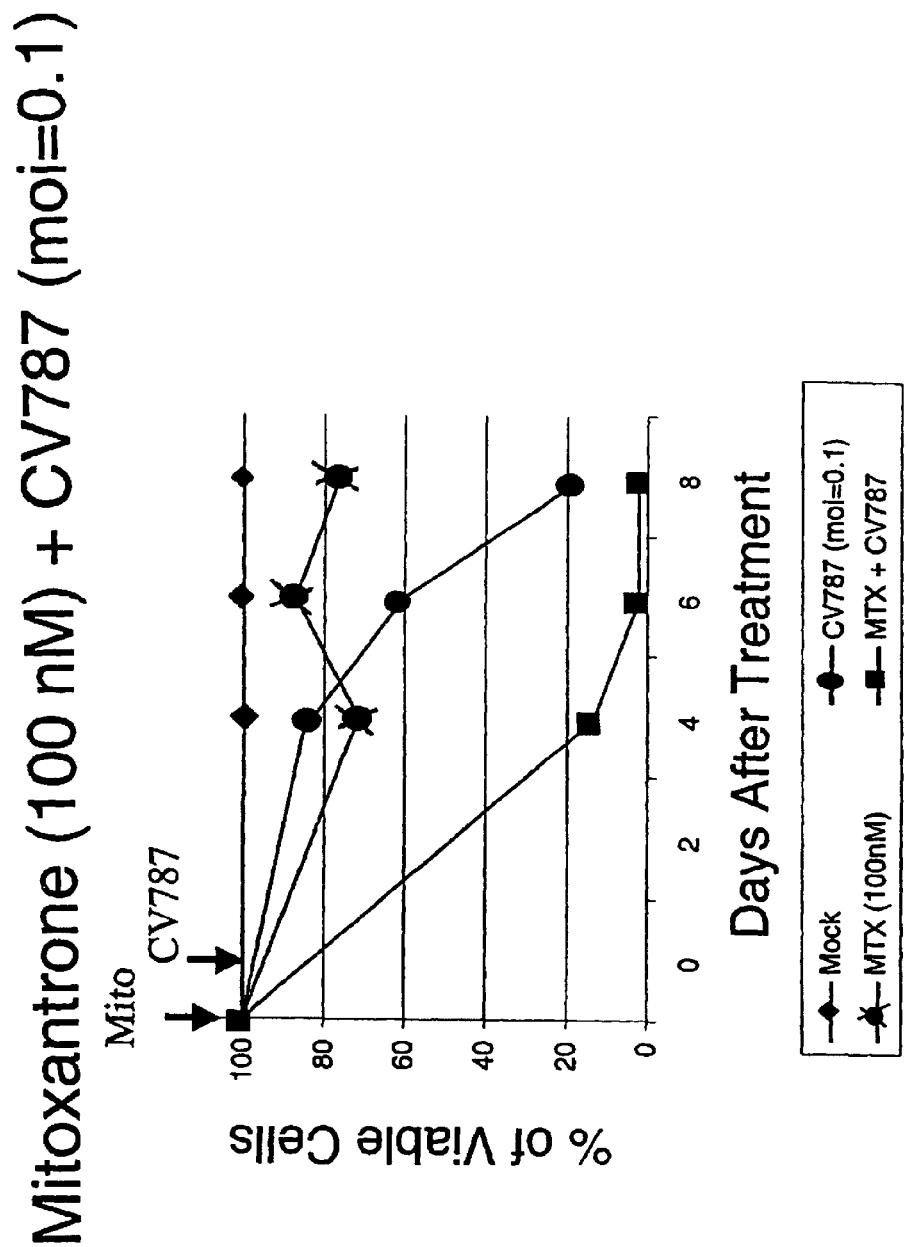
FIG. 5 is a graph depicting percent viable LNCaP prostate tumor cells treated with CV787 adenovirus vector (solid circles; MOI 0.1); CV787 and mitoxantrone (MTX; solid squares;); MTX alone (solid circles with "X"; 100 nM); and mock infected control (diamonds). For the combination administration, Mitoxantrone was administered first, 24 hrs prior to CV787.

To study potential synergy or enhancement in treatment when administering CV787 and chemotherapy in vitro, the effectiveness of the combined treatment at several concentrations of paclitaxel, ranging from 0–62.5 nM, or docetaxel, ranging from 125–250 nM, with CV787 at various MOIs, ranging from 0–10 MOI, was evaluated in the prostate carcinoma LNCaP cells. Cells were treated with CV787 and paclitaxel or docetaxel and the cell viability was determined at various time points after treatment by an MTT assay, as shown in FIGS. 2–4. FIG. 2 presents data for treatment with a combination of CV787 (MOI 0.01) and paclitaxel (6.25 nM), showing the synergistic cytotoxicity of the combination treatment compared to virus alone or chemotherapy alone. An enhanced cytotoxicity was observed in the combination treatment between CV787 and paclitaxel. For example, CV787 at an MOI of 0.01 produced 85% cell survival 6 days after virus infection and paclitaxel at 6.25 nM showed 100% survival in LNCaP. When CV787 and paclitaxel were combined at these concentrations, cell survival dropped to 18%, demonstrating a greater effect than just an additive effect. To determine whether the timing of administration for the testing articles affected the combined oncolytic effect, LNCaP cells were treated with paclitaxel for 24 hours before or after infection with CV787. Results showed that there were no significant differences in oncolytic activity between cells treated with paclitaxel before or after infection with CV787.

Cytotoxicity was also measured for the combination treatment of CV787 and docetaxel, FIGS. 3 and 4, and synergistic effects were observed. LNCaP cells were infected with CV787 at an MOI of 0.01 after a 24 hour incubation with docetaxel at 3.12 nM and cell viability was determined by MTT, as shown in FIG. 3. The cell survival was 25% of the control at day 7 post treatment, whereas CV787 alone produced 95% cell survival and docetaxel alone showed 95% cell survival in prostate carcinoma LNCaP cells. No significant difference in the effectiveness of the combined therapy of docetaxel and CV787 infection was observed by varying the time of virus administration. As presented in FIG. 3, LNCaP cells treated with docetaxel for 24 hours, then infected with CV787 produced similar cell viability to the treatment of which the LNCaP cells were infected with CV787 24 hours prior to docetaxel FIG. 4.

The protocols described above were used to screen a number of different chemotherapeutic agents from various classes of chemotherapeutics. The results are presented in FIGS. 5–9 and are summarized in Table 5, below. The summarized results are for experiments in which drug was added 24 hours before the introduction of the virus, except in the case of doxorubicin, in which the virus was added 24 hours prior to the administration of the drug. FIGS. 3–4 compare the order of administration for a combination of docetaxel and CV787. CV787 was administered at MOI of either 0.1 or 0.01 as indicated in FIGS. 5–9. Chemotherapeutics were administered in the following amounts: paclitaxel (6.25 nM); docetaxel (3.12 nM); mitoxantrone (100 nM); etoposide (500 ng/ml); doxorubicin (50 ng/ml); cisplatin (8.25 $\mu$M); 5-fluorouracil (35 $\mu$M); estramustine (5 mg/ml); gemcitabine (50 ng/ml); flutamide (15 ng/ml); goserelin (50 $\mu$g/$\mu$g); leuprolide (5 nM); and vinblastine (80 mg/ml).

TABLE 5

Synergistic Effects of CV787/Chemotherapeutic Combinations

| VIRUS | TARGET/ CELL LINE | CHEMOTHERAPEUTIC AGENT | CLASS OF AGENT | SYNERGY |
|---|---|---|---|---|
| CV787 | Prostate cancer/ LNCaP | 5-Fluorouracil (5-FU) | Antimetabolites (acting as pseudosubstrate for essential enzymatic reactions) | Yes |
| CV787 | Prostate cancer/ LNCaP | Cisplatin | Alkylating agent (Plantinum-containing agents - Causing single- and double-strand break in DNA) | Yes |
| CV787 | Prostate cancer/ LNCaP | Doxorubicin | Antibiotics (anticycline; interrupting DNA replication and transcription, causing strand break) | Yes |
| CV787 | Prostate cancer/ LNCaP | Estramustine | Alkylating agent | Yes |
| CV787 | LNCaP | Etoposide | Plant alkaloid (inhibiting the assembly of microtubules and disrupting mitosis | Yes |
| CV787 | Prostate cancer/ LNCaP | Mitoxantrone | Antibiotics (anticycline) | Yes |
| CV787 | Prostate cancer/ LNCaP | TAXOTERE ™ (docetaxel) | Plant alkaloids | Yes |
| CV787 | Prostate cancer/ LNCaP | TAXOL ™ (paclitaxel) | Plant alkaloids | Yes |
| CV787 | Prostate cancer/ LNCaP | Gemcitabine | Antimetabolite | No |
| CV787 | Prostate cancer/ LNCaP | Flutamide | Anti-androgen | No |
| CV787 | Prostate cancer/ LNCaP | ZOLADEX ™ (goserelin) | Hormonal analog | No |
| CV787 | Prostate cancer/ LNCaP | LUPRON ™ (leuprolide) | Testosterone analog | No |
| CV787 | Prostate cancer/ LNCaP | Vinblastine | Plant alkaloids | No |

The following experiments were designed to test the specificity and viability of the replication-competent target cell-specific adenoviral vectors described herein in the presence of antineoplastic (chemotherapeutic) agents.

Virus Yield

Virus yield was determined to characterize the specificity of combination treatment of CV787 and paclitaxel or docetaxel. 5×10$^5$ 293, LNCaP, HBL-100 and OVCAR-3 cells were plated in duplicate into six-well plates. Twenty-four hours later, medium was aspirated and replaced with 1.0 ml of serum-free RPMI 1640 containing CV787 at a MOI of 1 PFU (plaque-forming unit) per cell. After a 4 hour incubation at 37° C. with 5% $CO_2$, cells were washed twice with pre-warmed phosphate buffered saline (PBS), and 2 ml of complete RPMI 1640 containing the indicated chemotherapeutic agents were added into each well in concentrations and amounts as indicated below. After an additional 72 hours, the cells were scraped into the culture medium, and the cells were lysed by three freeze-thaw cycles. The supernatant of each duplicate point was tested for virus production by triplicate plaque assay for 12 days under semisolid agarose on 293 cells. Yu et al. *Cancer Research* (1999) 59:1698.

Paclitaxel Does Not Inhibit CV787 Replication

Paclitaxel (TAXOL™) and docetaxel (TAXOTERE™) are antineoplastic agents belonging to the taxoid family. They are novel antimicrotubule agents that promote the assembly of microtubules from tubulin dimers and stabilize microtubules by preventing depolymerization. This stability results in the inhibition of the normal dynamic reorganization of the microtubule network that is essential for vital interphase and mitotic cellular functions. In addition, they induce abnormal arrays or "bundles" of microtubules throughout the cell cycle and multiple asters of microtubules during mitosis.

To examine the effect of paclitaxel on the virus replication, we ran a virus yield assay. LNCAP cells were infected with CV787 at a MOI of 0.1 for 4 hours, followed by incubation in RPMI 1640 containing paclitaxel at a final concentration of 6.25 nM. Cells were harvested 6 days post-infection and the number of infectious virus particles were determined on 293 cells by a standard plaque assay. As shown in the Figures, cells treated with CV787 and paclitaxel produced 7,000 pfu per cell, while the cells infected with CV787 alone generated about 4,600 pfu per cell, suggesting that paclitaxel does not inhibit CV787 replication.

In addition, the chemotherapeutics mitoxantrone, doxorubicin and etoposide were also tested with CV787 according to the above protocol. None of these chemotherapeutics, from different classes of agents, showed a reduction in viral yield compared to CV787 without chemotherapeutic agent.

Paclitaxel Does Not Alter CV787's Specificity

In order to evaluate whether addition of paclitaxel could change the specificity of CV787's oncolytic activity, we tested viral replication efficiency in four cell lines including a permissive cell line LNCaP, and two non-permissive cell lines, HBL-100 (breast epithelia) and OVCAR-3 (ovarian carcinoma). These three cell lines were infected with either CV787 at an MOI of 0.1 or CV787 and paclitaxel, with a final paclitaxel concentration of 6.25 nM in the medium. Progeny virus yield was determined 48 hours after infection by plaque assay on 293 cells. Results presented in FIG. 12 show that prostate cancer (LNCaP) treated with CV787 and paclitaxel produced a similar burst size to the cells infected with CV787 alone, which produced about 800 pfu per cell. CV787 replicated poorly in the non-prostate cancer cells tested (HBL-100 and OVCAR-3), producing 1000 to 10,000-fold lower virus yield compared to the burst size in LNCaP cells. Interestingly, the burst size in the LNCaP cells treated with CV787 and paclitaxel is similar to that in the cells infected by CV787 alone. These data indicate that CV787 in the presence of paclitaxel replicates efficiently in prostate cancer cells, but is still attenuated in non-prostate cancer cells. Combination treatment does not change CV787 replication efficiency in the non-prostate cells and retains a high selectivity. Similar results were obtained for combinations of CV787 and mitoxantrone (MXT) and doxorubicin (DOXO).

To further assess the specificity of the combination treatment of CV787 and paclitaxel, the viability of various infected cells was estimated using the MTT assay to measure mitochondrial activity. HEK-293, LNCaP, HBL-100 and OVCAR-3 cells were infected with CV787 at an MOI of 0.1 in the presence or absence of paclitaxel. The percentage of cell viability in the combination treatment group versus paclitaxel treatment group was plotted in FIG. 13. Combination of CV787 and paclitaxel was toxic to 293, a permissive production cell line, and LNCaP cells, prostate cancer cells, but not to HBL-100, normal breast epithelial cells, and OVCAR-3 cells, ovarian cancer cells. There were no surviving LNCaP cells 9 days after infection. In contrast, the viability of HBL-100 and OVCAR-3 cells treated with CV787 and paclitaxel was similar to that of cells treated with paclitaxel (ratio of cell survival between combination group and paclitaxel group was approximately 1). The results suggest that the presence of paclitaxel does not alter the cytotoxic effect of CV787.

Similar results were observed using the above protocols and a combination of CV787 and mitoxantrone FIG. 14.

In vivo Assesment

Using the PSA+ LNCaP xenograft model of prostate cancer, a single i.v. dose of $1 \times 10^8$ particles CV787 and docetaxel in combination eliminates large pre-existent distant tumors. Toxicity studies do not show a synergistic increase of toxicity of CV787 and taxane. These experiments demonstrate a synergistic antitumor efficacy for CV787 when combined with taxane, and demonstrate an in vivo single-does curative therapeutic index for CV787 of over 1000:1.

Cell Viability

MTT assays were performed by seeding LNCaP, HBL-100, OVCAR-3, HepG2, and 293 cells at 5000 cells per well in a 96 well plate (Falcon) 48 hr prior to infection as previously described (Denizot, 2000, *J Immunol. Methods* 89:271–7.) with modifications. Cells were either infected with CV787 at an MOI of 2 PFU/cell or treated with the indicated chemotherapeutic agents (Paclitaxel at 6.25 nM and Docetaxel at 3.12 nM). Cell viability was measured at the times indicated by removing the media and replacing it with 50 $\mu$l of a 1 mg/ml solution of MTT (3-(4,5-Dimethylthiazol-2-yly 2,5-diphenyl-2H-tetrazolium bromide) (Sigma, St. Louis, Mo.) and incubating for 3 hrs at 3 hrs at 37° C. After removing the MTT solution, the crystals remaining in the wells were solubilized by the addition of 50 $\mu$l of isopropanol followed by vigorous shaking. The absorbency was determined using a microplate reader (Molecular Dynamics) at 560 nm (test wavelength) and 690 nm (reference wavelength). The percentage of surviving cells was estimated by dividing the $OD_{550}$-$OD_{650}$ of virus infected cells by the $OD_{550}$-$OD_{650}$ of mock infected cells. 12 replica samples were taken for each time point and each experiment was repeated at least three times.

Statistical Analysis

The dose-response interactions between taxane and CV787 at the point of $IC_{50}$ were evaluated by the isobologram method of Steel and Peckham (Steel, 1993, *Int. J. Rad. Onc. Biol. Phys.* 5:85.) as modified by Aoe et al. (Aoe, K. et al. 1999, *Anticancer Res.* 19:291–299.) The $IC_{50}$ was defined as the concentration of drug that produced 50% cell growth inhibition, i.e. 50% reduction in absorbance. Cells were exposed to drugs sequentially for 24 h and cell viability was determined by the MTT assay after 6 days. The dose-response curves were plotted with CurveExpert (Version 1.34) on a semilog scale as a percentage of the control, the absorbance of which was obtained from the samples not exposed to the drugs. $IC_{50}$ value of CV787 and taxane in LNCaP was then determined. Based upon the dose-response curves of CV787 alone and taxane alone, isobolograms (three isoeffect curves, model 1 and model 2 lines) were computed. The envelope of additivity, surrounded by model 1 and model 2 isobologram lines, was constructed from the dose response curves of CV787 alone and taxane alone. The observed data were compared with the predicted maximum and minimum data for presence of synergism, additivity, or antagonism by a statistical analysis using the Stat View 4.01 software program (Abacus Concepts, Berkeley, Calif.). When the data points of the drug combination fall within the area surrounded by model 1 and/or model 2 lines (i.e. within the envelope of additivity), the combination is described as additive. A combination that gives data points to the left of the envelope of additivity can be described as supraadditive (synergism) and a combination that gives data points to the right of the envelope of additivity, can be described as subadditive (antagonistic) (Kano, Y. et al. 1998, *Cancer Chemo. Pharm.* 42:91–98.) Fractional tumor volume (FTV) relative to untreated controls was determined as described previously (Yokoyama, Y. et al., 2000, *Cancer Res.* 60:2190–2196.).

One-step Growth Curve and Virus Yield

One-step growth curves of CV787 in the presence or absence of docetaxel were performed in LNCAP cells to determine burst size. Monalayers of LNCaP cells were infected at a multiplicity of 2 PFU/cell with CV787. After a 4 hour incubation at 37° C. with 5% $CO_2$, cells were washed twice with pre-warmed PBS, and 2 ml of complete RPMI 1640 containing docetaxel at a concentration of either 0 nM or 3.12 nM was added into each well. At the indicated times thereafter, duplicate cell samples were harvested and lysed by three cycles of freeze-thawing. Virus was titered in triplicate (Yu, D. -C. et al., 1999, *Cancer Res.* 59:1498–1504.).

Virus yield was used to determine if CV787 retained specificity in the combination treatment of CV787 and taxane. $5 \times 10^5$ cells of 293, LNCaP, HBL-100, HepG2 and OVCAR-3 were plated in duplicate into six-well plates. Twenty-four hours later, medium was aspirated and replaced with 1.0 mi of serum-free RPMI 1640 containing CV787 at an MOI of 1 PFU (plaque-forming unit) per cell. After a 4 hour incubation at 37° C. with 5% CO2, cells were washed twice with pre-warmed PBS, and 2 ml of complete RPMI 1640 containing the indicated taxane was added to each well. After an additional 72 hours, cells were scraped into the culture medium, and lysed by three freeze-thaw cycles. Virus production was monitored by triplicate plaque assay (Yu, D. -C., et al., 1999, *Cancer Res.* 59:1498–1504.).

Immunoblots

LNCaP cells treated with CV787, taxane, or both CV787 and taxane, were incubated for the indicated times. Cells were washed with cold PBS, and lysed for 30 min on ice in 50 mM Tris, pH8.0, 150 mM NaCl, 1% IGEPAL CA360 (NP40 equivalent from Sigma), 0.5% sodium deoxycholate, and protease inhibitor cocktail (Roche, Palo Alto, Calif.). After 30 min centrifugation at 4° C., the supernatant was removed and protein concentration was determined by the ESL protein assay kit (Roche). Fifty micrograms of protein/lane were separated on 8–16% SDS-PAGE and electroblotted onto Hybond ECL membranes (Amersham Pharmacia, Buckinghamshire, England). The membrane were blocked overnight in PBST (PBS with 0.1% Tween-20) supplemented with 5% nonfat dry milk. Primary antibody incubation was done at room temperature for 2–3 hrs with PBST/1% nonfat dry milk diluted antibody, followed by wash and 1 hr incubation with diluted horseradish peroxidase-conjugated secondary antibody. Enhanced chemiluminescence (ECL; Amersham Pharmacia) was used for detection. Antibodies for p53 and poly-ADP-ribose-polymerase were from Roche. Antibodies against Fas/Fas-L, caspase 7, Bcl-2, Bcl-XL, Bax and secondary antibodies were purchased from Santa Cruz Biotechnology Inc. (Santa Cruz, Calif.). All antibodies were used according manufacturer's instruction. For quantifying the bands, the gels were scanned and bands were analyzed by Multi-Analyst software (Blo-Rad).

In vivo Antitumor Efficacy

Six to eight week old athymic Balb/c nu/nu mice were obtained from Simonson Laboratories (Gilroy, Calif.) and acclimatized to laboratory conditions one week prior to tumor implantation. Xenografts were established by injecting $1 \times 10^6$ LNCaP cells, suspended in 100 µd of RPM1 1640 and 100 µd of matrigel, subcutaneously near the small of the back. When tumors reached between 400 $mm^3$ and 600 $mm^3$, mice were randomized into groups of four. The first group received $1 \times 10^{10}$ particles of CV787 at day 1 via the tail vein intravenously (i.v.). CV787 was diluted in 0.1 ml lyophilized buffer (5% sucrose, 1% glycine, 1 mM $MgCl_2$, 0.05% Tween-80 in 10 mM Tris buffer) and injected into the tail vein using a 28-gauge needle. The second group was given taxane only. Paclitaxel was intraperitoneally administered at a dose of 20 mg/kg, daily for 4 days starting at day 2. Docetaxel was intravenously administered at a dose of 5 or 12.5 mg/kg at day 2, 5 and 8. The third group was given CV787 (i.v.) at day 1 and taxane at the same doses and schedule as the second group. As a control, a fourth group was treated with 0.1 ml of normal saline (i.e. control) i.v. at day 1 and then i.p. or i.v. for 4 days. The dose and route of administration of paclitaxel were selected according to studies in nude mice (Riondel, J. et al., 1986, *Cancer Chemother Pharmacol.* 17:137–42.) (Chahinian, A. P. et al.,1998, *J. Surg. Onc.* 67:104–111.). For docetaxel, the dose was selected based on the human clinical dose.(RPR Pharm. Inc., Collegeville, Pa.) and determined by a dose-range finding study in nude mice. Tumors were measured weekly in two dimensions by external caliper and volume was estimated by the formula [length (mm)×width $(mm)^2$]/2 (7). Animals were humanely killed when their tumor burden became excessive. Serum was harvested weekly by retro-orbital bleed. The difference in mean tumor volume between treatment groups was compared for statistical significance using the unpaired, two-tailed, t-test. Blood samples were collected at various time points for determining prostate-specific antigen. Federal and institutional guidelines for animal care were followed.

Immunohistochemistry

Four groups of mice (n=6) were treated with vehicle, CV787 ($1 \times 10^{10}$ particles per animal), paclitaxel (15 mg/kg) or a combination of CV787 and paclitaxel at these identical doses. Half the animals were sacrificed on day 9 and the other half on day 16. Tumors were fixed in 10% neutral buffered formalin, embedded in paraffin and sectioned using standard procedures. For detecting adenovirus, tissue sections were blocked with ready-to-use normal rabbit serum (Biogenex, San Carlos, Calif.) for 20 min and incubated with goat anti-Ad antibody (Biodesign International, Kennebunkport, Me.) diluted 1:200 in PBS for 30 min. Alkaline phosphatase staining was performed using Super Sensitive™ streptaviden-blotin alkaline phosphatase reagents and Fast Red™ chromogen (Biogenex) as suggested by the manufacturer. Sections were counterstained with Gill's hematoxylin and mounted with Gel Mount™ (Biomedia, Foster City, Calif.).

Apoptotic cells were detected using M30 monoclonal antibody with reagents from the M30 CytoDEATH™ kit (Roche Molecular Biochemicals, Indianapolis, Ind.) as suggested by the manufacturer. Paraffin-embedded tumor sections were heated in citric acid buffer for 15 min to retrieve antigen, hybridized with M30 antibody, then counterstained with Harries hematoxylin (Roche Molecular Biochemicals). The stained sections were analyzed under a light microscope and pictures of representative sections taken.

Isobolograms were also generated to show the synergy between CV787 and docetaxel. Dose-response curve analysis indicated that the $IC_{50}$ at day 5 in LNCaP cells for CV787 and docetaxel was 0.368 MOI and 8.14 nM, respectively. The combined data points fell to the left of the envelope of additivity, or restated the IC50 in LNCaP cells of CV787 in combination with docetaxel occurred at smaller doses than that predicted from the use of CV787 or docetaxel alone.

Thus, sequential exposure to CV787 followed by docetaxel produced synergistic effects.

To determine whether the timing of administration for the tested compounds affected the combined cytotoxic effect, LNCaP cells were treated with paclitaxel for 24 hours before or after infection with CV787. There were no significant differences in cytotoxic activity between cells treated with paclitaxel before infection, after infection, or simultaneously with CV787. Similar results were obtained for docetaxel.

Taxane Increases CV787 Burst Size in LNCaP Calls

Paclitaxel and docetaxel are antineoplastic agents belonging to the taxane family. They are novel antimicrotubule agents that promote the assembly of microtubulas from tubulin dimers and stabilize microtubules by preventing depolymerization. This stability results in the inhibition of the normal dynamic reorganization of the microtubule network that is essential for vital interphase and mitotic cellular functions (Blagosklonny, M. V. et al., 2000, *J. Urol.* 163:1022–6.). In addition, the taxanes induce abnormal arrays or "bundles" of microtubules throughout the cell cycle and multiple asters of microtubules during mitosis. One possible explanation for the synergy seen with taxane and CV787 is that taxane may augment the ability of CV787 to replicate in LNCaP cells.

To examine the effect of paclitaxel and docetaxel on virus replication, we performed the one-step growth curve. LNCaP cells were infected with CV787 at an MOI of 1 for 4 hrs, followed by incubation in RPMI 1640 containing docetaxel at a final concentration of 3.12 nM. Cells were harvested at various times post-infection and the number of infectious virus particles was determined on 293 cells by standard plaque assay (Yu, D. -C. et al., 1999, *Cancer Res.* 59:4200–4203.). Although the initial rate of increase of CV7137 in cells treated with CV787 and docetaxel was similar to that of cells treated with CV787 alone, a plateau was reached for CV787 at approximately 72 post-infection and at approximately 96 hours post-infection for CV787 and docetaxel. Cells treated with CV787 and docetaxel produced 30,000 PFU per cell, while the cells infected with CV787 alone generated about 15,000 PFU per cell. Thus, docetaxel does not inhibit CV787 replication, but actually increases virus replication efficiency. A similar results was obtained in a parallel study with paclitaxel.

Combination of Taxane and CV787Increases the p53 Expression

To address the synergistic mechanism behind combination treatment, LNCaP cells were treated with various agents and the expression of apoptotic related protein markers were compared by Western blot. The treatments for LNCaP cells were grouped as (1) docetaxel alone at 6.0 nM, (2) CV787 alone at, MOI 0.5, and (3) CV787 (MOI=0.5) and docetaxel (6.0 nM) together. For each treatment group, cells were collected at different time points and subjected to various antibodies by Western blot. Under these experimental conditions, in the first 48 hours after treatment, the combination of CV787 and taxane increased p53 expression up to 2 to 8-fold compared to virus alone or drug alone at 24 or 48 hours.

In contrast, the apoptotic indicators caspase-7 and poly-ADP-ribose-polymerase did not show a significant change. In addition, the combination of CV787 and taxane did not change Fas/Fas-L or Bcl-2, Bcl-XL, and Bax expression compared to the single agent group. Previously, it was suggested that paclitaxel-induced apoptosis was not mediated by Bcl–2 family change. In the current study, we did not observe a significant change of Bcl–2 expression in the cells treated with docetaxel alone, CV787 alone, or docetaxel and CV787. Liu and Stein has reported that paclitaxel treated LNCaP cells experienced alteration In bcl-XL and Bak expression. However, under our condition of low concentration of docetaxel, there was no dramatic change detected. From the increased p53 expression, p53-dependent apoptosis may play a major role in the synergy of CV787 and taxane.

Synergistic Efficacy of Taxane With CV787 in vivo

The in vivo antitumor efficacy of CV767 in combination with taxane was assessed in the LNCaP mouse xenograft model. We have shown previously that a single intravenous administration of CV787 at $1 \times 10^{11}$ particles per animal can eliminate subcutaneous xenograft tumors in 6 weeks (Yu, D. -C. et al. (1999) supra. This data was extended using studies up through 10 weeks. Established human prostate tumors (LNCaP cells) were treated with either vehicle, CV787 ($1 \times 10^{11}$ particles per animal), paclitaxel (20 mg/kg), or both CV787 and paclitaxel. For the combination treatment, animals were intravenously injected with either CV787 or vehicle, and twenty-four hours later, paclitaxel was administered intraperitoneally (i.p.) daily for four days. The tumor volume data shows that there was a significant decrease in tumor volume between control and all treatment groups. In this study, single doses of CV787 or 4 doses of paclitaxel over four days were effective in producing partial tumor regression 7 weeks or 2 weeks after treatment, whereas the combination produced a near complete regression within 2 weeks. Four weeks after treatment, relative tumor volume decreased to 3% of baseline (from 418 mm$^3$ to 14 mm$^3$) for the combination treatment group and 31% of baseline for the paclitaxel group, but increased to 216% of baseline for the vehicle-treated group and 162% of baseline for the CV787 group. These changes were statistically significant by Students t-test (p<0.05) for the comparison of the combination treatment of CV787 with paclitaxel to any of the vehicles, CV787 or paclitaxel, alone. Additionally, serum PSA levels in mice injected with vehicle increased, whereas the levels in mice injected with CV787 and paclitaxel decreased to ~2% of their staffing values within 4 weeks.

Combination therapy showed more than additive effect (e.g. synergy) on tumor growth inhibition. On day 21, there was 4.4-fold improvement in anti-tumor activity in the combination group when compared with the expected additive effect. At this time point, CV787 alone or paclitaxel alone inhibited tumor growth by 20% or 70%, respectively (fractional tumor volume, 0.815 mm$^3$ and 0.287 mm$^3$ respectively) when compared with the control group. With time, there was a progressive improvement in anti-tumor activity. On day 42, CV787 and paclitaxel combination group showed a 9.2-fold higher inhibition of tumor growth over additive effect (expected fractional tumor volume). These data demonstrated a synergistic efficacy between CV787 and paclitaxel in LNCaP xenografts.

A synergistic effect was also observed in the combination treatment of xenograft tumors with CV787 and docetaxel. Results from LNCaP prostate tumor xenografts treat with CV787 and docetaxel, both administered intravenously: in the combination treatment group, animals were intravenously injected with docetaxel (5.0 mg/kg) on day 2, day 5 and day 8, following a single intravenous injection of CV787 ($1 \times 10^{10}$ particles per animal) on day 1. Both CV787 and docetaxel appear to be effective in producing stabilization of tumor growth in the LNCaP mouse model, whereas a combination of the two produce a complete regression within 5 weeks. Analysis on fractional tumor volume, indicated a synergistic effect between CV787 and docetaxel in LNCaP xenografts. For example, on day 42, CV787 and docetaxel combination group showed a 6.4-fold higher inhibition of tumor growth over an additive effect.

To further investigate the dose range for CV787 treatment in combination with docetaxel, we fixed the dose of docetaxel at 12.5 mg/kg and varied the dose of CV787 from $1 \times 10^8$, $1 \times 10^9$, to $1 \times 10^{10}$ particles per animal. Treatment with CV787 alone or docetaxel alone resulted in tumor growth inhibition. However, the combination of CV787 and docetaxel had the greatest effect of the treatments tested. Complete regression was achieved in the animals treated with docetaxel and CV787 at a dose of either $1\times10^{10}$, $1\times10^{9}$, or $1\times10^{8}$ particles. Synergy of anti-tumor activity was also evident using $1\times10^{7}$ particles per animal but complete regression was not observed. These changes were statistically significant by the Student's t-test for the comparison of combination treatment of CV787 and docetaxel to any of the vehicle, CV787 alone, or docetaxel alone treatments, with no statistical difference between the three combination treatment groups. Recall the complete response dose of CV787 alone is $1\times10^{11}$ particles per animal (Yu, D. -C. et al., 1999, Supra. Thus, the combination of CV787 and docetaxel produces a complete response with 1000-fold less virus, compared to the use of CV787 alone.

Virus replication within LNCaP tumors was documented by immunohistochemical staining of tumor sections using polyclonal antibodies to Adenovirus type 5 (Chen, Y. et al., 2000, *Hum. Gone Ther.* 11:1153–1567.) No evidence of virus replication was found in the tumors treated with either vehicle or paclitaxel, whereas evidence of necrosis and multifocal inflammation was observed in a small portion of tumors treated with paclitaxel. In the CV787-treated tumors, while positively stained cells were visible throughout the tumors, infected cells were predominantly located near the tumor vasculature. The most intriguing phenomena were in the samples treated with both the virus and paclitaxel. While few virus-infected cells were detected, most of the cells in the sections were empty and virtually devoid of cellular content. The remaining cells were much smaller and appeared to have undergone a morphological change.

Tumor cells were also tested for apoptosis using the M30 CytoDEATH™ detection kit, which recognizes a specific caspase cleavage site within cytokeratin 18 in early events of apoptosis. Three tumors from each group, CV787 alone, paclitaxel, or both CV787 and paclitaxel, were analyzed 9 days after the start of dosing. Few apoptotic cells were detected in the paclitaxel-treated tumor, while a significant amount of apoptotic cells along the blood vessel were present in the CV787-infected tumors. However, combination treatment produced more apoptotic cells than in the any of the other samples. In conclusion, the immunohistochemical analysis of CV787 treated tumors suggests that both virus replication-dependent cytolysis and apoptosis contribute to the antitumor effect of CV787 and taxane.

Finally, and of clinical significance are two other results. First, healthier animals, characterized by body weight, were observed in the combination treatment group as compared to groups treated with either agent alone. Of particular interest is the transient weight loss using docetaxel alone, from which animals are protected from by the use of CV787 in combination with docetaxel. Indeed, animals treated with both CV787 and taxotere gain 24% more weight than untreated control animals (Table 2). Second, formal toxicology studies in Balb/C mice failed to show synergistic toxicity from the combined use of docetaxel and CV787.

Example 2

In vitro Treatment of HepG2 and Hep3B Tumor Cells With Replication Competent Target Cell-specific Adenoviral Vector CV790 and Chemotherapy Regimen for in vitro Study of Adenoviral Vector and Chemotherapeutic Agent A preliminary experiment was performed to compare three different protocols: Adding virus first, drug first or virus and drug together (FIGS. 15–17). HepG2 and Hep3B cells were treated with 10 ng/ml doxorubicin and 0.01 MOI of CV790. FIG. 15 shows a synergistic effect in the panel of virus infection first. Virus first indicates administration of the virus about 10–14 hrs before drug application. Drug first indicates administration of the chemotherapeutic agent 10–14 hrs before virus infection FIG. 16. The results of administration of adenovirus vector and drug together are shown in FIG. 17. For the combination of CV790 and doxorubicin, virus first administration resulted in the greatest killing of liver cancer cells. This order of administration was not the most effective for CV787 combined with paclitaxel (TAXOL™) or docetaxel (TAXOTERE™).

In order to study the killing effect of virus and drug on liver cancer cells, an in vitro cell viability study (MTT assay) was carried out using chemotherapeutic agents and the CV790 adenovirus on HepG2 and Hep3B hepatoma cells. Protocols for cell growth and MTT assay were as described as in Example 1. CV790 was constructed according to methods known in the art with the E1A and E1B genes under the control of the α-fetoprotein promoter (approximately 0.8 kb), with an intact E3 region. The structure of CV790 can be summarized as AFP/E1A, AFP/E1B, E2, E3, E4. The hepatoma cells were grown in well plates, then treated with CV790 and various chemotherapeutic agents, as shown in FIGS. 15–22. After treatment, cells were incubated with MTT and cell viability at different time points from days 2–10 were compared. The MTT assay determines the number of cancerous cells still viable after treatment with the CV790/chemotherapy combination. Dead cells are equal to 1-the percentage of viable cells.

The following is the list of chemotherapeutic agents (drugs) and the sources for the drugs used in this study.
1. 5-Fluorouracil, (Sigma, St. Louis, Mo.) catalog number F-6627
2. Doxorubicin hydrochloride, (Sigma, St. Louis, Mo.) catalog number D-1 515
3. Cis-platinum (if)-diammine dichloride (cisplatin), (Sigma, St. Louis, Mo.) catalog number P-4394
4. 5-azacytidine, (Sigma, St. Louis, Mo.) catalog number A-2385
5. Mitomycin C, (Sigma, St. Louis, Mo.) catalog number M-0505
6. TAXOL™, (Mead Johnson oncology products, N.J.) catalog number C 0015-3475–30
7. Gemcitabine, (Lilly, Ind.) catalog number nC 0002–7501–01
8. Etoposide, (Bristol Laboratories, N.J.) catalog number nC 0015-3095-20
9. Mitoxantrone, (Immunex Corp., Seattle, Wash.), catalog number NDC 58406-640-03

Screening of Chemotherapeutic Agents for Synergistic Effects With CV790

The cytotoxicity of different chemotherapeutic agents combined with CV790 in Hep3B and HepG2 hepatoma cells were tested using the methodology described in Example 1 and above, with virus added before treatment with chemotherapeutic agent. The results are shown in FIGS. 18–22 and summarized in Table 6, below. These results correspond to the virus first regimen described above. Doxorubicin, mitomycin C, mitoxantrone, cisplatin, gemcitabine, 5-azacytidine, etoposide and TAXOL™ displayed synergistic effects of cytotoxicity when combined with CV790 compared to the cytotoxicity of the drug or virus alone. 5-Fluorouracil did not show synergistic effects with respect to virus and chemotherapy alone. For the experiments summarized in Table 6 the administered dose of CV790 was either MOI 0.1 or 0.01, as shown in the Figures. The chemotherapeutic agents were administered in the following amounts: doxorubicin (50 ng/ml); cisplatin (10 μg/ml); taxol (6.5 ng/ml); 5-fluorouracil (100 μg/ml); mitoxantrone (100 nM); mitomycin C (10 μg/ml); 5-azacytidine (10 μg/ml); etoposide (1 μg/ml); and gemcitabine (50 ng/ml).

TABLE 6

Synergistic Effects of CV790/Chemotherapeutic Combinations

| Virus | Cell line | Chemotherapeutic agent | Class of agent | SYNERGY |
|---|---|---|---|---|
| CV790 | HepG2, Hep3B | 5-Fluorouracil | Antimetabolites | No |
| CV790 | HepG2, Hep3B | 5-Azacytidine | Antimetabolite (DNA damaging agent) | Yes |
| CV790 | HepG2, Hep3B | Cisplatin | Alkylating agent (Plantinum-containing agents) | Yes |
| CV790 | HepG2, Hep3B | Doxorubicin | Antibiotics (anticycline) | Yes |
| CV790 | HepG2, Hep3B | TAXOL ™ (paclitaxel) | Plant alkaloids | Yes |
| CV790 | HepG2, Hep3B | Etoposide | Plant alkaloids | Yes |
| CV790 | HepG2, Hep3B | Gemcitabine | Antimetabolite (DNA damaging agent) | Yes |
| CV790 | HepG2, Hep3B | Mitomycin C | Antibiotics | Yes |
| CV790 | HepG2, Hep3B | Mitoxantrone | Antibiotics (anticycline) | Yes |

Example 3

In vitro Treatment of HepG2 and Hep3B Tumor Cells With Replication-competent AFP-producing Cell-specific Adenoviral Vector CV790 and Combination Chemotherapy In addition to screening single chemotherapeutic agents co-administered with replication-competent target cell-specific adenoviral vectors, a screen was completed of a number of combination chemotherapy regimens which were co-administered with CV790, a hepatoma specific adenoviral vector. Examples of such combination or multiple drug chemotherapy regimens can be found in Table 2. The protocols for the administration of the drugs and virus were as described in Examples 1 and 2, as was the monitoring of cell viability by MTT assay. The regimen followed was the virus first regimen. A range of drug concentrations were tested.

Treatment of hepatoma cells (Hep3B and HepG2) with a combination of multiple chemotherapy drugs plus CV790 showed a synergistic enhancement of cytotoxicity toward the hepatoma cells compared to the treatment of the hepatoma cells with either the virus alone or the multiple drug combination alone. Results are summarized in Table 7 below.

TABLE 7

Synergistic effects of CV790/Combination Chemotherapeutics

| VIRUS | CELL LINE | CHEMOTHERAPEUTIC AGENT | CLASS OF AGENT | SYNERGY |
|---|---|---|---|---|
| CV790 | HepG2, Hep3B | Doxorubicin & Cisplatin | Anticycline antibiotics & Plantinum-containing agents | Yes |
| CV790 | HepG2, Hep3B | Doxorubicin & Mitomycin C | Anticycline antibiotics | Yes |
| CV790 | HepG2, Hep3B | Doxorubicin & Mitoxantrone | Anticycline antibiotics | Yes |
| CV790 | HepG2, Hep3B | Doxorubicin & TAXOL ™ | Anticycline antibiotics & Plant alkaloids | Yes |

Example 4

Treatment of Prostate Tumor Xenografts With CV787 and Chemotherapeutic Agents After a synergistic effect was observed in vitro for the suppression of tumor cell growth with combinations of CV787 and a number of chemotherapeutic agents, a subset of these agents were examined for evidence of synergistic results in suppressing tumor growth in vivo. In vivo studies indicated that the combination of CV787 with paclitaxel or docetaxel could eliminate tumors within 2–4 weeks with ten-fold less virus ($1 \times 10^7$ particles per mm$^3$ for intratumoral administration, $1 \times 10^{10}$ particle per animal for intravenous administration) compared to a previously effective dose for virus alone. Yu et al. (1999) *Cancer Res.* 59:4200. Below are described detailed examples for CV787 and paclitaxel and CV787 and docetaxel.

Six to eight week old athymic Balb/c nu/nu mice were obtained from Simonson Laboratories (Gilroy, Calif.) and acclimatized to laboratory conditions one week prior to tumor implantation. Xenografts were established by injecting $1 \times 10^6$ LNCaP cells subcutaneously near the small of the back suspended in 100 μl of RPMI 1640 and 100 μl of maltrigel (Collaborative Biochemical Products). When tumors reached between 400 mm$^3$ and 600 mm$^3$, mice were randomized in groups of four each to receive either $1 \times 10^{10}$ particles of CV787 at day 1 via the tail vein or paclitaxel, 20 mg/kg intraperitoneally (i.p.) daily for 4 days starting at day 2, versus controls treated with normal saline 0.1 ml i.v. at day 1 and then i.p. for 4 days. In addition, another group of mice received the combination of CV787 and paclitaxel at the same doses and schedule as above. CV787 was diluted in lyophilized buffer and injected into tail vein in a volume of 0.1 ml using a 28-gauge needle. The dose and route of administration of paclitaxel were selected according to studies in nude mice by Riondel et al., (1986) *Cancer Chemother Pharmacol.* 17:137. These authors conducted acute toxicity studies of paclitaxel in nude mice and selected the unit dose of 12.5 mg/kg daily, being ½0th of the LD50 dose (lethal dose for 50% of animals). Tumors were measured weekly in two dimensions by external caliper and volume was estimated by the formula [length (mm)×width (mm)$^2$]/2. Animals were humanely killed when their tumor burden became excessive. Serum was harvested weekly by retro-orbital bleed. The difference in mean tumor volume between treatment groups was compared for statistical significance using the unpaired, two-tailed, t-test. Blood samples were collected at various time points for determining prostate-specific antigen (PSA). The level of PSA is directly related to tumor size, and tumor regression is accompanied by a fall in PSA levels.

Anti-tumor Efficacy of the Combined Therapy of Intratumorally Administered CV787 With Paclitaxel The in vivo antitumor efficacy of intratumorally administered CV787 and the interaction of CV787 in the combination with paclitaxel was assessed in the LNCaP mouse xenograft model as described above. The following treatments were administered (n=6 per treatment group):

Vehicle (negative control).

CV787 (active control) at a dose of $1\times10^7$ particles per mm$^3$ of tumor, at day 1.

Paclitaxel at a dose of 15 mg/kg of animal weight, starting at day 2, daily for four days.

CV787 ($1\times10^7$ particles per mm) and paclitaxel (15 mg/kg), scheduled as above.

All treatment groups received identical injections of the active agent or vehicle control into both the tumor and peritoneum. Tumor volume was measured just before the injection of test articles and once a week for 6 weeks thereafter.

The following changes in average tumor volumes were measured 6 weeks after treatment. Average tumor volume increased in vehicle-treated animals from 425 mm$^3$ to 983 mm$^3$ (231% of baseline) 6 weeks after treatment and in the paclitaxel group from 405 mm$^3$ to 630 mm$^3$ (166% of baseline) FIG. 23. Tumor volumes in the CV787 $1\times10^7$ particles/mm$^3$ group dropped from 419 to 379 mm$^3$ (90% of baseline) whereas the average tumor volume in the combination treatment group of CV787 with paclitaxel decreased from 413 mm$^3$ to 45 mm$^3$ (11% of baseline) within six weeks after treatment. These changes were statistically significant by Student's t-test for the comparison of combination treatment of CV787 with paclitaxel to any of the vehicles, CV787 alone or paclitaxel alone treatment. It is suggested that the combination of CV787 with paclitaxel produces a synergistically enhanced anti-tumor efficacy, more effective than virus treatment alone or paclitaxel treatment alone.

Anti-tumor Efficacy of the Combined Therapy of Intravenously Administered CV787 With Paclitaxel In vivo studies of intravenously administered CV787 in conjunction with paclitaxel or docetaxel were performed in the same mouse xenograft model as used for the intratumoral injection study. All test articles were administered via tail vein except that paclitaxel was injected intraperitoneally into animals.

The efficacy of intravenously administered CV787 and paclitaxel was assessed as described above. The following treatments were administered in this study:

Vehicle (negative control).

CV787 (active control) at a dose of $1\times10^{10}$ particles per animal at day 1.

Paclitaxel at a dose of 20 mg/kg of animal weight, starting at day 2, daily for 4 days.

CV787 ($1\times10^{10}$ particles/animal) and paclitaxel (20 mg/kg), scheduled as above.

Tumor volumes were measured just before the injection of test articles and once a week for 10 weeks thereafter.

In this study, single doses of CV787 and paclitaxel both appeared to be effective in producing tumor regression in the LNCaP mouse model, whereas the combination produced a complete regression in 4 weeks FIG. 25. Four weeks after treatment, relative tumor volume decreased to 3%. of baseline (from 418 mm$^3$ to 14 mm$^3$) for the combination treatment group and 216% of baseline for the vehicle-treated group, 31% of baseline for the paclitaxel group and 162% of baseline for the CV787 group. Ten weeks after treatment, 100% of the animals in the combination therapy group were tumor free, and animals were followed for 90 days without tumor regrowth. Relative tumor volume in the CV787-treated group decreased to 28% of baseline, while the tumors in the paclitaxel-treated group progressively grew back to 149% of baseline. This result indicated that paclitaxel alone could not cure cancers in this xenograft model. CV787 appeared to be highly effective and virus alone took a relatively long period of time to cure cancer at this dose level. However, the combination of CV787 and paclitaxel effectively eliminated tumors within 4 weeks after administration. In summary, the combination of paclitaxel with intravenously administered CV787 was far more effective than chemotherapy or virus treatment alone.

FIG. 24 depicts the change in tumor growth upon varying does of paclitaxel (TAXOL ™) and CV787 combined with paclitaxel (TAXOL™). paclitaxel (TAXOL™) at 10 mg/kg has approximately the same efficacy over a 5 week period as does paclitaxel (TAXOL™) at 2 mg/kg when combined with CV787 ($1\times10^{10}$ particles). Each of these treatments merely arrests tumor growth while not actually causing and regression of the tumor. A dose of 2 mg/kg of paclitaxel (TAXOL™) alone, however, leads to progressive enlargement of the tumor. A combination of paclitaxel (TAXOL™) at 10 mg/kg combined with a $1\times10^{10}$ particle dose of CV787, however, leads to complete suppression of tumor growth by the third week of the in vivo trial.

Anti-tumor Efficacy of the Combined Therapy of Intravenously Administered CV787 and Docetaxel The efficacy of intravenously administered CV787 and docetaxel was also assessed as described above. All test articles were administered into animals via tail vein. The following treatments were administered in this study:

Vehicle (negative control).

CV787 (active control) at a dose of $1\times10^{10}$ particles per animal at day 1.

Docetaxel at a dose of 10 mg/kg of animal weight, starting at day 2, daily for 4 days.

CV787 ($1\times10^{10}$ particles/animal) and paclitaxel (10 mg/kg), scheduled as above.

Tumor volumes were measured just before the injection of test articles and once a week for 6 weeks thereafter.

In this study, single dose of CV787 and docetaxel both appeared to be effective in producing tumor regression in the LNCaP mouse model, whereas the combination produced a complete regression within 4 weeks. Four weeks after treatment, relative tumor volume decreased to 2% of baseline for the combination treatment group and 226% of baseline for the vehicle-treated group, 49% of baseline for the docetaxel group and 132% of baseline for the CV787 group. These changes were statistically significant by the Student's t-test for the comparison of combination treatment of CV787 and docetaxel to any of the vehicle, CV787 alone or docetaxel alone treatment. It is suggested that the combination of CV787 and docetaxel produces an enhanced anti-tumor efficacy, much better than virus alone or docetaxel alone.

An alternate presentation of these data are found in FIG. 28 in which the data are reported as tumor volumes.

Following the successful treatment of the LNCaP xenografts with the above-described method, the dosage of docetaxel was decreased by 50% to 5 mg/kg and the CV787 dose was maintained at $1\times10^{10}$ particles. As shown in FIG. 29 significant regression of the tumor is observed for the CV787/docetaxel combination therapy by week 3. At week 4 the tumor volume is less than the tumor volume which remains steady for the remainder of the experiment. The minimum tumor volume for docetaxel alone, approximately 50% of the original tumor volume, is reached by week 1, however, in the following weeks tumor growth resumes and by week 6 has reached the starting tumor volume. Treatment with a tenfold higher dose of CV787 ($1\times10^{11}$ particles) is significantly more effective than the lower dose of CV787 ($1\times10^{10}$ particles) or docetaxel alone, but is slower to regress tumor growth and even at week 6 does not equal the reduction in tumor volume as the combination of CV787 ($1\times10^{10}$ particles) and docetaxel (5 mg/kg).

In summary, in vivo studies showed that direct intratumoral or intravenous injection of CV787 in conjunction with paclitaxel or docetaxel has an enhanced anti-tumor efficacy, resulting in a significantly lower tumor burden observed in the combination treatment. The virus dose in the combination treatment was 10-fold lower than our previously effective dose for virus treatment alone, $1\times10^{11}$ particles and a hundred percent of treated animals had complete tumor regression within 4 weeks in the intravenous administration regimen. These data provide supportive evidence for the potential development of a combination clinical regimen of CV787 with paclitaxel or docetaxel for clinical treatment of prostate cancer.

A number of other chemotherapeutic agents were screened for synergistic effect when combined with CV787 for the in vivo treatment of cancer. Results are summarized in Table 8, below, and representative data shown in FIGS. 23, 25–27.

Table 8 also includes data for the CN706 adenoviral vector, a replication-competent prostate cell-specific adenoviral construct (see Table 4). CV787 was administered in amounts ranging between $1\times10^7$ particles/mm$^3$, and $1\times10^{11}$ particles, as indicated in the Figures. Chemotherapeutic agents were administered in the following amounts: paclitaxel (TAXOL™; 2 mg/kg to 20 mg/kg as shown); docetaxel (TAXOTERE™; 5–10 mg/kg, as shown); mitoxantrone (3 mg/kg); estramustine (14 mg/kg daily at days 2–5, 7–11, 13–17, and 20–24);cisplatin (4 mg/kg); and 5-fluorouracil (30 mg/kg).

TABLE 8

Synergistic effects of Adenovirus/Chemotherapeutic Combinations in vivo

| Virus | Cell line | Chemotherapeutic agent | Class of agent | Synergy |
|---|---|---|---|---|
| CV706 | Prostate cancer xenografts | 5-Fluorouracil | Antimetabolites | Yes |
| CV787 | Prostate cancer xenografts | Cisplatin | Alkylating Agent (Plantinum-containing agents) | Yes |
| CV787 | Prostate cancer xenografts | Estramustine | Alkylating agent | Yes |
| CV787 | Prostate cancer xenografts | Mitoxantrone | Antibiotics (anticycline) | No |
| CV787 | Prostate cancer xenografts | TAXOTERE ™ (docetaxel) | Plant Alkaloids | Yes |
| CV787 | Prostate cancer xenografts | TAXOL ™ (paclitaxel) | Plant alkaloids | Yes |

Example 5

Treatment of Hep3B Tumor Xenografts With Replication-competent Hepatoma Specific CV790 and Doxorubicin and Hepatoma Specific CV890 and Doxorubicin CV790 is an AFP producing hepatocellular carcinoma specific adenovirus, with E1A and E1B under the control of an identical AFP promoter (827 bp) and enhancer with an E3 region. The CV890 adenovirus construct is also a hepatoma or liver-specific adenoviral mutant with the E1A and E1B genes under transcriptional control of 827 bp AFP promoter, wherein E1B is under translational control of EMCV IRES and having an intact E3 region. The structure of CV890 therefore reads as AFP/E1A, IRES/E1B, E2, E3, E4. In vivo studies of the efficacy of combinations of CV790 and doxorubicin and CV890 and doxorubicin were performed according to the protocols described in detail in Example 4, with minor alterations which are described below.

Xenografts in the study of CV790 and CV890 combined with chemotherapeutic agents utilized liver carcinoma Hep3B cells, instead of LNCaP prostate carcinoma. Virus, CV790 or CV890, was administered by a single intravenous injection of $1\times10^{11}$ particles through the tail veins of the nude mice. One day after virus delivery, a single dose of doxorubicin was given to each animal by i.p. injection. The doxorubicin dose was 10 mg/kg for both doxorubicin alone and doxorubicin combined with virus treatments. Tumor volume was measured once a week for six weeks according to the protocol in Example 4.

Both CV790/doxorubicin and CV890/doxorubicin treatment of the hepatoma showed synergistic results. Four weeks after treatment with either CV790/doxorubicin or CV890/doxorubicin the relative tumor volume was less than 10%. Unlike mice treated with either virus alone or doxorubicin alone, after week 4, the relative tumor volume did not increase for either the either CV790/doxorubicin or CV890/doxorubicin treated mice. At week 6 in the control mice, the relative tumor volume was approximately 1000% in the CV790 study and approximately 600% in the CV890 study 4 weeks after treatment. The relative tumor volumes of mice treated with virus alone were 250% (CV790) and 520% (CV890) while the relative tumor volumes for mice treated with doxorubicin alone were 450% with 280% in the CV790 study and 500% in the CV890 study. These results are shown in FIG. 30 (CV790/doxorubicin) and FIG. 31 (CV890/doxorubicin).

Example 6

In vitro Treatment of Tumor Cells With Combined Target Cell-specific Adenoviral Vector CV787 and Radiation Therapy LNCaP prostate carcinoma cells were pre-seeded in 96 well plates in the RPMI medium at 10,000 cells per well. After infection with CV787 (0.01 MOI) according to above described protocols (Example 1), the cells were incubated at 37° C. with 5% $CO_2$ for 24 hours, and then irradiated as monolayers using Cesium 137 gamma rays (used for all radiation studies) at a dose of 2 Gy. An MTT assay as described in Example 1 was performed to determine cell viability (1-% of viable cells=dead cells). The results are shown in FIGS. 10; 32; 33; 34; 35; and 36. The results show that the combined adenoviral/radiation treatment is synergistically enhanced over treatment with either virus or radiation alone.

FIG. 33 summarizes the results of a comparison of the treatment of LNCaP prostate carcinoma cells with 6 Gy radiation combined with CV787 (MOI 0.1), 6 Gy radiation alone, CV787 treatment alone, or no treatment. Protocols for the treatment are as described above for CV787 and 2 Gy radiation. Synergistic results were observed for the combined treatment of adenovirus and radiation compared to either treatment alone.

In FIG. 32 the same procedure was followed as those described above with the treatment consisting of CV787 (MOI 0.1) and 6 Gy radiation, except that the virus was added 24 hours after LNCaP cells were irradiated. The results indicate that virus treatment either before or after irradiation leads to synergy in terms of cell killing.

To establish a dose response curve, LNCaP cells were prepared and treated as described above, with CV787 (MOI 0.01) administered first, followed after 24 hours with varying doses of radiation. Separate cell cultures were irradiated with an increasing dose of radiation starting at 0 Gy, up to 8 Gy (CV787 was kept at the same level of multiplicity of infection of 0.01), then 6 days after irradiation, the cells were subjected to a MTT assay as described above in Example 1. FIG. 36 shows the resulting dose response curve, with nearly 100% cell death at day 6 for an 8 Gy dose of radiation.

To determine the effect of radiation on the viability of the replication-competent target cell-specific adenoviral vectors, virus yield was measured according to the protocol described in Example 8. LNCaP prostate carcinoma cells were seeded in well plates as described in Example 1 and above, then treated with either radiation (6 Gy) followed by administration of CV787 (MOI 0.1) 24 hours later or treated with CV787 (MOI 0.1) followed 24 hours later by irradiation (6 Gy), as described above in this example. These results were compared to the virus yield determined in LNCaP cells treated with CV787 (MOI 0.1) alone. In both cases, with either radiation administered first FIG. 34 or virus administered first FIG. 35, the virus yield over time is comparable to the virus yield in LNCap cells which are not treated with radiation. These results indicate that the combination treatment produces more virus than virus alone.

Example 7

Construction of a Replication-competent Adenovirus Vector Comprising an AFP-TRE and an EMCV IRES The encephalomyocarditis virus (ECMV) IRES as depicted in Table 12 was introduced between the E1A and E1B regions of a replication-competent adenovirus vector specific for cells expressing AFP as follows. Table 12 shows the 519 base pair IRES segment which was PCR amplified from Novagen's pCITE vector by primers A/B as listed in Table 9. A 98 base pair deletion in the E1A promoter region was created in PXC.1, a plasmid which contains the leftmost 16 mu of Ad5. Plasmid pXC.1 (McKinnon (1982) *Gene* 19:33–42) contains the wild-type left-hand end of Ad5, from Adenovirus 5 nt 22 to 5790 including the inverted terminal repeat, the packaging sequence, and the E1a and E1b genes in vector pBR322. pBHG10 (Bett. et al. (1994) *Proc. Natl. Acad. Sci. USA* 91:8802–8806; Microbix Biosystems Inc., Toronto) provides the right-hand end of Ad5, with a deletion in E3. The resultant plasmid, CP306 (PCT/US98/16312), was used as the backbone in overlap PCR to generate CP624. To place a SalI site between E1a and E1b, primers C/D, E/F (Table 9) were used to amplify CP306, plasmid derived from pXC.1 and lacking the E1a promoter. After first round PCR using CP306 as template and primers C/D, E/F, the resultant two DNA fragments were mixed together for another round of overlapping PCR with primers C/F. The overlap PCR product was cloned by blunt end ligation to vector. The resultant plasmid, CP624 (Table 10), contains 100 bp deletion in E1a/E1b intergenic region and introduces SalI site into the junction. On this plasmid, the endogenous E1a promoter is deleted, and the E1a polyadenylation signal and the E1b promoter are replaced by the SalI site. Next, the SalI fragment of CP625 was cloned into the SalI site in CP624 to generate CP627 (Table 10). CP627 has an EMCV IRES connecting adenovirus essential genes E1a and E1b. In CP627, a series of different tumor-specific promoters can be placed at the PinAI site in front of E1a to achieve transcriptional control on E1 expression.

TABLE 9

| Primer | Sequence | | Note |
|---|---|---|---|
| A. | 5'-GACGTCGACTAATTCCGGTTATTTTCCA | SEQ ID NO:19 | For PCR EMCV IRES, GTCGAC is a SalI site. |
| B. | 5'-GACGTCGACATCGTGTTTTTCAAAGGAA | SEQ ID NO:20 | For PCR EMCV IRES, GTCGAC is a SalI site. |
| C. | 5'-CCTGAGACGCCCGACATCACCTGTG | SEQ ID NO:21 | Ad5 sequence to 1314 to 1338. |
| D. | 5'-<u>GTCGACCATTCAGCAAACAAAGGCGTTAAC</u> | SEQ ID NO:22 | Antisense of Ad5 sequence 1572 to 1586. GTCGAC is a SalI site. Underline region overlaps with E. |
| E. | 5'-<u>TGCTGAATGGTCGACATGGAGGCTTGGGAG</u> | SEQ ID NO:23 | Ad5 sequence 1714 to 1728. GTCGAC is a SalI site. Underline region overlaps with D. |
| F. | 5'-CACAAACCGCTCTCCACAGATGCATG | SEQ ID NO:24 | Antisense of Ad5 sequence 2070 to 2094. |

For generating a liver cancer-specific virus, an about 0.8 kb AFP promoter fragment as shown in Table 14 was placed into the PinAl site of CP627 thereby yielding plasmid CP686. Full-length viral genomes were obtained by recombination between CP686 and a plasmid containing a right arm of an adenovirus genome. The right arms used in virus recombination were pBHGE3 (Microbix Biosystems Inc.), containing an intact E3 region, and pBHG11 or pBHG10 (Bett et al. (1994) containing a deletion in the E3 region.

The virus obtained by recombination of CP686 with a right arm containing an intact E3 region was named CV890. The virus obtained by recombination of CP686 with a right arm containing a deleted E3 region (pBHG 10) was named CV840. The structure of all viral genomes was confirmed by conducting PCR amplifications that were diagnostic for the corresponding specific regions.

Therefore, adenovirus vector designated CV890 comprises 0.8 kb AFP promoter, E1A, a deletion of the E1A promoter, EMCV IRES, E1B a deletion of the E1B promoter and an intact E3 region. Adenovirus vector CV840 comprises AFP promoter, E1A, a deletion of the E1A promoter, EMCV IRES, E1B, a deletion of the E1B promoter and a deleted E3 region.

TABLE 10

| Plasmid designation | Brief description |
|---|---|
| CP306 | An E1A promoter deleted plasmid derived from pXC.1 |
| CP624 | Overlap PCR product from CP306 to generate 100 bp deletion and introduce a Sal1 site at E1A and E1B junction; E1A and E1B promoter deleted in E1A/E1B intergenic region. |
| CP625 | EMCV IRES element ligated to PCR-blunt vector (Invitrogen pCR ® blunt vector). |
| CP627 | IRES element derived from CP625 by Sal1 digestion and ligated to CP624 Sal1 site placing IRES upstream from E1B. |
| CP628 | Probasin promoter derived from CP251 by PinA1 digestion and cloned into PinA1 site on CP627. |
| CP629 | HCMV IE promoter amplified from pCMV beta (Clontech) with PinA1 at 5' and 3' ends ligated into CP627 PinA1 site. |
| CP630 | A 163 bp long VEGF IRES fragment (Table 1) cloned into the Sal1 site on CP628. |
| CP686 | AFP promoter from CP219 digested with PinA1 and cloned into PinA1 site on CP627. |

Example 8

Construction of a Replication-competent Adenovirus Vector With a Probasin TRE and an EMCV IRES The probasin promoter as shown in Table 14 was inserted at the PinAl site of plasmid CP627 (see Example 8) to generate CP628, which contains a probasin promoter upstream of E1A and an EMCV IRES between E1A and E1B. Full-length viral genomes were obtained by recombination between CP628 and a plasmid containing a right arm of an adenovirus genome. The right arms used in virus recombination were pBHGE3, containing an intact E3 region, and pBHG11 or pBHG10 containing a deletion in the E3 region. The structure of all viral genomes was confirmed by conducting PCR amplifications that were diagnostic for the corresponding specific regions.

Therefore, adenovirus designated CV 834 comprises probasin promoter, E1A, a deletion of the E1A promoter, EMCV IRES, E1B, a deletion of the E1B endogenous promoter and a deleted E3 region.

Example 9

Construction of a Replication-competent Adenovirus Vector With a hCMV-TRE and an EMCV IRES The hCMV immediate early gene (IE) promoter from plasmid CP629, originally derived from pCMVBeta (Clonetech, Palo Alto) was inserted at the PinAl site of plasmid CP627 (see Example 8) to generate CP629, containing a CMV IE promoter upstream of E1A and an RES between E1A and E1B. Full-length viral genomes were obtained by recombination between CP629 and a plasmid containing a right arm of an adenovirus genome. The right arms used in virus recombination were pBHGE3, containing an intact E3 region, and pBHG11 or pBHG10 containing a deletion in the E3 region. The structure of all viral genomes was confirmed by conducting PCR amplifications that were diagnostic for the corresponding specific regions.

Therefore, adenovirus vector designated CV835 comprises hCMV-IE promoter, E1A, a deletion of the E1A promoter, EMCV IRES, E1B a deletion in the E1B endogenous promoter and a deleted E3 region. CV835 lacks the hCMV enhancer and is therefore not tissue specific. By adding the hCMV IE enhancer sequence to CV835, the vector is made tissue specific.

Example 10

Comparison of Dual TRE Vectors With Single TRE/IRES-containing Vectors

Two liver cancer-specific adenovirus vectors, CV790 and CV733 (also designated CN790 and CN733, respectively), were generated and characterized. See PCT/US98/04084. These viruses contain two AFP TREs, one upstream of E1A and one upstream of E1B. They differ in that CV790 contains an intact E3 region, while the E3 region is deleted in CV733. Replication of these two viruses was compared with that of the newly generated IRES-containing viruses, CV890 and CV840 (see Example 1).

Virus replication was compared, in different cell types, using a virus yield assay as described in Example 4. Cells were infected with each type of virus and, 72 hrs after infection, virus yield was determined by a plaque assay. The results indicate that vectors containing an IRES between E1A and E1B (CV890 and CV840), in which E1B translation is regulated by the IRES, replicate to similar extents as normal adenovirus and viruses with dual AFP TREs, in AFP-producing cells such as 293 cells and hepatoma cells. In SK-Hep-1 (liver cells), PA-1 (ovarian carcinoma) and LNCAP cells (prostate cells) the IRES-containing viruses do not replicate as well as dual TRE or wild-type adenoviruses, indicating that the IRES-containing viruses have higher specificity for hepatoma cells. Based on these results, it is concluded that IRES-containing vectors have unaltered replication levels, but are more stable and have better target cell specificity, compared to dual-TRE vectors.

Example 11

Uroplakin Adenoviral Constructs Containing an EMCV IRES

A number of E3-containing viral constructs were prepared which contained uroplakin II sequences (mouse and/or human) as well as an EMCV internal ribosome entry site (IRES). The viral constructs are summarized in Table 11. All of these vectors lacked an E1A promoter and retained the E1A enhancer.

The 519 base pair EMCV IRES segment was PCR amplified from Novage's pCITE vector by primers A/B:
primer A: 5'-GACGTCGACTAATTCCGGTTATTTT-CCA SEQ ID NO: 19
primer B 5'-GACGTCGACATCGTGTTTTTCAAAGG-AA SEQ ID NO: 20 (GTCGAC is a SalI site).
The EMCV IRES element was ligated to PCR blunt vector (Invitrogen pCR® blunt vector).
CP1066
The 1.9 kb-(-1885 to +1) fragment of mouse UPII from CP620 was digested with AflIII (blunted) and HindIII and inserted into pGL3-Basic from CP620 which had been digested with XhoI (blunted) and HindIII to generate CP1066.
CP1086
The 1.9 kb mouse UPII insert was digested with PinAI and ligated with CP269 (CMV driving E1A and IRES driving E1B with the deletions of E1A/E1B endogenous promoter) which was similarly cut by PinAI.
CP1087
The 1 kb (-1128 to +1) human UPII was digested with PinAI from CP665 and inserted into CP629 which had been cut by PinAI and purified (to elute CMV).
CP1088
The 2.2 kb (-2225 to +1) human UPII was amplified from CP657 with primer 127.2.1 (5'-AGGACCGGTCACT-ATAGGGCACGCGTGGT-3'(SEQ ID NO: 25)) PLUS 127.2.2(5'-AGGACCGGTGGGATGCTGGGCTGGGA-GGTGG-3'(SEQ ID NO: 26)) and digested with PinI and ligated with CP629 cut with PinAI.
CP627 is an Ad5 plasmid with an internal ribosome entry site (IRES) from encephelomycarditis virus (EMCV) at the junction of E1A and E1B. First, CP306 (Yu et al., 1999) was amplified with primer pairs 96.74.3/96.74.6 and 96.74.4/96.74.5.
The two PCR products were mixed and amplified with primer pairs 96.74.3 and 96.74.5. The resultant PCR product contains a 100 bp deletion in E1A-E1B intergenic region and a new SalI site at the junction. EMCV IRES fragment was amplified from pCITE-3a(+) (Novagen) using primers 96.74.1 and 96.74.2. The SalI fragment containing IRES was placed into SalI site to generate CP627 with the bicistronic E1A-IRES-E1B cassette. CP629 is a plasmid with CMV promoter amplified from pCMVbeta (Clontech) with primer 99.120.1 and 99.120.2 and cloned into PinAI site of CP627.
CP657 is a plasmid with 2.2 kb 5' flanking region of human UP II gene in pGL3-Basic (Promega). The 2.2 kb hUPII was amplified by PCR from GenomeWalker product with primer 100.113.1 and 100.113.2 and TA-cloned into pGEM-T to generate CP655.
The 2.2 kb insert digested from SacII (blunt-ended) and KpnI was cloned into pGL3-Basic at HindIII (blunted) and KpnI to create CP657.
CP1089
The 1 kb (-965 to +1) mouse UPII was digested by PinAI from CP263 and inserted into CN422 (PSE driving E1A and GKE driving E1B with the deletions of E1A/E1B endogenous promoter) cut by PinAI and purified and further digested with EagI and ligated with 1 kb (-1128 to +1) human UPII cut from CP669 with EagI.
CP1129
The 1.8 kb hUPII fragment with PinAI site was amplified from CP657 with primer 127.50.1 and 127.2.2 and cloned into PinAI site of CP629.
CP1131
CP686 was constructed by replacing the CMV promoter in CP629 with an AFP fragment from CP219. A 1.4 kb DNA fragment was released from CP686 by digesting it with BssHII, filling with Klenow, then digesting with BglII. This DNA fragment was then cloned into a similarly cut CP686 to generate CP1199. In CP1199, most of the E1B 19-KDa region was deleted. The 1.8 kb hUPII fragment with PinAI site was amplified from CP657 by PCR with primer 127.50.1 and 127.2.2 and inserted into similarly digested CP1199 to create CP1131.

The plasmids above were all co-transfected with pBHGE3 to generate CV874 (from CP1086), CV875 (from CP1087), CV876 (from 1088) and CV877 (from CP1089), CV882 (from CP1129) and CV884 (from CP1131). CP1088, CP1129 and CP1131 were cotransfected with pBHGE3 for construction of CV876, CV892 and CV884, respectively by lipofectAMINE (Gibco/BRL) for 11–14 days. pBHGE3 was purchased from Microbix, Inc., and was described previously. The cells were lysed by three freeze-thaw cycles and plaqued on 293 cells for a week. The single plaques were picked and amplified by infection in 293 cells for 3–5 days. The viral DNAs were isolated from the lysates and the constructs were confirmed by PCR with primer 31.166.1/51.176 for CV876 and primer 127.50.1/51.176 for CV882 and CV884 at E1 region and primer 32.32.1/2 for all three viruses at E3 region.

TABLE 11

| Name | Vector | Ad 5 Vector | E1A TRE | E1B TRE | E3 |
|---|---|---|---|---|---|
| CV874 | CP1086 | pBHGE3 | 1.9 kb mUPII | IRES | intact |
| CV875 | CP1087 | pBHGE3 | 1.0 kb hUPII | IRES | intact |
| CV876 | CP1088 | pBHGE3 | 2.2 kb hUPII | IRES | intact |
| CV877 | CP1089 | pBHGE3 | 1.0 kb mUPII | 1.0 kb hUPII (E1B promoter deleted) | intact |
| CV882 | CP1129 | pBHGE3 | 1.8 kb hUPII | IRES | intact |
| CV884 | CP1131 | pBHGE3 | 1.8 kb hUPii | IRES (E1B 19-kDa deleted) | intact |

Viruses are tested and characterized as described above.
Primer sequences:

| | | |
|---|---|---|
| 96.74.1 | GACGTCGACATCGTGTTTTTCAAAGGAA | SEQ ID NO:20 |
| 96.74.2 | GACGTCGACTAATTCCGGTTATTTTCCA | SEQ ID NO:19 |
| 96.74.3 | CCTGAGACGCCCGACATCACCTGTG | SEQ ID NO:21 |
| 96.74.4 | TGCTGAATGGTCGACATGGAGGCTTGGGAG | SEQ ID NO:23 |
| 96.74.5 | CACAACCGCTCTCCACAGATGCATG | SEQ ID NO:24 |
| 96.74.6 | GTCGACCATTCAGCAAACAAAGGCGTTAAC | SEQ ID NO:22 |
| 100.113.1 | AGGGGTACCCACTATAGGGCACGCGTGGT | SEQ ID NO:27 |
| 100.113.2 | ACCCAAGCTTGGGATGCTGGGCTGGGAGGTGG | SEQ ID NO:28 |
| 127.2.2 | AGGACCGGTGGGATGCTGGGCTGGGAGGTGG | SEQ ID NO:26 |
| 127.50.1 | AGGACCGGTCAGGCTTCACCCCAGACCCAC | SEQ ID NO:29 |

-continued

| | | |
|---|---|---|
| 31.166.1 | TGCGCCGGTGTACACAGGAAGTGA | SEQ ID NO:30 |
| 32.32.1 | GAGTTTGTGCCATCGGTCTAC | SEQ ID NO:31 |
| 32.32.2 | AATCAATCCTTAGTCCTCCTG | SEQ ID NO:32 |
| 51.176 | GCAGAAAAATCTTCCAAACACTCCC | SEQ ID NO:33 |
| 99.120.1 | ACGTACACCGGTCGTTACATAACTTAC | SEQ ID NO:34 |
| 99.120.2 | CTAGCAACCGGTCGGTTCACTAAACG | SEQ ID NO:35 |

Example 12

Construction of a Replication-competent Adenovirus Vector With a Tyrosinase TRE and EMCV IRES CP621 is a plasmid containing a human tyrosinase enhancer and promoter elements in a PinAI fragment. This fragment is ligated to the PinAI site on CP627 to generate CP1078. CP1078 is combined with pBHGE3 to generate anew melanoma specific virus, CV859. Table 14 depicts the polynucleotide sequence of the PinAI fragment which contains a tyrosinase promoter and enhancer.

Example 13

Construction of a Replication-competent Adenovirus Vector With a Probasin-TRE and a VEGF IRES Using a strategy similar to that described in Example 8, the IRES fragment from the mouse vascular endothelial growth factor (VEGF) gene is amplified and cloned into CP628 at the SalI site. Table 12 depicts the IRES fragment obtainable from vascular endothelial growth factor (VEGF) mRNA. In order to clone this fragment into the E1a/E1b intergenic region, two pieces of long oligonucleotide are synthesized. The sense oligonucleotide is shown in the Table, whereas the second piece is the corresponding antisense one. After annealing the two together to create a duplex, the duplex is subjected to SalI digestion and the resulting fragment is cloned into the SalI site on CP628. The resulting plasmid, CP630, has a probasin promoter in front of E1a and an VEGF IRES element in front of E1b. This plasmid is used to construct a prostate cancer-specific virus comprising the VEGF IRES element.

Example 14

Construction of a Replication-competent Adenovirus Vector With an AFP-TRE and a VEGF IRES Using a strategy similar to Example 8, a PinAI fragment which contains AFP TRE can be obtained. This AFP TRE is cloned into the PinAI site in front of E1A on CP628 yielding plasmid CP1077. This plasmid has the AFP TRE for E1 transcriptional control and the VEGF IRES element before E1b. CP1077 can be recombined with pBHGE3 to generate a liver-specific adenovirus, designated as CV858.

Example 15

Construction of a Replication-competent AdenovirusVector With a hKLK2-TRE and a EMCV IRES Using a strategy similar to Example 1, the TRE fragment from human glandular kallikrein II as shown in Table 14 was cloned into the PinAI site in CP627. The resultant plasmid, CP1079, is cotransfected with pBHGE3 to create CV860.

Example 16

Construction of a Replication-Competent Adenovir Vector with a CEA-TRE and a EMCVIRES Using a strategy similar to Example 1, the TRE fragment from Carcinembryonic antigen (CEA)(Table 14, SEQ ID NO:14) is used to construct virus designated CV873. A PinAI fragment containing the CEA-TRE was cloned into the PinAI site in front of E1A of CP627 or the transcriptional control. The resultant plasmid CP1080 is used together with pBHGE3 to generate CV873.

Example 17

Adenovirus Vectors With Urothelial Cell-specific TREs

A number of plasmid constructs were generated as intermediates for adenovirus type 5 (Ad 5) vector constructs. The plasmid constructs were based on plasmid CP321 (Yu et al., 1999, Cancer Res. 59:4200–4203), which contains a prostate-specific enhancer inserted at a PinAI site upstream of the E1A gene and at a EagI site upstream of the E1B gene. Constructs were created by inserting various UPII-derived 5'-flanking DNA sequences into the PinAI and EagI sites and removing the prostate-specific enhancer. Characteristics of the plasmid CP669 are E1A TRE 1.0 kb hUPII and E1B TRE 1.0 kb mUPI and lacked the E1A promoter and which contained the E1A enhancer. Infectious recombinant adenoviral vectors was produced by co-transfecting 293 cells with the UPII 5'-flanking DNA/E1 constructs and an Ad 5 backbone vector (pBHG10 or pBHGE3, Microbix, Inc.) as described in Yu et al. (id.) to produce CV829,which has an intact E3 region.

Example 18

In vitro Characterization of Melanocyte-specific TRE-containing Adenoviral Constructs An especially useful objective in the development of melanocyte cell-specific adenoviral vectors is to treat patients with melanoma. Methods are described below for measuring the activity of a melanocyte-specific TRE and thus for determining whether a given cell allows a melanocyte-specific TRE to function.

Cells and Culture Methods

Host cells such as, HepG2 (liver); Lovo (colon); LNCaP (prostate); PMEL (melanoma); SKMel (melanoma); G361 (melanoma) and MeWo cells are obtained at passage 9 from the American Type Culture Collection (Rockville, Md.). MeWo cells are maintained in RPMI 1640 medium (RPMI) supplemented with 10% fetal bovine serum (FBS; Intergen Corp.), 100 units/mL of penicillin, and 100 units/mL streptomycin. MeWo cells being assayed for luciferase expression are maintained in 10% strip-serum (charcoal/dextran treated fetal bovine serum to remove T3, T4, and steroids; Gemini Bioproduct, Inc., Calabasas, Calif.) RPMI.

Transfections of MeWo Cells

For transfections, MeWo cells are plated out at a cell density of $5 \times 10^5$ cells per 6-cm culture dish (Falcon, N.J.) in complete RPMI. DNAs are introduced into MeWo cells after being complexed with a 1:1 molar lipid mixture of N-[1-(2,3-dioleyloxy)propyl-N,N,N-trimethylammonium chloride (DOTAP™; Avanti Polar Lipids, Ala.) and dioleoyl-phosphatidylethanolamine (DOPE™; Avanti Polar Lipids, Ala.); DNA/lipid complexes are prepared in serum-free RPMI at a 2:1 molar ratio. Typically, 8 µg (24.2 nmole) of DNA is diluted into 200 µL of incomplete RPMI and added dropwise to 50 nmole of transfecting, lipids in 200 µL of RPMI with gentle vortexing to insure homogenous mixing of components. The DNA/lipid complexes are allowed to anneal at room temperature for 15 minutes prior to their addition to MeWo cells. Medium is removed from MeWo cells and replaced with 1 mL of serum-free RPMI followed by the dropwise addition of DNA/lipid complexes. Cells are incubated with complexes for 4–5 hours at 37° C., 5% $CO_2$. Medium was removed and cells washed once with PBS. The cells were then trypsinized and resuspended in 10% strip-serum RPMI (phenol red free). Cells were replated into an opaque 96-well tissue culture plate (Falcon, N.J.) at a cell density of 40,000 cells/well per 100 µL media and assayed.

Plaque Assays

To determine whether the adenoviral constructs described above replicate preferentially in melanocytes, plaque assays are performed. Plaquing efficiency is evaluated in the following cell types: melanoma cells (MeWo), prostate tumor cell lines (LNCaP), breast normal cell line (HBL-100), ovarian tumor cell line (OVCAR-3, SK-OV-3), and human embryonic kidney cells (293). 293 cells serve as a positive control for plaquing efficiency, since this cell line expresses Ad5 E1A and E1B proteins. For analyzing constructs comprising a melanocyte-specific TRE, cells that allow a melanocyte-specific TRE to function, such as the cell lines provided above and cells that do not allow such function, such as HuH7, HeLa, PA-1, or G361, are used. The plaque assay is performed as follows: Confluent cell monolayers are seeded in 6-well dishes eighteen hours before infection. The monolayers are infected with 10-fold serial dilutions of each virus. After infecting monolayers for four hours in serum-free media (MEM), the medium is removed and replaced with a solution of 0.75% low melting point agarose and tissue culture media. Plaques are scored two weeks after infection.

Example 19

In vitro and in vivo assays of Anti-tumor Activity

An especially useful objective in the development of urothelial cell-specific adenoviral vectors is to treat patients with bladder cancer. An initial indicator of the feasibility is to test the vector(s) for cytotoxic activity against cell lines and tumor xenografts grown subcutaneously in Balb/c nu/nu mice.

In vitro Characterization of CV876
Virus Yield Assay for CV876

$5 \times 10^5$ 293, RT-4, SW780, PA-1, G361, MKNI, HBL-100, Fibroblast (from lung) and Smooth muscle cells (from bladder) were plated into each well of six-well plates. Twenty-four hours later, medium was aspirated and replaced with 1 ml of serum-free RPMI 1640 containing CV802 (wt.Ad5 with E3) or CV876 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

Unlike wt. Ad5, CV802 which grows well in all of the cells tested, CV876 replicates much better in permissive cells (293, RT-4 and SW780) than in non-permissive cells (PA-1, G361, MKN1, HBL-100 and primary cells) by about 100–10000 fold. Noticeably, the replication in SW780 for CV876 is about 100 fold less than CV802, which indicates the limitation of this virus in efficacy.

Growth Curve Experiment for CV876

$5 \times 10^5$ RT-4, PA-1, Smooth muscle and Fibroblast cells were plated into each well of six-well plates. Twenty-four hours later, medium was aspirated and replaced with 1 ml of serum-free RPMI 1640 containing CV802 (wt.Ad5 with 133) or CV876 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three freeze-thaw cycles. The lysates were tested for virus production by triplicate plaque assay for 8–10 days under semisolid agarose on 293 cells.

Very similar as in virus yield assay, CV876 replicates well only in RT-4 but not in primary cells and PA-1 over a 120 h period of time. However, CV876 does show a delay of replication in RT-4 compared to CV802.

Cytopathic Effect Assay for CV876

$5 \times 10^5$ 293, RT-4, SW780, PA-1, MKN1 and LNCap were plated into each well of six-well plates. Twenty-four hours later, medium was aspirated and replaced with 1 ml of serum-free RPMI 1640 containing CV802 (wt.Ad5 with E3) or CV876 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV876 only kills the permissive cells (293, RT-4 and SW780) but not the non-permissive cells (PA-1, MKN-1 and LNCap).

MTT Assay for CV876

$2 \times 10^4$ 293, RT-4, SW780, MKN1, PA-1, HBL-100, Smooth muscle cells (from bladder) and Fibroblast (from lung) were plated into each well of 96-well plates. Twenty-four hours later, the cells were infected with CV802 and CV876 at increasing MOI from 0.001 to 10 in complete RPMI 1640. A rapid colorimetric assay for cell growth and survival was run at different time point of day 1, 3, 5, 7 and 10. The medium was replaced by 50 ul of MTT at 1 mg/ml solution, which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV876 shows efficacy only in permissive cells but not in non-permissive cells. Again, in RT-4 and SW780, CV876 kills the cells much slower than CV802.

In vitro Characterization of CV882
Virus Yield Assay for CV882

$5 \times 10^5$ 293, RT-4, SW780, G361, LNCap, HBL-100, MKNI, PA-1, Fibroblast and Smooth muscle cells were plated into each well of six-well plates. Twenty-four hours later, medium was aspirated and replaced with 1 ml of serum-free RPMI 1640 containing CV802 (wt.Ad5 with E3) or CV882 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

The replication of CV882 in permissive cells (293, RT-4 and SW780) is comparable to CV802 (the difference is less than 100 fold) while it shows over 1000–1000000 fold difference in non-permissive cells (G361, LNCap, HBL-100, MKN1, PA-1 and primary cells).

Growth Curve Experiment for CV882

$5\times10^5$ RT-4, PA-1, and Fibroblast cells were plated into each well of six-well plates. Twenty-four hours later, medium was aspirated and replaced with 1 ml of serum-free RPMI 1640 containing CV802 (wt.Ad5 with E3) or CV882 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three, freeze-thaw cycles. The lysates were tested for virus production by triplicate plaque assay for 8–10 days under semisolid agarose on 293 cells.

Very similar as in virus yield assay, CV882 replicates well only in RT-4 but not in primary cells and PA-1 over a 120 h period of time. Additionally, CV882 shows better replication in RT-4 compared to CV876.

Cytopathic Effect Assay for CV882

$5\times10^5$ 293, RT-4, SW780, HBL-100, G361, PA-1 and Fibroblast cells were plated into each well of six-well plates. Twenty-four hours later, medium was aspirated and replaced with 1 ml of serum-free RPNI 1640 containing CV802 (wt.Ad5 with E3) or CV882 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV882 only kills the permissive cells (293, RT-4 and SW780) but not the non-permissive cells (HBL-100, G361, PA-1 and Fibroblast cells).

MTT Assay for CV882

$2\times10^4$ RT-4, SW780, PA-1, HBL-100, U 18 and Fibroblast were plated into each well of 96-well plates. Twenty-four hours later, the cells were infected with CV802 and CV882 at increasing MOI from 0.001 to 10 in complete RPMI 1640. A rapid colorimetric assay for cell growth and survival was run at different time points of day 1, 3, 5, 7 and 10. The medium was replaced by 50ul of MTT at 1 mg/ml solution, which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV882 shows efficacy only in permissive cells but not in non-permissive cells.

In vitro Characterization of CV884

Virus Yield Assay for CV884

$5\times10^5$ 293, RT-4, SW780, G361, LNCap, HBL-100, MKN1, PA-1, Fibroblast and Smooth muscle cells were plated into each well of six-well plates. Twenty-four hours later, medium was aspirated and replaced with 1 ml of serum-free RPMI 1640 containing CV802 (wt.Ad5 with E3) or CV984 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

The replication of CV884 is very similar as CV802 in permissive cells (293, RT-4 and SW780) but shows over 1000 fold difference with CV802 in non-permissive cells (G361, LNCap, HBL-100, MKN1, PA-1 and primary cells). CV884 shows better efficacy than CV876 and CV882 without losing much specificity.

Growth Curve Experiment for CV884

$5\times10^5$ RT-4, PA-1, Smooth muscle and Fibroblast cells were plated into each well of six-well plates. Twenty-four hours later, medium was aspirated and replaced with 1 ml of serum-free RPMI 1640 containing CV802 (wt.Ad5 with E3) or CV884 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three freeze-thaw cycles. The lysates were tested for virus production by triplicate plaque assay for 8–10 days under semisolid agarose on 293 cells.

Very similar as in virus yield assay, CV884 replicates very well only in RT-4 (similar as CV802) but not in primary cells and PA-1. Again, the replication of CV884 is better than CV882 and CV876.

Cytopathic Effect Assay for CV884

$5\times10^5$ 293, RT-4, SW780, G361, PA-1 and Fibroblast cells were plated into each well of six-well plates. Twenty-four hours later, medium was aspirated and replaced with 1 ml of serum-free RPMI 1640 containing CV802 (wt.Ad5 with E3) or CV884 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV884 only kills the permissive cells (293, RT-4 and SW780) but not the non-permissive cells (G361, PA-I and Fibroblast cells).

MTT Assay for CV884

$2\times10^4$ 293, RT-4, SW780, U118, Fibroblast and Smooth muscle cells were plated into each well of 96-well plates. Twenty-four hours later, the cells were infected with CV802 and CV884 at increasing MOI from 0.001 to 10 in complete RPMI 1640. A rapid colorimetric assay for cell growth and survival was run at different time points of day 1, 3, 5, 7 and 10. The medium was replaced by 50 ul of MTT at 1 mg/ml solution which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV884 shows strong efficacy (similar as wt. Ad5) only in permissive cells but not in non-permissive cells.

In vivo Activity of CV808

Mice were given subcutaneous (SC) injections of $1\times10^6$ sW780 cells. When tumors grew to about 500 mm$^3$, CV808 was introduced into the mice ($5\times10^7$ PFU of virus in 0.1 ml PBS and 10% glycerol) intratumorally. Control mice received vehicle alone. Tumor sizes were measured weekly. The data indicate that CV808 was effective at suppressing tumor growth.

While it is highly possible that a therapeutic based on the viruses described here would be given intralesionally (i.e., direct injection), it would also be desirable to determine if intravenous (IV) administration of adenovirus vector can affect tumor growth. If so, then it is conceivable that the virus could be used to treat metastatic tumor deposits inaccessible to direct injection. For this experiment, groups of mice bearing bladder epithelial tumors are inoculated with $10^8$ to $10^{10}$ PFU of an adenoviral vector by tail vein injection, or with buffer used to carry the virus as a negative control. The effect of IV injection of the adenoviral vector on tumor size is compared to vehicle treatment.

Example 20

Synergistic Effect of CV 890 With Chemotherapeutics

Materials and Methods

Cells

Hepatocellular carcinoma cell lines HepG2, Hep3B, PLC/PRF/5, SNU449, and Sk-Hep-1, Chang liver cell (human normal liver cells), as well as other tumor cell lines PA-1 (ovarian carcinoma), UM-UC-3 (bladder carcinoma), SW 780 (bladder carcinoma), HBL100 (breast epithelia), Colo 201 (Colon adenocarcinoma), U 118 MG (glioblastoma) and LNCaP (prostate carcinoma) were obtained from the American Type Culture Collection. HuH-7 (liver carcinoma) was a generous gift of Dr. Patricia Marion (Stanford University). 293 cells (human embryonic kidney containing the E1 region of Adenovirus) were purchased from Microbix, Inc. (Toronto, Canada). The primary cells nBdSMC (normal human bladder smooth muscle cells), nHLFC (normal human lung fibroblast cells), and nHMEC (normal human mammary epithelial cells) were purchased from Clonetics (San Diego, Calif.). All tumor cell lines were maintained in RPMI 1640 (BioWhittaker, Inc.) supplemented with 10% fetal bovine serum (Irvine Scientific), 100 U/ml penicillin and 100 ug/ml streptomycin. Primary cells were maintained in accordance with vendor instructions (Clonetics, San Diego). Cells were tested for the expression of AFP by immunoassay (Genzyme Diagnostics, San Carlos, Calif.).

Virus Yield and One-step Growth Curves

Six well dishes (Falcon) were seeded with $5 \times 10^5$ cells per well of calls of interest 24 hrs prior to infection. Cells were infected at an multiplicity of infection (MOI) of 2 PFU/cell for three hours in serum-free media. After 3 hours, the virus containing media was removed, monolayers were washed three times with PBS, and 4 ml of complete media (RPMI1640+10% FBS) was added to each well. 72 hours post infection, cells were scraped into the culture medium and lysed by three cycles of freeze-thaw.

The one-step growth curves time points were harvested at various time points after infection. Two independent infections of each virus cell-combination were titered in duplicate on 293 cells (Yu et al., 1999, *Cancer Research*, 59:1498–1504.

Northern Blot Analysis

Hep3B or HBL100 cells were infected at an MOI of 20 PFU/cell (plaque forming unit per cell) with either CV802 or CV890 and harvested 24 hours post infection. Total cell RNA was purified using the RNeasy protocol (Qiagen). The Northern blot was conducted using NorthernMax Plus reagents (Ambion, Austin, Tex.). 5 ug of RNA was fractionated on a 1% agarose, formaldehyde-based denaturing gel and transferred to a BrightStar-Plus (Ambion) positively charged membrane by capillary transfer. The antisense RNA probes for E1A (adenovirus genome 501 bp to 1141 bp) or E1B (1540 bp-3910 bp) were PCR products cloned in pGEM-T easy (Promega) and transcription labeled with $[\alpha^{32}P]$ UTP. Blots were hybridized at 68° C. for 14 hours with ZipHyb solution and washed using standard methods (Ambion). Membranes were exposed to BioMax film (Kodak).

Western Blot Analysis

Hep3B or HBL100 cells were infected at MOI of 20 PFU/cell with either CV802 or CV890 and harvested 24 hours post infection. Cells were washed with cold PBS and lysed for 30 min on ice in (50 mM Tris, pH8.0, 150 mM NaCl, 1% IGEPAL CA360 a NP40 equivalent (Sigma), 0.5% sodium deoxycholate, and protease inhibitor cocktail from (Roche, Palo Alto, Calif.). After 30 min centrifugation at 4 C, the supernatant was harvested and the protein concentration determined with protein assay ESL kit (Roche). Fifty micrograms of protein per lane were separated on 816% SDS-PAGE and electroblotted onto Hybond ECL membrane (Amersham Pharmacia, Piscataway, N.J.). The membrane was blocked overnight in PBST (PBS with 0.1% Tween-20) supplemented with 5% nonfat dry milk. Primary antibody incubation was done at room temperature for 2–3 hrs with PBST/1% milk diluted antibody, followed by wash and 1 hr incubation with diluted horseradish peroxidase-conjugated secondary antibody (Santa Cruz Biotechnology Inc., Santa Cruz, Calif.). Enhanced chemiluminescence (ECL; Amersham Pharmacia) was used for the detection. E1A antibody (clone M58) was from NeoMarkers (Fremont, Calif.), E1B-21 kD antibody was from Oncogene (Cambridge, Mass.). All antibodies were used according manufacturer's instruction.

Cell Viability Assay and Statistical Analysis

To determine the cell killing effect of virus and chemotherapeutic agent in combination treatment, a cell viability assay was conducted as previously described with modifications (Denizot, 1986, Journal Immunology. Methods, 89:271–277). On 96 well plates, cells of interest were seeded at 10,000 calls per well 48 hr prior to infection. Cells were then treated with virus alone, drug alone, or in combination. Cell viability was measured at different time points by removing the media, adding 50 μl of 1 mg/ml solution of MTT (3-(4,5-Dimethylthiazol-2-yl)-2,5-diphenyl-$^2$H-tetrazolium bromide) (Sigma, St. Louis, Mo.) and incubating for 3 hrs at 37° C. After removing the MTT solution, the crystals remaining in the wells were solubilized by the addition of 50 μl of isopropanol followed by 30 C incubation for 0.5 hr. The absorbency was determined on a microplate reader (Molecular Dynamics) at 560 nm (test wavelength) and 690 nm (reference wavelength). The percentage of surviving cells was estimated by dividing the $OD_{550}$–$OD_{650}$ of virus or drug treated cells by the $OD_{550}$-$OD_{650}$ of control cells. 6 replica samples were taken for each time point and each experiment was repeated at least three times.

For statistical analysis, CurveExpert (shareware by Daniel Hyams, version 1.34) was used to plot the dose-response curves for virus and drugs. Based upon the dose-response curves, the isobologramms were made according to the original theory of Steel and Peckham (1993, *Int. J. Rad. Onc. Biol. Phys.*, 5:85) and method described in Aoe et al. (1999, *Anticancer Res.* 19:291–299).

Animal Studies

Six to eight week old athymic BALB/C nu/nu mice were obtained from Simonson Laboratories (Gilroy, Calif.) and acclimated to laboratory conditions one week prior to tumor implantation. Xenografts were established by injecting $1 \times 10^6$ Hep3B, HepG2 or LNCAP cells suspended in 100 μl of RPMI 1640 media subcutaneously. When tumors reached between 200 mm$^3$ and 300 mm$^3$, mice were randomized and dosed with 100 μl of test article via intratumoral or the tail vein injection. Tumors were measured in two dimensions by external caliper and volume was estimated by the formula [length (mm)×width (mm)$^2$]/2. Animals were humanely killed when their tumor burden became excessive. Serum was harvested weekly by retro-orbital bleed. The level of AFP in the serum was determined by AFP Immunoassay kit (Genzyme Diagnostics, San Carlos, Calif.). The difference in mean tumor volume and mean serum AFP concentration between treatment groups was compared for statistical significance using the unpaired, two-tailed, t-test.

Transcription and Translation of E1A/E1B Bicistronic Cassette of CV890 in Different Cells In wild type adenovirus infection, E1A and E1B genes produce a family of alternatively spliced products. It has been found that there are five E1A mRNAs, among them 12S (880 nucleotides, nts) and 13S (1018 nts) mRNAs are the dominant ones that are expressed both early and late after infection. The 12S and 13S mRNAs encode the gene product of 243 amino acids (243R) and 289 amino acids (289R) respectively (reviewed by Shenk, 1996). The two major E1B transcripts that code for 19 kD and 55 kD proteins are 12S (1031 nts) and 22S (2287 nts) mRNAs. E1B 12S mRNA only codes the 19 kD product, whereas the 22S mRNA codes for both 19 kD and 55 kD products due to different initiation sites during translation. In the current study, the generation of E1A-IRES-E1B bicistronic cassette was expected to change the pattern of E1A and E1B transcripts in viral infection. Therefore, Northern blot analysis was conducted to evaluate the steady-state level of E1A and E1B transcripts. First, CV802 or CV890 were infected to Hep3B (AFP) or HBL100 (AFP) cells for 24 hours. The total RNA samples were separated on agarose gels and processed for Northern blot by hybridizing to antisense RNA probes. The Northern blot with E1A probe visualized the 12S and 13S mRNAs in both wild type CV802 infected cells. For CV890, E1A transcripts can only be seen in Hep3B cells, indicating the conditional transcription of E1A. It is of interest to find that in CV890, there is only one large transcript (about 3.5 Kb), whereas the 12S and 13S mRNAs are no longer present. This large transcript indicates the continuous transcription of E1A-IRES-E1B bicistronic cassette, suggesting an alteration of viral E1A splicing pattern in CV890. Transcription of E1B from CV890 also appears to be AFP-dependent. It is clear that both 12S and 22S mRNAs of E1B were present in wild type CV802 samples, whereas the 12S mRNA and an enlarged 22S mRNA (3.5 Kb) appeared in CV890 infected cells. Obviously, the identity of this enlarged mRNA is the same 3.5 Kb transcript as visualized in E1A blot, which is from the transcription of E1A/E1B bicistronic cassette. Therefore, the E1B mRNA is tagged after E1A mRNA in this large transcript. This large transcript contains all the coding information for E1A, E1B 19 kD and E1B 55 kD. The mRNA splice pattern that appears in CV802 is not valid in CV890, the 12S mRNA with E1B probe disappeared. Meanwhile, in the E1B Northern blot, due to the selection of our E1B probe (1540 bp-3910 bp), mRNA of the Adenovirus gene IX (3580 bp-4070 bp), the hexon-associated protein, was also detected. In CV890 infected Hep3B cells, gene IX expression is equivalent to that of CV802, whereas in CV890 infected HBL100, its expression was also completely shut down. This result further demonstrated that the AFP controlled E1A/E1B expression is the key for late gene expression as well as viral replication.

Results of the same samples in the Western blot also indicate that CV890 has AFP dependent expression of E1A and E1B. Under our experimental conditions, E1A expression level of CV890 in Hep3B cells is similar to that of CV802. However, when E1B 19 kD protein was detected, it was found that the expression level was much lower than CV802 E1A. Previously, it has been addressed that IRES-mediated second gene has less expression (Mizuguchi et al., 2000, Mol. Ther. 1:376–382). Taken together, CV890 infection in permissive Hep3B cells can produce normal amounts of E1A and lesser amounts of E1B proteins capable of initiating a normal productive infection. In AFP-cells, however, this process was attenuated due to a lack of E1A and E1B gene transcription and translation. These data demonstrated that the expression of both E1A and E1B genes are under the control of AFP TRE and the artificial E1A/E1B bicistronic cassette is functioning properly in CV890.

In vitro Replication Specificity of CV890 in Tumor Cells and Primary Cells

From in vitro comparison of virus yield, CV890 has a better specificity profile than CV732 (CV732 is an AFP-producing, cell-specific adenovirus variant in which the E1A gene is under control of AFP-TRE). In order to gain further insights of using CV890 in liver cancer therapy, more tumor cell lines and primary cells were tested to characterize in vitro virus replication. First, all cells in the study were analyzed for their AFP status by AFP immune assay. Based on AFP produced in the cells and media, all the cells were divided into three groups, high (>2.5 $\mu g/10^6$ cells/10 days), low (<0.6 $\mu g/10^6$ cells/10 days) and none (undetectable in our study) (Table 15). It was confirmed that replication of CV890 in different cell lines correlates well with the AFP status of the host cell. Among the group of liver cell lines, CV890 only replicates well in AFP$^+$ cells, including Hep3B, HepG2, Huh7, SNU449 and PLC/PRF/5. The amount of AFP required for the promoter activity seems very low as one of the hepatoma cell lines, SNU449, a previous reported AFP-cell (Park et al., 1995, Int. J. Cancer 62:276–282), produces very low AFP (about 60 ng/$10^6$ cells/10 days) compared to other cells. Nevertheless, even with very low amount of AFP, SNU449 cells can still support CV890 replication to the extent comparable to cells producing significantly higher levels of AFP such as HepG2. Compared to CV802, CV890 is attenuated 5,000 to 100,000 fold in cells that do not produce AFP, including the hepatoma cell Sk-Hep1 and Chang liver cell, other tumor cells and primary cells. Taken together the results indicate that CV890 has shown a good specificity profile from a broad spectrum of tumor cells. Among them, only the AFP$^+$ liver cells, AFP production level from high to low, are permissive for CV890.

In another experiment, CV890 was compared to CV802 for their single step growth curves on different cells. Results demonstrated that CV890 has a similar growth kinetics to wild-type CV802 in AFP$^+$ cells except that virus yields are slightly lower (2–8 fold) in low AFP producing cells. In consideration of experimental error, there is no dramatic difference in the replication of CV890 and CV802 in AFP$^+$ hepatoma cells. However, the growth curves of CV890 in AFP-cells showed clear attenuation. During a 5 day experiment, CV890 failed to replicate in AFP-cells including hepatoma cell (Change liver) and primary cells (nHLFC). From all the in vitro virus replication studies, it is clear that replication of CV890 is under the tight control of AFP-TRE and this adenovirus variant has an excellent specificity profile of preferentially targeting AFP producing hepatocellular carcinoma cells.

In vivo Specificity and Efficacy of CV890

CV890 specificity was also evaluated in animals bearing prostate cancer LNCaP xenografts. In this in vivo test, nude mice with prostate xenograft were intravenously injected with either CV890 or CV787, a prostate cancer specific adenovirus variant (Yu et al., 1999, Cancer Research, 59:4200–4203). Tumor volumes were documented and indicated that only CV787 had a significant antitumor efficacy in LNCaP xenografts, while tumors in the animals treated with CV890 grew, from 400 mm$^3$ to approximately 1200 mm$^3$ in six weeks, similar to the group treated with vehicle. This study indicates that CV890 does not attack LNCaP xenograft and keeps the good specificity profile under in vivo conditions.

To evaluate in vivo antitumor efficacy of CV890, different studies were carried out in the nude mouse model harboring human hepatoma xenografts. First, BALB/c nu/nu mice with HepG2 or Hep3B xenografts were established, animals were further challenged with single dose or multiple doses of CV890 into the tumor mass (intratumoral administration, IT) or via their tail vein (intravenous administration, IV). Tumor volume and the level of serum AFP were monitored weekly after the start of treatment, and hence the efficacy of the treatment was determined. The in vitro cytotoxicity study has demonstrated that CV890 has a better cytolytic effect than CV732. In order to further examine their antitumor activity, we first conducted animal study to compare CV890 to CV732. Animals harboring 300 mm$^3$ Hep3B xenograft were grouped (n=6) and injected with vehicle alone (control group), CV890 ($1\times10^{11}$ particles/dose, CV890 group), or CV732 ($1\times10^{11}$ particles/dose, CV732 group). The Hep3B xenograft is a very aggressive tumor model and tumors grow very fast. Most animals can not survive long because of excessive tumor burden. During a six week study, single intravenous administration of CV890 have shown significant tumor growth inhibition, whereas control mice had over 10 fold tumor growth at week 5. In the group treated with CV732, single dose IV injection also reduced the tumor growth as compared to control group, however, it was much less effective compared to CV890. For example, the average tumor volume of the CV890 treated group dropped from 312 mm$^3$ to 219 mm$^3$, while tumor volume increased from 308 mm$^3$ to 1542 mm$^3$ 5 weeks after treatment in control. Both control group and the CV732 group were terminated at week 5 because excessive tumor size. Previously, CV732 has been demonstrated to restrict the hepatoma tumor from growth after 5 doses of intravenous administration. Similar efficacy can be achieved with just a single intravenous administration of CV890, indicating that under in vivo conditions, CV890 has better efficacy than CV732 in hepatoma xenografts. In this experiment, 4 out of five CV890 treated mice were tumor free three weeks after treatment. However, in CV732 group, xenografts in two mice stopped growing but none of treated animals were tumor free through the six-week experiment. There was no tumor reduction in this group or the control group of animals. By statistical analysis, the differences in mean relative tumor volumes and serum AFP concentrations between CV890 treated and CV732 treated or vehicle treated tumors are significant ($p<0.01$)). Taken together, these studies suggest that CV890 has a significant antitumor activity and its oncolytic efficacy is better than CV732, an adenovirus variant similar to AvE1a04I, in which the AFP TRE was applied to control E1A alone (Hallenback et al, 1999, *Hum. Gene. Ther.,* 10:1721–1733).

Synergistic Antitumor Efficacy of CV890 in Combination With Chemotherapeutic Agents In this example, different chemotherapeutic agents were tested in combination with CV890 for their in vitro killing effect in Hep3B or HepG2 cells. Drug concentrations were optimized to the extent that they would not generate extensive cytotoxic effect on their own. Under such conditions, some agents had shown higher cell killing effect in combination with CV890. Among them, doxorubicin, a drug currently used in treatment of HCC showed synergistic cytotoxicity with CV890. In experiments using doxorubicin together with CV890 on Hep3B cells, doxorubicin at 10 ng/ml did not generate cytotoxicity, whereas CV890 at an MOI of 0.01 (pfu/cell) only had about 35% of cell killed at day 9. However, when both were applied together, 90% cells were killed 9 days after treatment. In order to determine the potential synergistic effect from the combination treatment, the MTT cell viability data were subjected to further statistical analysis. FIG. 38 shows a representative IC$_{50}$ isobologram of doxorubicin and CV890 on Hep3B cells at day 5. First, the dose-response curves of doxorubicin alone or CV890 alone were made. Based on the original theory of Steel and Peckham (1993) and method by Aoe et al. (1999), three isoeffect curves (mode 1 and mode 2a, 2b) were constructed. From this isobologram, several data points were in the synergy or additive area, indicating that combination of CV890 and doxorubicin provides synergistic effect on killing of Hep3B cells.

Although CV890 alone has good antitumor activity, we applied combination therapy with doxorubicin for in vivo evaluation of synergy. Animals harboring 300 mm$^3$ Hep3B xenografts were grouped (n=6) and injected with vehicle alone (control group), CV890 alone ($1\times10^{11}$ particles/dose, CV890 group), doxorubicin alone (10 mg/kg, doxorubicin group), or CV890 in combination with doxorubicin (combination group). FIG. 38 shows weekly change of the relative tumor size normalized to 100% at day 1. In this experiment, by week six, all animals in the control group had excessive tumor which has increased by 700% of baseline, whereas in CV890 group and combination group, animals had either tumor free or tumor reduction. Of the eight Hep3B xenografts, treated with CV890, three animals (37.5%) had no palpable tumor at week 5, another three animals had tumor regressed by more than 60%. In combination group, four out of eight animals were tumor free from week 5, another four animals had tumor reduction about 90%. All the animals in the CV890 and combination group were alive and tumor was suppressed even ten weeks following treatment whereas the control animals were sacrificed for excessive tumor burden after week 6. Furthermore, CV890 also caused a drop in the serum AFP concentration in these mice. Statistical analysis shows that differences in mean relative tumor volumes and serum AFP concentrations between CV890 and vehicle treated group or combination and doxorubicin treated group are significant at different times ($p<0.005$).

The strong efficacy in the combination treatment shows that single IV injection of CV890 in combination of doxorubicin can eradicate aggressive Hep3B xenografts in most of the animals.

TABLE 15

AFP production in different tumor cells

| CELLS | AFP (ng/10$^6$ cells/10 days) | |
|---|---|---|
| Hep3B | 2645 | High |
| HepG2 | 3140 | |
| HuH7 | 4585 | |
| SNU449 | 60 | Low |
| PLC/PRF/5 | 600 | |
| Chang | 0 | None |
| SK-Hep1 | 0 | |
| HBL100 | 0 | |
| PA-1 | 0 | |
| LoVo | 0 | |

Example 21

CV706 in Combination With Irradiation Produces Synergy

Materials and Methods

Cell Culture and Virus

The human LNCaP (prostate carcinoma), OVCAR-3 (ovary carcinoma) and HBL-100 (breast epithelia) cell lines were obtained from the American Type Culture Collection (ATCC, Rockville, Md.). The human embryonic kidney cell line, 293, which expresses the Adenoviral E1A and E1B gene products, was purchased from Microbix Biosystem, Inc. (Toronto, Canada). Cells were maintained at 37° C. with 5% $CO_2$ in RPMI 1640 supplemented with 10% fetal bovine serum (FBS, Hyclone, Utah), 100 units/ml penicillin and 100 µg/ml of streptomycin (Life Technologies, Gaithersburg, Md.).

CV706 is a prostate-specific replication competent Adenovirus variant. One prostate-specific transcription response element (TRE), the human prostate-specific antigen promoter and enhancer (PSE), was inserted upstream of the E1A encoding region in the viral genome (Rodriguez et al., 1997, Cancer Research, 57: 2559–2563). Similarly, CV787 is also a prostate-specific replication competent Adenovirus variant, which contain two prostate-specific TREs, the probasin promoter and PSE, inserted upstream of the E1A and E1B encoding regions in the viral genome, respectively (Yu et al., 1999, supra). Both CV706 and CV787 are currently in clinical trials for organ-confined prostate cancer and metastatic hormone refractory prostate cancer (DeWeese et al., 2001).

Cell Viability and Irradiation

MTT assays were performed to measure cell viability as described by (Yu et al, 1999, supra). Briefly, HBL-100, OVCAR-3 and LNCaP cells ($2 \times 10^4$ cells/well, 96 well plate) were either infected with CV706 or CV787 at various MOI (from 0.0001 to 1) or treated with irradiation at the indicated dosages. Cells were incubated in growth medium for 24 hr to allow for viral replication. After 24 hr, cells were exposed to a single dose of γ-irradiation (0–40 Gy) (Mark 1 Research Irradiator Model #1608A, Caesium 137 source). Cell viability was measured at the times indicated by removing the media and replacing it with 50 µl of 1 mg/ml solution of MTT (3-(4,5-Dimethylthiazol-2-yl)-2,5-diphenyl-2H-tetrazolium bromide) (Sigma, St. Louis, Mo.) and incubating for 3 hrs at 37° C. After removing the MIT solution, the crystals remaining in the wells were solubilized by the addition of 50 µl of isopropanol and placed in a 30° C. incubator for 30 min for the crystals to dissolve. Plates were vibrated for 10 sec prior to reading. The absorbency was determined on a microplate reader (Molecular Dynamics) at 560 nm (test wavelength) and 690 nm (reference wavelength). At least, 8 replica samples were taken for each time point and the percentage of surviving cells was estimated by dividing the $OD_{560}$-$OD_{690}$ of virus infected cells by the $OD_{560}$-$OD_{690}$ of mock infected cells.

Statistical Analysis

The dose-response interactions between CV706 and irradiation at the point of $IC_{50}$ were evaluated by the isobologram method of Steel and Peckham as modified by Aoe et al. (Aoe et al. 1999, Anticancer Res. 19:291–299). The $IC_{50}$ defined as the concentration of drug that produced 50% cell growth inhibition, i.e. 50% reduction in absorbance. Isobolograms (three isoeffect curves, model 1 and model 2) were computed as described previously (Yu et al., 2001). Fractional tumor volume (FTV) relative to untreated controls was determined based on the method described previously (Yokoyama et al., 2000; Yu et al., 2001, Cancer Research).

On Step Growth Curve and Virus Yield

One-step growth curve of CV706 in the presence and absence of irradiation were performed in LNCaP cells to determine burst size. Monolayers of LNCaP cells were infected with CV706 at MOIs 0.01, 0.1 and 1. After 24 hour incubation at 37° C. with 5% $CO_2$, cells were exposed to a single dose of γ-irradiation at 10 Gy. At the indicated times thereafter, duplicate cell samples were harvested and lysed by three cycles of freeze-thawing. Virus yield was determined by plaque assay as described in (Yu et al., 1999, Cancer Research, 59:1498–1504).

In vivo Antitumor Efficacy

Six to eight week old athymic Balb/c nu/nu mice were obtained from Simonson Laboratories (Gilroy, Calif.) and acclimatized to laboratory conditions one week prior to tumor implantation. Xenografts were established either by injecting $1 \times 10^6$ LNCaP cells subcutaneously near the small of the back suspended in 100 µl of RPMI 1640 and 100 µl of matrigel (back tumor) or by injecting cells into the right gastrocnemius muscle (i.m.) (leg tumor). When tumors reached between 300 $mm^3$ and 500 $mm^3$, mice were randomized into groups of four. The first group received CV706 at day 0 via intratumoral (i.t.) administration. CV706 was diluted by PBS containing 10% glycerol and injected into tumor as 0.4 µl of diluted virus ($1 \times 10^7$ particles) per $mm^3$ of tumor using a 28-gauge needle. The second group was given irradiation only. For irradiation mice were immobilized in lucite chambers and their whole body was shielded with lead except for the tumor bearing sites on their back or tumor-bearing hind leg. This tumor-bearing site in back or leg was irradiated with a Mark 1 Research Irradiator (Model #1 608A, J.H. Shepherd Associates) at various doses (0, 5, 10 and 20 Gy) 1 day after CV706 injection or mock injection. The third group was given CV706 (i.t.) at day 0 and irradiated at the same doses at day 1. As a control, a fourth group was treated with virus dilution buffer (i.e. control) i.t. at day 0. Tumors were measured weekly in two dimensions by external caliper and volume for back tumors was estimated by the formula [length (mm)×width $(mm)^2$]/2 (Yu et al., 1999b). Volumes of i.m. leg tumors were determined using the following formula (Alfieri and Hahn, 1978, Cancer Research, 38:3006–3011): volume $(cm^3)$=d'3−$(0.6)^2$d', where d' is the average diameter of the tumor-bearing leg (cm), and the product $(0.6)^2$d' is the correction factor for normal leg volume. Animals were humanely killed when their tumor burden became excessive. The difference in relative tumor volumes between treatment groups was compared for statistical significance using the type 2 (two-sample equal variance), two-tailed, t-test. Blood samples were collected at various time points by retro-orbital bleed for determining prostate-specific antigen. Federal and institutional guidelines for animal care were followed.

Histochemistry Analysis

Four groups of mice (n=6) were treated with vehicle, CV706 ($1 \times 10^7$ particles per $mm^3$ of tumor), irradiation (10 Gy) or a combination of CV706 and irradiation. Half the animals were sacrificed on day 7 and the other half on day 14. The tumor samples were embedded in paraffin blocks and 4-µm sections were cut and stained with Hematoxylin and Eosin (H&E). Histology methods for detecting Adenovirus antigens were as described (Yu et al., 1999, Cancer Research, 59:4200–4203). The necrotic cells were scored on coded slides at light microscopy at ×400 magnification. The number of necrosis was based on scoring 500 points per section as either necrotic or nonnecrotic. The average necrosis score was calculated based on counting in 10 fields distributed evenly across the area of tumor section. The light-microscopic features used to identify necrosis included cell size, indistinct cell border, eosinophilic cytoplasm, loss or condensation of the nucleus, and associated inflammation (Milross et al., 2000). To assess the effect of CV706, irradiation or the combination treatment on tumor vascularization, the number of blood vessels was counted at a magnification of ×400 and the average blood vessels were calculated from 10 fields distributed evenly across the area of whole tumor section. Apoptotic cells were detected using TUNEL assay (Roche Molecular Biochemicals, Indianapolis, Ind.) as suggested by the manufacturer. The morphological features used to identify apoptosis in the tumor sections have been previously described, associated with positive terminal deoxynucleotidyl transferase-mediated nick end labeling staining (Milross, et al., 2000). The apoptotic cells were scored on coded slides at ×400 magnification and average score of apoptotic cells was calculated from 10 fields of nonnecrotic areas selected randomly across each tumor section.

Results

CV706 in Combination With Irradiation Produce Synergistic Cytotoxicity in Prostate Carcinoma LNCaP Cells To study the potential interaction between a prostate-specific Adenovirus variant CV706 and radiation in vitro, the effectiveness of combined treatment of several combinations of CV706 and irradiation at various doses was evaluated in the PSA-producing prostate carcinoma LNCaP cell line. LNCaP cells were either mock-infected, or infected with CV706. One day later, cells received a single dose of γ-irradiation (0, 5Gy, 10Gy and 20Gy) and the cell viability was then determined at various time points by the MTT assay. Several viral MOIs and radiation doses were tested to determine the dose-response curves in LNCaP cells, such that the selected dose shows greater combined efficacy with radiation or virus, but minimal cell killing when treated with the same dose of virus alone or radiation alone. Infecting LNCaP cells with CV706 at an MOI of 0.01 resulting in 80% cell survival 5 days after infection, while irradiation at a dose of 10 Gy resulted in 78% survival 5 days after treatment. However, when CV787 and radiation were combined at these doses, cell survival dropped to 20% 5 days after treatment. Cell viability dropped further to 8% 9 days after combination treatment, while cells treated with virus at MOI 0.01 alone or radiation 10 Gy alone retained 70% or 60% cell viability, respectively.

Isobolograms were generated from the models to determine the presence of synergy, additivity, or antagonism between CV706 and irradiation. The results indicate that sequential exposure to CV706 followed by irradiation produced synergistic cytotoxicity. The enhanced cytotoxicity was also observed in LNCaP cells when CV787, a second prostate-specific Adenovirus variant, was combined with radiation Taken together, our in vitro data demonstrate that prostate-specific Adenovirus variants in combination with irradiation produce synergistic cell cytotoxicity in prostate carcinoma LNCaP cells.

Irradiation Increases CV706 Burst Size in LNCaP Cells

Irradiation kills mammalian cells in the reproductive (also known as clonogenic) death pathway. DNA is the target, and double-stranded breaks in the DNA are regarded as the specific lesions that initiate this lethal response. Most radiation induced DNA double-stranded breaks are rapidly repaired by constitutively expressed DNA repair mechanisms. Residual unrepaired or misrepaired breaks lead to genetic instability and to increased frequency of mutations and chromosomal aberrations (Garzotto et al., 1999). Because of its small target size, the adenoviral genome (36 kb) is far less likely to sustain radiation-induced damage as it is $10^5$-fold smaller than that of human cells ($3\times10^6$ kb).

To examine the effect of irradiation on virus replication, we performed a one-step growth curve. LNCAP cells were infected with CV706 at an MOI of 0.1 for 24 hrs, followed by irradiation at a dose of 10 Gy. Cells were harvested at various times post-infection and the number of infectious virus particles was determined on 293 cells by standard plaque assay (Yu et al., 1999, supra). Although the initial rate of increase of CV706 in cells treated with CV706 and irradiation was similar to that of cells treated with CV706 alone, cells treated with CV706 and irradiation produced a larger burst size than CV706 alone. For example, cells treated with CV706 and irradiation produced 8,000 PFU per cell 9 days post-infection, while the cells infected with CV706 alone generated about 500 PFU per cell 9 days after virus infection. A bigger virus burst size was also observed in the combination treatment of irradiation and CV706 at MOIs 0.01 or 1. Cells treated with CV706 at MOI of 0.01, and 1 produced 15 and 3500 PFU per cell, whereas cells treated with CV706 at MOI of 0.01 and 1 combined with irradiation, produced 4750, and 8700 PFU per cell respectively, at 9 days after virus infection. Thus, irradiation does not inhibit CV706 replication, but significantly increases virus propagation.

Cytotoxicity of CV706 in Combination With Irradiation Remains to be Specific to Prostate Cancer Cells In order to evaluate whether the addition of radiation could change the specificity of CV706's cytotoxic activity, we assess the specificity of the combination treatment of CV706 and radiation by measuring viability of various infected cell lines using the MTT assay. LNCaP, HBL-100 and OVCAR-3 cells were infected with CV706 at an MOI of 0.01 for 24 hrs, followed by a single dose of radiation at 10 Gy. The percentage of cell viability versus time post treatment was plotted. The combination of CV706 and radiation was toxic to LNCaP cells, but not to HBL-100 and OVCAR-3 cells. There were few surviving LNCAP cells 9 days after infection. In contrast, the viability of HBL-100 and OVCAR-3 cells treated with CV706 and radiation was more than 90% throughout the course of the experiment, similar to that of cells treated with radiation alone. This data suggests that combination with irradiation does not alter CV706's specificity.

Synergistic Efficacy of CV706 in Combination With Irradiation in vivo

The in vivo antitumor efficacy of CV706 in combination with irradiation was assessed in the LNCaP mouse xenograft model. We have shown previously that a single intratumoral administration of CV706 at $5\times10^8$ particles per mm$^3$ of tumor can eliminate subcutaneous xenograft tumors in 6 weeks (Rodriguez et al., 1997,supra) Established human prostate cancer xenografts (LNCaP cells) were treated with either vehicle, CV706 ($1\times10^7$ particles/mm$^3$), irradiation (10 Gy), or both CV706 and irradiation. For the combination treatment, animals were intratumorally injected with either CV706 or vehicle, and 24 hours later, animals received a single dose of irradiation. In this study, a single dose of 10 Gy was used because it caused a tumor growth delay in a previous pilot study. The dose of $1\times10^7$ particles per mm$^3$ of tumor was selected based on our previous studies on its antitumor efficacy (Yu et al., 1999, supra.

The tumor volume data shows that there was a significant decrease in tumor volume between control and all treatment groups. In all cases although single doses of CV706 or irradiation were effective in producing tumor growth inhibition, the combination of the two showed significant tumor regression. For example, tumor volume of the group treated with irradiation (10 Gy) was 119.76% of baseline 6 weeks after treatment, while the tumor volume of the group treated with CV706 was 97.39% of baseline 6 weeks after administration. However, when CV706 was combined with irradiation at similar doses, a statistically significant drop in the relative tumor volume (4% of baseline) was observed ($p<0.01$). Additionally, relative PSA level in serum of mice was also monitored for anti-tumor efficacy. Relative PSA level in mice increased to 370% of baseline 6 weeks after receiving vehicle treatment, increased to 139% after receiving irradiation alone, reduced to 84% of baseline after being treated with CV706 alone, whereas the PSA levels in mice treated with CV706 and irradiation decreased to less than 1% of their starting values within 6 weeks.

After 7 days, combination treatment showed more than additive effect on tumor growth inhibition at all the time points studied. On day 21, there was more than 2-fold improvement in anti-tumor activity in the combination group when compared with the expected additive effect. At this time point, both CV706 and irradiation (10 Gy) per se inhibited tumor growth by 26% and 34%, respectively (fractional tumor volume, 0.7419 $mm^3$ and 0.6645 $mm^3$, respectively) when compared with the control group. This anti-tumor activity further improved with time. On day 42, the group treated with the combination of CV706 and irradiation showed a 6.69-fold higher inhibition of tumor growth over the expected fractional tumor volume. These observation further strengthen the idea of synergy between CV706 and irradiation in the eradication of LNCaP xenografts.

Enhanced antitumor efficacy was also observed in the animal model in which the prostate cancer tumors are implanted in hind limb of mice. In this study, tumors were produced by inoculation of $1\times10^6$ cells into limb muscle. Those tumors which were attained a volume of 200 $mm^3$ to 300 $mm^3$ were randomized into four groups and treated as described above for back tumors. As before the weekly tumor volume measurements showed that combination treatment of CV706 and irradiation led to significant antitumor activity in comparison to either CV706 or irradiation. For example, tumor volume of the group treated with irradiation (20 Gy) was 70% of baseline 4 weeks after treatment, while the tumor volume of the group treated with CV706 ($5\times10^7$ particle per $mm^3$ of tumor) was 75% of baseline 4 weeks after administration. However, when CV706 was combined with irradiation at these dose levels, the tumor volume dropped to 8% of baseline.

A series of experiments were then designed to examine the effects of various factors, including the sequencing of the agents, timing of irradiation following virus administration and irradiation fractionation. The effect of order of administration for the tested agents was examined in an in vivo study using back tumor xenograft model. LNCaP xenografts were irradiated 24 hr before or after CV706 administration. Weekly measured tumor volume indicated that treatment with CV706 prior to irradiation was significantly superior to irradiation followed by CV706.

The second study was designed to evaluate the timing of irradiation following virus administration. Tumors were treated with CV706 at day 0 and followed by irradiation at various periods of time. The results of average tumor volume indicated that similar antitumor efficacy was achieved when tumors treated with CV706 at day 0 following by irradiation 1 day or 4 days after virus administration, both eliminated tumors within 6 weeks after treatment. However, the antitumor activity was decreased when the tumors were treated with irradiation 7 days after CV706 administration.

The third study was designed to assess the effect of radiation fractionation on antitumor efficacy. Animals with human prostate cancer tumors on their backs were randomized into five groups. Two of which were treated with either CV706 at day 0 followed by a single dose of radiation at 10 Gy on day 1, or CV706 at day 0 followed with four fractional doses of radiation at 2.5 Gy on day 1, 2, 6 and 8. Weekly measured tumor volume data indicated that both treatments eliminated the pre-existing tumors 6 weeks after treatment and produced an synergistic antitumor activity when compared to either agent alone. However, no significant difference in antitumor efficacy was observed between these two combination groups as long as the total doses of irradiation was the same.

Synergistic antitumor efficacy of CV706 in combination irradiation was further documented by tumor histological analysis. First of all, more necrotic cells were observed in the tumors treated with CV706 plus irradiation compared with either agent alone. The amount of necrosis in tumors treated with CV706 alone was higher than control tumor or tumor treated with radiation. Evidence of necrosis and multifocal inflammation was observed in a small portion of tumors treated with radiation. In the tumor treated with both the virus and radiation, a few virus-infected cells were detected. Most of the cells in the sections were empty and virtually devoid of cellular content. Significantly increases in the extent of necrosis was a dominant histological feature, which makes up about 95% of the tumor mass in this treatment group. The average necrosis scores in a x 400 magnification for the tumors treated with vehicle, radiation, CV706 and both were 5.4±2.17, 67±48.24, 258.2±80.76 and 461.6±37.87, respectively. The presence of mass necrosis in the tumors treated with CV706 or CV706 plus radiation suggests that the induction of necrosis greatly attributes CV706 or CV706 plus radiation's anti-tumor efficacy in vivo. Student T test showed that tumor cell necrosis caused by CV706 in combination with radiation was significantly greater than by CV706 ($p<0.03$) and irradiation perse ($p<0.0001$). This observation is in agreement with the number of apoptotic cells observed in the treated tumors. The number of apoptotic cells, detected using TUNEL assay (Milross et al., 2000) in the tumors treated with CV706 and irradiation is 16-fold higher than vehicle, 8.8-fold higher than irradiation and 3.2-fold higher than CV706.

Secondly, a significant reduction in blood vessel numbers was observed in the tumors treated with CV706 in combination with irradiation. Average number of blood vessel observed at a magnification of 400x in tumors treated with vehicle, CV706, radiation or the combination of CV706 and radiation were 87.5±6.3, 27.5±8.9, 58.5±3.1 and 4.5±1.9, respectively. Significantly reduced numbers of blood vessels in the tumors treated with combination in comparison to CV706 alone or irradiation alone ($p<0.01$) suggest that the reduction of tumor vascularization may contribute to enhanced tumor regression. It is unclear at this time as to the precise mechanism by which this reduction in blood vessel number is achieved. The possibility for such an eventuality through direct damage of endothelial cells or indirectly through the destruction of tumor vasculature by extensive necrosis seems highly possible. CD31 is expressed constitutively on the surface of adult and embryonic endothelial cells and has been used as a marker to detect angiogenesis (Giatromanolaki et al., 1997, Clin. Can. Res. 3 (12pt 1): 2485–92). Immunohistochemical staining was performed to examine the effect of treatment on tumor angiogenesis by using monoclonal antibody against CD31 (Horak et al., 1992). Tumors treated with CV706 followed by irradiation showed a significantly lower level of CD31 positive vessel when compared to radiation (p=0.003) or CV706 alone (p=0.03). When compared to untreated mice, CV706/radiation treated mice exhibited significantly lower (4-fold) CD31 positive blood vessel counts (p<0.0001), whereas, radiation treated or CV706 treated mice displayed 1.6-fold (p=0.03) or 2.1-fold (p=0.004) lower CD31 positive blood vessel counts. These observations suggest that CV706 in combination with radiation may be inhibiting tumor angiogenesis to a significant extent.

Finally, treatment employing the combination seems to have a beneficial effect on the general health of the treated animals in comparison to the individual treatment. The quality of life of the treated animals seems to be greatly improved as evidenced by the general appearance and significant gain in the body weight. Indeed, animals treated with both CV706 and irradiation gain 38% more weight than untreated control animals, 22% more than CV706 treated animals and 25% more weight than irradiation treated animals. The combination treatment seems to protect the animals from the transient weight loss observed in the case of animals treated with irradiation alone.

TABLE 12

IRES Sequences

SEQ ID NO:1 A 519 base pair IRES obtainable from encephelomycarditis virus (EMCV).

1 GAC*GTCGAC*TAATTCCGGTTATTTTCCACCATATTGCCGTCTTTTGG
CAA

*Sal*I

51 TGTGAGGGCCCGGAAACCTGGCCCTGTCTTCTTGACGAGCATTCCTA
GGG

101 GTCTTTCCCCTCTCGCCAAAGGAATGCAAGGTCTGTTGAATGTCGTG
AAG

151 GAAGGAGTTCCTCTGGAAGCTTCTTGAAGACAAACAACGTCTGTAGC
GAC

201 CCTTTGCAGGCAGCGGAACCCCCCACCTGGCGACAGGTGCCTCTGCG
GCC

251 AAAAGCCACGTGTATAAGATACACCTGCAAAGGCGGCACAACCCCAG
TGC

301 CACGTTGTGAGTTGGATAGTTGTGGAAAGAGTCAAATGGCTCTCCTC
AAG

351 CGTATTCAACAAGGGGCTGAAGGATGCCCAGAAGGTACCCCATTGTA
TGG

401 GATCTGATCTGGGGCCTCGGTGCACATGCTTTACATGTGTTTAGTCG
AGG

451 TTAAAAAACGTCTAGGCCCCCCGAACCACGGGGACGTGGTTTTCCTT
TGA

*Sal*I

501 AAAACACGAT*GTCGAC*GTC

SEQ ID NO:2 An IRES obtainable from vascular endothelial growth factor (VEGF).

1 ACGTA*GTCGAC*AGCGCAGAGGCTTGGGGCAGCCGAGCGGCAGCCAGG
CCC

*Sal*I

51 CGGCCCGGGCCTCGGTTCCAGAAGGGAGAGGAGCCCGCCAAGGCGCG
CAA

101 GAGAGCGGGCTGCCTCGCAGTCCGAGCCGGAGAGGGAGCGCGAGCCG
CGC

151 CGGCCCCGGACGGCCTCCGAAACCATG*GTCGAC*ACGTA

*Sal*I

SEQ ID NO:3 A 5'UTR region of HCV.
1
GCCAGCCCCCTGATGGGGCGACACTCCGCCATGAATCACTCCCCTG
TGAGGAACTACTG

61
TCTTCACGCAGAAAGCGTCTAGCCATGGCGTTAGTATGAGTGTCGTG
CAGCCTCCAGGAC

121 CCCCCCTCCCGGGAGAGCCATAGTGGTCTGCGGAACCGGTGAGTACA
CCGGAATTGCCAG

181 GACGACCGGGTCCTTTCTTGGATTAACCCGCTCAATGCCTGGAGATT
TGGGCGTGCCCCC

241 GCAAGACTGCTAGCCGAGTAGTGTTGGGTCGCGAAAGGCCTTGTGGT
ACTGCCTGATAGG

301 GTGCTTGCGAGTGCCCCGGGAGGTCTCGTAGACCGTGCACC (341)

SEQ ID NO:4 5'UTR region of BiP SEQ ID NO:4
1
CCCGGGGTCACTCCTGCTGGACCTACTCCGACCCCCTAGGCCGGGAG
TGAAGGCGGGACT

61
TGTGCGGTTACCAGCGGAAATGCCTCGGGGTCAGAAGTCGCAGGAGA
GATAGACAGCTGC

121 TGAACCAATGGGACCAGCGGATGGGGCGGATGTTATCTACCATTGGT
GAACGTTAGAAAC

181 GAATAGCAGCCAATGAATCAGCTGGGGGGGCGGAGCAGTGACGTTTA
TTGCGGAGGGGGC

241 CGCTTCGAATCGGCGGCGGCCAGCTTGGTGGCCTGGGCCAATGAACG
GCCTCCAACGAGC

301 AGGGCCTTCACCAATCGGCGGCCTCCACGACGGGGCTGGGGGAGGGT
ATATAAGCCGAGT

361 AGGCGACGGTGAGGTCGACGCCGGCCAAGACAGCACAGACAGATTGA
CCTATTGGGGTGT

421 TTCGCGAGTGTGAGAGGGAAGCGCCGCGGCCTGTATTTCTAGACCTG
CCCTTCGCCTGGT

481 TCGTGGCGCCTTGTGACCCCGGGCCCCTGCCGCCTGCAAGTCGAAAT
TGCGCTGTGCTCC

541 TGTGCTACGGCCTGTGGCTGGACTGCCTGCTGCTGCCCAACTGGCTG
GCAAGATG (595)

SEQ ID NO:5 A 5'UTR of PDGF SEQ ID NO:5

```
  1 GTTTGCACCTCTCCCTGCCCGGGTGCTCGAGCTGCCGTTGCAAAGC
                                        CAACTTTGGAAAAA
 61 GTTTTTTGGGGGAGACTTGGGCCTTGAGGTGCCCAGCTCCGCGCTTT
                                        CCGATTTTGGGGG
121 CTTTCCAGAAAATGTTGCAAAAAAGCTAAGCCGGCGGGCAGAGGAAA
                                        ACGCCTGTAGCCG
181 GCGAGTGAAGACGAACCATCGACTGCCGTGTTCCTTTTCCTCTTGGA
                                        GGTTGGAGTCCCC
241 TGGGCGCCCCCACACCCCTAGACGCCTCGGCTGGTTCGCGACGCAGC
                                        CCCCCGGCCGTGG
301 ATGCTGCACTCGGGCTCGGGATCCGCCCAGGTAGCCGGCCTCGGACC
                                        CAGGTCCTGCGCC
361 CAGGTCCTCCCCTGCCCCCAGCGACGGAGCCGGGGCCGGGGCGGC
                                        GGCGCCGGGGCA
421 TGCGGGTGAGCCGCGGCTGCAGAGGCCTGAGCGCCTGATCGCCGCGG
                                        ACCTGAGCCGAGC
481 CCACCCCCTCCCCAGCCCCCCACCCTGGCCGCGGGGCGGCGCGCT
                                        CGATCTACGCGTC
541 CGGGGCCCCGCGGGGCCGGGCCCGGAGTCGGCATG (575)
```

TABLE 13

Literature References For IRES

| IRES Host | Example | Reference |
|---|---|---|
| Picornavirus | HAV | Glass et al., 1993. Virol 193:842–852 |
| | EMCV | Jang & Wimmer, 1990. Gene Dev 4:1560–1572 |
| | Poliovirus | Borman et al., 1994. EMBO J 13:3149–3157 |
| HCV and pestivirus | HCV | Tsukiyama-Kohara et al., 1992. J Virol 66:1476–1483 |
| | BVDV | Frolov I et al., 1998. RNA. 4:1418–1435 |
| Leishmania virus | LRV-1 | Maga et al., 1995. Mol Cell Biol 15:4884–4889 |
| Retroviruses | MoMLV VL30 (Harvey murine sarcoma virus) | Torrent et al., 1996. Hum Gene Ther 7:603–612 |
| | REV | Lopez-Lastra et al., 1997. Hum Gene Ther 8:1855–1865 |
| Eukaryotic mRNA | BiP | Macejak & Sarnow, 1991. Nature 353:90–94 |
| | antennapedia mRNA | Oh et al., 1992. Gene & Dev 6:1643–1653 |
| | FGF-2 | Vagner et al., 1995. Mol Cell Biol 15:35–44 |
| | PDGF-B | Bernstein et al., 1997. J Biol Chem 272:9356–9362 |
| | IGFII | Teerink et al., 1995. Biochim Biophys Acta 1264:403–408 |
| | eIF4G | Gan & Rhoads, 1996. J Biol Chem 271:623–626 |
| | VEGF | Stein et al., 1998. Mol Cell Biol 18:3112–3119; Huez et al., 1998. Mol Cell Biol 18:6178–6190 |

TABLE 14

TRE Sequences

Nucleotide sequence of a human uroplakin II 5' flanking region. Position +1 (the translational start site) is denoted with an asterisk. SEQ ID NO:6 (number 1 of SEQ ID NO:6 corresponds to position -2239 with respect to the translational start site).

```
TCGATAGGTA CCCACTATAG GCACGCGTG GTCGACGGCC CGGGCTGGTC
1                                                            50

TGGCAACTTC AAGTGTGGGC CTTTCAGACC GGCATCATCA GTGTTACGGG
51                                                          100

GAAGTCACTA GGAATGCAGA ATTGATTGAG CACGGTGGCT CACACCTGTA
101                                                         150

ATCCCAACAC TCTGGGAGGC CAAGGCAGGT GGATCACTTG TGGTCAGGAG
151                                                         200

TTTGAGACCA GCCTGGCCAA CATGGTGAAA CCTCATCTCT ACTAAAAATA
201                                                         250

CAAAAATTAG CTGGGAATGG TGGCACATGC CTATAATCCC AGTTACTCAG
251                                                         300

GAGGCTGAGG CAGGAGAATC ATTTGAACCT GGGAGGCAGA GGTTGCAGTG
301                                                         350

AGCCGAGATC ACGCCACTGC ACTCCAGCCT GGGTGACACA GCGAGACTCT
351                                                         400

GTCTCAAAAA AAAAAAAATG CAGAATTTCA GGCTTCACCC CAGACCCACT
401                                                         450
```

TABLE 14-continued

TRE Sequences

```
GCATGACTGC ATGAGAAGCT GCATCTTAAC AAGATCCCTG GTAATTCATA
451                                                500

CGCATATTAA ATTTGGAGAT GCACTGGCGT AAGACCCTCC TACTCTCTGC
501                                                550

TTAGGCCCAT GAGTTCTTCC TTTACTGTCA TTCTCCACTC ACCCCAAACT
551                                                600

TTGAGCCTAC CCTTCCCACC TTGGCGGTAA GGACACAACC TCCCTCACAT
601                                                650

TCCTACCAGG ACCCTAAGCT TCCCTGGGAC TGAGGAAGAT AGAATAGTTC
651                                                700

GTGGAGCAAA CAGATATACA GCAACAGTCT CTGTACAGCT CTCAGGCTTC
701                                                750

TGGAAGTTCT ACAGCCTCTC CCGACAAAGT ATTCCACTTT CCACAAGTAA
751                                                800

CTCTATGTGT CTGAGTCTCA GTTTCCACTT TTCTCTCTCT CTCTCTCTCT
801                                                850

CAACTTTCTG AGACAGAGTT TCACTTAGTC GCCCAGGCTG GAGTGCAGGG
851                                                900

GCACAATCTC GGCTCACTGC AACCTCCACC TCCTGGGTTC AAGTGTTTCT
901                                                950

CCTGTCTCAG CCTCCCGAGT AGCTGGGATT ACAGGCACAC ACCACCGCGT
951                                               1000

TAGTTTTTGT ATTTTTGGTA GAGATGGTGT TTCGCCATAT TGGCCAGGCT
1001                                              1050

GATCTCGAAC TCCTGACCTC AGGTGATCCG CCCACCTCGG CCTCCCAAAG
1051                                              1100

TGCTGGGATT ACAGGCATGA GCCACCACGC CCGGCTGATC TCTTTTCTAT
1101                                              1150

TTTAATAGAG ATCAAACTCT CTGTGTTGCC TAGGCTGGTC TTGAACTCCT
1151                                              1200

GGCCTCGAGT GATCCTCCCA CCTTGGCCTC CCAAAGTGTT GAGATTACAG
1201                                              1250

GCATGAGCCA CTGTGCCTGG CCTCAGTTCT ACTACAAAAG GAAGCCAGTA
1251                                              1300

CCAGCTACCA CCCAGGGTGG CTGTAGGGCT ACAATGGAGC ACACAGAACC
1301                                              1350

CCTACCCAGG GCCCGGAAGA AGCCCCGACT CCTCTCCCCT CCCTCTGCCC
1351                                              1400

AGAACTCCTC CGCTTCTTTC TGATGTAGCC CAGGGCCGGA GGAGGCAGTC
1401                                              1450

AGGGAAGTTC TGTCTCTTTT TCATGTTATC TTACGAGGTC TCTTTTCTCC
1451                                              1500

ATTCTCAGTC CAACAAATGG TTGCTGCCCA AGGCTGACTG TGCCCACCCC
1501                                              1550

CAACCCCTGC TGGCCAGGGT CAATGTCTGT CTCTCTGGTC TCTCCAGAAG
1551                                              1600

TCTTCCATGG CCACCTTCGT CCCCACCCTC CAGAGGAATC TGAAACCGCA
1601                                              1650

TGTGCTCCCT GGCCCCCACA GCCCCTGCCT CTCCCAGAGC AGCAGTACCT
1651                                              1700

AAGCCTCAGT GCACTCCAAG AATTGAAACC CTCAGTCTGC TGCCCCTCCC
1701                                              1750
```

TABLE 14-continued

TRE Sequences

```
CACCAGAATG TTTCTCTCCC ATTCTTACCC ACTCAAGGCC CTTTCAGTAG
1751                                                1800

CCCCTTGGAG TATTCTCTTC CTACATATCA GGGCAACTTC CAAACTCATC
1801                                                1850

ACCCTTCTGA GGGGTGGGGG AAAGACCCCC ACCACATCGG GGGAGCAGTC
1851                                                1900

CTCCAAGGAC TGGCCAGTCT CCAGATGCCC GTGCACACAG GAACACTGCC
1901                                                1950

TTATGCACGG GAGTCCCAGA AGAAGGGGTG ATTTCTTTCC CCACCTTAGT
1951                                                2000

TACACCATCA AGACCCAGCC AGGGCATCCC CCCTCCTGGC CTGAGGGCCA
2001                                                2050

GCTCCCCATC CTGAAAAACC TGTCTGCTCT CCCCACCCCT TTGAGGCTAT
2051                                                2100

AGGGCCCAAG GGGCAGGTTG GACTGGATTC CCCTCCAGCC CCTCCCGCCC
2101                                                2150

CCAGGACAAA ATCAGCCACC CCAGGGGCAG GGCCTCACTT GCCTCAGGAA
2151                                                2200

CCCCAGCCTG CCAGCACCTA TTCCACCTCC CAGCCCAGCA
2201                                     2239
```

Nucleotide sequence of a mouse uroplakin II 5' flanking region. The transitional start site is denoted with an asterisk. SEQ ID NO:7 (number 1 of SEQ ID NO:7 correspond to position-3592 with respect to the translational start site).

```
CTCGAGGATCTCGGCCCTCTTTCTGCATCCTTGTCCTAAATCATTTTCAT
1                                                 50

ATCTTGCTAGACCTCAGTTTGAGAGAAACGAACCTTCTCATTTTCAAGTT
51                                               100

GAAAAAAAAAAGAGGTTCAAAGTGGCTCACTCAAAGTTACAAGCCAACAC
101                                              150

TCACCACTACGAGTACAATGGCCACCATTAGTGCTGGCATGCCCCAGGAG
151                                              200

ACAGGCATGCATATTATTCTAGATGACTGGGAGGCAGAGGGGTGGCCTAG
201                                              250

TGAGGTCAGACTGTGGACAGATCAGGCAGATGTGGGTTCTGATCCCAATT
251                                              300

CCTCAGGCCGCAGAACTACTGTGGTTCAAGAAGGGGACAAAAGGACTGCA
301                                              350

GTCCGGAACAGGAGGTCCATTTGAGAGCTGACTGAGCAGAAGAGGAAAGT
351                                              400

GAAGAACTTCTGGGGCAAGAGCTTACCCTACTTTACAGCTTTGTTGTCTT
401                                              450

CTTTACTCCAGGGGCGTCCCTGGTACTCAGTAAATGTCTGTTGGCTTGAG
451                                              500

GAACATATGTGTAAGGAGGAAGGAGAGGGAACTTGAGGGAGTTAAGACTC
501                                              550

AAGAATCAATCAAGGAGAGGACAGCAGAGAAGACAGGGTTTGGGAGAGAG
551                                              600

ACTCCAGACATTGGCCCTGGTTCCCTTCTTGGCCACTGTGAAACCCTCCA
601                                              650

GAGGAACTGAGTGCTGTGGCTTTAAATGATCTCAGCACTGTCAGTGAAGC
651                                              700

GCTCTGCTCAAAGAGTTATCCTCTTGCTCCTGTGCCGGGGCCTCCCCCTC
701                                              750

CTCTCAGCTCCCAAACCCTTCTCAGCCACTGTGATGGCATAATTAGATGC
751                                              800

GAGAGCTCAGACCGTCAGGTCTGCTCCAGGAACCACCCATTTTCCCCAAC
801                                              850

CCCAGAGAAAGGTCCTAGTGGAAAAGTGGGGGCCACTGAAGGGCTGATGG
851                                              900

GGTTCTGTCCTTTCCCCCATGCTGGGTGGACTTAAAGTCTGCGATGTGTG
900                                              950

TAGGGGGTAGAAGACAACAGAACCTGGGGGCTCCGGCTGGGAGCAGGAGG
951                                             1000

AACTCTCACCAGACGATCTCCAAATTTACTGTGCAATGGACGATCAGGAA
1001                                            1050

ACTGGTTCAGATGTAGCTTCTGATACAGTGGGTCTGAGGTAAAACCCGAA
1051                                            1100

ACTTAATTTCTTTCAAAAATTTAAAGTTGCATTTATTATTTTATATGTGT
1101                                            1150

GCCCATATGTGTGCCACAGTGTCTATGTGGAGGTCAGAGGGCAAGTTGTG
1151                                            1200

GGCATTGGCTCTCTCCTTTCATAATGTGGCTTCTGGGGACCAAAATGTCA
1201                                            1250

GGCATGGTGGCAAGAGCTTTTACCTGTTGAGCCATCTCATGGTTTCGTAA
1251                                            1300
```

-continued

```
AACTTCCTATGACGCTTACAGGTAACGCAGAGACACAGACTCACATTTGG
1301                                              1350

AGTTAGCAGATGCTGTATTGGTGTAAACACTCATACACAGACACACACAC
1351                                              1400

ATACTCATACACACACACACACACTTATCACATGCACACACATACTCGTA
1401                                              1450

TACACACAGACACACACACATGCACTCTCACATTCACATATTCATACACA
1451                                              1500

TCCACACACACACTCATCCACACACACAGACACACATACTCATCCACACA
1501                                              1550

CACACACACACATACTCATACACACACACAGACACACATACTCATACACA
1551                                              1600

CACACAGACACACACATATAATCATACATACACAGACACACTCATACATG
1601                                              1650

TGCACACACACACTCATCCACACACACACACTCATACACACACACACTCA
1651                                              1700

TACACACACACACTCATACACACACACACGAGGTTTTTCTCAGGCTGCCT
1701                                              1750

TTGGGTGGAGACTGGAACTGATTTCTGTTTTTCAGCTCCTTGGCTTTTTG
1751                                              1800

TCCCTTTAGATGAGATCTCCTCCTCACTTTACACACAGAAAGATCACACA
1801                                              1850

CGAGGGAGAACTGGCGGTGCGGAAGAGGGCTACACGGTAGGGTGTCAGGG
1851                                              1900

TCAGGAGATCTTCCTGGCAAGTCTCAAACCTCCACATAGCACAGTGTTTA
1901                                              1950

CGTGAGGATTTAGGAGGAATCAGGAAGAGGATTGGTTTACTGCAGAGCAG
1951                                              2000

ACCATATAGGTCCACTCCTAAGCCCCATTTGAAATTAGAAGTGAGACAGT
2001                                              2050

GTGGGATAAAAAGAGCAGATCTCTGGTCACATTTTTAAAGGGATATGAGG
2051                                              3000

GTCCTGTGCCTTTAAGCCTTCCCATCTCCCTCCAATCCCCCCTCACCTTC
2101                                              2150

CCCACCCTAACCCTCCCCAGGTTTCTGGAGGAGCAGAGTTGCGTCTTCTC
2151                                              2200

CCTGCCCTGCCGAGCTGCTCACTGGCTGCTCTAGAGGCTGTGCTTTGCGG
2201                                              2250

TCTCCATGGAAACCATTAGTTGCTAAGCAACTGGAGCATCATCTGTGCTG
2251                                              2300

AGCTCAGGTCCTATCGAGTTCACCTAGCTGAGACACCCACGCCCCTGCAG
2301                                              2350

CCACTTTGCAGTGACAAGCCTGAGTCTCAGGTTCTGCATCTATAAAAACG
2351                                              2400

AGTAGCCTTTCAGGAGGGCATGCAGAGCCCCTGGCCAGCGTCTAGAGGA
2401                                              2450

GAGGTGACTGAGTGGGCCATGTCACTCGTCCATGGCTGGAGAACCTCCA
2451                                              2500

TCAGTCTCCCAGTTAGCCTGGGGCAGGAGAGAACCAGAGGAGCTGTGGCT
2501                                              2550

GCTGATTGGATGATTTACGTACCCAATCTGTTGTCCCAGGCATCGAACCC
2551                                              2600

CAGAGCGACCTGCACACATGCCACCGCTGCCCCGCCCTCCACCTCCTCTG
2601                                              2650

CTCCTGGTTACAGGATTGTTTTGTCTTGAAGGGTTTTGTTGTTGCTACTT
2651                                              2700

TTTGCTTTGTTTTTTCTTTTTTAACATAAGGTTTCTCTGTGTAGCCCTAG
2701                                              2750

CTGTCCTGGAACTCACTCTGTAGACCAGGCTGGCCTCAAACTCAGAAATC
2751                                              2800

CACCTTCCTCCCAAGTGCTGGGATTAAAGGCATTCGCACCATCGCCCAGC
2801                                              2850

CCCCGGTCTTGTTTCCTAAGGTTTTCCTGCTTTACTCGCTACCCGTTGCA
2851                                              2900

CAACCGCTTGCTGTCCAAGTCTGTTTGTATCTACTCCACCGCCCACTAGC
2901                                              2950

CTTGCTGGACTGGACCTACGTTTACCTGGAAGCCTTCACTAACTTCCCTT
2951                                              3000

GTCTCCACCTTCTGGAGAAATCTGAAGGCTCACACTGATACCCTCCGCTT
3001                                              3050

CTCCCAGAGTCGCAGTTTCTTAGGCCTCAGTTAAATACCAGAATTGGATC
3051                                              3100

TCAGGCTCTGCTATCCCCACCCTACCTAACCAACCCCCTCCTCTCCCATC
3101                                              3150

CTTACTAGCCAAAGCCCTTTCAACCCTTGGGCTTTTCCTACACCTACAC
3151                                              3200

ACCAGGGCAATTTTAGAACTCATGGCTCTCCTAGAAAACGCCTACCTCCT
3201                                              3250

TGGAGACTGACCCTCTACAGTCCAGGAGGCAGACACTCAGACAGAGGAAC
3251                                              3300

TCTGTCCTTCAGTCGCGGGAGTTCCAGAAAGAGCCATACTCCCCTGCAGA
3301                                              3350

GCTAACTAAGCTGCCAGGACCCAGCCAGAGCATCCCCCTTTAGCCGAGGG
3351                                              3400

CCAGCTCCCCAGAATGAAAAACCTGTCTGGGGCCCCTCCCTGAGGCTACA
3401                                              3450

GTCGCCAAGGGGCAAGTTGGACTGGATTCCCAGCAGCCCCTCCCACTCCG
3451                                              3500

AGACAAAATCAGCTACCCTGGGGCAGGCCTCATTGGCCCCAGGAAACCCC
3501                                              3550

AGCCTGTCAGCACCTGTTCCAGGATCCAGTCCCAGCGCAGTA
3551                                    3592
```

AFP-TRE. SEQ ID NO:8.

```
1
    GCATTGCTGTGAACTCTGTACTTAGGACTAAACTTTGAGCAATAACA
                                      CACATAGATTGAG
61
    GATTGTTTGCTGTTAGCATACAAACTCTGGTTCAAAGCTCCTCTTTA
                                      TTGCTTGTCTTGG
121 AAAATTTGCTGTTCTTCATGGTTTCTCTTTTCACTGCTATCTATTTT
                                      TCTCAACCACTCA
181 CATGGCTACAATAACTGTCTGCAAGCTTATGATTCCCAAATATCTAT
                                      CTCTAGCCTCAAT
241 CTTGTTCCAGAAGATAAAAAGTAGTATTCAAATGCACATCAACGTCT
                                      CCACTTGGAGGGC
```

-continued

```
301 TTAAAGACGTTTCAACATACAAACCGGGGAGTTTTGCCTGGAATGTT
                                     TCCTAAAATGTGT
361 CCTGTAGCACATAGGGTCCTCTTGTTCCTTAAAATCTAATTACTTTT
                                        AGCCCAGTGCTCA
421 TCCCACCTATGGGGAGATGAGAGTGAAAAGGGAGCCTGATTAATAAT
                                       TACACTAAGTCAA
481 TAGGCATAGAGCCAGGACTGTTTGGGTAAACTGGTCACTTTATCTTA
                                      AACTAAATATATC
541 CAAAACTGAACATGTACTTAGTTACTAAGTCTTTGACTTTATCTCAT
                                      TCATACCACTCAG
601 CTTTATCCAGGCCACTTATGAGCTCTGTGTCCTTGAACATAAAATAC
                                      AAATAACCGCTAT
661 GCTGTTAATTATTGGCAAATGTCCCATTTTCAACCTAAGGAAATACC
                                      ATAAAGTAACAGA
721 TATACCAACAAAAGGTTACTAGTTAACAGGCATTGCCTGAAAAGAGT
                                      ATAAAAGAATTTC
781 AGCATGATTTTCCATATTGTGCTTCCACCACTGCCAATAACA
                                                (822)
```

```
Probasin -TRE SEQ ID NO:9
      -426
5'-AAGCTTCCACAAGTGCATTTAGCCTCTCCAGTATTGCTGATGAATCC

ACAGTTCAGGTTCAATGGCGTTCAAAACTTGATCAAAAATGACCAGACTT

TATATTTACACCAACATCTATCTGATTGGAGGAATGGATAATAGTCATCA

TGTTTAAACATCTACCATTCCAGTTAAGAAAATATGATAGCATCTT

GTTCTTAGTCTTTTTCTTAATAGGGACATAAAGCCCACAAATAAAAATAT
ARE-1

GCCTGAAGAATGGGACAGGCATTGGGCATTGTCCATGCCTAGTAAAGTA

CTCCAAGAACCTATTTGTATACTAGATGACACAATGTCAATGTCTGTGTA
ARE-2

CAACTGCCAACTGGGATGCAAGACACTGCCCATGCCAATCATCCTGAAAA
                                          CAAT box
                                        +1
GCAGCTATAAAAGCAGGAAGCTACTCTGCACCTTGTCAGTAGGTCCAGA
      TATAA box                    Transcription site
      +28
TACCTACAG-3'
```

```
Tyrosinase-TRE SEQ ID NO:10
    PinA1 end

1       CCGGTTGAAAATGATAAGTTGAATTCTGTCTTCGAGAACATAGAAAGAA

51       TTATGAAATGCCAACATGTGGTTACAAGTAATGCAGACCCAAGGCTCCCC

101       AGGGACAAGAAGTCTTGTGTTAACTCTTTGTGGCTCTGAAAGAAAGAGAG

151       AGAGAAAAGATTAAGCCTCCTTGTGGAGATCATGTGATGACTTCCTGATT

201       CCAGCCAGAGCGAGCATTTCCATGGAAACTTCTCTTCCTCTTCACTCGAG

251       ATTACTAACCTTATTGTTAATATTCTAACCATAAGAATTAAACTATTAAT

301       GGTGAATAGAGTTTTTCACTTTAACATAGGCCTATCCCACTGGTGGGATA

351       CGAGCCAATTCGAAAGAAAAAGTCAGTCATGTGCTTTTCAGAGGATGAAA

401       GCTTAAGATAAAGACTAAAAGTGTTTGATGCTGGAGGTGGGAGTGGTATT

451       ATATAGGTCTCAGCCAAGACATGTGATAATCACTGTAGTAGTAGCTGGAA

501       AGAGAAATCTGTGACTCCAATTAGCCAGTTCCTGCAGACCTTGTGA
                                                      PinA1 end
```

```
Human glandular kallikrein-TRE SEQ ID NO:11
gaattcagaa ataggggaag gttgaggaag gacactgaac tcaaagggga tacagtgatt    60
ggtttatttg tcttctcttc acaacattgg tgctggagga attcccaccc tgaggttatg   120
aagatgtctg aacacccaac acatagcact ggagatatga gctcgacaag agtttctcag   180
ccacagagat tcacagccta gggcaggagg acactgtacg ccaggcagaa tgacatggga   240
attgcgctca cgattggctt gaagaagcaa ggactgtggg aggtgggctt tgtagtaaca   300
```

-continued

```
agagggcagg gtgaactctg attcccatgg gggaatgtga tggtcctgtt acaaattttt      360
caagctggca gggaataaaa cccattacgg tgaggacctg tggagggcgg ctgccccaac      420
tgataaagga aatagccagg tgggggcctt tcccattgta gggggacat  atctggcaat      480 agaagccttt gagacccttt aggtacaag  tactgaggca gcaaataaaa tgaaatctta      540
tttttcaact ttatactgca tgggtgtgaa gatatatttg tttctgtaca ggggtgagg       600 gaaggaggg  gaggaggaaa gttcctgcag gtctggtttg gtcttgtgat ccaggggtc       660 ttggaactat ttaaattaaa ttaaattaaa acaagcgact gttttaaatt aaattaaatt      720
aaattaaatt ttactttatt ttatcttaag ttctgggcta catgtgcagg acgtgcagct      780
ttgttacata ggtaaacgtg tgccatggtg gtttgctgta cctatcaacc catcacctag      840
gtattaagcc cagcatgcat tagctgtttt tcctgacgct ctccctctcc ctgactccca      900
caacaggccc cagtgtgtgt tgttccctc  cctgtgtcca tgtgttctca ttgttcagct      960
cccacttata agtgagaaca tgtggtgttt ggttttctgt ttctgtgtta gtttgctgag     1020
gataatggct tccacctcca tccatgttcc tgcaaaggac gtgatcttat tcttttttat     1080
ggttgcatag aaattgtttt tacaaatcca attgatattg tatttaatta caagttaatc     1140
taattagcat actagaagag attacagaag atattaggta cattgaatga ggaaatatat     1200
aaaataggac gaaggtgaaa tattaggtag gaaaagtata atagttgaaa gaagtaaaaa     1260
aaaatatgca tgagtagcag aatgtaaaag aggtgaagaa cgtaatagtg acttttttaga    1320 ccagattgaa ggacagagac agaaaaattt taaggaattg ctaaaccatg tgagtgttag     1380
aagtacagtc aataacatta aagcctcagg aggagaaaaa aataggaaag gaggaaatat     1440
gtgaataaat agtagagaca tgtttgatgg attttaaaat atttgaaaga cctcacatca     1500
aaggattcat accgtgccat tgaagaggaa gatgaaaag  ccaagaagcc agatgaaagt     1560
tagaaatatt attggcaaag cttaaatgtt aaaagtccta gagagaaagg atggcagaaa     1620
tattggcggg aaagaatgca gaacctagaa tataaattca tcccaacagt ttggtagtgt     1680
gcagctgtag cctttttctag ataatacact attgtcatac atcgcttaag cgagtgtaaa    1740
atggtctcct cactttattt atttatatat ttatttagtt ttgagatgga gcctcgctct     1800
gtctcctagg ctggagtgca atagtgcgat accactcact gcaacctctg cctcctctgt     1860
tcaagtgatt ttcttacctc agcctcccga gtagctggga ttacaggtgc gtgccaccac     1920
acccggctaa ttttttgtatt ttttgtagag acggggtttt gccatgttgg ccaggctggt    1980
cttgaactcc tgacatcagg tgatccacct gccttggcct cctaaagtgc tgggattaca     2040
ggcatgagcc accgtgccca accactttat ttatttttta tttttatttt taaatttcag     2100
cttctatttg aaatacaggg ggcacatata taggattgtt acatgggtat attgaactca     2160
ggtagtgatc atactaccca acaggtaggt tttcaaccca ctccccctct tttcctcccc     2220
attctagtag tgtgcagtgt ctattgttct catgtttatg tctatgtgtg ctccaggttt     2280
agctcccacc tgtaagtgag aacgtgtggt atttgatttt ctgtccctgt gttaattcac     2340
ttaggattat ggcttccagc tccattcata ttgctgtaaa ggatatgatt catttttcat     2400
ggccatgcag tattccatat tgcgtataga tcacattttc tttctttttt tttttgaga     2460 cggagtcttg ctttgctgcc taggctggag tgcagtagca cgatctcggc tcactgcaag     2520
cttcacctcc ggggttcacg tcattcttct gtctcagctt cccaagtagc tgggactaca     2580
ggcgcccgcc accacgtccg gctaattttt ttgtgtgttt ttagtagaga tggggggtttc    2640 actgtgttag ccaggatggt cttgatctcc tgaccttgtg gtccacctgc ctcggtctcc     2700
```

-continued

```
caaagtgctg ggattacagg ggtgagccac tgcgcccggc ccatatatac cacattttct    2760
ttaaccaatc caccattgat gggcaactag gtagattcca tggattccac agttttgcta    2820
ttgtgtgcag tgtggcagta gacatatgaa tgaatgtgtc ttttttggtat aatgatttgc    2880 attcctttgg gtatacagtc attaatagga gtgctgggtt gaacggtggc tctgtttaaa    2940
attctttgag aattttccaa actgtttgcc atagagagca aactaattta catttccacg    3000
aacagtatat aagcattccc ttttctccac agctttgtca tcatggtttt tttttttctt    3060
tattttaaaa aagaatatgt tgttgttttc ccagggtaca tgtgcaggat gtgcaggttt    3120
gttacatagg tagtaaacgt gagccatggt ggtttgctgc acctgtcaac ccattacctg    3180
ggtatgaagc cctgcctgca ttagctcttt tccctaatgc tctcactact gccccaccct    3240
caccctgaca gggcaaacag acaacctaca gaatgggagg aaattttgc aatctattca    3300 tctgacaaag gtcaagaata tccagaatct acaaggaact taagcaaatt tttacttttt    3360
aataatagcc actctgactg gcgtgaaatg gtatctcatt gtggttttca tttgaatttc    3420
tctgatgatc agtgacgatg agcattttt catatttgtt ggctgcttgt acgtcttttg    3480
agaagtgtct cttcatgcct tttggccact ttaatgggat tattttttgc ttttttagttt    3540 aagttcctta tagattctgg atattagact tcttattgga tgcatagttt gtgaatactc    3600
tcttccattc tgtaggttgt ctgtttactc tattgatggc ttcttttgct gtgccgaagc    3660
atcttagttt aattagaaac cacctgccaa tttttgtttt tgttgcaatt gcttttgggg    3720
acttagtcat aaactctttg ccaaggtctg ggtcaagaag agtatttcct aggttttctt    3780
ctagaatttt gaaagtctga atgtaaacat ttgcatttt aatgcatctt gagttagttt    3840
ttgtatatgt gaaaggtcta ctctcatttt ctttccctct ttctttcttt ctttcttttc    3900
tttctttctt tctttctttc tttctttctt tcttctttc tttcttttg tccttctttc    3960 tttctttctt tctctttctt tctctctttc tttttttttt ttgatggagt attgctctgt    4020
tgcccaggct gcagtgcagc ggcacgatct cggctcactg caacctctgc ctcctgggtt    4080
caactgattc tcctgcatca gccttccaag tagctgggat tataggcgcc cgccaccacg    4140
cccgactaat ttttgtattt ttagtagaga cggggttgtg ccatgttggc caggctggtt    4200
tgaaactcct gacctcaaac gatctgcctg ccttggcctc ccaaagtgct gggattacag    4260
gtgtgagcca ctgtgcccag ccaagaatgt cattttctaa gaggtccaag aacctcaaga    4320
tattttggga ccttgagaag agaggaattc atacaggtat tacaagcaca gcctaatggc    4380
aaatctttgg catggcttgg cttcaagact ttaggctctt aaaagtcgaa tccaaaaatt    4440
tttataaaag ctccagctaa gctaccttaa aaggggcctg tatggctgat cactcttctt    4500
gctatacttt acacaaataa acaggccaaa tataatgagg ccaaaattta ttttgcaaat    4560
aaattggtcc tgctatgatt tactcttggt aagaacaggg aaaatagaga aaaatttaga    4620
ttgcatctga cctttttttc tgaattttta tatgtgccta caatttgagc taaatcctga    4680
attattttct ggttgcaaaa actctctaaa gaagaacttg gttttcattg tcttcgtgac    4740
acatttatct ggctctttac tagaacagct ttcttgtttt tggtgttcta gcttgtgtgc    4800
cttacagttc tactcttcaa attattgtta tgtgtatctc atagttttcc ttcttttgag    4860
aaaactgaag ccatggtatt ctgaggacta gagatgactc aacagagctg gtgaatctcc    4920
tcatatgcaa tccactgggc tcgatctgct tcaaattgct gatgcactgc tgctaaagct    4980
atacatttaa aaccctcact aaaggatcag ggaccatcat ggaagaggag gaaacatgaa    5040
attgtaagag ccagattcgg ggggtagagt gtggaggtca gagcaactcc accttgaata    5100
```

-continued

```
agaaggtaaa gcaacctatc ctgaaagcta acctgccatg gtggcttctg attaacctct      5160
gttctaggaa gactgacagt ttgggtctgt gtcattgccc aaatctcatg ttaaattgta      5220
atccccagtg ttcggaggtg ggacttggtg gtaggtgatt cggtcatggg agtagatttt      5280
cttctttgtg gtgttacagt gatagtgagt gagttctcgt gagatctggt catttaaaag      5340
tgtgtggccc ctcccctccc tctcttggtc ctcctactgc catgtaagat acctgctcct      5400
gctttgcctt ctaccataag taaaagcccc ctgaggcctc cccagaagca gatgccacca      5460
tgcttcctgt acagcctgca gaaccatcag ccaattaaac ctcttttctg tataaattac      5520
cagtcttgag tatctctttta cagcagtgtg agaacggact aatacaaggg tctccaaaat      5580
tccaagttta tgtattcttt cttgccaaat agcaggtatt taccataaat cctgtcctta      5640
ggtcaaacaa ccttgatggc atcgtacttc aattgtctta cacattcctt ctgaatgact      5700
cctcccctat ggcatataag ccctgggtct tgggggataa tggcagaggg gtccaccatc      5760
ttgtctggct gccacctgag acacggacat ggcttctgtt ggtaagtctc tattaaatgt      5820
ttctttctaa gaaactggat ttgtcagctt gtttctttgg cctctcagct tcctcagact      5880
ttggggtagg ttgcacaacc ctgcccacca cgaaacaaat gtttaatatg ataaatatgg      5940
atagatataa tccacataaa taaaagctct tggagggccc tcaataattg ttaagagtgt      6000
aaatgtgtcc aaagatggaa aatgtttgag aactactgtc ccagagattt tcctgagttc      6060
tagagtgtgg gaatatagaa cctggagctt ggcttcttca gcctagaatc aggagtatgg      6120
ggctgaagtc tgaagcttgg cttcagcagt ttggggttgg cttccggagc acatatttga      6180
catgttgcga ctgtgatttg gggtttggta tttgctctga atcctaatgt ctgtccttga      6240
ggcatctaga atctgaaatc tgtggtcaga attctattat cttgagtagg acatctccag      6300
tcctggttct gccttctagg gctggagtct gtagtcagtg acccggtctg gcatttcaac      6360
ttcatataca gtgggctatc ttttggtcca tgtttcaacc aaacaaccga ataaaccatt      6420
agaacctttc cccacttccc tagctgcaat gttaaaccta ggatttctgt ttaataggtt      6480
catatgaata atttcagcct gatccaactt tacattcctt ctaccgttat tctacaccca      6540
ccttaaaaat gcattcccaa tatattccct ggattctacc tatatatggt aatcctggct      6600
ttgccagttt ctagtgcatt aacatacctg atttacattc ttttactttta aagtggaaat      6660 aagagtccct ctgcagagtt caggagttct caagatggcc cttacttctg acatcaattg      6720
agatttcaag ggagtcgcca agatcatcct caggttcagt gattgctggt agccctcata      6780
taactcaatg aaaagctgtta tgctcatggc tatggtttat tacagcaaaa gaatagagat      6840
gaaaatctag caagggaaga gttgcatggg gcaaagacaa ggagagctcc aagtgcagag      6900
attcctgttg ttttctccca gtggtgtcat ggaaagcagt atcttctcca tacaatgatg      6960
tgtgataata ttcagtgtat tgccaatcag ggaactcaac tgagccttga ttatattgga      7020
gcttggttgc acagacatgt cgaccacctt catggctgaa ctttagtact tagcccctcc      7080
agacgtctac agctgatagg ctgtaaccca acattgtcac cataaatcac attgttagac      7140
tatccagtgt ggcccaagct cccgtgtaaa cacaggcact ctaaacaggc aggatatttc      7200
aaaagcttag agatgacctc ccaggagctg aatgcaaaga cctggcctct ttgggcaagg      7260
agaatccttt accgcacact ctccttcaca gggttattgt gaggatcaaa tgtggtcatg      7320
tgtgtgagac accagcacat gtctggctgt ggagagtgac ttctatgtgt gctaacattg      7380
ctgagtgcta agaagtatt aggcatggct ttcagcactc acagatgctc atctaatcct      7440
cacaacatgg ctacagggtg ggcactacta gcctcatttg acagaggaaa ggactgtgga      7500
```

```
taagaagggg gtgaccaata ggtcagagtc attctggatg caaggggctc cagaggacca      7560
tgattagaca ttgtctgcag agaaattatg gctggatgtc tctgcccegg aaaggggat       7620 gcactttcct tgacccccta tctcagatct tgactttgag gttatctcag acttcctcta      7680
tgataccagg agcccatcat aatctctctg tgtcctctcc ccttcctcag tcttactgcc      7740
cactcttccc agctccatct ccagctggcc aggtgtagcc acagtaccta actctttgca      7800
gagaactata aatgtgtatc ctacaggga gaaaaaaaaa aagaactctg aaagagctga       7860
cattttaccg acttgcaaac acataagcta acctgccagt tttgtgctgg tagaactcat      7920
gagactcctg ggtcagaggc aaaagatttt attacccaca gctaaggagg cagcatgaac      7980
tttgtgttca catttgttca ctttgccccc caattcatat gggatgatca gagcagttca      8040
ggtggatgga cacaggggtt tgtggcaaag gtgagcaacc taggcttaga aatcctcaat      8100
cttataagaa ggtactagca aacttgtcca gtctttgtat ctgacggaga tattatcttt      8160
ataattgggt tgaaagcaga cctactctgg aggaacatat tgtatttatt gtcctgaaca      8220
gtaaacaaat ctgctgtaaa atagacgtta actttattat ctaaggcagt aagcaaacct      8280
agatctgaag gcgataccat cttgcaaggc tatctgctgt acaaatatgc ttgaaaagat      8340
ggtccagaaa agaaaacggt attattgcct ttgctcagaa gacacacaga aacataagag      8400
aaccatggaa aattgtctcc caacactgtt cacccagagc cttccactct tgtctgcagg      8460
acagtcttaa catcccatca ttagtgtgtc taccacatct ggcttcaccg tgcctaacca      8520
agatttctag gtccagttcc ccaccatgtt tggcagtgcc ccactgccaa ccccagaata      8580
agggagtgct cagaattccg aggggacatg ggtgggatc agaacttctg ggcttgagtg       8640 cagaggggc ccatactcct tggttccgaa ggaggaagag gctggaggtg aatgtccttg       8700
gaggggagga atgtgggttc tgaactctta aatccccaag ggaggagact ggtaaggtcc      8760
cagcttccga ggtactgacg tgggaatggc ctgagaggtc taagaatccc gtatcctcgg      8820
gaaggagggg ctgaaattgt gagggttga gttgcagggg tttgttagct tgagactcct       8880
tggtgggtcc ctgggaagca aggactggaa ccattggctc cagggtttgg tgtgaaggta      8940
atgggatctc ctgattctca aagggtcaga ggactgagag ttgcccatgc tttgatcttt      9000
ccatctactc cttactccac ttgagggtaa tcacctactc ttctagttcc acaagagtgc      9060
gcctgcgcga gtataatctg cacatgtgcc atgtcccgag gcctgggggca tcatccactc     9120 atcattcagc atctgcgcta tgcgggcgag gccggcgcca tgacgtcatg tagctgcgac      9180
tatccctgca gcgcgcctct cccgtcacgt cccaaccatg gagctgtgga cgtgcgtccc      9240
ctggtggatg tggcctgcgt ggtgccaggc cggggcctgg tgtccgataa agatcctaga      9300
accacaggaa accaggactg aaaggtgcta gagaatggcc atatgtcgct gtccatgaaa      9360
tctcaaggac ttctgggtgg agggcacagg agcctgaact tacgggtttg ccccagtcca     9420
ctgtcctccc aagtgagtct cccagatacg aggcactgtg ccagcatcag cttcatctgt      9480
accacatctt gtaacaggga ctacccagga ccctgatgaa caccatggtg tgtgcaggaa      9540 gaggggtga aggcatggac tcctgtgtgg tcagagccca gaggggccca tgacgggtgg      9600
ggaggaggct gtggactggc tcgagaagtg ggatgtggtt gtgtttgatt cctttggcc       9660 agataaagtg ctggatatag cattgaaaac ggagtatgaa gaccagttag aatggagggt      9720
caggttggag ttgagttaca gatgggtaa aattctgctt cggatgagtt tggggattgg       9780
caatctaaag gtggtttggg atggcatggc tttgggatgg aaataggttt gttttatgt       9840 tggctgggaa gggtgtgggg attgaattgg ggatgaagta ggtttagttt tggagataga     9900
```

```
atacatggag ctggctattg catgcgagga tgtgcattag tttggtttga tctttaaata    9960
aaggaggcta ttagggttgt cttgaattag attaagttgt gttgggttga tgggttgggc   10020
ttgtgggtga tgtggttgga ttgggctgtg ttaaattggt ttgggtcagg ttttggttga   10080
ggttatcatg gggatgagga tatgcttggg acatggattc aggtggttct cattcaagct   10140
gaggcaaatt tcctttcaga cggtcattcc agggaacgag tggttgtgtg ggggaaatca   10200
ggccactggc tgtgaatatc cctctatcct ggtcttgaat tgtgattatc tatgtccatt   10260
ctgtctcctt cactgtactt ggaattgatc tggtcattca gctggaaatg ggggaagatt   10320
ttgtcaaatt cttgagacac agctgggtct ggatcagcgt aagccttcct tctggtttta   10380 ttaacagat gaaatcacat ttttttttc aaaatcacag aaatcttata gagttaacag   10440
tggactctta taataagagt taacaccagg actcttattc ttgattcttt tctgagacac   10500
caaaatgaga tttctcaatg ccaccctaat tctttttttt tttttttttt ttttgagac   10560 acagtctggg tcttttgctc tgtcactcag gctggagcgc agtggtgtga tcatagctca   10620
ctgaaccctt gacctcctgg acttaaggga tcctcctgct tcagcctcct gagtagatgg   10680
ggctacaggt gcttgccacc acacctggct aattaaattt tttttttttt tttgtagaga   10740
aagggtctca ctttgttgcc ctggctgatc ttgaacttct gacttcaagt gattcttcag   10800
ccttggactc ccaaagcact gggattgctg gcatgagcca ctcaccgtgc ctggcttgca   10860
gcttaatctt ggagtgtata aacctggctc ctgatagcta gacatttcag tgagaaggag   10920
gcattggatt ttgcatgagg acaattctga cctaggaggg caggtcaaca ggaatccccg   10980
ctgtacctgt acgttgtaca ggcatggaga atgaggagtg aggaggccgt accggaaccc   11040
catattgttt agtggacatt ggattttgaa ataataggga acttggtctg ggagagtcat   11100
atttctggat tggacaatat gtggtatcac aaggttttat gatgagggag aaatgtatgt   11160
ggggaaccat tttctgagtg tggaagtgca agaatcagag agtagctgaa tgccaacgct   11220
tctatttcag gaacatggta agttggaggt ccagctctcg ggctcagacg ggtataggga   11280
ccaggaagtc tcacaatccg atcattctga tatttcaggg catattaggt ttggggtgca   11340
aaggaagtac ttgggactta ggcacatgag actttgtatt gaaaatcaat gattggggct   11400
ggccgtggtg ctcacgcctg taatctcatc actttgggag accgaagtgg gaggatggct   11460
tgatctcaag agttggacac cagcctaggc aacatggcca gaccctctct ctacaaaaaa   11520
attaaaaatt agctggatgt ggtggtgcat gcttgtggtc tcagctatcc tggaggctga   11580
gacaggagaa tcggttgagt ctgggagttc aaggctacag ggagctgcga tcacgccgct   11640
gcactccagc ctgggaaaca gagtgagact gtctcagaat ttttttaaaa aagaatcagt   11700
gatcatccca acccctgttg ctgttcatcc tgagcctgcc ttctctggct tgttcccta   11760 gatcacatct ccatgatcca taggccctgc ccaatctgac ctcacaccgt gggaatgcct   11820
ccagactgat ctagtatgtg tggaacagca agtgctggct ctccctcccc ttccacagct   11880
ctgggtgtgg gagggggttg tccagcctcc agcagcatgg ggagggcctt ggtcagcatc   11940
taggtgccaa caggcaagg gcggggtcct ggagaatgaa ggctttatag ggctcctcag   12000
ggaggccccc cagccccaaa ctgcaccacc tggccgtgga caccggt                12047
```

HRE-TRE SEQ ID NO:12
ccccgagg cagtgcat gaggctcagg gcgtgcgt gagtcgcagcga
gaccccg gggtgcag gccgga

PSA-TRE SEQ ID NO:13

| | | | | | |
|---|---|---|---|---|---|
| aagcttctag | ttttcttttc | ccggtgacat | cgtggaaagc | actagcatct ctaagcaatg | 60 |
| atctgtgaca | atattcacag | tgtaatgcca | tccagggaac | tcaactgagc cttgatgtcc | 120 |
| agagatttt | gtgttttttt | ctgagactga | gtctcgctct | gtgccaggct ggagtgcagt | 180 |
| ggtgcaacct | tggctcactg | caagctccgc | ctcctgggtt | cacgccattc tcctgcctca | 240 |
| gcctcctgag | tagctgggac | tacaggcacc | cgccaccacg | cctggctaat ttttttgtat | 300 |
| ttttagtaga | gatgggtttt | cactgtgtta | gccaggatgg | tctcagtctc ctgacctcgt | 360 |
| gatctgccca | ccttggcctc | ccaaagtgct | gggatgacag | gcgtgagcca ccgcgcctgg | 420 |
| ccgatatcca | gagatttttt | gggggctcc | atcacacaga | catgttgact gtcttcatgg | 480 |
| ttgacttta | gtatccagcc | cctctagaaa | tctagctgat | atagtgtggc tcaaaacctt | 540 |
| cagcacaaat | cacaccgtta | gactatctgg | tgtgcccaa | accttcaggt gaacaaaggg | 600 |
| actctaatct | ggcaggatac | tccaaagcat | tagagatgac | ctcttgcaaa gaaaagaaa | 660 |
| tggaaagaa | aagaaagaa | aggaaaaaaa | aaaaaaaaa | gagatgacct ctcaggctct | 720 |
| gagggggaaac | gcctgaggtc | tttgagcaag | gtcagtcctc | tgttgcacag tctccctcac | 780 |
| agggtcattg | tgacgatcaa | atgtggtcac | gtgtatgagg | caccagcaca tgcctggctc | 840 |
| tggggagtgc | cgtgtaagtg | tatgcttgca | ctgctgaatg | gctgggatgt gtcagggatt | 900 |
| atcttcagca | cttacagatg | ctcatctcat | cctcacagca | tcactatggg atgggtatta | 960 |
| ctggcctcat | tgatggaga | aagtggctgt | ggctcagaaa | ggggggacca ctagaccagg | 1020 |
| gacactctgg | atgctgggga | ctccagagac | catgaccact | caccaactgc agagaaatta | 1080 |
| attgtggcct | gatgtccctg | tcctggagag | ggtggaggtg | gaccttcact aacctcctac | 1140 |
| cttgacccctc | tcttttaggg | ctctttctga | cctccaccat | ggtactagga ccccattgta | 1200 |
| ttctgtaccc | tcttgactct | atgaccccca | ccgcccactg | catccagctg ggtcccctcc | 1260 |
| tatctctatt | cccagctggc | cagtgcagtc | tcagtgccca | cctgtttgtc agtaactctg | 1320 |
| aaggggctga | cattttactg | acttgcaaac | aaataagcta | actttccaga gttttgtgaa | 1380 |
| tgctggcaga | gtccatgaga | ctcctgagtc | agaggcaaag | gcttttactg ctcacagctt | 1440 |
| agcagacagc | atgaggttca | tgttcacatt | agtacacctt | gccccccca aatcttgtag | 1500 |
| ggtgaccaga | gcagtctagg | tggatgctgt | gcagaagggg | tttgtgccac tggtgagaaa | 1560 |
| cctgagatta | ggaatcctca | atcttatact | gggacaactt | gcaaacctgc tcagcctttg | 1620 |
| tctctgatga | agatattatc | ttcatgatct | tggattgaaa | acagacctac tctggaggaa | 1680 |
| catattgtat | cgattgtcct | tgacagtaaa | caaatctgtt | gtaagagaca ttatctttat | 1740 |
| tatctaggac | agtaagcaag | cctggatctg | agagagatat | catcttgcaa ggatgcctgc | 1800 |
| tttacaaaca | tccttgaaac | aacaatccag | aaaaaaaaag | gtgttactgt cttttgctcag | 1860 |
| aagacacaca | gatacgtgac | agaaccatgg | agaattgcct | cccaacgctg ttcagccaga | 1920 |
| gccttccacc | ctttctgcag | gacagtctca | acgttccacc | attaaatact tcttctatca | 1980 |
| catcccgctt | ctttatgcct | aaccaaggtt | ctaggtcccg | atcgactgtg tctggcagca | 2040 |

-continued

```
ctccactgcc aaacccagaa taaggcagcg ctcaggatcc cgaagggca tggctgggga      2100 tcagaacttc tgggtttgag tgaggagtgg gtccaccctc ttgaatttca aggaggaag      2160 aggctggatg tgaaggtact gggggaggga aagtgtcagt tccgaactct taggtcaatg      2220
agggaggaga ctggtaaggt cccagctccc gaggtactga tgtgggaatg gcctaagaat      2280
ctcatatcct caggaagaag gtgctggaat cctgaggggt agagttctgg gtatatttgt      2340
ggcttaaggc tctttggccc ctgaaggcag aggctggaac cattaggtcc agggtttggg      2400
gtgatagtaa tgggatctct tgattcctca agagtctgag gatcgagggt tgcccattct      2460
tccatcttgc cacctaatcc ttactccact tgagggtatc accagccctt ctagctccat      2520
gaaggtcccc tgggcaagca caatctgagc atgaaagatg ccccagaggc cttgggtgtc      2580
atccactcat catccagcat cacactctga gggtgtggcc agcaccatga cgtcatgttg      2640
ctgtgactat ccctgcagcg tgcctctcca gccacctgcc aaccgtagag ctgcccatcc      2700
tcctctggtg ggagtggcct gcatggtgcc aggctgaggc ctagtgtcag acagggagcc      2760
tggaatcata gggatccagg actcaaaagt gctagagaat ggccatatgt caccatccat      2820
gaaatctcaa gggcttctgg gtggagggca cagggacctg aacttatggt ttcccaagtc      2880
tattgctctc ccaagtgagt ctcccagata cgaggcactg tgccagcatc agccttatct      2940
ccaccacatc ttgtaaaagg actacccagg gccctgatga acaccatggt gtgtacagga      3000
gtagggggtg gaggcacgga ctcctgtgag gtcacagcca agggagcatc atcatgggtg      3060
gggaggaggc aatggacagg cttgagaacg gggatgtggt tgtatttggt tttctttggt      3120
tagataaagt gctgggtata ggattgagag tggagtatga agaccagtta ggatggagga      3180
tcagattgga gttgggttag ataaagtgct gggtatagga ttgagagtgg agtatgaaga      3240
ccagttagga tggaggatca gattggagtt gggttagaga tggggtaaaa ttgtgctccg      3300
gatgagtttg ggattgacac tgtggaggtg gtttgggatg gcatggcttt gggatggaaa      3360
tagatttgtt ttgatgttgg ctcagacatc cttggggatt gaactgggga tgaagctggg      3420
tttgattttg gaggtagaag acgtggaagt agctgtcaga tttgacagtg gccatgagtt      3480
ttgtttgatg gggaatcaaa caatggggga agacataagg gttggcttgt taggttaagt      3540
tgcgttgggt tgatggggtc ggggctgtgt ataatgcagt tggattggtt tgtattaaat      3600
tgggttgggt caggttttgg ttgaggatga gttgaggata tgcttgggga caccggatcc      3660
atgaggttct cactggagtg gagacaaact tcctttccag gatgaatcca gggaagcctt      3720
aattcacgtg taggggaggt caggccactg gctaagtata tccttccact ccagctctaa      3780
gatggtctta aattgtgatt atctatatcc acttctgtct ccctcactgt gcttggagtt      3840
tacctgatca ctcaactaga aacaggggaa gattttatca aattcttttt ttttttttt      3900 tttttttgag acagagtctc actctgttgc ccaggctgga gtgcagtggc gcagtctcgg      3960
ctcactgcaa cctctgcctc ccaggttcaa gtgattctcc tgcctcagcc tcctgagttg      4020
ctgggattac aggcatgcag caccatgccc agctaatttt tgtattttta gtagagatgg      4080
ggtttcacca atgtttgcca ggctggcctc gaactcctga cctggtgatc cacctgcctc      4140
agcctcccaa agtgctggga ttacaggcgt cagccaccgc gcccagccac ttttgtcaaa      4200
ttcttgagac acagctcggg ctggatcaag tgagctactc tggttttatt gaacagctga      4260
aataaccaac ttttggaaa ttgatgaaat cttacggagt taacagtgga ggtaccaggg      4320
ctcttaagag ttcccgattc tcttctgaga ctacaaattg tgattttgca tgccacctta      4380
atcttttttt tttttttttt aaatcgaggt ttcagtctca ttctatttcc caggctggag      4440
```

-continued

```
ttcaatagcg tgatcacagc tcactgtagc cttgaactcc tggccttaag agattctcct      4500
gcttcggtct cccaatagct aagactacag tagtccacca ccatatccag ataattttta      4560
aattttttgg ggggccgggc acagtggctc acgcctgtaa tcccaacacc atgggaggct      4620
gagatgggtg gatcacgagg tcaggagttt gagaccagcc tgaccaacat ggtgaaactc      4680
tgtctctact aaaaaaaaaa aaatagaaa attagccgg gcgtggtggc acacggcacc       4740
tgtaatccca gctactgagg aggctgaggc aggagaatca cttgaaccca gaaggcagag      4800
gttgcaatga gccgagattg cgccactgca ctccagcctg ggtgacagag tgagactctg      4860
tctcaaaaaa aaaaaatttt ttttttttt ttgtagagat ggatcttgct ttgtttctct       4920
ggttggcctt gaactcctgg cttcaagtga tcctcctacc ttggcctcgg aaagtgttgg      4980
gattacaggc gtgagccacc atgactgacc tgtcgttaat cttgaggtac ataaacctgg      5040
ctcctaaagg ctaaaggcta atatttgtt ggagaagggg cattggattt tgcatgagga       5100
tgattctgac ctgggagggc aggtcagcag gcatctctgt tgcacagata gagtgtacag      5160
gtctggagaa caaggagtgg ggggttattg gaattccaca ttgtttgctg cacgttggat      5220
tttgaaatgc tagggaactt tgggagactc atatttctgg gctagaggat ctgtggacca      5280
caagatcttt ttatgatgac agtagcaatg tatctgtgga gctggattct gggttgggag      5340
tgcaaggaaa agaatgtact aaatgccaag acatctattt caggagcatg aggaataaaa      5400
gttctagttt ctggtctcag agtggtgcat ggatcaggga gtctcacaat ctcctgagtg      5460
ctggtgtctt agggcacact gggtcttgga gtgcaaagga tctaggcacg tgaggctttg      5520
tatgaagaat cggggatcgt acccaccccc tgtttctgtt tcatcctggg catgtctcct      5580
ctgcctttgt cccctagatg aagtctccat gagctacaag ggcctggtgc atccagggtg      5640
atctagtaat tgcagaacag caagtgctag ctctccctcc ccttccacag ctctgggtgt      5700
ggaggggggt tgtccagcct ccagcagcat ggggagggcc ttggtcagcc tctgggtgcc      5760
agcagggcag gggcggagtc ctggggaatg aaggttttat agggctcctg ggggaggctc      5820
cccagcccca agctt                                                      5835

CEA TRE SEQ ID NO:14
aagcttttta gtgctttaga cagtgagctg gtctgtctaa cccaagcgac ctgggctcca       60
tactcagccc cagaagtgaa gggtgaagct gggtggagcc aaaccaggca agcctaccct      120
cagggctccc agtggcctga gaaccattgg acccaggacc cattacttct agggtaagga     180
aggtacaaac accagatcca accatggtct gggggacag ctgtcaaatg cctaaaaata       240
tacctgggag aggagcaggc aaactatcac tgccccaggt tctctgaaca gaaacagagg      300
ggcaacccaa agtccaaatc caggtgagca ggtgcaccaa atgcccagag atatgacgag      360
gcaagaagtg aaggaaccac ccctgcatca aatgttttgc atgggaagga aaggggggtt      420
gctcatgttc ccaatccagg agaatgcatt tgggatctgc cttcttctca ctccttggtt      480
agcaagacta agcaaccagg actctggatt tggggaaaga cgtttatttg tggaggccag     540
tgatgacaat cccacgaggg cctaggtgaa gagggcagga aggctcgaga cactggggac      600
tgagtgaaaa ccacacccat gatctgcacc acccatggat gctccttcat tgctcacctt      660
tctgttgata tcagatggcc ccattttctg taccttcaca gaaggacaca ggctagggtc      720
tgtgcatggc cttcatcccc ggggccatgt gaggacagca ggtgggaaag atcatgggtc      780 ctcctggggtc ctgcagggcc agaacattca tcacccatac tgacctccta gatgggaatg     840
```

-continued

```
gcttccctgg ggctgggcca acggggcctg ggcaggggag aaaggacgtc aggggacagg      900
gaggaagggt catcgagacc cagcctggaa ggttcttgtc tctgaccatc caggatttac      960
ttccctgcat ctacctttgg tcatttccc tcagcaatga ccagctctgc ttcctgatct      1020
cagcctccca ccctggacac agcacccag tccctggccc ggctgcatcc acccaatacc      1080
ctgataaccc aggacccatt acttctaggg taaggagggt ccaggagaca gaagctgagg      1140
aaaggtctga agaagtcaca tctgtcctgg ccagagggga aaaaccatca gatgctgaac      1200
caggagaatg ttgacccagg aaagggaccg aggacccaag aaaggagtca gaccaccagg      1260
gtttgcctga gaggaaggat caaggccccg agggaaagca gggctggctg catgtgcagg      1320
acactggtgg ggcatatgtg tcttagattc tccctgaatt cagtgtccct gccatggcca      1380
gactctctac tcaggcctgg acatgctgaa ataggacaat ggccttgtcc tctctcccca      1440
ccatttggca agagacataa aggacattcc aggacatgcc ttcctgggag gtccaggttc      1500
tctgtctcac acctcaggga ctgtagttac tgcatcagcc atggtaggtg ctgatctcac      1560
ccagcctgtc caggcccttc cactctccac tttgtgacca tgtccaggac cacccctcag      1620
atcctgagcc tgcaaatacc ccttgctgg gtgggtggat tcagtaaaca gtgagctcct      1680
atccagcccc cagagccacc tctgtcacct tcctgctggg catcatccca ccttcacaag      1740
cactaaagag catggggaga cctggctagc tgggtttctg catcacaaag aaaataatcc      1800
cccaggttcg gattcccagg gctctgtatg tggagctgac agacctgagg ccaggagata      1860
gcagaggtca gccctaggga gggtgggtca tccacccagg ggacagggt gcaccagcct      1920
tgctactgaa agggcctccc caggacacg ccatcagccc tgcctgagag ctttgctaaa      1980
cagcagtcag aggaggccat ggcagtggct gagctcctgc tccaggcccc aacagaccag      2040
accaacagca caatgcagtc cttccccaac gtcacaggtc accaaaggga aactgaggtg      2100
ctacctaacc ttagagccat caggggagat aacagcccaa tttcccaaac aggccagttt      2160
caatcccatg acaatgacct ctctgctctc attcttccca aaataggacg ctgattctcc      2220
cccaccatgg atttctccct tgtcccggga gccttttctg cccctatga tctgggcact      2280
cctgacacac acctcctctc tggtgacata tcagggtccc tcactgtcaa gcagtccaga      2340
aaggacagaa ccttggacag cgcccatctc agcttcaccc ttcctccttc acagggttca      2400
gggcaaagaa taaatggcag aggccagtga gcccagagat ggtgacaggc agtgacccag      2460
gggcagatgc ctggagcagg agctggcggg gccacaggga gaaggtgatg caggaaggga      2520
aacccagaaa tgggcaggaa aggaggacac aggctctgtg gggctgcagc ccaggggttgg      2580
actatgagtg tgaagccatc tcagcaagta aggccaggtc ccatgaacaa gagtgggagc      2640
acgtggcttc ctgctctgta tatgggggtgg gggattccat gccccataga accagatggc      2700
cggggttcag atggagaagg agcaggacag gggatcccca ggataggagg accccagtgt      2760
ccccacccag gcaggtgact gatgaatggg catgcaggt cctcctgggc tgggctctcc      2820
cttttgtccct caggattcct tgaaggaaca tccggaagcc gaccacatct acctggtggg      2880
ttctggggag tccatgtaaa gccaggagct tgtgttgcta ggagggtca tggcatgtgc      2940
tgggggcacc aaagagagaa acctgagggc aggcaggacc tggtctgagg aggcatggga      3000
gcccagatgg ggagatggat gtcaggaaag gctgccccat cagggagggt gatagcaatg      3060
gggggtctgt gggagtgggc acgtgggatt ccctgggctc tgccaagttc cctcccatag      3120
tcacaacctg ggacactgc ccatgaaggg gcgcctttgc ccagccagat gctgctggtt      3180
ctgcccatcc actaccctct ctgctccagc cactctgggt cttctccag atgccctgga      3240
```

-continued

```
cagccctggc ctgggcctgt cccctgagag gtgttgggag aagctgagtc tctggggaca   3300
ctctcatcag agtctgaaag gcacatcagg aaacatccct ggtctccagg actaggcaat   3360
gaggaaaggg ccccagctcc tccctttgcc actgagaggg tcgaccctgg gtggccacag   3420
tgacttctgc gtctgtccca gtcaccctga accacaaca aaaccccagc cccagaccct   3480
gcaggtacaa tacatgtggg gacagtctgt acccagggga agccagttct ctcttcctag   3540
gagaccgggc ctcaggggctg tgcccggggc aggcggggc agcacgtgcc tgtccttgag   3600
aactcgggac cttaagggtc tctgctctgt gaggcacagc aaggatcctt ctgtccagag   3660
atgaaagcag ctcctgcccc tcctctgacc tcttcctcct tcccaaatct caaccaacaa   3720
ataggtgttt caaatctcat catcaaatct tcatccatcc acatgagaaa gcttaaaacc   3780
caatggattg acaacatcaa gagttggaac aagtggacat ggagatgtta cttgtggaaa   3840
tttagatgtg ttcagctatc gggcaggaga atctgtgtca aattccagca tggttcagaa   3900
gaatcaaaaa gtgtcacagt ccaaatgtgc aacagtgcag gggataaaac tgtggtgcat   3960
tcaaactgag ggatattttg gaacatgaga aaggaaggga ttgctgctgc acagaacatg   4020
gatgatctca cacatagagt tgaaagaaag gagtcaatcg cagaatagaa aatgatcact   4080
aattccacct ctataaagtt tccaagagga aaacccaatt ctgctgctag agatcagaat   4140
ggaggtgacc tgtgccttgc aatggctgtg agggtcacgg gagtgtcact tagtgcaggc   4200
aatgtgccgt atcttaatct gggcagggct ttcatgagca cataggaatg cagacattac   4260
tgctgtgttc attttacttc accgaaaaag aagaataaaa tcagccgggc gcggtggctc   4320
acgcctgtaa tcccagcact ttagaaggct gaggtgggca gattacttga ggtcaggagt   4380
tcaagaccac cctggccaat atggtgaaac cccggctcta ctaaaaatac aaaaattagc   4440
tgggcatggt ggtgcgcgcc tgtaatccca gctactcggg aggctgaggc tggacaattg   4500
cttggaccca ggaagcagag gttgcagtga gccaagattg tgccactgca ctccagcttg   4560
ggcaacagag ccagactctg taaaaaaaaa aaaaaaaaa aaaaaagaa agaaagaaaa   4620 agaaagaaa gtataaaatc tctttgggtt aacaaaaaaa gatccacaaa acaaacacca   4680
gctcttatca aacttacaca actctgccag agaacaggaa acacaaatac tcattaactc   4740
acttttgtgg caataaaacc ttcatgtcaa aaggagacca ggacacaatg aggaagtaaa   4800
actgcaggcc ctacttgggt gcagagaggg aaaatccaca aataaaacat taccagaagg   4860
agctaagatt tactgcattg agttcattcc ccaggtatgc aaggtgattt taacacctga   4920
aaatcaatca ttgcctttac tacatagaca gattagctag aaaaaaatta caactagcag   4980
aacagaagca atttggcctt cctaaaattc cacatcatat catcatgatg gagacagtgc   5040
agacgccaat gacaataaaa agagggacct ccgtcacccg gtaaacatgt ccacacagct   5100
ccagcaagca cccgtcttcc cagtgaatca ctgtaacctc ccctttaatc agccccaggc   5160
aaggctgcct gcgatggcca cacaggctcc aacccgtggg cctcaacctc cgcagaggc   5220 tctcctttgg ccaccccatg gggagagcat gaggacaggg cagagccctc tgatgcccac   5280
acatggcagg agctgacgcc agagccatgg gggctggaga gcagagctgc tggggtcaga   5340
gcttcctgag gacacccagg cctaagggaa ggcagctccc tggatggggg caaccaggct   5400
ccgggctcca acctcagagc ccgcatggga ggagccagca ctctaggcct ttcctagggt   5460
gactctgagg ggaccctgac acgacaggat cgctgaatgc acccgagatg aaggggccac   5520
cacgggaccc tgctctcgtg gcagatcagg agagagtggg acaccatgcc aggccccat   5580 ggcatggctg cgactgaccc aggccactcc cctgcatgca tcagcctcgg taagtcacat   5640
```

```
gaccaagccc aggaccaatg tggaaggaag gaaacagcat cccctttagt gatggaaccc    5700
aaggtcagtg caaagagagg ccatgagcag ttaggaaggg tggtccaacc tacagcacaa    5760
accatcatct atcataagta gaagccctgc tccatgaccc ctgcatttaa ataaacgttt    5820
gttaaatgag tcaaattccc tcaccatgag agctcacctg tgtgtaggcc catcacacac    5880
acaaacacac acacacacac acacacacac acacacacac acagggaaag tgcaggatcc    5940
tggacagcac caggcaggct tcacaggcag agcaaacagc gtgaatgacc catgcagtgc    6000
cctgggcccc atcagctcag agaccctgtg agggctgaga tggggctagg caggggagag    6060
acttagagag ggtggggcct ccagggaggg ggctgcaggg agctgggtac tgccctccag    6120
ggagggggct gcaggagct gggtactgcc ctccagggag ggggctgcag ggagctgggt    6180
actgccctcc agggaggggg ctgcaggag ctgggtactg ccctccaggg aggggctgc    6240 agggagctgg gtactgccct ccagggaggc aggagcactg ttcccaacag agagcacatc    6300
ttcctgcagc agctgcacag acacaggagc ccccatgact gccctgggcc agggtgtgga    6360
ttccaaattt cgtgccccat tgggtgggac ggaggttgac cgtgacatcc aagggcatc    6420 tgtgattcca aacttaaact actgtgccta caaaatagga aataacccta cttttctac    6480 tatctcaaat tccctaagca caagctagca ccctttaaat caggaagttc agtcactcct    6540
ggggtcctcc catgccccca gtctgacttg caggtgcaca gggtggctga catctgtcct    6600
tgctcctcct cttggctcaa ctgccgcccc tcctgggggt gactgatggt caggacaagg    6660
gatcctagag ctggccccat gattgacagg aaggcaggac ttggcctcca ttctgaagac    6720 tagggtgtc aagagagctg ggcatcccac agagctgcac aagatgacgc ggacagaggg    6780
tgacacaggg ctcagggctt cagacgggtc gggaggctca gctgagagtt cagggacaga    6840
cctgaggagc ctcagtggga aaagaagcac tgaagtggga agttctggaa tgttctggac    6900
aagcctgagt gctctaagga aatgctccca ccccgatgta gcctgcagca ctggacggtc    6960
tgtgtacctc cccgctgccc atcctctcac agccccgcc tcagggaca caactcctgc    7020 cctaacatgc atctttcctg tctcattcca cacaaaggg cctctggggt ccctgttctg    7080
cattgcaagg agtggaggtc acgttcccac agaccaccca gcaacagggt cctatggagg    7140
tgcggtcagg aggatcacac gtccccccat gcccagggga ctgactctgg gggtgatgga    7200
ttggcctgga ggccactggt cccctctgtc cctgagggga atctgcaccc tggaggctgc    7260
cacatccctc ctgattcttt cagctgaggg cccttcttga aatcccaggg aggactcaac    7320
ccccactggg aaaggcccag tgtggacggt tccacagcag cccagctaag gcccttggac    7380
acagatcctg agtgagagaa cctttaggga cacaggtgca cggccatgtc cccagtgccc    7440
acacagagca gggcatctg gaccctgagt gtgtagctcc cgcgactgaa cccagccctt    7500
ccccaatgac gtgacccctg gggtggctcc aggtctccag tccatgccac caaaatctcc    7560
agattgaggg tcctcccttg agtccctgat gcctgtccag gagctgcccc ctgagcaaat    7620
ctagagtgca gagggctggg attgtggcag taaaagcagc cacatttgtc tcaggaagga    7680
aagggaggac atgagctcca ggaagggcga tggcgtcctc tagtgggcgc ctcctgttaa    7740
tgagcaaaaa ggggccagga gagttgagag atcaggctg gccttggact aaggctcaga    7800
tggagaggac tgaggtgcaa agaggggct gaagtagggg agtggtcggg agagatggga    7860
ggagcaggta aggggaagcc ccagggaggc cgggggaggg tacagcagag ctctccactc    7920
ctcagcattg acatttgggg tggtcgtgct agtgggttc tgtaagttgt agggtgttca    7980
gcaccatctg gggactctac ccactaaatg ccagcaggac tccctcccca agctctaaca    8040
```

```
                                -continued
accaacaatg tctccagact ttccaaatgt ccoctggaga gcaaaattgc ttctggcaga      8100
atcactgatc tacgtcagtc tctaaaagtg actcatcagc gaaatccttc acctcttggg      8160
agaagaatca caagtgtgag aggggtagaa actgcagact tcaaaatctt tccaaaagag      8220
ttttacttaa tcagcagttt gatgtcccag gagaagatac atttagagtg tttagagttg      8280
atgccacatg gctgcctgta cctcacagca ggagcagagt gggttttcca agggcctgta      8340
accacaactg gaatgacact cactgggtta cattacaaag tggaatgtgg ggaattctgt      8400
agactttggg aagggaaatg tatgacgtga gcccacagcc taaggcagtg gacagtccac      8460
tttgaggctc tcaccatcta ggagacatct cagccatgaa catagccaca tctgtcatta      8520
gaaaacatgt tttattaaga ggaaaaatct aggctagaag tgctttatgc tcttttttct      8580
ctttatgttc aaattcatat acttttagat cattccttaa agaagaatct atcccctaa       8640 gtaaatgtta tcactgactg gatagtgttg gtgtctcact cccaacccct gtgtggtgac      8700
agtgccctgc ttccccagcc ctgggccctc tctgattcct gagagctttg ggtgctcctt      8760
cattaggagg aagagaggaa gggtgttttt aatattctca ccattcaccc atccacctct      8820
tagacactgg gaagaatcag ttgcccactc ttggatttga tcctcgaatt aatgacctct      8880
atttctgtcc cttgtccatt tcaacaatgt gacaggccta agaggtgcct tctccatgtg      8940
atttttgagg agaaggttct caagataagt tttctcacac ctctttgaat tacctccacc      9000
tgtgtcccca tcaccattac cagcagcatt tggaccettt ttctgttagt cagatgcttt      9060
ccacctcttg agggtgtata ctgtatgctc tctacacagg aatatgcaga ggaaatagaa      9120
aaagggaaat cgcattacta ttcagagaga agaagaccett tatgtgaatg aatgagagtc      9180
taaaatccta agagagccca tataaaatta ttaccagtgc taaaactaca aaagttacac      9240
taacagtaaa ctagaataat aaaacatgca tcacagttgc tggtaaagct aaatcagata      9300 ttttttttctt agaaaaagca ttccatgtgt gttgcagtga tgacaggagt gcccttcagt      9360
caatatgctg cctgtaattt ttgttccctg gcagaatgta ttgtcttttc tcccctttaaa     9420 tcttaaatgc aaaactaaag gcagctcctg ggcccectcc ccaaagtcag ctgcctgcaa      9480
ccagccccac gaagagcaga ggcctgagct tccctggtca aaatagggg ctagggagct       9540 taaccttgct cgataaagct gtgttcccag aatgtcgctc ctgttcccag gggcaccagc      9600
ctggagggtg gtgagcctca ctggtggcct gatgcttacc ttgtgccctc acaccagtgg      9660
tcactggaac cttgaacact tggctgtcgc ccggatctgc agatgtcaag aacttctgga      9720
agtcaaatta ctgcccactt ctccagggca gataccctgtg aacatccaaa accatgccac     9780
agaaccctgc ctggggtcta caacacatat ggactgtgag caccaagtcc agccctgaat      9840
ctgtgaccac ctgccaagat gcccctaact gggatccacc aatcactgca catggcaggc      9900
agcgaggctt ggaggtgctt cgccacaagg cagccccaat ttgctgggag tttcttggca     9960
cctggtagtg gtgaggagcc ttgggaccct caggattact ccccttaagc atagtgggga   10020
cccttctgca tccccagcag gtgccccgct cttcagagcc tctctctctg aggtttaccc   10080 agaccectgc accaatgaga ccatgctgaa gcctcagaga gagagatgga gctttgacca   10140
ggagccgctc ttccttgagg gccagggcag ggaaagcagg aggcagcacc aggagtggga   10200
acaccagtgt ctaagccect gatgagaaca gggtggtctc tcccatatgc ccataccagg   10260
cctgtgaaca gaatcctcct tctgcagtga caatgtctga gaggacgaca tgtttcccag   10320
cctaacgtga agccatgccc atctacccac tgcctactgc aggacagcac caacccagga   10380
gctgggaagc tgggagaaga catggaatac ccatggcttc tcaccttcct ccagtccagt   10440
```

```
gggcaccatt tatgcctagg acacccacct gccggcccca ggctcttaag agttaggtca   10500
cctaggtgcc tctgggaggc cgaggcagga gaattgcttg aacccgggag gcagaggttg   10560
cagtgagccg agatcacacc actgcactcc agcctgggtg acagaatgag actctgtctc   10620
aaaaaaaaag agaaagatag catcagtggc taccaagggc tagggcaggg ggaaggtgga   10680
gagttaatga ttaatagtat gaagtttcta tgtgagatga tgaaaatgtt ctggaaaaaa   10740
aaatatagtg gtgaggatgt agaatattgt gaatataatt aacggcattt aattgtacac   10800
ttaacatgat taatgtggca tattttatct tatgtatttg actacatcca agaaacactg   10860
ggagagggaa agcccaccat gtaaaataca cccaccctaa tcagatagtc ctcattgtac   10920
ccaggtacag gcccctcatg acctgcacag gaataactaa ggatttaagg acatgaggct   10980
tcccagccaa ctgcaggtgc acaacataaa tgtatctgca aacagactga gagtaaagct   11040
gggggcacaa acctcagcac tgccaggaca cacacccttc tcgtggattc tgactttatc   11100
tgacccggcc cactgtccag atcttgttgt gggattggga caaggaggt cataaagcct    11160 gtccccaggg cactctgtgt gagcacacga gacctcccca ccccccacc gttaggtctc     11220 cacacataga tctgaccatt aggcattgtg aggaggactc tagcgcgggc tcagggatca   11280
caccagagaa tcaggtacag agaggaagac ggggctcgag gagctgatgg atgacacaga   11340
gcagggttcc tgcagtccac aggtccagct caccctggtg taggtgcccc atcccctga    11400 tccaggcatc cctgacacag ctccctcccg gagcctcctc ccaggtgaca catcagggtc   11460
cctcactcaa gctgtccaga gagggcagca ccttggacag cgcccacccc acttcactct   11520
tcctccctca cagggctcag ggctcaggc tcaagtctca gaacaaatgg cagaggccag    11580
tgagcccaga gatggtgaca gggcaatgat ccaggggcag ctgcctgaaa cgggagcagg   11640
tgaagccaca gatgggagaa gatggttcag gaagaaaaat ccaggaatgg gcaggagagg   11700
agaggaggac acaggctctg tggggctgca gcccaggatg ggactaagtg tgaagacatc   11760
tcagcaggtg aggccaggtc ccatgaacag agaagcagct cccacctccc ctgatgcacg   11820
gacacacaga gtgtgtggtg ctgtgccccc agagtcgggc tctcctgttc tggtccccag   11880
ggagtgagaa gtgaggttga cttgtccctg ctcctctctg ctaccccaac attcaccttc   11940
tcctcatgcc cctctctctc aaatatgatt tggatctatg tccccgccca aatctcatgt   12000
caaattgtaa accccaatgt tggaggtggg gccttgtgag aagtgattgg ataatgcggg   12060
tggattttct gctttgatgc tgtttctgtg atagagatct cacatgatct ggttgtttaa   12120
aagtgtgtag cacctctccc ctctctctct ctctctctta ctcatgctct gccatgtaag   12180
acgttcctgt ttcccttca ccgtccagaa tgattgtaag ttttctgagg cctccccagg     12240
agcagaagcc actatgcttc ctgtacaact gcagaatgat gagcgaatta aacctctttt   12300
ctttataaat tacccagtct caggtatttc tttatagcaa tgcgaggaca gactaataca   12360
atcttctact cccagatccc cgcacacgct tagccccaga catcactgcc cctgggagca   12420
tgcacagcgc agcctcctgc cgacaaaagc aaagtcacaa aaggtgacaa aaatctgcat   12480
ttggggacat ctgattgtga aagagggagg acagtacact tgtagccaca gagactgggg   12540
ctcaccgagc tgaaacctgg tagcacttttg gcataacatg tgcatgaccc gtgttcaatg   12600
tctagagatc agtgttgagt aaaacagcct ggtctggggc cgctgctgtc cccacttccc   12660
tcctgtccac cagagggcgg cagagttcct cccaccctgg agcctcccca ggggctgctg   12720
acctccctca gccgggccca cagcccagca gggtccaccc tcacccgggt cacctcggcc   12780
cacgtcctcc tcgccctccg agctcctcac acggactctg tcagctcctc cctgcagcct   12840
```

-continued

```
atcggccgcc cacctgaggc ttgtcggccg cccacttgag gcctgtcggc tgccctctgc    12900
aggcagctcc tgtcccctac accccctcct tccccgggct cagctgaaag ggcgtctccc    12960
agggcagctc cctgtgatct ccaggacagc tcagtctctc acaggctccg acgcccccta    13020
tgctgtcacc tcacagccct gtcattacca ttaactcctc agtcccatga agttcactga    13080
gcgcctgtct cccggttaca ggaaaactct gtgacaggga ccacgtctgt cctgctctct    13140
gtggaatccc agggcccagc ccagtgcctg acacggaaca gatgctccat aaatactggt    13200
taaatgtgtg ggagatctct aaaaagaagc atatcacctc cgtgtggccc ccagcagtca    13260
gagtctgttc catgtggaca caggggcact ggcaccagca tgggaggagg ccagcaagtg    13320
cccgcggctg ccccaggaat gaggcctcaa cccccagagc ttcagaaggg aggacagagg    13380
cctgcaggga atagatcctc cggcctgacc ctgcagccta atccagagtt cagggtcagc    13440
tcacaccacg tcgaccctgg tcagcatccc tagggcagtt ccagacaagg ccggaggtct    13500
cctcttgccc tccaggggt gacattgcac acagacatca ctcaggaaac ggattcccct    13560
ggacaggaac ctggctttgc taaggaagtg gaggtggagc tggtttcca tcccttgctc    13620 caacagaccc ttctgatctc tcccacatac ctgctctgtt cctttctggg tcctatgagg    13680
accctgttct gccaggggtc cctgtgcaac tccagactcc ctcctggtac caccatgggg    13740
aaggtggggt gatcacagga cagtcagcct cgcagagaca gagaccaccc aggactgtca    13800
gggagaacat ggacaggccc tgagccgcag ctcagccaac agacacggag agggagggtc    13860
cccctggagc cttccccaag gacagcagag cccagagtca cccacctccc tccaccacag    13920
tcctctcttt ccaggacaca aagacacct cccctccac atgcaggatc tggggactcc    13980
tgagacctct gggcctgggt ctccatccct gggtcagtgg cggggttggt ggtactggag    14040
acagagggct ggtccctccc cagccaccac ccagtgagcc tttttctagc ccccagagcc    14100
acctctgtca ccttcctgtt gggcatcatc ccaccttccc agagccctgg agagcatggg    14160
gagacccggg accctgctgg gtttctctgt cacaaaggaa aataatcccc ctggtgtgac    14220
agacccaagg acagaacaca gcagaggtca gcactgggga agacaggttg tcctcccagg    14280 ggatggggt ccatccacct tgccgaaaag atttgtctga ggaactgaaa atagaaggga    14340
aaaaagagga gggacaaaag aggcagaaat gagaggggag gggacagagg acacctgaat    14400
aaagaccaca cccatgaccc acgtgatgct gagaagtact cctgccctag gaagagactc    14460
```

↪ transcription start site
```
agggcagagg gaggaaggac agcagaccag acagtcacag cagccttgac aaaacgttcc    14520
tggaactcaa gctcttctcc acagaggagg acagagcaga cagcagagac catggagtct    14580
ccctcggccc ctccccacag atggtgcatc ccctggcaga ggctcctgct cacaggtgaa    14640
gggaggacaa cctgggagag ggtgggagga gggagctggg gtctcctggg taggacaggg    14700
ctgtgagacg gacagagggc tcctgttgga gcctgaatag ggaagaggac atcagagagg    14760
gacaggagtc acaccagaaa aatcaaattg aactggaatt ggaaaggggc aggaaaacct    14820
caagagttct attttcctag ttaattgtca ctggccacta cgttttaaa aatcataata    14880 actgcatcag atgacacttt aaataaaaac ataaccaggg catgaaacac tgtcctcatc    14940
cgcctaccgc ggacattgga aaataagccc caggctgtgg agggccctgg gaaccctcat    15000
gaactcatcc acaggaatct gcagcctgtc ccaggcactg gggtgcaacc aagatc       15056
```

Mucin-TRE SEQ ID NO:15

```
cgagcggccc ctcagcttcg gcgcccagcc ccgcaaggct cccggtgacc actagagggc    60
gggaggagct cctggccagt ggtggagagt ggcaaggaag gaccctaggg ttcatcggag   120
cccaggttta ctcccttaag tggaaatttc ttcccccact cctccttggc tttctccaag   180
gagggaaccc aggctgctgg aaagtccggc tggggcgggg actgtgggtt caggggagaa   240
cggggtgtgg aacgggacag ggagcggtta aagggtggg gctattccgg gaagtggtgg    300
ggggagggag cccaaaacta gcacctagtc cactcattat ccagccctct tatttctcgg   360
ccgctctgct tcagtggacc cggggagggc ggggaagtgg agtgggagac ctaggggtgg   420
gcttcccgac cttgctgtac aggacctcga cctagctggc tttgttcccc atccccacgt   480
tagttgttgc cctgaggcta aaactagagc ccaggggccc caagttccag actgcccctc   540
cccctcccc cggagccagg gagtggttgg tgaaaggggg aggccagctg gagaacaaac     600
gggtagtcag ggggttgagc gattagagcc cttgtaccct acccaggaat ggttggggag   660
gaggaggaag aggtaggagg taggggaggg ggcggggttt tgtcacctgt cacctgctcg   720
ctgtgcctag ggcgggcggg cggggagtgg ggggaccggt ataaagcggt aggcgcctgt   780
gcccgctcca cctctcaagc agccagcgcc tgcctgaatc tgttctgccc cctccccacc   840
catttcacca ccaccatg                                                 858
```

αFP-TRE SEQ ID NO:16

```
gaattcttag aaatatgggg gtaggggtgg tggtggtaat tctgttttca ccccataggt    60
gagataagca ttgggttaaa tgtgctttca cacacacatc acatttcata agaattaagg   120
aacagactat gggctggagg actttgagga tgtctgtctc ataacacttg ggttgtatct   180
gttctatggg gcttgtttta agcttggcaa cttgcaacag ggttcactga ctttctcccc   240
aagcccaagg tactgtcctc ttttcatatc tgttttgggg cctctggggc ttgaatatct   300
gagaaaatat aaacatttca ataatgttct gtggtgagat gagtatgaga gatgtgtcat   360
tcatttgtat caatgaatga atgaggacaa ttagtgtata atccttagt acaacaatct    420
gagggtaggg gtggtactat tcaatttcta tttataaaga tacttatttc tatttattta   480
tgcttgtgac aaatgttttg ttcgggacca caggaatcac aaagatgagt ctttgaattt   540
aagaagttaa tggtccagga ataattacat agcttacaaa tgactatgat ataccatcaa   600
acaagaggtt ccatgagaaa ataatctgaa aggtttaata agttgtcaaa ggtgagaggg   660
ctcttctcta gctagagact aatcagaaat acattcaggg ataattattt gaatagacct   720
taagggttgg gtacattttg ttcaagcatt gatggagaag gagagtgaat atttgaaaac   780
attttcaact aaccaaccac ccaatccaac aaacaaaaaa tgaaaagaat ctcagaaaca   840
gtgagataag agaaggaatt ttctcacaac ccacacgtat agctcaactg ctctgaagaa   900
gtatatatct aatatttaac actaacatca tgctaataat gataataatt actgtcattt   960
tttaatgtct ataagtacca ggcatttaga agatattatt ccatttatat atcaaaataa  1020
acttgagggg atagatcatt ttcatgatat atgagaaaaa ttaaaaacag attgaattat  1080
ttgcctgtca tacagctaat aattgaccat aagacaatta gatttaaatt agttttgaat  1140
ctttctaata ccaaagttca gtttactgtt ccatgttgct tctgagtggc ttcacagact  1200
tatgaaaaag taaacggaat cagaattaca tcaatgcaaa agcattgctg tgaactctgt  1260
acttaggact aaactttgag caataacaca catagattga ggattgtttg ctgttagcat  1320
```

-continued

```
acaaactctg gttcaaagct cctctttatt gcttgtcttg gaaaatttgc tgttcttcat   1380
ggtttctctt ttcactgcta tctattttc tcaaccactc acatggctac aataactgtc   1440
tgcaagctta tgattcccaa atatctatct ctagcctcaa tcttgttcca gaagataaaa   1500
agtagtattc aaatgcacat caacgtctcc acttggaggg cttaaagacg tttcaacata   1560
caaaccgggg agttttgcct ggaatgtttc ctaaaatgtg tcctgtagca catagggtcc   1620
tcttgttcct taaaatctaa ttacttttag cccagtgctc atcccaccta tggggagatg   1680
agagtgaaaa gggagcctga ttaataatta cactaagtca ataggcatag agccaggact   1740
gtttgggtaa actggtcact ttatcttaaa ctaaatatat ccaaaactga acatgtactt   1800
agttactaag tctttgactt tatctcattc ataccactca gctttatcca ggccacttat   1860
ttgacagtat tattgcgaaa acttcctaac tggtctcctt atcatagtct tatcccctt    1920 tgaaacaaaa gagacagttt caaaatacaa atatgatttt tattagctcc cttttgttgt   1980
ctataatagt cccagaagga gttataaact ccatttaaaa agtctttgag atgtggccct   2040
tgccaacttt gccaggaatt cccaatatct agtattttct actattaaac tttgtgcctc   2100
ttcaaaactg cattttctct cattcccctaa gtgtgcattg ttttcccttaa ccggttggtt    2160 tttccaccac cttttacatt ttcctggaac actatacct ccctcttcat ttgggcccacc    2220 tctaatttc tttcagatct ccatgaagat gttacttcct ccaggaagcc ttatctgacc    2280
cctccaaaga tgtcatgagt tcctcttttc attctactaa tcacagcatc catcacacca   2340
tgttgtgatt actgatacta ttgtctgttt ctctgattag gcagtaagct caacaagagc   2400
tacatggtgc ctgtctcttg ttgctgatta ttcccatcca aaaacagtgc ctggaatgca   2460
gacttaacat tttattgaat gaataaataa accccatct atcgagtgct actttgtgca    2520
agacccggtt ctgaggcatt tatatttatt gatttattta attctcattt aaccatgaag   2580
gaggtactat cactatccctt attttatagt tgataaagat aaagcccaga gaaatgaatt   2640
aactcaccca agtcatgta gctaagtgac agggcaaaaa ttcaaaccag ttccccaact    2700
ttacgtgatt aatactgtgc tatactgcct ctctgatcat atggcatgga atgcagacat   2760
ctgctccgta aggcagaata tggaaggaga ttggaggatg acacaaaacc agcataatat   2820
cagaggaaaa gtccaaacag gacctgaact gatagaaaag ttgttactcc tggtgtagtc   2880
gcatcgacat cttgatgaac tggtggctga cacaacatac attggcttga tgtgtacata   2940
ttatttgtag ttgtgtgtgt attttttatat atatatttgt aatattgaaa tagtcataat   3000
ttactaaagg cctaccattt gccaggcatt tttacatttg tcccctctaa tcttttgatg   3060
agatgatcag attggattac ttggccttga agatgatata tctacatcta tatctatatc   3120
tatatctata tctatatcta tatctatatc tatatctata tatgtatatc agaaaagctg   3180
aaatatgttt tgtaaagtta taaagatttc agactttata gaatctggga tttgccaaat   3240 gtaaccccttt tctctacatt aaacccatgt tggaacaaat acatttatta ttcattcatc   3300
aaatgttgct gagtcctggc tatgaaccag acactgtgaa agcctttggg atattttgcc   3360
catgcttggg caagcttata tagtttgctt cataaaactc tatttcagtt cttcataact   3420
aatacttcat gactattgct tttcaggtat tccttcataa caaatacttt ggctttcata   3480
tatttgagta aagtcccct tgaggaagag tagaagaact gcactttgta aatactatcc    3540
tggaatccaa acggatagac aaggatggtg ctacctcttt ctggagagta cgtgagcaag   3600
gcctgttttg ttaacatgtt ccttaggaga caaaacttag gagagacacg catagcagaa   3660
aatggacaaa aactaacaaa tgaatgggaa ttgtacttga ttagcattga agaccttgtt   3720
```

-continued

```
tatactatga taaatgtttg tatttgctgg aagtgctact gacggtaaac ccttttttgtt    3780 taaatgtgtg ccctagtagc ttgcagtatg atctattttt taagtactgt acttagctta    3840
tttaaaaatt ttatgtttaa aattgcatag tgctctttca ttgaagaagt tttgagagag    3900
agatagaatt aaaattcactt atcttaccat ctagagaaac ccaatgttaa aactttgttg    3960
tccattattt ctgtctttta ttcaacattt tttttagagg gtgggaggaa tacagaggag    4020
gtacaatgat acacaaatga gagcactctc catgtattgt tttgtcctgt ttttcagtta    4080
acaatatatt atgagcatat ttccatttca ttaaatattc ttccacaaag ttattttgat    4140
ggctgtatat caccctactt tatgaatgta ccatattaat ttatttcctg gtgtgggtta    4200
tttgatttta taatcttacc tttagaataa tgaaacacct gtgaagcttt agaaaatact    4260
ggtgcctggg tctcaactcc acagattctg atttaactgg tctgggttac agactaggca    4320
ttgggaattc aaaaagttcc cccagtgatt ctaatgtgta gccaagatcg ggaacccttg    4380
tagacaggga tgataggagg tgagccactc ttagcatcca tcatttagta ttaacatcat    4440
catcttgagt tgctaagtga atgatgcacc tgacccactt tataaagaca catgtgcaaa    4500
taaaattatt ataggacttg gtttattagg gcttgtgctc taagttttct atgttaagcc    4560
atacatcgca tactaaatac tttaaaatgt accttattga catacatatt aagtgaaaag    4620
tgtttctgag ctaaacaatg acagcataat tatcaagcaa tgataatttg aaatgaattt    4680
attattctgc aacttaggga caagtcatct ctctgaattt tttgtacttt gagagtattt    4740
gttatatttg caagatgaag agtctgaatt ggtcagacaa tgtcttgtgt gcctggcata    4800
tgataggcat ttaatagttt taaagaatta atgtatttag atgaattgca taccaaatct    4860
gctgtctttt ctttatggct tcattaactt aatttgagag aaattaatta ttctgcaact    4920
tagggacaag tcatgtcttt gaatattctg tagtttgagg agaatatttg ttatatttgc    4980
aaaataaaat aagtttgcaa gttttttttt tctgccccaa agagctctgt gtccttgaac    5040
ataaaataca aataaccgct atgctgttaa ttattggcaa atgtcccatt ttcaacctaa    5100
ggaaatacca taaagtaaca gatataccaa caaaaggtta ctagttaaca ggcattgcct    5160
gaaaagagta taaagaatt tcagcatgat tttccatatt gtgcttccac cactgccaat    5220
aaca                                                                 5224
```

---

We claim:

1. A method for suppressing tumor growth in a mammal comprising:
administering to a mammal a synergistic combination of
   a replication competent, target tumor cell-specific adenovirus, said adenovirus comprising an adenoviral gene essential for replication under transcriptional control of a prostate-specific antigen (PSA)-TRE wherein said target tumor cell-specific adenovirus results in virus replication-dependent cytolysis; and
   at least one antineoplastic agent selected from the group consisting of paclitaxel and docetaxel, in a combined dosage effective to substantially reduce the numbers of said targeted solid tumor cell population to a level more than additive when compared to administration of the adenovirus and antineoplastic agent alone, wherein said tumor growth in said mammal is suppressed.

2. The method according to claim 1, wherein said adenovirus is administered by site-specific injection.

3. The method according to claim 1, wherein said adenovirus is administered by intravenous injection.

4. The method according to claim 1, wherein said adenoviral gene essential for replication is an adenoviral early gene.

5. The method of claim 4, wherein the adenoviral early gene is E1A.

6. The method of claim 4, wherein the adenoviral early gene is E1B.

7. The method of claim 6, wherein E1B has a deletion of the 19-kDa region.

8. The method of claim 1, wherein said at least one antineoplastic agent is paclitaxel.

9. The method of claim 1, wherein said at least one antineoplastic agent is docetaxel.

* * * * *

SEQUENCE LISTING

<160> NUMBER OF SEQ ID NOS: 35

<210> SEQ ID NO 1
<211> LENGTH: 519
<212> TYPE: DNA
<213> ORGANISM: Artificial Sequence
<220> FEATURE:
<223> OTHER INFORMATION: IRES from encephelomycarditis virus (EMCV)

<400> SEQUENCE: 1

```
gacgtcgact aattccggtt attttccacc atattgccgt cttttggcaa tgtgagggcc      60
cggaaacctg gccctgtctt cttgacgagc attcctaggg gtctttcccc tctcgccaaa     120
ggaatgcaag gtctgttgaa tgtcgtgaag gaagcagttc ctctggaagc ttcttgaaga     180
caaacaacgt ctgtagcgac cctttgcagg cagcggaacc cccacctgg cgacaggtgc      240 ctctgcggcc aaaagccacg tgtataagat acacctgcaa aggcggcaca acccccagtgc    300
```

```
cacgttgtga gttggatagt tgtggaaaga gtcaaatggc tctcctcaag cgtattcaac    360
aaggggctga aggatgccca gaaggtaccc cattgtatgg gatctgatct ggggcctcgg    420
tgcacatgct ttacatgtgt ttagtcgagg ttaaaaaacg tctaggcccc ccgaaccacg    480
gggacgtggt tttcctttga aaaacacgat gtcgacgtc                           519
```

<210> SEQ ID NO 2
<211> LENGTH: 188
<212> TYPE: DNA
<213> ORGANISM: Artificial Sequence
<220> FEATURE:
<223> OTHER INFORMATION: IRES from vascular endothelial growth factor
      (VEGF)

<400> SEQUENCE: 2

```
acgtagtcga cagcgcagag gcttggggca gccgagcggc agccaggccc cggcccgggc     60
ctcggttcca gaagggagag gagcccgcca aggcgcgcaa gagagcgggc tgcctcgcag    120
tccgagccgg agagggagcg cgagccgcgc cggccccgga cggcctccga aaccatggtc    180
gacacgta                                                             188
```

<210> SEQ ID NO 3
<211> LENGTH: 341
<212> TYPE: DNA
<213> ORGANISM: Artificial Sequence
<220> FEATURE:
<223> OTHER INFORMATION: 5' UTR region of HCV

<400> SEQUENCE: 3

```
gccagccccc tgatgggggc gacactccgc catgaatcac tcccctgtga ggaactactg     60
tcttcacgca gaaagcgtct agccatggcg ttagtatgag tgtcgtgcag cctccaggac    120 ccccctccc gggagagcca tagtggtctg cggaaccggt gagtacaccg gaattgccag    180
gacgaccggg tcctttcttg gattaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac c                        341
```

<210> SEQ ID NO 4
<211> LENGTH: 595
<212> TYPE: DNA
<213> ORGANISM: Artificial Sequence
<220> FEATURE:
<223> OTHER INFORMATION: 5' UTR region of BiP

<400> SEQUENCE: 4

```
cccggggtca ctcctgctgg acctactccg accccctagg ccgggagtga aggcgggact     60
tgtgcggtta ccagcggaaa tgcctcgggg tcagaagtcg caggagagat agacagctgc    120
tgaaccaatg ggaccagcgg atgggcggga tgttatctac cattggtgaa cgttagaaac    180
gaatagcagc caatgaatca gctgggggg cggagcagtg acgtttattg cggagggggc    240
cgcttcgaat cggcggcggc cagcttggtg gcctgggcca atgaacgggc tccaacgagc    300
agggccttca ccaatcggcg gcctccacga cggggctggg ggagggtata taagccgagt    360
aggcgacggt gaggtcgacg ccggccaaga cagcacagac agattgacct attgggtgt    420 ttcgcgagtg tgagagggaa gcgccgcggc ctgtatttct agacctgccc ttcgcctggt    480
tcgtggcgcc ttgtgacccc gggccctctg cgcctgcaag tcgaaattgc gctgtgctcc    540
tgtgctacgg cctgtggctg gactgcctgc tgctgcccaa ctggctggca agatg         595
```

<210> SEQ ID NO 5
<211> LENGTH: 575
<212> TYPE: DNA
<213> ORGANISM: Artificial Sequence
<220> FEATURE:
<223> OTHER INFORMATION: 5' UTR of PDGF

<400> SEQUENCE: 5

| | | | | | |
|---|---|---|---|---|---|
| gtttgcacct | ctccctgccc | gggtgctcga | gctgccgttg | caaagccaac | tttggaaaaa | 60 |
| gttttttggg | ggagacttgg | gccttgaggt | gcccagctcc | gcgctttccg | attttggggg | 120 |
| cttttccagaa | aatgttgcaa | aaagctaag | ccggcgggca | gaggaaaacg | cctgtagccg | 180 |
| gcgagtgaag | acgaaccatc | gactgccgtg | ttccttttcc | tcttggaggt | tggagtcccc | 240 |
| tgggcgcccc | cacacccta | gacgcctcgg | ctggttcgcg | acgcagcccc | ccggccgtgg | 300 |
| atgctgcact | cgggctcggg | atccgcccag | gtagccggcc | tcggacccag | gtcctgcgcc | 360 |
| caggtcctcc | cctgccccc | agcgacggag | ccggggccgg | gggcggcggc | gccggggca | 420 |
| tgcgggtgag | ccgcggctgc | agaggcctga | gcgcctgatc | gccgcggacc | tgagccgagc | 480 |
| ccaccccct | ccccagcccc | ccaccctggc | cgcgggggcg | gcgcgctcga | tctacgcgtc | 540 |
| cggggccccg | cggggccggg | cccggagtcg | gcatg | | | 575 |

<210> SEQ ID NO 6
<211> LENGTH: 2240
<212> TYPE: DNA
<213> ORGANISM: Artificial Sequence
<220> FEATURE:
<223> OTHER INFORMATION: Human uroplakin II 5' flanking region

<400> SEQUENCE: 6

| | | | | | |
|---|---|---|---|---|---|
| tcgataggta | cccactatag | ggcacgcgtg | gtcgacggcc | cgggctggtc | tggcaacttc | 60 |
| aagtgtgggc | ctttcagacc | ggcatcatca | gtgttacggg | gaagtcacta | ggaatgcaga | 120 |
| attgattgag | cacggtggct | cacacctgta | atcccaacac | tctgggaggc | caaggcaggt | 180 |
| ggatcacttg | tggtcaggag | tttgagacca | gcctggccaa | catggtgaaa | cctcatctct | 240 |
| actaaaaata | caaaaattag | ctgggaatgg | tggcacatgc | ctataatccc | agttactcag | 300 |
| gaggctgagg | caggagaatc | atttgaacct | gggaggcaga | ggttgcagtg | agccgagatc | 360 |
| acgccactgc | actccagcct | gggtgacaca | gcgagactct | gtctcaaaaa | aaaaaaaatg | 420 |
| cagaatttca | ggcttcaccc | cagacccact | gcatgactgc | atgagaagct | gcatcttaac | 480 |
| aagatccctg | gtaattcata | cgcatattaa | atttggagat | gcactggcgt | aagaccctcc | 540 |
| tactctctgc | ttaggcccat | gagttcttcc | tttactgtca | ttctccactc | accccaaact | 600 |
| ttgagcctac | ccttcccacc | ttggcggtaa | ggacacaacc | tccctcacat | tcctaccagg | 660 |
| accctaagct | tccctgggac | tgaggaagat | agaatagttc | gtggagcaaa | cagatataca | 720 |
| gcaacagtct | ctgtacagct | ctcaggcttc | tggaagttc | acagcctctc | ccgacaaagt | 780 |
| attccacttt | ccacaagtaa | ctctatgtgt | ctgagtctca | gtttccactt | ttctctctct | 840 |
| ctctctctct | caactttctg | agacagagtt | tcacttagtc | gcccaggctg | gagtgcaggg | 900 |
| gcacaatctc | ggctcactgc | aacctccacc | tcctgggttc | aagtgttct | cctgtctcag | 960 |
| cctcccgagt | agctgggatt | acaggcacac | accaccgcgt | tagttttgt | attttggta | 1020 |
| gagatggtgt | ttcgccatat | tggccaggct | gatctcgaac | tcctgacctc | aggtgatccg | 1080 |
| cccacctcgg | cctcccaaag | tgctgggatt | acaggcatga | gccaccacgc | ccggctgatc | 1140 |
| tcttttctat | tttaatagag | atcaaactct | ctgtgttgcc | taggctggtc | ttgaactcct | 1200 |

-continued

| | |
|---|---|
| ggcctcgagt gatcctccca ccttggcctc ccaaagtgtt gagattacag gcatgagcca | 1260 |
| ctgtgcctgg cctcagttct actacaaaag gaagccagta ccagctacca cccagggtgg | 1320 |
| ctgtagggct acaatggagc acacagaacc cctacccagg gcccggaaga agccccgact | 1380 |
| cctctcccct ccctctgccc agaactcctc cgcttctttc tgatgtagcc cagggccgga | 1440 |
| ggaggcagtc agggaagttc tgtctctttt tcatgttatc ttacgaggtc tcttttctcc | 1500 |
| attctcagtc caacaaatgg ttgctgccca aggctgactg tgcccacccc caaccctgc | 1560 |
| tggccagggt caatgtctgt ctctctggtc tctccagaag tcttccatgg ccaccttcgt | 1620 |
| ccccaccctc cagaggaatc tgaaaccgca tgtgctccct ggcccccaca gccctgcct | 1680 |
| ctcccagagc agcagtacct aagcctcagt gcactccaag aattgaaacc ctcagtctgc | 1740 |
| tgcccctccc caccagaatg tttctctccc attcttaccc actcaaggcc ctttcagtag | 1800 |
| ccccttggag tattctcttc ctacatatca gggcaacttc caaactcatc cccttctga | 1860 |
| ggggtgggg aaagaccccc accacatcgg gggagcagtc ctccaaggac tggccagtct | 1920 |
| ccagatgccc gtgcacacag gaacactgcc ttatgcacgg gagtcccaga gaaggggtg | 1980 |
| atttctttcc ccaccttagt tacaccatca agacccagcc agggcatccc ccctcctggc | 2040 |
| ctgagggcca gctccccatc ctgaaaaacc tgtctgctct ccccacccct ttgaggctat | 2100 |
| agggcccaag gggcaggttg gactggattc ccctccagcc cctcccgccc ccaggacaaa | 2160 |
| atcagccacc ccaggggcag ggcctcactt gcctcaggaa ccccagcctg ccagcaccta | 2220 |
| ttccacctcc cagcccagca | 2240 |

<210> SEQ ID NO 7
<211> LENGTH: 3592
<212> TYPE: DNA
<213> ORGANISM: Artificial Sequence
<220> FEATURE:
<223> OTHER INFORMATION: Mouse uroplakin II 5' flanking region

<400> SEQUENCE: 7

| | |
|---|---|
| ctcgaggatc tcggccctct ttctgcatcc ttgtcctaaa tcattttcat atcttgctag | 60 |
| acctcagttt gagagaaacg aaccttctca ttttcaagtt gaaaaaaaaa agaggttcaa | 120 |
| agtggctcac tcaaagttac aagccaacac tcaccactac gagtacaatg ccaccatta | 180 |
| gtgctggcat gccccaggag acaggcatgc atattattct agatgactgg gaggcagagg | 240 |
| ggtggcctag tgaggtcaga ctgtggacag atcaggcaga tgtgggttct gatcccaatt | 300 |
| cctcaggccg cagaactact gtggttcaag aaggggacaa aaggactgca gtccggaaca | 360 |
| ggaggtccat ttgagagctg actgagcaga agaggaaagt gaagaacttc tggggcaaga | 420 |
| gcttacccta ctttacagct ttgttgtctt ctttactcca ggggcgtccc tggtactcag | 480 |
| taaatgtctg ttggcttgag gaacatatgt gtaaggagga aggagaggga acttgaggga | 540 |
| gttaagactc aagaatcaat caaggagagg acagcagaga agacagggtt tgggagagag | 600 |
| actccagaca ttgccctgg ttcccttctt ggccactgtg aaaccctcca gaggaactga | 660 |
| gtgctgtggc tttaaatgat ctcagcactg tcagtgaagc gctctgctca aagagttatc | 720 |
| ctcttgctcc tgtgccgggg cctcccctc ctctcagctc ccaaacccctt ctcagccact | 780 |
| gtgatggcat aattagatgc gagagctcag accgtcaggt ctgctccagg aaccacccat | 840 |
| tttccccaac cccagagaaa ggtcctagtg gaaaagtggg ggccactgaa gggctgatgg | 900 |
| ggttctgtcc tttcccccat gctgggtgga cttaaagtct gcgatgtgtg taggggtag | 960 |

-continued

```
aagacaacag aacctggggg ctccggctgg gagcaggagg aactctcacc agacgatctc  1020
caaatttact gtgcaatgga cgatcaggaa actggttcag atgtagcttc tgatacagtg  1080
ggtctgaggt aaaacccgaa acttaatttc tttcaaaaat ttaaagttgc atttattatt  1140
ttatatgtgt gcccatatgt gtgccacagt gtctatgtgg aggtcagagg gcaagttgtg  1200
ggcattggct ctctcctttc ataatgtggc ttctggggac caaaatgtca ggcatggtgg  1260
caagagcttt tacctgttga gccatctcat ggtttcgtaa acttcctat gacgcttaca   1320
ggtaacgcag agacacagac tcacatttgg agttagcaga tgctgtattg gtgtaaacac  1380
tcatacacag acacacacac atactcatac acacacacac acacttatca catgcacaca  1440
catactcgta tacacacaga cacacacaca tgcactctca cattcacata ttcatacaca  1500
tccacacaca cactcatcca cacacacaga cacacatact catccacaca cacacacaca  1560
catactcata cacacacaca gacacacata ctcatacaca cacacagaca cacatata    1620
atcatacata cacagacaca ctcatacatg tgcacacaca cactcatcca cacacacaca  1680
ctcatacaca cacacactca tacacacaca cactcataca cacacacacg aggttttct   1740
caggctgcct ttgggtggag actggaactg atttctgttt ttcagctcct ggcttttg    1800
tccctttaga tgagatctcc tcctcacttt acacacagaa agatcacaca cgagggagaa  1860
ctggcggtgc ggaagagggc tacacggtag ggtgtcaggg tcaggagatc ttcctggcaa  1920
gtctcaaacc tccacatagc acagtgttta cgtgaggatt taggaggaat caggaagagg  1980
attggtttac tgcagagcag accatatagg tccactccta agccccattt gaaattagaa  2040
gtgagacagt gtgggataaa aagagcagat ctctggtcac attttttaaag ggatatgagg 2100
gtcctgtgcc tttaagcctt cccatctccc tccaatcccc cctcaccttc cccacccta a 2160
ccctccccag gtttctggag gagcagagtt gcgtcttctc cctgccctgc cgagctgctc  2220
actggctgct ctagaggctg tgctttgcgg tctccatgga aaccattagt tgctaagcaa  2280
ctggagcatc atctgtgctg agctcaggtc ctatcgagtt cacctagctg agacacccac  2340
gccctgcag ccactttgca gtgacaagcc tgagtctcag gttctgcatc tataaaaacg   2400
agtagccttt caggagggca tgcagagccc cctggccagc gtctagagga gaggtgactg  2460
agtgggccca tgtcactcgt ccatggctgg agaacctcca tcagtctccc agttagcctg  2520
gggcaggaga gaaccagagg agctgtggct gctgattgga tgatttacgt acccaatctg  2580
ttgtcccagg catcgaaccc cagagcgacc tgcacacatg ccaccgctgc ccgccctcc   2640
acctcctctg ctcctggtta caggattgtt ttgtcttgaa gggttttgtt gttgctactt  2700
tttgctttgt tttttctttt ttaacataag gtttctctgt gtagccctag ctgtcctgga  2760
actcactctg tagaccaggc tggcctcaaa ctcagaaatc caccttcctc caagtgctg   2820
ggattaaagg cattcgcacc atcgcccagc ccccggtctt gtttcctaag gttttcctgc  2880
tttactcgct acccgttgca caaccgcttg ctgtccaagt ctgtttgtat ctactccacc  2940
gcccactagc cttgctggac tggacctacg tttacctgga agccttcact aacttcccct  3000
gtctccacct tctggagaaa tctgaaggct cacactgata ccctccgctt ctcccagagt  3060
cgcagtttct taggcctcag ttaaataccc gaattggatc tcaggctctg ctatccccac  3120
cctacctaac caacccccct ctctcccatc cttactagcc aaagcccttt caacccttgg  3180
ggcttttcct acacctacac accagggcaa ttttagaact catggctctc ctagaaaacg  3240
cctacctcct tggagactga ccctctacag tccaggaggc agacactcag acagaggaac  3300
tctgtccttc agtcgcggga gttccagaaa gagccatact cccctgcaga gctaactaag  3360
```

```
ctgccaggac ccagccagag catccccctt tagccgaggg ccagctcccc agaatgaaaa    3420
acctgtctgg ggcccctccc tgaggctaca gtcgccaagg ggcaagttgg actggattcc    3480
cagcagcccc tcccactccg agacaaaatc agctaccctg gggcaggcct cattggcccc    3540
aggaaacccc agcctgtcag cacctgttcc aggatccagt cccagcgcag ta            3592

<210> SEQ ID NO 8
<211> LENGTH: 822
<212> TYPE: DNA
<213> ORGANISM: Artificial Sequence
<220> FEATURE:
<223> OTHER INFORMATION: APF-TRE

<400> SEQUENCE: 8
gcattgctgt gaactctgta cttaggacta aactttgagc aataacacac atagattgag     60
gattgtttgc tgttagcata caaactctgg ttcaaagctc ctctttattg cttgtcttgg    120
aaaatttgct gttcttcatg gtttctcttt tcactgctat ctattttttct caaccactca   180 catggctaca ataactgtct gcaagcttat gattcccaaa tatctatctc tagcctcaat    240
cttgttccag aagataaaaa gtagtattca aatgcacatc aacgtctcca cttggagggc    300
ttaaagacgt ttcaacatac aaaccgggga gttttgcctg gaatgtttcc taaaatgtgt    360
cctgtagcac atagggtcct cttgttcctt aaaatctaat tacttttagc ccagtgctca    420
tcccacctat ggggagatga gagtgaaaag ggagcctgat taataattac actaagtcaa    480
taggcataga gccaggactg tttgggtaaa ctggtcactt tatcttaaac taaatatatc    540
caaaactgaa catgtactta gttactaagt ctttgacttt atctcattca taccactcag    600
ctttatccag gccacttatg agctctgtgt ccttgaacat aaaatacaaa taaccgctat    660
gctgttaatt attggcaaat gtcccatttt caacctaagg aaataccata agtaacaga    720 tataccaaca aaaggttact agttaacagg cattgcctga aaagagtata aagaatttc    780 agcatgattt tccatattgt gcttccacca ctgccaataa ca                       822

<210> SEQ ID NO 9
<211> LENGTH: 451
<212> TYPE: DNA
<213> ORGANISM: Artificial Sequence
<220> FEATURE:
<223> OTHER INFORMATION: Probasin-TRE

<400> SEQUENCE: 9 aag ctt cca caa gtg cat tta gcc tct cca gta ttg ctg atg aat cca      48 cag ttc agg ttc aat ggc gtt caa aac ttg atc aaa aat gac cag act      96 tta tat tta cac caa cat cta tct gat tgg agg aat gga taa tag tca     144 tca tgt tta aac atc tac cat tcc agt aaa gaa aat atg ata gca tct     192 tgt tct tag tct ttt tct taa tag gga cat aaa gcc cac aaa taa aaa     240 tat gcc tga aga atg gga cag gca ttg ggc att gtc cat gcc tag taa     288 agt act cca aga acc tat ttg tat act aga tga cac aat gtc aat gtc     336 tgt gta caa ctg cca act ggg atg caa gac act gcc cat gcc aat cat     384 cct gaa aag cag cta aaa aaa gca gga agc tac tct gca cct tgt cag     432 tag gtc cag ata cct aca g                                            451

<210> SEQ ID NO 10
```

<211> LENGTH: 546
<212> TYPE: DNA
<213> ORGANISM: Artificial Sequence
<220> FEATURE:
<223> OTHER INFORMATION: Tyrosinase-TRE

<400> SEQUENCE: 10

| | | | | | |
|---|---|---|---|---|---|
| ccggttgaaa | atgataagtt | gaattctgtc | ttcgagaaca | tagaaaagaa | ttatgaaatg | 60 |
| ccaacatgtg | gttacaagta | atgcagaccc | aaggctcccc | agggacaaga | agtcttgtgt | 120 |
| taactctttg | tggctctgaa | agaaagagag | agagaaaaga | ttaagcctcc | ttgtggagat | 180 |
| catgtgatga | cttcctgatt | ccagccagag | cgagcatttc | catggaaact | tctcttcctc | 240 |
| ttcactcgag | attactaacc | ttattgttaa | tattctaacc | ataagaatta | aactattaat | 300 |
| ggtgaataga | gttttcact | ttaacatagg | cctatcccac | tggtgggata | cgagccaatt | 360 |
| cgaaagaaaa | agtcagtcat | gtgcttttca | gaggatgaaa | gcttaagata | aagactaaaa | 420 |
| gtgtttgatc | ctggaggtgg | gagtggtatt | ataggtct | cagccaagac | atgtgataat | 480 |
| cactgtagta | gtagctggaa | agagaaatct | gtgactccaa | ttagccagtt | cctgcagacc | 540 |
| ttgtga | | | | | | 546 |

<210> SEQ ID NO 11
<211> LENGTH: 12047
<212> TYPE: DNA
<213> ORGANISM: Artificial Sequence
<220> FEATURE:
<223> OTHER INFORMATION: Human glandular kallikrein-TRE

<400> SEQUENCE: 11

| | | | | | |
|---|---|---|---|---|---|
| gaattcagaa | ataggggaag | gttgaggaag | gacactgaac | tcaaagggga | tacagtgatt | 60 |
| ggtttatttg | tcttctcttc | acaacattgg | tgctggagga | attcccaccc | tgaggttatg | 120 |
| aagatgtctg | aacacccaac | acatagcact | ggagatatga | gctcgacaag | agtttctcag | 180 |
| ccacagagat | tcacagccta | gggcaggagg | acactgtacg | ccaggcagaa | tgacatggga | 240 |
| attgcgctca | cgattggctt | gaagaagcaa | ggactgtggg | aggtgggctt | tgtagtaaca | 300 |
| agagggcagg | gtgaactctg | attcccatgg | gggaatgtga | tggtcctgtt | acaaattttt | 360 |
| caagctggca | gggaataaaa | cccattacgg | tgaggacctg | tgagggcgg | ctgccccaac | 420 |
| tgataaagga | aatagccagg | tgggggcctt | tcccattgta | gggggacat | atctggcaat | 480 |
| agaagccttt | gagacccttt | agggtacaag | tactgaggca | gcaaataaaa | tgaaatctta | 540 |
| tttttcaact | ttatactgca | tgggtgtgaa | gatatatttg | tttctgtaca | ggggtgagg | 600 |
| gaaaggaggg | gaggaggaaa | gttcctgcag | gtctggtttg | gtcttgtgat | ccagggggtc | 660 |
| ttggaactat | ttaaattaaa | ttaaattaaa | acaagcgact | gttttaaatt | aaattaaatt | 720 |
| aaattaaatt | ttactttatt | ttatcttaag | ttctgggcta | catgtgcagg | acgtgcagct | 780 |
| ttgttacata | ggtaaacgtg | tgccatggtg | gtttgctgta | cctatcaacc | catcacctag | 840 |
| gtattaagcc | cagcatgcat | tagctgtttt | tcctgacgct | ctccctctcc | ctgactccca | 900 |
| caacaggccc | cagtgtgtgt | tgttcccctc | cctgtgtcca | tgtgttctca | ttgttcagct | 960 |
| cccacttata | agtgagaaca | tgtggtgttt | ggttttctgt | ttctgtgtta | gtttgctgag | 1020 |
| gataatggct | tccacctcca | tccatgttcc | tgcaaaggac | gtgatcttat | tcttttttat | 1080 |
| ggttgcatag | aaattgtttt | tacaaatcca | attgatattg | tatttaatta | caagttaatc | 1140 |
| taattagcat | actagaagag | attacagaag | atattagta | cattgaatga | ggaaatatat | 1200 |
| aaaataggac | gaaggtgaaa | tattaggtag | gaaaagtata | atagttgaaa | gaagtaaaaa | 1260 |

-continued

```
aaaatatgca tgagtagcag aatgtaaaag aggtgaagaa cgtaatagtg acttttttaga    1320 ccagattgaa ggacagagac agaaaaattt taaggaattg ctaaaccatg tgagtgttag    1380
aagtacagtc aataacatta aagcctcagg aggagaaaag aataggaaag gaggaaatat    1440
gtgaataaat agtagagaca tgtttgatgg attttaaaat atttgaaaga cctcacatca    1500
aaggattcat accgtgccat tgaagaggaa gatggaaaag ccaagaagcc agatgaaagt    1560
tagaaatatt attggcaaag cttaaatgtt aaaagtccta gagagaaagg atggcagaaa    1620
tattggcggg aaagaatgca gaacctagaa tataaaattca tcccaacagt ttggtagtgt    1680
gcagctgtag cctttctag ataatacact attgtcatac atcgcttaag cgagtgtaaa    1740
atggtctcct cactttattt atttatatat ttatttagtt ttgagatgga gcctcgctct    1800
gtctcctagg ctggagtgca atagtgcgat accactcact gcaacctctg cctcctctgt    1860
tcaagtgatt tcttacctc agcctcccga gtagctggga ttacaggtgc gtgccaccac    1920
acccggctaa ttttttgtatt ttttgtagag acggggtttt gccatgttgg ccaggctggt    1980
cttgaactcc tgacatcagg tgatccacct gccttggcct cctaaagtgc tgggattaca    2040
ggcatgagcc accgtgccca accactttat ttatttttta tttttatttt taaatttcag    2100
cttctatttg aaatacaggg ggcacatata taggattgtt acatgggtat attgaactca    2160
ggtagtgatc atactaccca acaggtaggt tttcaaccca ctccccctct tttcctcccc    2220
attctagtag tgtgcagtgt ctattgttct catgtttatg tctatgtgtg ctccaggttt    2280
agctcccacc tgtaagtgag aacgtgtggt atttgatttt ctgtccctgt gttaattcac    2340
ttaggattat ggcttccagc tccattcata ttgctgtaaa ggatatgatt cattttttcat    2400 ggccatgcag tattccatat tgcgtataga tcacattttc tttcttttt tttttttgaga    2460 cggagtcttg ctttgctgcc taggctggag tgcagtagca cgatctcggc tcactgcaag    2520
cttcacctcc ggggttcacg tcattcttct gtctcagctt cccaagtagc tgggactaca    2580
ggcgcccgcc accacgtccg gctaattttt ttgtgtgttt ttagtagaga tggggggtttc    2640 actgtgttag ccaggatggt cttgatctcc tgaccttgtg gtccacctgc ctcggtctcc    2700
caaagtgctg ggattacagg ggtgagccac tgcgcccggc ccatatatac cacattttct    2760
ttaaccaatc caccattgat gggcaactag gtagattcca tggattccac agttttgcta    2820
ttgtgtgcag tgtggcagta gacatatgaa tgaatgtgtc ttttttggtat aatgatttgc    2880 attccttttgg gtatacagtc attaatagga gtgctgggtt gaacggtggc tctgtttaaa    2940
attctttgag aattttccaa actgtttgcc atagagagca aactaattta catttccacg    3000
aacagtatat aagcattccc ttttctccac agctttgtca tcatggttttt tttttttctt    3060 tattttaaaa aagaatatgt tgttgttttc ccagggtaca tgtgcaggat gtgcaggttt    3120
gttacatagg tagtaaacgt gagccatggt ggtttgctgc acctgtcaac ccattacctg    3180
ggtatgaagc cctgcctgca ttagctcttt tccctaatgc tctcactact gccccaccct    3240
caccctgaca gggcaaacag acaacctaca gaatgggagg aaattttttgc aatctattca    3300 tctgacaaag gtcaagaata tccagaatct acaaggaact taagcaaatt tttactttttt    3360 aataatagcc actctgactg gcgtgaaatg gtatctcatt gtggttttca tttgaatttc    3420
tctgatgatc agtgacgatg agcatttttt catatttgtt ggctgcttgt acgtcttttg    3480
agaagtgtct cttcatgcct tttggccact ttaatgggat tattttttgc ttttttagttt    3540 aagttcctta tagattctgg atattagact tcttattgga tgcatagttt gtgaatactc    3600
```

```
tcttccattc tgtaggttgt ctgtttactc tattgatggc ttcttttgct gtgccgaagc    3660
atcttagttt aattagaaac cacctgccaa tttttgtttt tgttgcaatt gcttttgggg    3720
acttagtcat aaactctttg ccaaggtctg ggtcaagaag agtatttcct aggttttctt    3780
ctagaatttt gaaagtctga atgtaaacat ttgcatttt aatgcatctt gagttagttt     3840
ttgtatatgt gaaaggtcta ctctcatttt cttccctct ttctttcttt ctttctttc     3900 tttcttcttt tctttctttc tttctttctt tcttctttc tttctttttg tccttctttc    3960 tttcttctt tctctttctt tctctctttc tttttttttt ttgatggagt attgctctgt    4020
tgcccaggct gcagtgcagc ggcacgatct cggctcactg caacctctgc ctcctgggtt    4080
caactgattc tcctgcatca gccttccaag tagctgggat tataggcgcc cgccaccacg    4140
cccgactaat ttttgtattt ttagtagaga cggggtttgtg ccatgttggc caggctggtt   4200
tgaaactcct gacctcaaac gatctgcctg ccttggcctc ccaaagtgct gggattacag    4260
gtgtgagcca ctgtgcccag ccaagaatgt cattttctaa gaggtccaag aacctcaaga    4320
tattttggga ccttgagaag agaggaattc atacaggtat tacaagcaca gcctaatggc    4380
aaatctttgg catggcttgg cttcaagact ttaggctctt aaaagtcgaa tccaaaaatt    4440
tttataaaag ctccagctaa gctaccttaa aaggggcctg tatggctgat cactcttctt    4500
gctatacttt acacaaataa acaggccaaa tataatgagg ccaaaattta ttttgcaaat    4560
aaattggtcc tgctatgatt tactcttggt aagaacaggg aaaatagaga aaaatttaga    4620
ttgcatctga cctttttttc tgaattttta tatgtgccta caatttgagc taaatcctga    4680
attattttct ggttgcaaaa actctctaaa gaagaacttg gttttcattg tcttcgtgac    4740
acatttatct ggctctttac tagaacagct ttcttgtttt tggtgttcta gcttgtgtgc    4800
cttacagttc tactcttcaa attattgtta tgtgtatctc atagttttcc ttcttttgag    4860
aaaactgaag ccatggtatt ctgaggacta gagatgactc aacagagctg gtgaatctcc    4920
tcatatgcaa tccactgggc tcgatctgct tcaaattgct gatgcactgc tgctaaagct    4980
atacatttaa aaccctcact aaaggatcag ggaccatcat ggaagaggag gaaacatgaa    5040
attgtaagag ccagattcgg ggggtagagt gtggaggtca gagcaactcc accttgaata    5100
agaaggtaaa gcaacctatc ctgaaagcta acctgccatg gtggcttctg attaacctct    5160
gttctaggaa gactgacagt ttgggtctgt gtcattgccc aaatctcatg ttaaattgta    5220
atccccagtg ttcggaggtg ggacttggtg gtaggtgatt cggtcatggg agtagatttt    5280
cttctttgtg gtgttacagt gatagtgagt gagttctcgt gagatctggt catttaaaag    5340
tgtgtggccc ctcccctccc tctcttggtc ctcctactgc catgtaagat acctgctcct    5400
gctttgcctt ctaccataag taaaagcccc ctgaggcctc cccagaagca gatgccacca    5460
tgcttcctgt acagcctgca gaaccatcag ccaattaaac ctcttttctg tataaattac    5520
cagtcttgag tatctctta cagcagtgtg agaacggact aatacaaggg tctccaaaat    5580
tccaagttta tgtattcttt cttgccaaat agcaggtatt taccataaat cctgtcctta    5640
ggtcaaacaa ccttgatggc atcgtacttc aattgtctta cacattcctt ctgaatgact    5700
cctcccctat ggcatataag ccctgggtct tggggataa tggcagaggg gtccaccatc     5760
ttgtctggct gccacctgag acacggacat ggcttctgtt ggtaagtctc tattaaatgt    5820
ttctttctaa gaaactggat ttgtcagctt gtttctttgg cctctcagct tcctcagact    5880
ttggggtagg ttgcacaacc ctgcccacca cgaaacaaat gtttaatatg ataaatatgg    5940
atagatataa tccacataaa taaaagctct tggagggccc tcaataattg ttaagagtgt    6000
```

-continued

```
aaatgtgtcc aaagatggaa aatgtttgag aactactgtc ccagagattt tcctgagttc      6060
tagagtgtgg gaatatagaa cctggagctt ggcttcttca gcctagaatc aggagtatgg      6120
ggctgaagtc tgaagcttgg cttcagcagt ttggggttgg cttccggagc acatatttga      6180
catgttgcga ctgtgatttg gggtttggta tttgctctga atcctaatgt ctgtccttga      6240
ggcatctaga atctgaaatc tgtggtcaga attctattat cttgagtagg acatctccag      6300
tcctggttct gccttctagg gctggagtct gtagtcagtg acccggtctg gcatttcaac      6360
ttcatataca gtgggctatc ttttggtcca tgtttcaacc aaacaaccga ataaaccatt      6420
agaacctttc cccacttccc tagctgcaat gttaaaccta ggatttctgt ttaataggtt      6480
catatgaata atttcagcct gatccaactt tacattcctt ctaccgttat tctacaccca      6540
ccttaaaaat gcattcccaa tatattccct ggattctacc tatatatggt aatcctggct      6600
ttgccagttt ctagtgcatt aacatacctg atttacattc ttttacttta aagtggaaat      6660
aagagtccct ctgcagagtt caggagttct caagatggcc cttacttctg acatcaattg      6720
agatttcaag ggagtcgcca agatcatcct caggttcagt gattgctggt agccctcata      6780
taactcaatg aaagctgtta tgctcatggc tatggtttat tacagcaaaa gaatagagat      6840
gaaaatctag caaggaaga gttgcatggg gcaaagacaa ggagagctcc aagtgcagag      6900
attcctgttg ttttctccca gtggtgtcat ggaaagcagt atcttctcca tacaatgatg      6960
tgtgataata ttcagtgtat tgccaatcag ggaactcaac tgagccttga ttatattgga      7020
gcttggttgc acagacatgt cgaccacctt catggctgaa ctttagtact tagcccctcc      7080
agacgtctac agctgatagg ctgtaaccca acattgtcac cataaatcac attgttagac      7140
tatccagtgt ggcccaagct cccgtgtaaa cacaggcact ctaaacaggc aggatatttc      7200
aaaagcttag agatgacctc ccaggagctg aatgcaaaga cctggcctct ttgggcaagg      7260
agaatccttt accgcacact ctccttcaca gggttattgt gaggatcaaa tgtggtcatg      7320
tgtgtgagac accagcacat gtctggctgt ggagagtgac ttctatgtgt gctaacattg      7380
ctgagtgcta agaaagtatt aggcatggct ttcagcactc acagatgctc atctaatcct      7440
cacaacatgg ctacagggtg ggcactacta gcctcatttg acagaggaaa ggactgtgga      7500
taagaagggg gtgaccaata ggtcagagtc attctggatg caaggggctc cagaggacca      7560
tgattagaca ttgtctgcag agaaattatg gctggatgtc tctgccccgg aaaggggggat     7620 gcactttcct tgacccccta tctcagatct tgactttgag gttatctcag acttcctcta      7680
tgataccagg agcccatcat aatctctctg tgtcctctcc ccttcctcag tcttactgcc      7740
cactcttccc agctccatct ccagctggcc aggtgtagcc acagtaccta actctttgca      7800
gagaactata aatgtgtatc ctacagggga gaaaaaaaa aagaactctg aaagagctga      7860
cattttaccg acttgcaaac acataagcta acctgccagt tttgtgctgg tagaactcat      7920
gagactcctg ggtcagaggc aaaagatttt attacccaca gctaaggagg cagcatgaac      7980
tttgtgttca catttgttca cttttgcccc caattcatat gggatgatca gagcagttca      8040
ggtggatgga cacaggggtt tgtggcaaag gtgagcaacc taggcttaga aatcctcaat      8100
cttataagaa ggtactagca aacttgtcca gtctttgtat ctgacggaga tattatcttt      8160
ataattgggt tgaaagcaga cctactctgg aggaacatat tgtatttatt gtcctgaaca      8220
gtaaacaaat ctgctgtaaa atagacgtta actttattat ctaaggcagt aagcaaacct      8280
agatctgaag gcgataccat cttgcaaggc tatctgctgt acaaatatgc ttgaaaagat      8340
```

-continued

```
ggtccagaaa agaaaacggt attattgcct ttgctcagaa gacacacaga aacataagag    8400
aaccatggaa aattgtctcc caacactgtt cacccagagc cttccactct tgtctgcagg    8460
acagtcttaa catcccatca ttagtgtgtc taccacatct ggcttcaccg tgcctaacca    8520
agatttctag gtccagttcc ccaccatgtt tggcagtgcc ccactgccaa ccccagaata    8580
agggagtgct cagaattccg agggacatg ggtgggatc agaacttctg ggcttgagtg    8640
cagaggggc ccatactcct tggttccgaa ggaggaagag gctggaggtg aatgtccttg    8700
gaggggagga atgtgggttc tgaactctta aatccccaag ggaggagact ggtaaggtcc    8760
cagcttccga ggtactgacg tgggaatggc ctgagaggtc taagaatccc gtatcctcgg    8820
gaaggagggg ctgaaattgt gaggggttga gttgcagggg tttgttagct tgagactcct    8880
tggtgggtcc ctgggaagca aggactgaaa ccattggctc cagggtttgg tgtgaaggta    8940
atgggatctc ctgattctca aagggtcaga ggactgagag ttgcccatgc tttgatcttt    9000
ccatctactc cttactccac ttgagggtaa tcacctactc ttctagttcc acaagagtgc    9060
gcctgcgcga gtataatctg cacatgtgcc atgtcccgag gcctgggca tcatccactc    9120
atcattcagc atctgcgcta tgcgggcgag gccggcgcca tgacgtcatg tagctgcgac    9180
tatccctgca gcgcgcctct cccgtcacgt cccaaccatg gagctgtgga cgtgcgtccc    9240
ctggtggatg tggcctgcgt ggtgccaggc cggggcctgg tgtccgataa agatcctaga    9300
accacaggaa accaggactg aaaggtgcta gagaatggcc atatgtcgct gtccatgaaa    9360
tctcaaggac ttctgggtgg agggcacagg agcctgaact tacgggtttg ccccagtcca    9420
ctgtcctccc aagtgagtct cccagatacg aggcactgtg ccagcatcag cttcatctgt    9480
accacatctt gtaacaggga ctacccagga ccctgatgaa caccatggtg tgtgcaggaa    9540
gagggggtga aggcatggac tcctgtgtgg tcagagccca gaggggcca tgacgggtgg    9600
ggaggaggct gtggactggc tcgagaagtg ggatgtggtt gtgtttgatt cctttggcc    9660
agataaagtg ctggatatag cattgaaaac ggagtatgaa gaccagttag aatggagggt    9720
caggttggag ttgagttaca gatggggtaa aattctgctt cggatgagtt tggggattgg    9780
caatctaaag gtggtttggg atggcatggc tttgggatgg aaataggttt gttttatgt    9840
tggctgggaa gggtgtgggg attgaattgg ggatgaagta ggtttagttt tggagataga    9900
atacatggag ctggctattg catgcgagga tgtgcattag tttggtttga tctttaaata    9960
aaggaggcta ttagggttgt cttgaattag attaagttgt gttgggttga tgggttgggc    10020
ttgtgggtga tgtggttgga ttgggctgtg ttaaattggt ttgggtcagg ttttggttga    10080
ggttatcatg gggatgagga tatgcttggg acatggattc aggtggttct cattcaagct    10140
gaggcaaatt tcctttcaga cggtcattcc agggaacgag tggttgtgtg ggggaaatca    10200
ggccactggc tgtgaatatc cctctatcct ggtcttgaat tgtgattatc tatgtccatt    10260
ctgtctcctt cactgtactt ggaattgatc tggtcattca gctggaaatg ggggaagatt    10320
ttgtcaaatt cttgagacac agctgggtct ggatcagcgt aagccttcct tctggtttta    10380
ttgaacagat gaaatcacat ttttttttttc aaaatcacag aaatcttata gagttaacag    10440
tggactctta taataagagt taacaccagg actcttattc ttgattcttt tctgagacac    10500
caaaatgaga tttctcaatg ccaccctaat tcttttttttt tttttttttt ttttttgagac    10560
acagtctggg tcttttgctc tgtcactcag gctggagcgc agtggtgtga tcatagctca    10620
ctgaacccett gacctcctgg acttaaggga tcctcctgct tcagcctcct gagtagatgc    10680
ggctacaggt gcttgccacc acacctggct aattaaattt tttttttttt tttgtagaga    10740
```

-continued

```
aagggtctca ctttgttgcc ctggctgatc ttgaacttct gacttcaagt gattcttcag    10800
ccttggactc ccaaagcact gggattgctg gcatgagcca ctcaccgtgc ctggcttgca    10860
gcttaatctt ggagtgtata aacctggctc ctgatagcta gacatttcag tgagaaggag    10920
gcattggatt ttgcatgagg acaattctga cctaggaggg caggtcaaca ggaatccccg    10980
ctgtacctgt acgttgtaca ggcatggaga atgaggagtg aggaggccgt accggaaccc    11040
catattgttt agtggacatt ggattttgaa ataataggga acttggtctg ggagagtcat    11100
atttctggat tggacaatat gtggtatcac aaggttttat gatgagggag aaatgtatgt    11160
ggggaaccat tttctgagtg tggaagtgca agaatcagag agtagctgaa tgccaacgct    11220
tctatttcag gaacatggta agttggaggt ccagctctcg ggctcagacg ggtataggga    11280
ccaggaagtc tcacaatccg atcattctga tatttcaggg catattaggt ttgggtgca    11340 aaggaagtac ttgggactta ggcacatgag actttgtatt gaaaatcaat gattggggct    11400
ggccgtggtg ctcacgcctg taatctcatc actttgggag accgaagtgg gaggatggct    11460
tgatctcaag agttggacac cagcctaggc aacatggcca gaccctctct ctacaaaaaa    11520
attaaaaatt agctggatgt ggtggtgcat gcttgtggtc tcagctatcc tggaggctga    11580
gacaggagaa tcggttgagt ctgggagttc aaggctacag ggagctgcga tcacgccgct    11640
gcactccagc ctgggaaaca gagtgagact gtctcagaat tttttaaaa aagaatcagt     11700 gatcatccca acccctgttg ctgttcatcc tgagcctgcc ttctctggct ttgttcccta    11760
gatcacatct ccatgatcca taggccctgc ccaatcgac ctcacaccgt gggaatgcct    11820
ccagactgat ctagtatgtg tggaacagca agtgctggct ctccctcccc ttccacagct    11880
ctgggtgtgg gaggggttg tccagcctcc agcagcatgg ggagggcctt ggtcagcatc    11940
taggtgccaa cagggcaagg gcggggtcct ggagaatgaa ggctttatag ggctcctcag    12000
ggaggccccc cagccccaaa ctgcaccacc tggccgtgga caccggt                  12047
```

<210> SEQ ID NO 12
<211> LENGTH: 67
<212> TYPE: DNA
<213> ORGANISM: Artificial Sequence
<220> FEATURE:
<223> OTHER INFORMATION: HRE-TRE

<400> SEQUENCE: 12

```
ccccgaggca gtgcatgagg ctcagggcgt gcgtgagtcg cagcgagacc ccggggtgca     60
ggccgga                                                              67
```

<210> SEQ ID NO 13
<211> LENGTH: 5835
<212> TYPE: DNA
<213> ORGANISM: Artificial Sequence
<220> FEATURE:
<223> OTHER INFORMATION: PSA-TRE

<400> SEQUENCE: 13

```
aagcttctag ttttcttttc ccggtgacat cgtggaaagc actagcatct ctaagcaatg     60
atctgtgaca atattcacag tgtaatgcca tccagggaac tcaactgagc cttgatgtcc    120
agagattttt gtgttttttt ctgagactga gtctcgctct gtgccaggct ggagtgcagt    180
ggtgcaacct tggctcactg caagctccgc ctcctgggtt cacgccattc tcctgcctca    240
gcctcctgag tagctgggac tacaggcacc cgccaccacg cctggctaat tttttgtat    300
```

-continued

| | |
|---|---|
| ttttagtaga gatggggttt cactgtgtta gccaggatgg tctcagtctc ctgacctcgt | 360 |
| gatctgccca ccttggcctc ccaaagtgct gggatgacag gcgtgagcca ccgcgcctgg | 420 |
| ccgatatcca gagatttttt ggggggctcc atcacacaga catgttgact gtcttcatgg | 480 |
| ttgacttta gtatccagcc cctctagaaa tctagctgat atagtgtggc tcaaaacctt | 540 |
| cagcacaaat cacaccgtta gactatctgg tgtgcccaa accttcaggt gaacaaaggg | 600 |
| actctaatct ggcaggatac tccaaagcat tagagatgac ctcttgcaaa gaaaaagaaa | 660 |
| tggaaaagaa aaagaaagaa aggaaaaaaa aaaaaaaaa gagatgacct ctcaggctct | 720 |
| gaggggaaac gcctgaggtc tttgagcaag gtcagtcctc tgttgcacag tctccctcac | 780 |
| agggtcattg tgacgatcaa atgtggtcac gtgtatgagg caccagcaca tgcctggctc | 840 |
| tggggagtgc cgtgtaagtg tatgcttgca ctgctgaatg gctgggatgt gtcagggatt | 900 |
| atcttcagca cttacagatg ctcatctcat cctcacagca tcactatggg atgggtatta | 960 |
| ctggcctcat tgatggaga aagtggctgt ggctcagaaa gggggaccca ctagaccagg | 1020 |
| gacactctgg atgctgggga ctccagagac catgaccact caccaactgc agagaaatta | 1080 |
| attgtggcct gatgtccctg tcctggagag ggtggaggtg gaccttcact aacctcctac | 1140 |
| cttgaccctc tcttttaggg ctctttctga cctccaccat ggtactagga ccccattgta | 1200 |
| ttctgtaccc tcttgactct atgaccccca ccgcccactg catccagctg ggtcccctcc | 1260 |
| tatctctatt cccagctggc cagtgcagtc tcagtgccca cctgtttgtc agtaactctg | 1320 |
| aaggggctga cattttactg acttgcaaac aaataagcta actttccaga gttttgtgaa | 1380 |
| tgctggcaga gtccatgaga ctcctgagtc agaggcaaag gcttttactg ctcacagctt | 1440 |
| agcagacagc atgaggttca tgttcacatt agtacacctt gccccccca aatcttgtag | 1500 |
| ggtgaccaga gcagtctagg tggatgctgt gcagaagggg tttgtgccac tggtgagaaa | 1560 |
| cctgagatta ggaatcctca atcttatact gggacaactt gcaaacctgc tcagcctttg | 1620 |
| tctctgatga agatattatc ttcatgatct tggattgaaa acagacctac tctggaggaa | 1680 |
| catattgtat cgattgtcct tgacagtaaa caaatctgtt gtaagagaca ttatctttat | 1740 |
| tatctaggac agtaagcaag cctggatctg agagagatat catcttgcaa ggatgcctgc | 1800 |
| tttacaaaca tccttgaaac aacaatccag aaaaaaaaag gtgttactgt ctttgctcag | 1860 |
| aagacacaca gatacgtgac agaaccatgg agaattgcct cccaacgctg ttcagccaga | 1920 |
| gccttccacc ctttctgcag gacagtctca acgttccacc attaaatact tcttctatca | 1980 |
| catcccgctt ctttatgcct aaccaaggtt ctaggtcccg atcgactgtg tctggcagca | 2040 |
| ctccactgcc aaacccagaa taaggcagcg ctcaggatcc cgaagggca tggctgggga | 2100 |
| tcagaacttc tgggtttgag tgaggagtgg gtccaccctc ttgaatttca aaggaggaag | 2160 |
| aggctggatg tgaaggtact gggggaggga aagtgtcagt tccgaactct taggtcaatg | 2220 |
| agggaggaga ctggtaaggt cccagctccc gaggtactga tgtgggaatg gcctaagaat | 2280 |
| ctcatatcct caggaagaag gtgctggaat cctgagggt agagttctgg gtatatttgt | 2340 |
| ggcttaaggc tctttggccc ctgaaggcag aggctggaac cattaggtcc agggtttggg | 2400 |
| gtgatagtaa tgggatctct tgattcctca agagtctgag gatcgagggt tgcccattct | 2460 |
| tccatcttgc cacctaatcc ttactccact tgagggtatc accagccctt ctagctccat | 2520 |
| gaaggtcccc tgggcaagca caatctgagc atgaaagatg ccccagaggc cttgggtgtc | 2580 |
| atccactcat catccagcat cacactctga gggtgtggcc agcaccatga cgtcatgttg | 2640 |
| ctgtgactat ccctgcagcg tgcctctcca gccacctgcc aaccgtagag ctgcccatcc | 2700 |

```
tcctctggtg ggagtggcct gcatggtgcc aggctgaggc ctagtgtcag acagggagcc    2760
tggaatcata gggatccagg actcaaaagt gctagagaat ggccatatgt caccatccat    2820
gaaatctcaa gggcttctgg gtggagggca cagggacctg aacttatggt ttcccaagtc    2880
tattgctctc ccaagtgagt ctcccagata cgaggcactg tgccagcatc agccttatct    2940
ccaccacatc ttgtaaaagg actacccagg gccctgatga acaccatggt gtgtacagga    3000 gtaggggtg gaggcacgga ctcctgtgag gtcacagcca agggagcatc atcatgggtg     3060
gggaggaggc aatggacagg cttgagaacg gggatgtggt tgtatttggt tttctttggt    3120
tagataaagt gctgggtata ggattgagag tggagtatga agaccagtta ggatggagga    3180
tcagattgga gttgggttag ataaagtgct gggtatagga ttgagagtgg agtatgaaga    3240
ccagttagga tggaggatca gattggagtt gggttagaga tggggtaaaa ttgtgctccg    3300
gatgagtttg ggattgacac tgtggaggtg gtttgggatg gcatggcttt gggatggaaa    3360
tagatttgtt ttgatgttgg ctcagacatc cttggggatt gaactgggga tgaagctggg    3420
tttgattttg gaggtagaag acgtggaagt agctgtcaga tttgacagtg gccatgagtt    3480
ttgtttgatg gggaatcaaa caatggggga agacataagg gttggcttgt taggttaagt    3540
tgcgttgggt tgatggggtc ggggctgtgt ataatgcagt tggattggtt tgtattaaat    3600 tgggttggt caggttttgg ttgaggatga gttgaggata tgcttgggga caccggatcc     3660
atgaggttct cactgagtg gagacaaact tcctttccag gatgaatcca gggaagcctt     3720
aattcacgtg tagggaggt caggccactg gctaagtata tccttccact ccagctctaa     3780
gatggtctta aattgtgatt atctatatcc acttctgtct ccctcactgt gcttggagtt    3840
tacctgatca ctcaactaga aacagggaa gattttatca aattctttt ttttttttt      3900 ttttttgag acagagtctc actctgttgc ccaggctgga gtgcagtggc gcagtctcgg     3960
ctcactgcaa cctctgcctc ccaggttcaa gtgattctcc tgcctcagcc tcctgagttg    4020
ctgggattac aggcatgcag caccatgccc agctaatttt tgtattttta gtagagatgg    4080
ggtttcacca atgtttgcca ggctggcctc gaactcctga cctggtgatc cacctgcctc    4140
agcctcccaa agtgctggga ttacaggcgt cagccaccgc gcccagccac ttttgtcaaa    4200
ttcttgagac acagctcggg ctggatcaag tgagctactc tggttttatt gaacagctga    4260
aataaccaac ttttttggaaa ttgatgaaat cttacggagt taacagtgga ggtaccaggg    4320
ctcttaagag ttcccgattc tcttctgaga ctacaaattg tgattttgca tgccaccttta   4380 atcttttttt ttttttttt aaatcgaggt ttcagtctca ttctatttcc caggctggag    4440
ttcaatagcg tgatcacagc tcactgtagc cttgaactcc tggccttaag agattctcct    4500
gcttcggtct cccaatagct aagactacag tagtccacca ccatatccag ataatttta    4560 aattttttgg gggccgggc acagtggctc acgcctgtaa tcccaacacc atgggaggct     4620
gagatgggtg gatcacgagg tcaggagttt gagaccagcc tgaccaacat ggtgaaactc    4680
tgtctctact aaaaaaaaa aaatagaaa aattagccgg gcgtggtggc acacggcacc      4740
tgtaatccca gctactgagg aggctgaggc aggagaatca cttgaaccca gaaggcagag    4800
gttgcaatga gccgagattg cgccactgca ctccagcctg ggtgacagag tgagactctg    4860
tctcaaaaaa aaaaatttt tttttttttt ttgtagagat ggatcttgct ttgtttctct     4920
ggttggcctt gaactcctgg cttcaagtga tcctcctacc ttggcctcgg aaagtgttgg    4980
gattacaggc gtgagccacc atgactgacc tgtcgttaat cttgaggtac ataaacctgg    5040
```

-continued

```
ctcctaaagg ctaaaggcta aatatttgtt ggagaagggg cattggattt tgcatgagga      5100
tgattctgac ctgggagggc aggtcagcag gcatctctgt tgcacagata gagtgtacag      5160
gtctggagaa caaggagtgg ggggttattg gaattccaca ttgtttgctg cacgttggat      5220
tttgaaatgc tagggaactt tgggagactc atatttctgg gctagaggat ctgtggacca      5280
caagatcttt ttatgatgac agtagcaatg tatctgtgga gctggattct gggttgggag      5340
tgcaaggaaa agaatgtact aaatgccaag acatctattt caggagcatg aggaataaaa      5400
gttctagttt ctggtctcag agtggtgcat ggatcaggga gtctcacaat ctcctgagtg      5460
ctggtgtctt agggcacact gggtcttgga gtgcaaagga tctaggcacg tgaggctttg      5520
tatgaagaat cggggatcgt acccaccccc tgtttctgtt tcatcctggg catgtctcct      5580
ctgcctttgt cccctagatg aagtctccat gagctacaag ggcctggtgc atccagggtg      5640
atctagtaat tgcagaacag caagtgctag ctctccctcc ccttccacag ctctgggtgt      5700 gggaggggt tgtccagcct ccagcagcat ggggagggcc ttggtcagcc tctggtgcc      5760 agcagggcag gggcggagtc ctggggaatg aaggttttat agggctcctg ggggaggctc      5820
cccagcccca agctt                                                      5835
```

<210> SEQ ID NO 14
<211> LENGTH: 15056
<212> TYPE: DNA
<213> ORGANISM: Artificial Sequence
<220> FEATURE:
<223> OTHER INFORMATION: CEA TRE

<400> SEQUENCE: 14

```
aagcttttta gtgctttaga cagtgagctg gtctgtctaa cccaagtgac ctgggctcca       60
tactcagccc cagaagtgaa gggtgaagct gggtggagcc aaaccaggca agcctaccct      120
cagggctccc agtggcctga gaaccattgg acccaggacc cattacttct agggtaagga      180
aggtacaaac accagatcca accatggtct gggggacag ctgtcaaatg cctaaaaata      240
tacctgggag aggagcaggc aaactatcac tgccccaggt tctctgaaca gaaacagagg      300
ggcaacccaa agtccaaatc caggtgagca ggtgcaccaa atgcccagag atatgacgag      360
gcaagaagtg aaggaaccac ccctgcatca aatgttttgc atgggaagga aaggggggtt      420
gctcatgttc ccaatccagg agaatgcatt tgggatctgc cttcttctca ctccttggtt      480
agcaagacta agcaaccagg actctggatt tggggaaaga cgtttatttg tggaggccag      540
tgatgacaat cccacgaggg cctaggtgaa gagggcagga aggctcgaga cactggggac      600
tgagtgaaaa ccacacccat gatctgcacc acccatggat gctccttcat tgctcacctt      660
tctgttgata tcagatggcc ccatttctg taccttcaca gaaggacaca ggctagggtc      720
tgtgcatggc cttcatcccc ggggccatgt gaggacagca ggtgggaaag atcatgggtc      780
ctcctgggtc ctgcagggcc agaacattca tcacccatac tgacctccta gatgggaatg      840
gcttccctgg ggctgggcca acggggcctg gcaggggag aaaggacgtc aggggacagg      900
gaggaagggt catcgagacc cagcctgaa ggttcttgtc tctgaccatc caggatttac      960
ttccctgcat ctacctttgg tcattttccc tcagcaatga ccagctctgc ttcctgatct     1020
cagcctccca ccctggacac agcacccag tccctggccc ggctgcatcc acccaatacc     1080
ctgataaccc aggacccatt acttctaggg taaggagggt ccaggagaca gaagctgagg     1140 aaggtctga agaagtcaca tctgtcctgg ccagagggga aaaaccatca gatgctgaac     1200
caggagaatg ttgacccagg aaagggaccg aggacccaag aaaggagtca gaccaccagg     1260
```

```
gtttgcctga gaggaaggat caaggccccg agggaaagca gggctggctg catgtgcagg      1320
acactggtgg ggcatatgtg tcttagattc tccctgaatt cagtgtccct gccatggcca      1380
gactctctac tcaggcctgg acatgctgaa ataggacaat ggccttgtcc tctctcccca      1440
ccatttggca agagacataa aggacattcc aggacatgcc ttcctgggag gtccaggttc      1500
tctgtctcac acctcaggga ctgtagttac tgcatcagcc atggtaggtg ctgatctcac      1560
ccagcctgtc caggcccttc cactctccac tttgtgacca tgtccaggac cacccctcag      1620
atcctgagcc tgcaaatacc cccttgctgg gtgggtggat tcagtaaaca gtgagctcct      1680
atccagcccc cagagccacc tctgtcacct tcctgctggg catcatccca ccttcacaag      1740
cactaaagag catggggaga cctggctagc tgggtttctg catcacaaag aaaataatcc      1800
cccaggttcg gattcccagg gctctgtatg tggagctgac agacctgagg ccaggagata      1860
gcagaggtca gccctaggga gggtgggtca tccacccagg ggacagggt gcaccagcct       1920 tgctactgaa agggcctccc caggacagcg ccatcagccc tgcctgagag ctttgctaaa      1980
cagcagtcag aggaggccat ggcagtggct gagctcctgc tccaggcccc aacagaccag      2040
accaacagca caatgcagtc cttccccaac gtcacaggtc accaaaggga aactgaggtg      2100
ctacctaacc ttagagccat caggggagat aacagcccaa tttcccaaac aggccagttt      2160
caatcccatg acaatgacct ctctgctctc attcttccca aaataggacg ctgattctcc      2220
cccaccatgg atttctccct tgtcccggga gccttttctg cccctatga tctgggcact       2280 cctgacacac acctcctctc tggtgacata tcagggtccc tcactgtcaa gcagtccaga      2340
aaggacagaa ccttggacag cgcccatctc agcttcaccc ttcctccttc acagggttca      2400
gggcaaagaa taaatggcag aggccagtga gcccagagat ggtgacaggc agtgacccag      2460
gggcagatgc ctggagcagg agctggcggg gccacaggga aaggtgatg caggaaggga       2520 aacccagaaa tgggcaggaa aggaggacac aggctctgtg gggctgcagc ccagggttgg      2580
actatgagtg tgaagccatc tcagcaagta aggccaggtc ccatgaacaa gagtgggagc      2640
acgtggcttc ctgctctgta tatggggtgg gggattccat gccccataga accagatggc      2700
cggggttcag atggagaagg agcaggacag gggatcccca ggataggagg accccagtgt      2760
ccccacccag gcaggtgact gatgaatggg catgcagggt cctcctgggc tgggctctcc      2820
ctttgtccct caggattcct tgaaggaaca tccggaagcc gaccacatct acctggtggg      2880
ttctggggag tccatgtaaa gccaggagct tgtgttgcta ggagggtca tggcatgtgc       2940 tggggcacc aaagagagaa acctgagggc aggcaggacc tggtctgagg aggcatggga       3000
gcccagatgg ggagatggat gtcaggaaag gctgccccat cagggagggt gatagcaatg      3060
gggggtctgt gggagtgggc acgtgggatt ccctggctc tgccaagttc cctcccatag       3120
tcacaacctg gggacactgc ccatgaaggg gcgccttgc ccagccagat gctgctggtt       3180
ctgcccatcc actaccctct ctgctccagc cactctgggt ctttctccag atgccctgga     3240
cagccctggc ctgggcctgt ccctgagag tgttgggag aagctgagtc tctgggaca        3300 ctctcatcag agtctgaaag gcacatcagg aaacatccct ggtctccagg actaggcaat      3360
gaggaaaggg ccccagctcc tcccttgcc actgagaggg tcgaccctgg gtggccacag      3420
tgacttctgc gtctgtccca gtcaccctga aaccacaaca aaacccagc cccagaccct       3480 gcaggtacaa tacatgtggg gacagtctgt acccagggga agccagttct ctcttcctag      3540
gagaccgggc ctcagggctg tgcccggggc aggcgggggc agcacgtgcc tgtccttgag      3600
```

```
aactcgggac cttaagggtc tctgctctgt gaggcacagc aaggatcctt ctgtccagag    3660
atgaaagcag ctcctgcccc tcctctgacc tcttcctcct tcccaaatct caaccaacaa    3720
ataggtgttt caaatctcat catcaaatct tcatccatcc acatgagaaa gcttaaaacc    3780
caatggattg acaacatcaa gagttggaac aagtggacat ggagatgtta cttgtggaaa    3840
tttagatgtg ttcagctatc gggcaggaga atctgtgtca aattccagca tggttcagaa    3900
gaatcaaaaa gtgtcacagt ccaaatgtgc aacagtgcag gggataaaac tgtggtgcat    3960
tcaaactgag ggatattttg gaacatgaga aggaaggga ttgctgctgc acagaacatg    4020
gatgatctca cacatagagt tgaaagaaag gagtcaatcg cagaatagaa aatgatcact    4080
aattccacct ctataaagtt tccaagagga aaacccaatt ctgctgctag agatcagaat    4140
ggaggtgacc tgtgccttgc aatggctgtg agggtcacgg gagtgtcact tagtgcaggc    4200
aatgtgccgt atcttaatct gggcagggct ttcatgagca cataggaatg cagacattac    4260
tgctgtgttc attttacttc accggaaaag aagaataaaa tcagccgggc gcggtggctc    4320
acgcctgtaa tcccagcact ttagaaggct gaggtgggca gattacttga ggtcaggagt    4380
tcaagaccac cctggccaat atggtgaaac cccggctcta ctaaaaatac aaaaattagc    4440
tgggcatggt ggtgcgcgcc tgtaatccca gctactcggg aggctgaggc tggacaattg    4500
cttggaccca ggaagcagag gttgcagtga gccaagattg tgccactgca ctccagcttg    4560
ggcaacagag ccagactctg taaaaaaaaa aaaaaaaaa aaaaaagaa agaaagaaaa    4620 agaaaagaaa gtataaaatc tctttgggtt aacaaaaaaa gatccacaaa acaaacacca    4680
gctcttatca aacttacaca actctgccag agaacaggaa acacaaatac tcattaactc    4740
acttttgtgg caataaaaacc ttcatgtcaa aaggagacca ggacacaatg aggaagtaaa    4800
actgcaggcc ctacttgggt gcagagaggg aaaatccaca aataaaacat taccagaagg    4860
agctaagatt tactgcattg agttcattcc ccaggtatgc aagtgatttt taacacctga    4920
aaatcaatca ttgcctttac tacatagaca gattagctag aaaaaaatta caactagcag    4980
aacagaagca atttggcctt cctaaaattc cacatcatat catcatgatg gagacagtgc    5040
agacgccaat gacaataaaa agagggacct ccgtcacccg gtaaacatgt ccacacagct    5100
ccagcaagca cccgtcttcc cagtgaatca ctgtaacctc ccctttaatc agccccaggc    5160
aaggctgcct gcgatggcca cacaggctcc aacccgtggg cctcaacctc ccgcagaggc    5220
tctcctttgg ccaccccatg gggagagcat gaggacaggg cagagccctc tgatgcccac    5280
acatggcagg agctgacgcc agagccatgg gggctggaga gcagagctgc tggggtcaga    5340
gcttcctgag gacacccagg cctaagggaa ggcagctccc tggatgggggg caaccaggct    5400 ccgggctcca acctcagagc ccgcatggga ggagccagca ctctaggcct ttcctagggt    5460
gactctgagg ggaccctgac acgacaggat cgctgaatgc acccgagatg aaggggccac    5520
cacgggaccc tgctctcgtg gcagatcagg agagagtggg acaccatgcc aggccccccat    5580 ggcatggctg cgactgaccc aggccactcc cctgcatgca tcagcctcgg taagtcacat    5640
gaccaagccc aggaccaatg tggaaggaag gaaacagcat cccctttagt gatgaaccc    5700 aaggtcagtg caaagagagg ccatgagcag ttaggaaggg tggtccaacc tacagcacaa    5760
accatcatct atcataagta gaagccctgc tccatgaccc ctgcatttaa ataaacgttt    5820
gttaaatgag tcaaattccc tcaccatgag agctcacctg tgtgtaggcc catcacacac    5880
acaaacacac acacacacac acacacacac acacacacac acagggaaag tgcaggatcc    5940
tggacagcac caggcaggct tcacaggcag agcaaacagc gtgaatgacc catgcagtgc    6000
```

```
cctgggcccc atcagctcag agaccctgtg agggctgaga tggggctagg caggggagag    6060
acttagagag ggtggggcct ccagggaggg ggctgcaggg agctgggtac tgccctccag    6120 ggaggggct gcaggagct gggtactgcc ctccagggag ggggctgcag ggagctgggt      6180
actgccctcc agggaggggg ctgcaggag ctgggtactg ccctccaggg aggggctgc      6240 agggagctgg gtactgccct ccagggaggc aggagcactg ttcccaacag agagcacatc    6300
ttcctgcagc agctgcacag acacaggagc ccccatgact gccctgggcc agggtgtgga    6360
ttccaaattt cgtgccccat tgggtgggac ggaggttgac cgtgacatcc aaggggcatc    6420
tgtgattcca aacttaaact actgtgccta caaatagga ataacccta cttttctac      6480 tatctcaaat tccctaagca caagctagca ccctttaaat caggaagttc agtcactcct    6540
ggggtcctcc catgccccca gtctgacttg caggtgcaca gggtggctga catctgtcct    6600
tgctcctcct cttggctcaa ctgccgcccc tctgggggt gactgatggt caggacaagg    6660
gatcctagag ctggccccat gattgacagg aaggcaggac ttggcctcca ttctgaagac    6720 tagggtgtc aagagagctg ggcatcccac agagctgcac aagatgacgc ggacagaggg    6780
tgacacaggg ctcagggctt cagacgggtc gggaggctca gctgagagtt cagggacaga    6840
cctgaggagc ctcagtggga aaagaagcac tgaagtggga agttctggaa tgttctggac    6900
aagcctgagt gctctaagga aatgctccca ccccgatgta gcctgcagca ctggacggtc    6960
tgtgtacctc cccgctgccc atcctctcac agccccgcc tctagggaca caactcctgc    7020
cctaacatgc atctttcctg tctcattcca cacaaaggg cctctggggt ccctgttctg    7080
cattgcaagg agtggaggtc acgttccac agaccaccca gcaacagggt cctatggagg    7140
tgcggtcagg aggatcacac gtccccccat gcccagggga ctgactctgg gggtgatgga    7200
ttggcctgga ggccactggt ccctctgtc cctgagggga atctgcaccc tggaggctgc    7260
cacatccctc ctgattcttt cagctgaggg cccttcttga atcccaggg aggactcaac    7320 ccccactggg aaaggcccag tgtggacggt tccacagcag cccagctaag gcccttggac    7380
acagatcctg agtgagagaa cctttaggga cacaggtgca cggccatgtc cccagtgccc    7440
acacagagca ggggcatctg gaccctgagt gtgtagctcc cgcgactgaa cccagcccct    7500
ccccaatgac gtgaccctg gggtggctcc aggtctccag tccatgccac caaaatctcc    7560
agattgaggg tcctcccttg agtccctgat gcctgtccag gagctgcccc ctgagcaaat    7620
ctagagtgca gagggctggg attgtggcag taaaagcagc cacatttgtc tcaggaagga    7680
aagggaggac atgagctcca ggaagggcga tggcgtcctc tagtgggcgc ctcctgttaa    7740
tgagcaaaaa ggggccagga gagttgagag atcaggctg gccttggact aaggctcaga    7800
tggagaggac tgaggtgcaa agaggggct gaagtagggg agtggtcggg agagatggga    7860
ggagcaggta aggggaagcc ccagggaggc cggggaggg tacagcagag ctctccactc    7920
ctcagcattg acatttgggg tggtcgtgct agtggggttc tgtaagttgt agggtgttca    7980
gcaccatctg gggactctac ccactaaatg ccagcaggac tccctcccca agctctaaca    8040
accaacaatg tctccagact ttccaaatgt cccctggaga gcaaaattgc ttctggcaga    8100
atcactgatc tacgtcagtc tctaaaagtg actcatcagc gaaatccttc acctcttggg    8160
agaagaatca caagtgtgag aggggtagaa actgcagact tcaaaatctt tccaaaagag    8220
ttttacttaa tcagcagttt gatgtcccag gagaagatac atttagagtg tttagagttg    8280
atgccacatg gctgcctgta cctcacagca ggagcagagt gggttttcca agggcctgta    8340
```

```
accacaactg gaatgacact cactgggtta cattacaaag tggaatgtgg ggaattctgt      8400
agactttggg aagggaaatg tatgacgtga gcccacagcc taaggcagtg gacagtccac      8460
tttgaggctc tcaccatcta ggagacatct cagccatgaa catagccaca tctgtcatta      8520
gaaaacatgt tttattaaga ggaaaaatct aggctagaag tgctttatgc tcttttttct      8580
ctttatgttc aaattcatat acttttagat cattccttaa agaagaatct atcccccctaa     8640 gtaaatgtta tcactgactg gatagtgttg gtgtctcact cccaaccect gtgtggtgac      8700 agtgccctgc ttccccagcc ctgggccctc tctgattcct gagagctttg ggtgctcctt      8760
cattaggagg aagagaggaa gggtgttttt aatattctca ccattcaccc atccacctct      8820
tagacactgg gaagaatcag ttgcccactc ttggatttga tcctcgaatt aatgacctct      8880
atttctgtcc cttgtccatt tcaacaatgt gacaggccta agaggtgcct tctccatgtg      8940 attttgagg agaaggttct caagataagt tttctcacac ctctttgaat tacctccacc      9000
tgtgtcccca tcaccattac cagcagcatt tggaccettt tctgttagt cagatgcttt      9060 ccacctcttg agggtgtata ctgtatgctc tctacacagg aatatgcaga ggaaatagaa      9120
aaagggaaat cgcattacta ttcagagaga agaagaccett tatgtgaatg aatgagagtc     9180
taaaatccta agagagccca tataaaatta ttaccagtgc taaaactaca aaagttacac      9240
taacagtaaa ctagaataat aaaacatgca tcacagttgc tggtaaagct aaatcagata      9300 ttttttttctt agaaaaagca ttccatgtgt gttgcagtga tgacaggagt gcccttcagt     9360
caatatgctg cctgtaattt ttgttccctg gcagaatgta ttgtcttttc tccctttaaa      9420
tcttaaatgc aaaactaaag gcagctcctg ggcccctcc ccaaagtcag ctgcctgcaa       9480
ccagccccac gaagagcaga ggcctgagct tccctggtca aaatagggg ctagggagct       9540 taaccttgct cgataaagct gtgttcccag aatgtcgctc ctgttcccag gggcaccagc      9600
ctggagggtg gtgagcctca ctggtggcct gatgcttacc ttgtgccctc acaccagtgg      9660
tcactggaac cttgaacact tggctgtcgc ccggatctgc agatgtcaag aacttctgga      9720
agtcaaatta ctgcccactt ctccagggca gataccetgtg aacatccaaa accatgccac    9780
agaaccctgc ctggggtcta caacacatat ggactgtgag caccaagtcc agccctgaat     9840
ctgtgaccac ctgccaagat gcccctaact gggatccacc aatcactgca catggcaggc     9900
agcgaggctt ggaggtgctt cgccacaagg cagccccaat ttgctgggag tttcttggca     9960
cctggtagtg gtgaggagcc ttgggaccct caggattact cccettaagc atagtgggga    10020 cccttctgca tccccagcag gtgccccgct cttcagagcc tctctctctg aggtttaccc    10080 agaccctgc accaatgaga ccatgctgaa gcctcagaga gagagatgga gctttgacca     10140
ggagccgctc ttccttgagg gccagggcag ggaaagcagg aggcagcacc aggagtggga    10200
acaccagtgt ctaagcccct gatgagaaca gggtggtctc tcccatatgc ccataccagg    10260
cctgtgaaca gaatcctcct tctgcagtga caatgtctga gaggacgaca tgtttcccag    10320
cctaacgtgc agccatgccc atctacccac tgcctactgc aggacagcac caacccagga    10380
gctgggaagc tgggagaaga catggaatac ccatggcttc tcaccttcct ccagtccagt    10440
gggcaccatt tatgcctagg acacccacct gccggcccca ggctcttaag agttaggtca    10500
cctaggtgcc tctgggaggc cgaggcagga gaattgcttg aacccgggag gcagaggttg    10560
cagtgagccg agatcacacc actgcactcc agcctgggtg acagaatgag actctgtctc    10620
aaaaaaaaag agaaagatag catcagtggc taccaagggc tagggcagg ggaaggtgga     10680 gagttaatga ttaatagtat gaagtttcta tgtgagatga tgaaaatgtt ctggaaaaaa    10740
```

```
aaatatagtg gtgaggatgt agaatattgt gaatataatt aacggcattt aattgtacac   10800
ttaacatgat taatgtggca tattttatct tatgtatttg actacatcca agaaacactg   10860
ggagagggaa agcccaccat gtaaaataca cccacccctaa tcagatagtc ctcattgtac   10920
ccaggtacag gcccctcatg acctgcacag gaataactaa ggatttaagg acatgaggct   10980
tcccagccaa ctgcaggtgc acaacataaa tgtatctgca aacagactga gagtaaagct   11040
gggggcacaa acctcagcac tgccaggaca cacacccttc tcgtggattc tgactttatc   11100
tgacccggcc cactgtccag atcttgttgt gggattggga caaggaggt cataaagcct    11160
gtccccaggg cactctgtgt gagcacacga gacctcccca cccccccacc gttaggtctc   11220
cacacataga tctgaccatt aggcattgtg aggaggactc tagcgcgggc tcagggatca   11280
caccagagaa tcaggtacag agaggaagac ggggctcgag gagctgatgg atgacacaga   11340
gcagggttcc tgcagtccac aggtccagct caccctggtg taggtgcccc atcccctga    11400
tccaggcatc cctgacacag ctccctcccg gagcctcctc ccaggtgaca catcagggtc   11460
cctcactcaa gctgtccaga gagggcagca ccttggacag cgcccacccc acttcactct   11520
tcctccctca cagggctcag ggctcagggc tcaagtctca gaacaaatgg cagaggccag   11580
tgagcccaga gatggtgaca gggcaatgat ccaggggcag ctgcctgaaa cgggagcagg   11640
tgaagccaca gatgggagaa gatggttcag gaagaaaaat ccaggaatgg gcaggagagg   11700
agaggaggac acaggctctg tggggctgca gcccaggatg ggactaagtg tgaagacatc   11760
tcagcaggtg aggccaggtc ccatgaacag agaagcagct cccacctccc ctgatgcacg   11820
gacacacaga gtgtgtggtg ctgtgccccc agagtcgggc tctcctgttc tggtccccag   11880
ggagtgagaa gtgaggttga cttgtccctg ctcctctctg ctaccccaac attccacttc   11940
tcctcatgcc cctctctctc aaatatgatt tggatctatg tccccgccca aatctcatgt   12000
caaattgtaa accccaatgt tggaggtggg gccttgtgag aagtgattgg ataatgcggg   12060
tggatttct gctttgatgc tgtttctgtg atagagatct cacatgatct ggttgtttaa    12120
aagtgtgtag cacctctccc ctctctctct ctctctctta ctcatgctct gccatgtaag   12180
acgttcctgt ttccccttca ccgtccagaa tgattgtaag ttttctgagg cctccccagg   12240
agcagaagcc actatgcttc ctgtacaact gcagaatgat gagcgaatta aacctctttt   12300
ctttataaat tacccagtct caggtatttc tttatagcaa tgcgaggaca gactaataca   12360
atcttctact cccagatccc cgcacacgct tagccccaga catcactgcc cctgggagca   12420
tgcacagcgc agcctcctgc cgacaaaagc aaagtcacaa aaggtgacaa aaatctgcat   12480
ttggggacat ctgattgtga aagagggagg acagtacact tgtagccaca gagactgggg   12540
ctcaccgagc tgaaacctgg tagcactttg gcataacatg tgcatgaccc gtgttcaatg   12600
tctagagatc agtgttgagt aaaacagcct ggtctgggc cgctgctgtc cccacttccc    12660
tcctgtccac cagagggcgg cagagttcct cccaccctgg agcctcccca ggggctgctg   12720
acctccctca gccgggccca cagcccagca gggtccaccc tcacccgggt cacctcggcc   12780
cacgtcctcc tcgccctccg agctcctcac acggactctg tcagctcctc cctgcagcct   12840
atcggccgcc cacctgaggc ttgtcggccg cccacttgag gcctgtcggc tgccctctgc   12900
aggcagctcc tgtcccctac accccctcct tcccgggct cagctgaaag ggcgtctccc    12960
agggcagctc cctgtgatct ccaggacagc tcagtctctc acaggctccg acgcccccta   13020
tgctgtcacc tcacagccct gtcattacca ttaactcctc agtcccatga agttcactga   13080
```

```
gcgcctgtct cccggttaca ggaaaactct gtgacaggga ccacgtctgt cctgctctct    13140
gtggaatccc agggcccagc ccagtgcctg acacggaaca gatgctccat aaatactggt    13200
taaatgtgtg ggagatctct aaaaagaagc atatcacctc cgtgtggccc ccagcagtca    13260
gagtctgttc catgtggaca caggggcact ggcaccagca tgggaggagg ccagcaagtg    13320
cccgcggctg ccccaggaat gaggcctcaa cccccagagc ttcagaaggg aggacagagg    13380
cctgcaggga atagatcctc cggcctgacc ctgcagccta atccagagtt cagggtcagc    13440
tcacaccacg tcgaccctgg tcagcatccc tagggcagtt ccagacaagg ccggaggtct    13500
cctcttgccc tccaggggt gacattgcac acagacatca ctcaggaaac ggattccct    13560 ggacaggaac ctggctttgc taaggaagtg gaggtggagc ctggtttcca tcccttgctc    13620
caacagaccc ttctgatctc tcccacatac ctgctctgtt cctttctggg tcctatgagg    13680
accctgttct gccaggggtc cctgtgcaac tccagactcc ctcctggtac caccatgggg    13740
aaggtggggt gatcacagga cagtcagcct cgcagagaca gagaccaccc aggactgtca    13800
gggagaacat ggacaggccc tgagccgcag ctcagccaac agacacggag agggagggtc    13860
cccctggagc cttccccaag gacagcagag cccagagtca cccacctccc tccaccacag    13920
tcctctcttt ccaggacaca caagacacct cccctccac atgcaggatc tggggactcc    13980
tgagacctct gggcctgggt ctccatccct gggtcagtgg cggggttggt ggtactggag    14040
acagagggct ggtccctccc cagccaccac ccagtgagcc tttttctagc ccccagagcc    14100
acctctgtca ccttcctgtt gggcatcatc ccaccttccc agagccctgg agagcatggg    14160
gagacccggg accctgctgg gtttctctgt cacaaaggaa aataatcccc ctggtgtgac    14220
agacccaagg acagaacaca gcagaggtca gcactgggga agacaggttg tcctcccagg    14280
ggatgggggt ccatccacct tgccgaaaag atttgtctga ggaactgaaa atagaaggga    14340
aaaaagagga gggacaaaag aggcagaaat gagaggggag gggacagagg acacctgaat    14400
aaagaccaca cccatgaccc acgtgatgct gagaagtact cctgccctag aagagactc    14460 agggcagagg gaggaaggac agcagaccag acagtcacag cagccttgac aaaacgttcc    14520
tggaactcaa gctcttctcc acagaggagg acagagcaga cagcagagac catggagtct    14580
ccctcggccc ctccccacag atggtgcatc ccctggcaga ggctcctgct cacaggtgaa    14640
gggaggacaa cctgggagag ggtgggagga gggagctggg gtctcctggg taggacaggg    14700
ctgtgagacg gacagagggc tcctgttgga gcctgaatag ggaagaggac atcagagagg    14760
gacaggagtc acaccagaaa aatcaaattg aactggaatt ggaaggggc aggaaaacct    14820 caagagttct attttcctag ttaattgtca ctggccacta cgttttttaaa aatcataata    14880 actgcatcag atgacacttt aaataaaaac ataaccaggg catgaaacac tgtcctcatc    14940
cgcctaccgc ggacattgga aaataagccc caggctgtgg agggccctgg gaaccctcat    15000
gaactcatcc acaggaatct gcagcctgtc ccaggcactg gggtgcaacc aagatc      15056
```

<210> SEQ ID NO 15
<211> LENGTH: 858
<212> TYPE: DNA
<213> ORGANISM: Artificial Sequence
<220> FEATURE:
<223> OTHER INFORMATION: Mucin-TRE

<400> SEQUENCE: 15

```
cgagcggccc ctcagcttcg gcgcccagcc ccgcaaggct cccggtgacc actagagggc      60
gggaggagct cctggccagt ggtggagagt ggcaaggaag gaccctaggg ttcatcggag     120
```

```
cccaggttta ctcccttaag tggaaatttc ttcccccact cctccttggc tttctccaag      180
gagggaaccc aggctgctgg aaagtccggc tggggcgggg actgtgggtt caggggagaa      240
cggggtgtgg aacgggacag ggagcggtta aagggtggg gctattccgg gaagtggtgg       300
ggggagggag cccaaaacta gcacctagtc cactcattat ccagccctct tatttctcgg      360
ccgctctgct tcagtggacc cggggagggc ggggaagtgg agtgggagac ctaggggtgg      420
gcttcccgac cttgctgtac aggacctcga cctagctggc tttgttcccc atccccacgt      480
tagttgttgc cctgaggcta aaactagagc ccaggggccc caagttccag actgcccctc      540
ccccctcccc cggagccagg gagtggttgg tgaaggggg aggccagctg gagaacaaac       600
gggtagtcag ggggttgagc gattagagcc cttgtaccct acccaggaat ggttggggag      660
gaggaggaag aggtaggagg tagggaggg ggcgggttt tgtcacctgt cacctgctcg        720
ctgtgcctag ggcgggcggg cggggagtgg ggggaccggt ataaagcggt aggcgcctgt      780
gcccgctcca cctctcaagc agccagcgcc tgcctgaatc tgttctgccc cctccccacc     840
catttcacca ccaccatg                                                    858

<210> SEQ ID NO 16
<211> LENGTH: 5224
<212> TYPE: DNA
<213> ORGANISM: Artificial Sequence
<220> FEATURE:
<223> OTHER INFORMATION: AlphaFP-TRE

<400> SEQUENCE: 16
gaattcttag aaatatgggg gtaggggtgg tggtggtaat tctgttttca ccccataggt       60
gagataagca ttgggttaaa tgtgctttca cacacacatc acatttcata agaattaagg      120
aacagactat gggctggagg actttgagga tgtctgtctc ataacacttg ggttgtatct      180
gttctatggg gcttgtttta agcttggcaa cttgcaacag ggttcactga ctttctcccc      240
aagcccaagg tactgtcctc ttttcatatc tgttttgggg cctctgggc ttgaatatct       300 gagaaaatat aaacatttca ataatgttct gtggtgagat gagtatgaga gatgtgtcat      360
tcatttgtat caatgaatga atgaggacaa ttagtgtata aatccttagt acaacaatct      420
gagggtaggg gtggtactat tcaatttcta tttataaaga tacttatttc tatttatttta    480 tgcttgtgac aaatgttttg ttcgggacca caggaatcac aaagatgagt ctttgaattt      540
aagaagttaa tggtccagga ataattcat agcttacaaa tgactatgat ataccatcaa       600
acaagaggtt ccatgagaaa ataatctgaa aggtttaata agttgtcaaa ggtgagaggg      660
ctcttctcta gctagagact aatcagaaat acattcaggg ataattattt gaatagacct      720
taagggttgg gtacattttg ttcaagcatt gatggagaag gagagtgaat atttgaaaac      780
attttcaact aaccaaccac ccaatccaac aaacaaaaaa tgaaaagaat ctcagaaaca      840
gtgagataag agaaggaatt ttctcacaac ccacacgtat agctcaactg ctctgaagaa      900
gtatatatct aatatttaac actaacatca tgctaataat gataataatt actgtcattt      960
tttaatgtct ataagtacca ggcatttaga agatattatt ccatttatat atcaaaataa     1020
acttgagggg atagatcatt ttcatgatat atgagaaaaa ttaaaaacag attgaattat     1080
ttgcctgtca tacagctaat aattgaccat aagacaatta gatttaaatt agttttgaat    1140 cttttctaata ccaagttca gtttactgtt ccatgttgct tctgagtggc ttcacagact    1200
tatgaaaaag taaacggaat cagaattaca tcaatgcaaa agcattgctg tgaactctgt    1260
```

```
acttaggact aaactttgag caataacaca catagattga ggattgtttg ctgttagcat    1320
acaaactctg gttcaaagct cctctttatt gcttgtcttg gaaaatttgc tgttcttcat    1380
ggtttctctt ttcactgcta tctattttt c tcaaccactc acatggctac aataactgtc    1440
tgcaagctta tgattcccaa atatctatct ctagcctcaa tcttgttcca gaagataaaa    1500
agtagtattc aaatgcacat caacgtctcc acttggaggg cttaaagacg tttcaacata    1560
caaaccgggg agttttgcct ggaatgtttc ctaaaatgtg tcctgtagca catagggtcc    1620
tcttgttcct taaaatctaa ttacttttag cccagtgctc atcccaccta tggggagatg    1680
agagtgaaaa gggagcctga ttaataatta cactaagtca ataggcatag agccaggact    1740
gtttgggtaa actggtcact ttatcttaaa ctaaatatat ccaaaactga acatgtactt    1800
agttactaag tctttgactt tatctcattc ataccactca gctttatcca ggccacttat    1860
ttgacagtat tattgcgaaa acttcctaac tggtctcctt atcatagtct tatcccettt    1920
tgaaacaaaa gagacagttt caaaatacaa atatgatttt tattagctcc ctttttgttgt    1980
ctataatagt cccagaagga gttataaact ccatttaaaa agtctttgag atgtggccct    2040
tgccaacttt gccaggaatt cccaatatct agtattttct actattaaac tttgtgcctc    2100
ttcaaaactg catttctct cattccctaa gtgtgcattg ttttcccttta ccggttggtt    2160
tttccaccac cttttacatt ttcctggaac actataccct ccctcttcat ttgcccacc    2220
tctaatttc tttcagatct ccatgaagat gttacttcct ccaggaagcc ttatctgacc    2280
cctccaaaga tgtcatgagt tcctcttttc attctactaa tcacagcatc catcacacca    2340
tgttgtgatt actgatacta ttgtctgttt ctctgattag gcagtaagct caacaagagc    2400
tacatggtgc ctgtctcttg ttgctgatta ttcccatcca aaaacagtgc ctggaatgca    2460
gacttaacat tttattgaat gaataaataa aaccccatct atcgagtgct actttgtgca    2520
agacccggtt ctgaggcatt tatatttatt gatttattta attctcattt aaccatgaag    2580
gaggtactat cactatcctt attttatagt tgataaagat aaagcccaga gaaatgaatt    2640
aactcaccca aagtcatgta gctaagtgac agggcaaaaa ttcaaaccag ttcccaact    2700
ttacgtgatt aatactgtgc tatactgcct ctctgatcat atggcatgga atgcagacat    2760
ctgctccgta aggcagaata tggaaggaga ttggaggatg acacaaaacc agcataatat    2820
cagaggaaaa gtccaaacag gacctgaact gatagaaaag ttgttactcc tggtgtagtc    2880
gcatcgacat cttgatgaac tggtggctga cacaacatac attggcttga tgtgtacata    2940
ttatttgtag ttgtgtgtgt attttttatat atatatttgt aatattgaaa tagtcataat    3000
ttactaaagg cctaccattt gccaggcatt tttacatttg tccccctctaa tcttttgatg    3060
agatgatcag attggattac ttggccttga agatgatata tctacatcta tatctatatc    3120
tatatctata tctatatcta tatctatatc tatatctata tatgtatatc agaaaagctg    3180
aaatatgttt tgtaaagtta taaagatttc agactttata gaatctggga tttgccaaat    3240
gtaacccctt tctctacatt aaacccatgt tggaacaaat acatttatta ttcattcatc    3300
aaatgttgct gagtcctggc tatgaaccag acactgtgaa agcctttggg atattttgcc    3360
catgcttggg caagcttata tagtttgctt cataaaactc tatttcagtt cttcataact    3420
aatacttcat gactattgct tttcaggtat tccttcataa caaatacttt ggctttcata    3480
tatttgagta aagtcccct tgaggaagag tagaagaact gcactttgta aatactatcc    3540
tggaatccaa acggatagac aaggatggtg ctacctcttt ctggagagta cgtgagcaag    3600
gcctgttttg ttaacatgtt ccttaggaga caaaacttag gagagacacg catagcagaa    3660
```

```
aatggacaaa aactaacaaa tgaatgggaa ttgtacttga ttagcattga agaccttgtt    3720
tatactatga taaatgtttg tatttgctgg aagtgctact gacggtaaac ccttttttgtt   3780 taaatgtgtg ccctagtagc ttgcagtatg atctatttt taagtactgt acttagctta    3840
tttaaaaatt ttatgtttaa aattgcatag tgctctttca ttgaagaagt tttgagagag    3900
agatagaatt aaattcactt atcttaccat ctagagaaac ccaatgttaa aactttgttg    3960
tccattattt ctgtctttta ttcaacattt tttttagagg gtgggaggaa tacagaggag    4020
gtacaatgat acacaaatga gagcactctc catgtattgt tttgtcctgt ttttcagtta    4080
acaatatatt atgagcatat ttccatttca ttaaatattc ttccacaaag ttattttgat    4140
ggctgtatat caccctactt tatgaatgta ccatattaat ttatttcctg gtgtgggtta    4200 tttgattta taatcttacc tttagaataa tgaaacacct gtgaagcttt agaaaatact     4260
ggtgcctggg tctcaactcc acagattctg atttaactgg tctgggttac agactaggca    4320
ttgggaattc aaaaagttcc cccagtgatt ctaatgtgta gccaagatcg ggaaccctg     4380 tagacaggga tgataggagg tgagccactc ttagcatcca tcatttagta ttaacatcat    4440
catcttgagt tgctaagtga atgatgcacc tgacccactt tataaagaca catgtgcaaa    4500
taaaattatt ataggacttg gtttattagg gcttgtgctc taagttttct atgttaagcc    4560
atacatcgca tactaaatac tttaaaatgt accttattga catacatatt aagtgaaaag    4620
tgtttctgag ctaaacaatg acagcataat tatcaagcaa tgataatttg aaatgaattt    4680
attattctgc aacttaggga caagtcatct ctctgaattt tttgtacttt gagagtattt    4740
gttatatttg caagatgaag agtctgaatt ggtcagacaa tgtcttgtgt gcctggcata    4800
tgataggcat ttaatagttt taagaatta atgtatttag atgaattgca taccaaatct     4860
gctgtctttt ctttatggct tcattaactt aatttgagag aaattaatta ttctgcaact    4920
tagggacaag tcatgtcttt gaatattctg tagtttgagg agaatatttg ttatatttgc    4980
aaaataaaat aagtttgcaa gtttttttt tctgccccaa agagctctgt gtccttgaac     5040
ataaaataca aataaccgct atgctgttaa ttattggcaa atgtcccatt ttcaacctaa    5100
ggaaatacca taaagtaaca gatataccaa caaaaggtta ctagttaaca ggcattgcct    5160
gaaaagagta taaagaatt tcagcatgat tttccatatt gtgcttccac cactgccaat     5220
aaca                                                                 5224

<210> SEQ ID NO 17
<211> LENGTH: 307
<212> TYPE: DNA
<213> ORGANISM: Artificial Sequence
<220> FEATURE:
<223> OTHER INFORMATION: Nucleotide sequence for ADP

<400> SEQUENCE: 17
gatgaccggc tcaaccatcg cgcccacaac ggactatcgc aacaccactg ctaccggact     60
aacatctgcc ctaaatttac cccaagttca tgcctttgtc aatgactggg cgagcttgga    120
catgtggtgg ttttccatag cgcttatgtt tgtttgcctt attattatgt ggcttatttg    180
ttgcctaaag cgcagacgcg ccagaccccc catctatagg cctatcattg tgctcaaccc    240
acacaatgaa aaaattcata gattggacgg tctgaaacca tgttctcttc ttttacagta    300
tgattaa                                                              307

<210> SEQ ID NO 18
```

```
<211> LENGTH: 101
<212> TYPE: PRT
<213> ORGANISM: Artificial Sequence
<220> FEATURE:
<223> OTHER INFORMATION: Amino acid sequence for ADP

<400> SEQUENCE: 18

Met Thr Gly Ser Thr Ile Ala Pro Thr Thr Asp Tyr Arg Asn Thr Thr
 1               5                  10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Ile Val Leu Asn Pro
65                  70                  75                  80

His Asn Glu Lys Ile His Arg Leu Asp Gly Leu Lys Pro Cys Ser Leu
                85                  90                  95

Leu Leu Gln Tyr Asp
            100

<210> SEQ ID NO 19
<211> LENGTH: 28
<212> TYPE: DNA
<213> ORGANISM: Artificial Sequence
<220> FEATURE:
<223> OTHER INFORMATION: PCR EMCV IRES (PCR primer 96.74.2)

<400> SEQUENCE: 19
gacgtcgact aattccggtt attttcca                                          28

<210> SEQ ID NO 20
<211> LENGTH: 28
<212> TYPE: DNA
<213> ORGANISM: Artificial Sequence
<220> FEATURE:
<223> OTHER INFORMATION: PCR EMCV IRES (PCR primer 96.74.1)

<400> SEQUENCE: 20
gacgtcgaca tcgtgttttt caaaggaa                                          28

<210> SEQ ID NO 21
<211> LENGTH: 25
<212> TYPE: DNA
<213> ORGANISM: Artificial Sequence
<220> FEATURE:
<223> OTHER INFORMATION: Ad5 sequence to 1314 to 1338
      (PCR primer 96.74.3)

<400> SEQUENCE: 21
cctgagacgc ccgacatcac ctgtg                                             25

<210> SEQ ID NO 22
<211> LENGTH: 30
<212> TYPE: DNA
<213> ORGANISM: Artificial Sequence
<220> FEATURE:
<223> OTHER INFORMATION: Antisense of Ad5 sequence 1572 to 1586
      (PCR primer 96.74.6)

<400> SEQUENCE: 22
gtcgaccatt cagcaaacaa aggcgttaac                                        30
```

```
<210> SEQ ID NO 23
<211> LENGTH: 30
<212> TYPE: DNA
<213> ORGANISM: Artificial Sequence
<220> FEATURE:
<223> OTHER INFORMATION: Ad5 sequence 1714 to 1728 (PCR primer 96.74.4)

<400> SEQUENCE: 23
tgctgaatgg tcgacatgga ggcttgggag                               30

<210> SEQ ID NO 24
<211> LENGTH: 26
<212> TYPE: DNA
<213> ORGANISM: Artificial Sequence
<220> FEATURE:
<223> OTHER INFORMATION: Antisense of Ad5 sequence 2070 to 2094
      (PCR primer 96.74.5)

<400> SEQUENCE: 24
cacaaaccgc tctccacaga tgcatg                                   26

<210> SEQ ID NO 25
<211> LENGTH: 29
<212> TYPE: DNA
<213> ORGANISM: Artificial Sequence
<220> FEATURE:
<223> OTHER INFORMATION: Human UPII (PCR primer 127.2.1)

<400> SEQUENCE: 25
aggaccggtc actatagggc acgcgtggt                                29

<210> SEQ ID NO 26
<211> LENGTH: 31
<212> TYPE: DNA
<213> ORGANISM: Artificial Sequence
<220> FEATURE:
<223> OTHER INFORMATION: Human UPII (PCR primer 127.2.2)

<400> SEQUENCE: 26
aggaccggtg ggatgctggg ctgggaggtg g                             31

<210> SEQ ID NO 27
<211> LENGTH: 29
<212> TYPE: DNA
<213> ORGANISM: Artificial Sequence
<220> FEATURE:
<223> OTHER INFORMATION: PCR primer 100.113.1

<400> SEQUENCE: 27
aggggtaccc actatagggc acgcgtggt                                29

<210> SEQ ID NO 28
<211> LENGTH: 32
<212> TYPE: DNA
<213> ORGANISM: Artificial Sequence
<220> FEATURE:
<223> OTHER INFORMATION: PCR primer 100.113.2

<400> SEQUENCE: 28
acccaagctt gggatgctgg gctgggaggt gg                            32

<210> SEQ ID NO 29
<211> LENGTH: 30
<212> TYPE: DNA
<213> ORGANISM: Artificial Sequence
<220> FEATURE:
```

```
<223> OTHER INFORMATION: PCR primer 127.50.1

<400> SEQUENCE: 29
aggaccggtc aggcttcacc ccagacccac                                    30

<210> SEQ ID NO 30
<211> LENGTH: 24
<212> TYPE: DNA
<213> ORGANISM: Artificial Sequence
<220> FEATURE:
<223> OTHER INFORMATION: PCR primer 31.166.1

<400> SEQUENCE: 30
tgcgccggtg tacacaggaa gtga                                          24

<210> SEQ ID NO 31
<211> LENGTH: 21
<212> TYPE: DNA
<213> ORGANISM: Artificial Sequence
<220> FEATURE:
<223> OTHER INFORMATION: PCR primer 32.32.1

<400> SEQUENCE: 31
gagtttgtgc catcggtcta c                                             21

<210> SEQ ID NO 32
<211> LENGTH: 21
<212> TYPE: DNA
<213> ORGANISM: Artificial Sequence
<220> FEATURE:
<223> OTHER INFORMATION: PCR primer 32.32.2

<400> SEQUENCE: 32
aatcaatcct tagtcctcct g                                             21

<210> SEQ ID NO 33
<211> LENGTH: 25
<212> TYPE: DNA
<213> ORGANISM: Artificial Sequence
<220> FEATURE:
<223> OTHER INFORMATION: PCR primer 51.176

<400> SEQUENCE: 33
gcagaaaaat cttccaaaca ctccc                                         25

<210> SEQ ID NO 34
<211> LENGTH: 27
<212> TYPE: DNA
<213> ORGANISM: Artificial Sequence
<220> FEATURE:
<223> OTHER INFORMATION: PCR primer 99.120.1

<400> SEQUENCE: 34
acgtacaccg gtcgttacat aacttac                                       27

<210> SEQ ID NO 35
<211> LENGTH: 26
<212> TYPE: DNA
<213> ORGANISM: Artificial Sequence
<220> FEATURE:
<223> OTHER INFORMATION: PCR primer 99.120.2

<400> SEQUENCE: 35
ctagcaaccg gtcggttcac taaacg                                        26
```